United States Patent [19]

Greenlee et al.

[11] Patent Number: 5,449,682
[45] Date of Patent: Sep. 12, 1995

[54] ANGIOTENSIN II ANTAGONISTS INCORPORATING A SUBSTITUTED BENZYL ELEMENT

[75] Inventors: William J. Greenlee, Teaneck, N.J.; David Hangauer, East Amherst, N.Y.; Arthur A. Patchett; Thomas F. Walsh, both of Westfield, N.J.; Kenneth J. Fitch, Scotch Plains, N.J.; Daljit S. Dhanoa; Ralph A. Rivero, both of Tinton Falls, N.J.

[73] Assignee: Merck & Co., Inc., Rahway, N.J.

[21] Appl. No.: 61,975

[22] Filed: May 17, 1993

Related U.S. Application Data

[60] Division of Ser. No. 744,557, Aug. 13, 1991, Pat. No. 5,240,938, which is a continuation-in-part of Ser. No. 671,551, Mar. 19, 1991, abandoned, which is a continuation-in-part of Ser. No. 479,786, Feb. 19, 1990, abandoned.

[51] Int. Cl.⁶ ............... A61K 31/495; A61K 31/505; C07D 471/04; C07D 235/04
[52] U.S. Cl. ..................... 514/381; 514/394; 548/254; 548/304.4
[58] Field of Search ............... 548/254, 304.4; 514/381, 394

[56] References Cited

U.S. PATENT DOCUMENTS

| | | | |
|---|---|---|---|
| 4,880,804 | 11/1989 | Carini et al. | 514/235.8 |
| 5,128,327 | 7/1992 | Chakravarty et al. | 514/81 |
| 5,151,435 | 9/1992 | Bagley et al. | 514/303 |
| 5,162,325 | 11/1992 | Chakravarty et al. | 514/259 |
| 5,177,074 | 1/1993 | Allen et al. | 514/234.2 |
| 5,177,095 | 1/1993 | Greenlee et al. | 514/384 |
| 5,183,810 | 2/1993 | Greenlee et al. | 514/63 |
| 5,198,438 | 3/1993 | Allen et al. | 514/235.8 |
| 5,236,928 | 8/1993 | Chakravarty et al. | 514/275 |
| 5,252,574 | 10/1993 | Allen et al. | 514/259 |
| 5,264,439 | 11/1993 | Greenlee et al. | 514/259 |

FOREIGN PATENT DOCUMENTS

| | | |
|---|---|---|
| 58696/90 | 1/1991 | Australia . |
| 0253310 | 1/1988 | European Pat. Off. . |
| 0260613 | 3/1988 | European Pat. Off. . |
| 0323841 | 7/1989 | European Pat. Off. . |
| 0324377 | 5/1990 | European Pat. Off. . |
| 0392317 | 10/1990 | European Pat. Off. . |
| 0399731 | 11/1990 | European Pat. Off. . |
| 0399732 | 11/1990 | European Pat. Off. . |
| 0400974 | 12/1990 | European Pat. Off. . |
| 0403158 | 12/1990 | European Pat. Off. . |
| 0403159 | 12/1990 | European Pat. Off. . |
| 409332 | 1/1991 | European Pat. Off. . |
| 0411766 | 2/1991 | European Pat. Off. . |
| 0412594 | 2/1991 | European Pat. Off. . |
| 0415886 | 3/1991 | European Pat. Off. . |
| 0419048 | 3/1991 | European Pat. Off. . |
| 429257 | 5/1991 | European Pat. Off. . |
| 430709 | 6/1991 | European Pat. Off. . |
| 434249 | 6/1991 | European Pat. Off. . |
| WO91/11909 | 8/1991 | WIPO . |
| WO91/11999 | 8/1991 | WIPO . |
| WO91/12001 | 8/1991 | WIPO . |
| WO91/12002 | 8/1991 | WIPO . |

*Primary Examiner*—Mukund J. Shah
*Assistant Examiner*—Matthew V. Grumbling
*Attorney, Agent, or Firm*—Valerie J. Camara; Mark R. Daniel; Joseph F. DiPrima

[57] ABSTRACT

Substituted heterocycles attached through a methylene bridge to novel substituted phenyl derivatives of the Formula I are useful as angiotensin II antagonists.

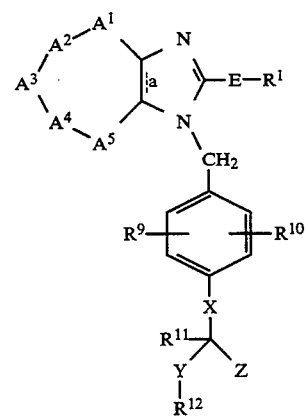

wherein the substituents are as defined in the claims.

11 Claims, No Drawings

ANGIOTENSIN II ANTAGONISTS INCORPORATING A SUBSTITUTED BENZYL ELEMENT

RELATED APPLICATIONS

The present application is a divisional application of application Ser. No. 744,557 filed on Aug. 13, 1991 (now issued to U.S. Pat. No. 5,240,938 on Aug. 31, 1993), which is a continuation in part of application Ser. No. 671,551 filed on Mar. 19, 1991 (now abandoned), which is a continuation in part of application Ser. No. 479,786 filed on Feb. 19, 1990 (now abandoned).

BACKGROUND OF THE INVENTION

The Renin-angiotensin system (RAS) plays a central role in the regulation of normal blood pressure and seems to be critically involved in hypertension development and maintenance as well as congestive heart failure. Angiotensin II (A II), is an octapeptide hormone produced mainly in the blood during the cleavage of angiotensin I by angiotensin converting enzyme (ACE) localized on the endothelium of blood vessels of lung, kidney, and many other organs. It is the end product of the renin-angiotensin system (RAS) and is a powerful arterial vasoconstrictor that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by partial agonist activity and lack of oral absorption [M. Antonaccio. *Clin. Exp. Hypertens.* A4, 27–46 (1982);. D. H. P. Streeten and G. H. Anderson, Jr. - *Handbook of Hypertension, Clinical Pharmacology of Antihypertensive Drugs*, ed. A. E. Doyle, Vol. 5, pp. 246–271, Elsevier Science Publisher, Amsterdam, The Netherlands, 1984].

Recently, several non-peptide compounds have been described as A II antagonists. Illustrative of such compounds are those disclosed in U.S. Pat. Nos. 4,207,324; 4,340,598; 4,576,958; 4,582,847; and 4,880,804 and in European Patent Applications 028,834; 245,637; 253,310; and 291,969; and in articles by A. T. Chiu, et al. [*Eur. J. Pharm. Exp. Therap*, 157, 13–21 (1988)]and by P. C. Wong, et al. [*J. Pharm. Exp. Therap*, 247, 1–7(1988)]. All of the U.S. patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,5,7-tetrahydro-2H-imidazo[4,5-c]-pyridine-6-carboxylic acid and analogs thereof as antihypertensive agents.

None of the compounds disclosed within this application or in any US Patent, European Applications or literature publication are of the type containing substituted heterocycles bonded through an alkyl bridge to a novel substituted phenyl of the type disclosed herein. The imidazole-5-, 6-, and 7-fused heterocycles have been disclosed in earlier U.S. patent applications focusing on the heterocyclic fragment of the antagonist design. The Ser. Nos. of these applications are 351,508; 358,971; 375,655; 360,673; 375,217; and 386,328 and are hereby incorporated by reference.

BRIEF DESCRIPTION OF THE INVENTION

This invention is directed to substituted heterocycles attached through a methylene bridge to novel substituted phenyl derivatives to give compounds of the Formula I, which are angiotensin II antagonists and are useful in the treatment of hypertension and congestive heart failure. Specifically, the compounds of this invention contain a heterocyclic moiety which is substituted at the specified positions and to which a methylene bridge connecting a novel substituted phenyl group as defined by the lower portion of Formula I, is attached. Additionally, pharmaceutically acceptable compositions of these novel compounds, as the sole therapeutically active ingredient and in combination with diuretics and other antihypertensive agents, including beta blockers, angiotensin converting enzyme inhibitors, calcium channel blockers or a combination thereof are disclosed and claimed. Further, methods of treating hypertension and congestive heart failure are described and claimed.

The compounds of this invention have central nervous system (CNS) activity. They are useful in the treatment of cognitive dysfunctions including Alzheimer's disease, amnesia and senile dementia. These compounds also have anxiolytic and antidepressant properties and are therefore, useful in the relief of symptoms of anxiety and tension and in the treatment of patients with depressed or dysphoric mental states.

DETAILED DESCRIPTION OF THE INVENTION

This invention relates to compounds of the general Formula I:

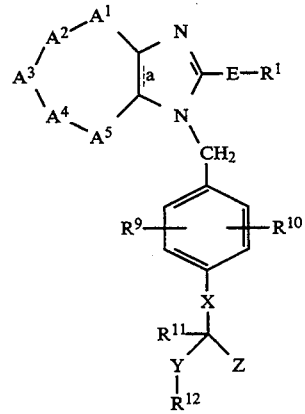

$R^1$ is:
(a) $(C_1-C_6)$-alkyl, $(C_2-C_6)$-alkenyl or $(C_2-C_6)$-alkynyl each of which is unsubstituted or substituted with a substituent selected from the group consisting of:
  i) aryl as defined below in $R^1(b)$,
  ii) $(C_3-C_7)$-cycloalkyl,
  iii) Cl, Br, I, F,
  iv) OH,
  v) $NH_2$,
  vi) $NH(C_1-C_4)$-alkyl,
  vii) $N[(C_1-C_4)$-alkyl$)]_2$,
  viii) $NHSO_2R^2$,
  ix) $CF_3$, x) COOR$^2$, or
xi) SO$_2$NHR$^{2a}$; and
(b) aryl, wherein aryl is defined as phenyl or naphthyl and is unsubstituted, mono- or disubstituted with substituents selected from the group consisting of:
i) Cl, Br, I, F,
ii) (C$_1$-C$_4$)-alkyl,
iii) (C$_1$-C$_4$)-alkoxy,
iv) NO$_2$
v) CF$_3$
vi) SO$_2$NR$^{2a}$R$^{2a}$,
vii) (C$_1$-C$_4$)-alkylthio,
viii) hydroxy,
ix) amino,
x) (C$_3$-C$_7$)-cycloalkyl,
xi) (C$_3$-C$_{10}$)-alkenyl; and
(c) heteroaryl, wherein heteroaryl is defined as a 5- or 6-membered heteroaromatic moiety, which can contain one or two members selected from the group consisting of N, O, S and wherein the heteroaryl is unsubstituted, mono- or disubstituted with substituents selected from the group consisting of:
i) Cl, Br, I, F,
ii) OH,
iii) SH,
iv) NO$_2$,
v) (C$_1$-C$_4$)-alkyl,
vi) (C$_2$-C$_4$)-alkenyl,
vii) (C$_2$-C$_4$)-alkynyl,
viii) (C$_1$-C$_4$)-alkoxy, or
ix) CF$_3$, or
(d) (C$_1$-C$_4$)-perfluoroalkyl; and
—A$^1$—A$^2$—A$^3$—A$^4$—A$^5$— is:
when A$^4$ and A$^5$ are absent, then —A$^1$—A$^2$—A$^3$— is:

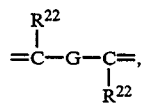 (a)

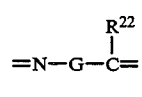 (b)

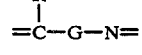 (c)

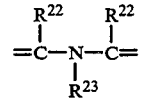 (d)

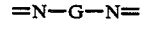 (e)

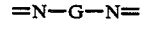 (f)

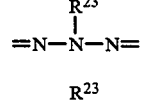 (g)

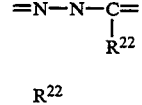 (h)

wherein a represents a single bond in these definitions of A in structure I but, hereafter will represent a double bond.

 (i)

 (j)

 (k)

 (l)

 (m)

 (n)

 (o)

 (p)

 (q)

 (r)

 (s)

 (t)

 (u)

 (v)

 (w)

 (x)

-continued
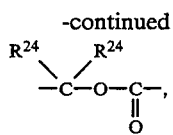 (y)
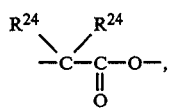 (z)
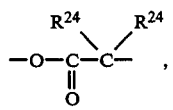 (ba)
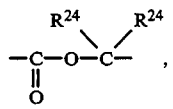 (bb)
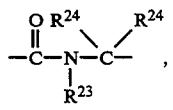 (bc)
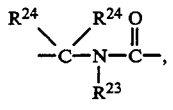 (bd)
when $A^4$ is present and $A^5$ is absent, then $-A^1-A^2-A^3-A^4-$ represents:
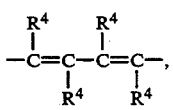 (be)
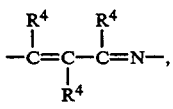 (bf)
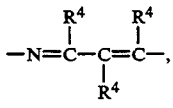 (bg)
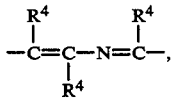 (bh)
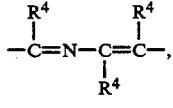 (bi)
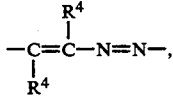 (bj)
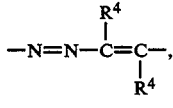 (bk)
-continued
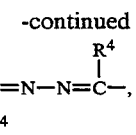 (bl)
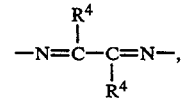 (bm)
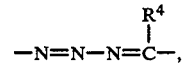 (bn)
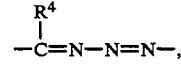 (bo)
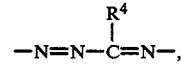 (bp)
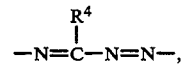 (bq)
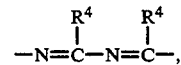 (br)
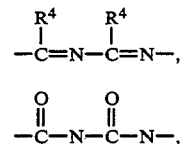 (bs)
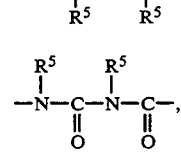 (bt)
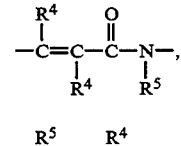 (bu)
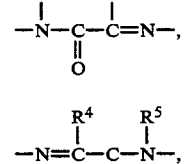 (bv)
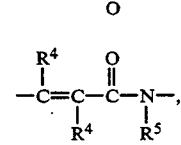 (bw)
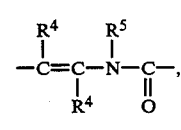 (bx)
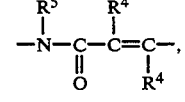 (by)
 (bz)
 (ca)

-continued (cb) 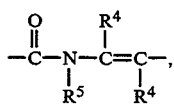

(cc) 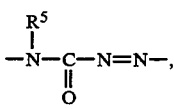

(cd) 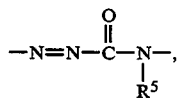

(ce) 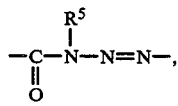

(cf) 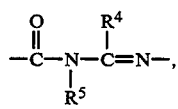

(cg) 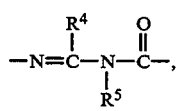

(ch) 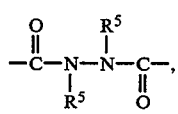

(ci) 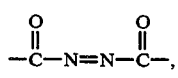

(cj) 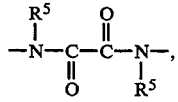

(ck) 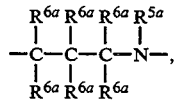

(cl) 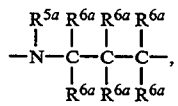

(cm) 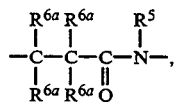

(cn) 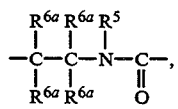

(co) 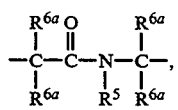

-continued (cp) 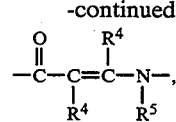

(cq) 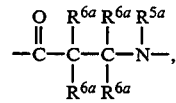

(cr) 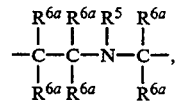

when $A^4$ and $A^5$ are present, then $-A^1-A^2-A^3-A^4-A^5-$ are:

(cs) 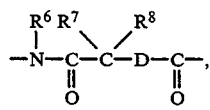

(ct) 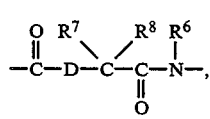

(cu) 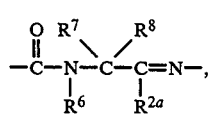

(cv) 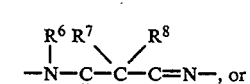

(cw) 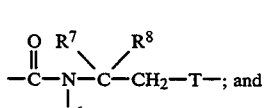

E is:
(a) a single bond,
(b) $-S(O)_n(CH_2)_s-$, or
(c) $-O-$; and
n is 0 to 2; and
s is 0 to 5; and
D is
(a) $-O-$, or
(b) $-N(R^6)-$; and
G is:
(a) $-O-$, or
(b) $-S(O)_n$; and
T is $-S-$, $-O-$ or $-N(R^{20})-$; and
$R^2$ is:
(a) H, or
(b) $(C_1-C_6)$-alkyl; and
$R^{2a}$ is:
(a) $R^2$,
(b) $CH_2$-aryl, or
(c) aryl; and
$R^4$ groups are independently:
(a) H,
(b) $(C_1-C_6)$-alkyl, $(C_2-C_6)$-alkenyl, or $(C_2-C_6)$-alkynyl, each of which is unsubstituted or substituted with:

i) OH,
ii) ($C_1$–$C_4$)-alkoxy,
iii) $CO_2R^2$,
iv) $OCOR^2$,
v) $CONHR^{2a}$,
vi) $CON(R^{2a})_2$,
vii) $N(R^{2a})C(=O)R^2$,
viii) $NH_2$,
ix) ($C_1$–$C_4$)-alkylamino,
x) di[($C_1$–$C_4$)-alkyl]amino,
xi) —S—($C_1$–$C_4$)-alkyl,
xii) aryl,
xiii) heteroaryl,
(c) Cl, Br, I, F,
(d) $CF_3$,
(e) $CO_2R^{2a}$,
(f) $C(=O)N(R^{2a})_2$, or
(g) —C(=O)-aryl,
(h) ($C_3$–$C_7$)-cycloalkyl,
(i) —$OR^{24}$,
(j) —SH,
(k) —$S(O)_n$-($C_1$–$C_4$)-alkyl,
(l) —$SO_3H$,
(m) —$NR^2R^{21}$,
(n) —$NR^2C(=O)R^{21}$,
(o) —$NR^2COOR^{21}$,
(p) —$SO_2NR^{2a}R^{2a}$,
(q) —$NO_2$,
(r) —$NHSO_2$-($C_1$–$C_4$)-alkyl, or
(s) when $R^4$ groups are on adjacent carbon atoms they may join to form a phenyl ring; and
$R^5$ is:
(a) H, or
(b) ($C_1$–$C_6$)-alkyl or ($C_2$–$C_6$)-alkenyl, optionally substituted with:
  i) hydroxy, or
  ii) ($C_1$–$C_4$)-alkoxy; and
$R^{5a}$ is
(a) $R^5$, or
(b) ($C_1$–$C_4$)-acyl; and
$R^6$ is:
(a) H,
(b) ($C_1C_6$)-alkyl, or
(c) ($C_1$–$C_6$)-alkyl substituted with hydroxy; and
$R^{6a}$ is:
(a) $R^6$, or
(b) ($C_1$–$C_6$)-alkyl substituted with:
  i) $CO_2R^2$,
  ii) $CONHR^2$,
  iii) $CON(R^2)_2$; and
$R^7$ and $R^8$ are independently:
(a) H,
(b) ($C_1$–$C_6$)-alkyl, ($C_2$–$C_6$)-alkenyl or ($C_2$–$C_6$)-alkynyl unsubstituted or substituted with a substituent selected from the group consisting of:
  i) hydroxy,
  ii) ($C_1$–$C_4$)-alkoxy,
  iii) ($C_1$–$C_4$)-alkylthio,
  iv) amino,
  v) ($C_1$–$C_4$)-alkylamino,
  vi) di($C_1$–$C_4$)-alkylamino,
  vii) carboxy,
  viii) carboxamido,
  ix) $CO_2R^{2a}$,
  x) $OC(O)R^{2a}$, or
  xi) guanidino, (c) phenyl or phenyl-($C_1$–$C_4$)-alkyl, wherein the phenyl group is unsubstituted or substituted with a member selected from the group consisting of:
  i) hydroxy,
  ii) Cl, Br, I, F,
  iii) ($C_1$–$C_4$)-alkyl,
  iv) ($C_1$–$C_4$)-alkoxy,
(d) imidazolyl-($C_1$–$C_4$)-alkyl, or
(e) indolyl-($C_1$–$C_4$)-alkyl; and
$R^9$ and $R^{10}$ are independently:
(a) H,
(b) ($C_1$–$C_6$)-alkyl, unsubstituted or substituted with ($C_3$–$C_7$)-cycloalkyl,
(c) ($C_2$–$C_6$)-alkenyl,
(d) ($C_2$–$C_6$)-alkynyl,
(e) Cl, Br, F, I,
(f) ($C_1$–$C_6$)-alkoxy,
(g) when $R^9$ and $R^{10}$ are on adjacent carbons, they can be joined to form a phenyl ring,
(h) perfluoro-($C_1$–$C_6$)-alkyl,
(i) ($C_3$–$C_7$)-cycloalkyl, unsubstituted or substituted with ($C_1$–$C_6$)-alkyl,
(j) aryl,
(k) ($C_1$–$C_6$)-alkyl-$S(O)_n$-$(CH_2)_n$-,
(l) hydroxy-($C_1$–$C_6$)-alkyl,
(m) -$CF_3$,
(n) -$CO_2R^{2a}$,
(o) -OH,
(p) -$NR^2R^{21}$,
(q) -[($C_1$–$C_6$)-alkyl]$NR^2R^{21}$,
(r) -$NO_2$,
(s) -$(CH_2)_n$-$SO_2$-$N(R^2)_2$,
(t) -$NR^2CO$-($C_1$–$C_4$)-alkyl, or
(u) -$CON(R^2)_2$;
X is:
(a) -O-,
(b) -$S(O)_n$-,
(c) -$NR^{13}$-,
(d) -$CH_2O$-,
(e) -$CH_2S(O)_n$-,
(f) -$CH_2NR^{13}$-,
(g) -$OCH_2$-,
(h) -$NR^{13}CH_2$-,
(i) -$S(O)_nCH_2$-,
(j) -$CH_2$-,
(k) -$(CH_2)_2$-,
(l) single bond, or
(m) -CH=, wherein Y and $R^{12}$ are absent forming a -C=C- bridge to the carbon bearing Z and $R^{11}$; and
Y is:
(a) single bond,
(b) -O-,
(c) -$S(O)_n$-,
(d) -$NR^{13}$-, or
(e) -$CH_2$-; and
except that X and Y are not defined in such a way that the carbon atom to which Z is attached also simultaneously is bonded to two heteroatoms (O, N, S, SO, $SO_2$);
$R^{11}$ and $R^{12}$ are independently:
(a) H,
(b) ($C_1$–$C_6$)-alkyl, unsubstituted or substituted with a substituent selected from the group consisting of:
  (i) aryl,
  (ii) ($C_3$–$C_7$)-cycloalkyl,
  (iii) $NR^2R^{21}$,
  (iv) morpholin-4-yl, (v) OH,
(vi) $CO_2R^{2a}$, or
(vii) $CON(R^2)_2$,
(c) aryl or aryl-$(C_1-C_2)$-alkyl, unsubstituted or substituted with 1 to 3 substitutents selected from the group consisting of:
(i) Cl, Br, I, F,
(ii) $(C_1-C_6)$-alkyl,
(iii) $[(C_1-C_5)$-alkenyl$]CH_2$-,
(iv) $[(C_1-C_5)$-alkynyl$]CH_2$-,
(v) $(C_1-C_6)$-alkyl-$S(O)_n$-$(CH_2)_n$-,
(vi) -$CF_3$,
(vii) -$CO_2R^{2a}$,
(viii) -OH,
(ix) -$NR^2R^{21}$,
(x) -$NO_2$,
(xi) -$NR^2COR^2$,
(xii) -$CON(R^2)_2$,
(xiii) -$G^1$-$[(C_1-C_6)$-alkyl$]$-$R^{27}$,
(xiv) -$N[CH_2CH_2]_2Q^1$, or
(xv) -$P(O)[O-(C_1-C_4)$-alkyl$]_2$,
and can additionally be substituted with 1 or 2 substituents selected from the group consisting of: Br, Cl or F,
(d) $(C_3-C_7)$-cycloalkyl, or
(e) when Y is single bond, $R^{11}$ and $R^{12}$ can be joined to form a fine of 5 to 7 carbon atoms, the ring can be benzo-fused and one carbon of which can be replaced with a heteroatom selected from the group consisting of: O, $S(O)_n$ and $NR^{26}$; and
$G^1$ is: a single bond, O, $S(O)_x$ or $NR^{27}$; and
$Q^1$ is: O, $S(O)_x$ or $NR^{26}$; and
$R^{13}$ is:
(a) H,
(b) $(C_1-C_6)$-alkyl,
(c) aryl,
(d) aryl-$(C_1-C_6)$-alkyl-$(C=O)$-,
(e) $(C_1-C_6)$-alkyl-$(C=O)$-,
(f) $[(C_2-C_5)$-alkenyl$]CH_2$-,
(g) $[(C_2-C_5)$-alkynyl$]CH_2$-, or
(h) aryl-$CH_2$-; and
Z is:
(a) -$CO_2H$,
(b) -$CO_2R^{28}$,
(c) -tetrazol-5-yl,
(d) -CONH(tetrazol-5-yl)
(e) -$CONHSO_2$-aryl,
(f) -$CONHSO_2$-$(C_1-C_8)$-alkyl, wherein the alkyl group is unsubstituted or substituted with a substituent selected from the group consisting of: -OH, -SH, -O$(C_1-C_4)$-alkyl, -S-$(C_1-C_4)$-alkyl, -$CF_3$, Cl, Br, F, I, -$NO_2$, -$CO_2H$, -$CO_2$-$(C_1-C_4)$-alkyl, -$NH_2$, -NH$[(C_1-C_4)$-alkyl$]$, or -N$[(C_1-C_4)$-alkyl$]_2$,
(g) -$CONHSO_2$-$(C_1-C_4)$-perfluoroalkyl,
(h) -$CONHSO_2$-heteroaryl,
(i) -$CONHSO_2NR^{2a}R^{2a}$,
(j) -$SO_2NHCO$-aryl,
(k) -$SO_2NHCO$-$(C_1-C_8)$-alkyl, wherein the alkyl group is unsubstituted or substituted with a substituent selected from the group consisting of: -OH, -SH, -O$(C_1-C_4)$-alkyl, -S-$(C_1-C_4)$-alkyl, -$CF_3$, Cl, Br, F, I, -$NO_2$, -$CO_2H$, -$CO_2$-$(C_1-C_4)$-alkyl, -$NH_2$, -NH$[(C_1-C_4)$-alkyl$]$, or -N$[(C_1-C_4)$-alkyl$]_2$,
(l) -$SO_2NHCO$-$(C_1-C_4)$-perfluoroalkyl,
(m) -$SO_2NHCO$-heteroaryl,
(n) -$SO_2CONR^{2a}R^{2a}$,
(o) -$PO(OH)_2$,
(p) -$PO(OR^2)_2$, or
(q) -$PO(OH)(OR^2)$; and $R^{20}$ is:
(a) H,
(b) $(C_1-C_6)$-alkyl,
(c) allyl,
(d) $(C_3-C_6)$-cycloalkyl,
(e) $(C_1-C_4)$-acyl,
(f) benzyl, or
(g) phenyl; and
$R^{21}$ is:
(a) H, or
(b) $(C_1-C_4)$-alkyl, unsubstituted or substituted with:
i) $NH_2$,
ii) NH$[(C_1-C_4)$-alkyl$]$,
iii) N$[(C_1-C_4)$-alkyl$]_2$,
iv) $CO_2H$,
v) $CO_2(C_1-C_4)$-alkyl,
vi) OH,
vii) $SO_3H$, or
viii) $SO_2NH_2$; and
$R^{22}$ groups are independently:
(a) H,
(b) $(C_1-C_6)$-alkyl, $(C_2-C_6)$-alkenyl or $(C_2-C_6)$-alkynyl each of which is unsubstituted or substituted with a substituent selected from the group consisting of: $(C_3-C_7)$-cycloalkyl, Cl, Br, I, F, -OH, -$NH_2$, -NH$[(C_1-C_4)$-alkyl$]$, -N$[(C_1-C_4)$-alkyl$]_2$, -$NHSO_2R^{25}$, -$CO_2R^{25}$, $(C_1-C_4)$-alkoxyl, $(C_1-C_4)$-alkylthio, $(C_1-C_4)$-acyl, or $C(=O)NH_2$,
(c) aryl,
(d) substituted aryl in which the substituents are V or W, as defined below,
(e) aryl-$(C_1-C_4)$-alkyl, which can be substituted with V or W as defined below,
(f) Cl, Br, I, F,
(g) hydroxyl,
(h) amino,
(i) NH$[(C_1-C_4)$-alkyl$]$,
(j) N$[(C_1-C_4)$-alkyl$]_2$,
(k) $(C_1-C_6)$-alkoxy,
(l) $CF_3$,
(m) $CO_2R^{25}$,
(n) $C(=O)N(R^{25})_2$,
(o) $N(R^{25})$-$C(=O)R^{25}$,
(p) $(C_1-C_4)$-alkylsulfonyl,
(q) $(C_1-C_4)$-alkylsulfinyl, or
(r) $(C_1-C_4)$-alkylthio; and
$R^{23}$ is:
(a) H,
(b) $(C_1-C_6)$-alkyl, $(C_2-C_6)$-alkenyl or $(C_2-C_6)$-alkynyl each of which is unsubstituted or substituted with a substituent selected from the group consisting of: $(C_3-C_7)$-cycloalkyl, Cl, Br, I, F, -OH, -$NH_2$, -NH$[(C_1-C_4)$-alkyl$]$, -N$[(C_1-C_4)$-alkyl$]_2$, -$NHSO_2R^{25}$, -$CO_2R^{25}$, $(C_1-C_4)$-alkoxyl, $(C_1-C_4)$-alkylthio, $(C_1-C_4)$-acyl, or $C(=O)NH_2$,
(c) -$C(=O)R^{25}$,
(d) -$CO_2R^{25}$,
(e) aryl, which is unsubstituted or substituted with substituents V or W,
(f) aryl-$(C_1-C_4)$-alkyl, which is unsubstituted or substituted with V or W; and
$R^{24}$ groups are independently:
(a) H,
(b) $(C_1-C_6)$-alkyl, $(C_2-C_6)$-alkenyl or $(C_2-C_6)$-alkynyl, each of which is unsubstituted or substituted with a substituent selected from the group consisting of: $(C_3-C_7)$-cycloalkyl, Cl, Br, I, F, -OH, -$NH_2$, -NH$[(C_1-C_4)$-alkyl$]$, -N$[(C_1-C_4)$-alkyl$]_2$, -NHSO$_2$R$^{25}$, -CO$_2$R$^{25}$, (C$_1$-C$_4$)-alkoxyl, (C$_1$-C$_4$)-alkylthio, (C$_1$-C$_4$)-acyl, or C(=O)NH$_2$,
(c) aryl or aryl-(C$_1$-C$_4$)-alkyl which is unsubstituted or substituted with V Or W; and V and W are each independently selected from:
(a) H,
(b) (C$_1$-C$_5$)-alkoxy,
(c) (C$_1$-C$_5$)-alkyl,
(d) hydroxy,
(e) -S(O)$_n$(C$_1$-C$_5$)-alkyl,
(f) -CN,
(g) -NO$_2$,
(h) -NR$^2$R$^{2a}$,
(i) [(C$_1$-C$_5$)-alkyl]-NR$^2$R$^{2a}$,
(j) -CO$_2$R$^{2a}$,
(k) -CO(C$_1$-C$_5$)-alkyl,
(l) CF$_3$,
(m) I, Br, Cl, F
(n) hydroxy-(C$_1$-C$_4$)-alkyl-,
(o) carboxy-(C$_1$-C$_4$)-alkyl-,
(p) -tetrazol-5-yl,
(q) -NHSO$_2$CF$_3$, or
(r) aryl; and R$^{25}$ is:
(a) H,
(b) (C$_1$-C$_6$)-alkyl,
(c) aryl, or
(d) aryl-(C$_1$-C$_5$)-alkyl; and R$^{26}$ is:
(a) H,
(b) (C$_1$-C$_4$)-alkyl,
(c) (C$_1$-C$_4$)-alkoxyl,
(d) aryl,
(e) aryl-(C$_1$-C$_4$)-alkyl,
(f) CO$_2$R$^{2a}$,
(g) CON(R$^2$)$_2$,
(h) SO$_2$R$^{2a}$,
(i) SO$_2$N(R$^2$)$_2$,
(j) P(O)[(C$_1$-C$_4$)-alkoxyl]$_2$, or
(k) imidazol-2-yl or imidazol-4-yl, in which the imidazolyl can be substituted with (C$_1$-C$_4$)-alkyl; and R$^{27}$ is:
(a) OH,
(b) NR$^2$R$^{21}$,
(c) CO$_2$R$^{2a}$,
(d) CON(R$^2$)$_2$,
(e) S(O)$_n$-(C$_1$-C$_4$)-alkyl,
(f) N(CH$_2$CH$_2$)$_2$Q; and R$^{28}$ is:
(a) (C$_1$-C$_4$)-alkyl,
(b) CHR$^{29}$-O-COR$^{30}$,
(c) CH$_2$CH$_2$-N[(C$_1$-C$_2$)-alkyl]$_2$,
(d) CH$_2$CH$_2$-N[CH$_2$CH$_2$]$_2$O,
(e) (CH$_2$CH$_2$O)$_y$-O-[(C$_1$-C$_4$)-alkyl], wherein y is 1 or 2,
(f) aryl or CH$_2$-aryl, where aryl is as defined above or optionally substituted with CO2-(C$_1$-C$_4$)-alkyl,

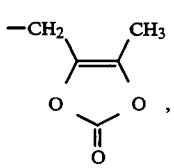 (g)

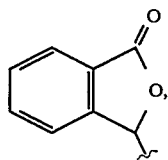 (h)

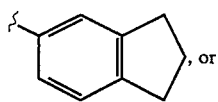, or (i)

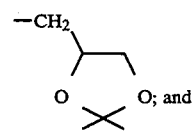 (j)

R$^{29}$ and R$^{30}$ independently are (C$_1$-C$_6$)-alkyl or phenyl.

Wherein a preferred embodiment is when:

R$^1$ is:
(a) (C$_1$-C$_6$)-alkyl or (C$_2$-C$_6$)-alkenyl or (C$_2$-C$_6$)-alkynyl each of which is unsubstituted or substituted with a substituent selected from the group consisting of:
  i) (C$_1$-C$_4$)-alkylthio,
  ii) (C$_1$-C$_4$)-alkoxy,
  iii) CF$_3$,
  iv) CF$_2$-CF$_3$, or
  v) (C$_3$-C$_5$)-cycloalkyl,
(b) (C$_1$-C$_4$)-perfluoroalkyl, or
(c) (C$_3$-C$_5$)-cycloalkyl; and -A$^1$-A$^2$-A$^3$-A$^4$-A$^5$- is:
when A$^4$ and A$^5$ are absent, then -A$^1$-A$^2$-A$^3$- is:

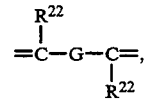 (a)

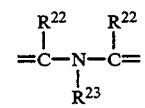 (b)

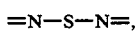 (c)

wherein a represents a single bond in these definitions of -A$^1$-A$^2$-A$^3$- in structure Ia but, hereafter will represent a double bond.

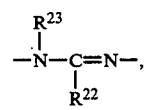 (d)

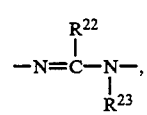 (e)

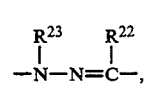 (f)

-continued
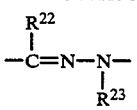 (g)
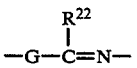 (h)
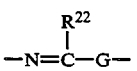 (i)
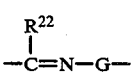 (j)
 (k)
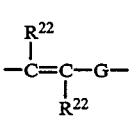 (l)
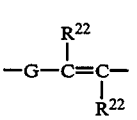 (m)
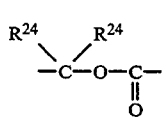 (n)
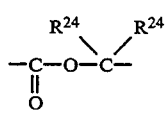 (o)
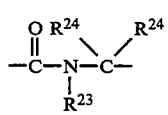 (p)
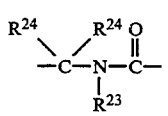 (q)
when $A^4$ is present and $A^5$ is absent, then $-A^1-A^2-A^3-A^4-$ represents:
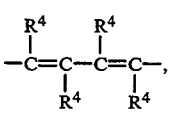 (r)
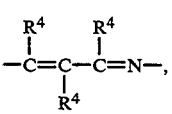 (s)
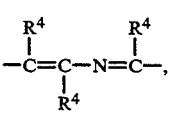 (t)
-continued
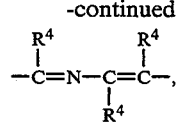 (u)
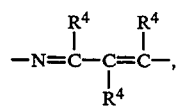 (v)
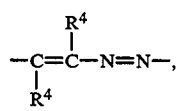 (w)
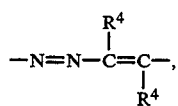 (x)
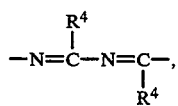 (y)
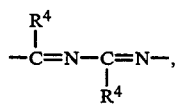 (z)
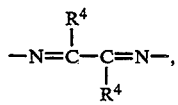 (aa)
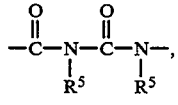 (ab)
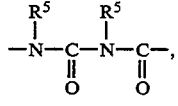 (ac)
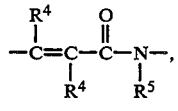 (ad)
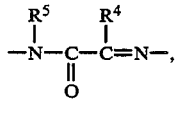 (ae)
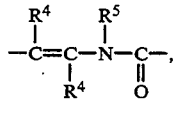 (af)
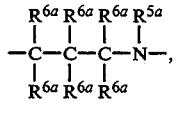 (ag)
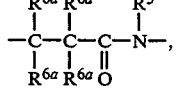 (ah)

-continued

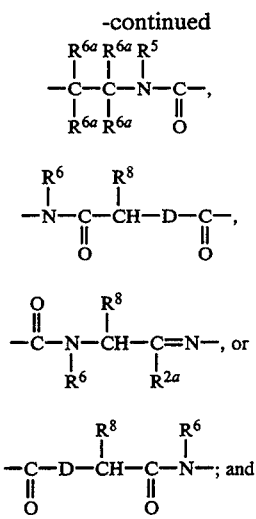

E is:
(a) single bond,
(b) -S-, or
(c) -O-; and
n is 0, 1, or 2; and
D is
(a) -O-, or
(b) -N($R^6$)-; and
G is:
(a) -O-, or
(b) -S(O)$_n$,
$R^2$ is:
(a) H, or
(b) ($C_1$-$C_6$)-alkyl; and
$R^{2a}$ is:
(a) $R^2$,
(b) benzyl, or
(c) phenyl; and
$R^4$ groups are independently:
(a) H,
(b) ($C_1$-$C_6$)-alkyl, which is unsubstituted or substituted with:
  i) OH,
  ii) $CO_2R^2$,
  iii) $NH_2$,
  iv) ($C_1$-$C_4$)-alkylamino.
  v) di[($C_1$-$C_4$)-alkyl]amino,
(c) Cl, Br, I, F,
(d) $CF_3$,
(e) $CO_2R^{2a}$,
(f) C(=O)$NR^{2a}R^{2a}$,
(g) -C(=O)-aryl,
(h) -$OR^{24}$,
(i) -S-($C_1$-$C_4$)-alkyl,
(j) -N[($C_1$-$C_4$)-alkyl]$_2$,
(k) -NHC (=O)($C_1$-$C_4$)-alkyl,
(l) -NHCOO($C_1$-$C_4$)-alkyl,
(m) -$SO_2NH$($C_1$-$C_4$)-alkyl,
(n) -$NO_2$,
(o) -$NHSO_2CH_3$,
(p) ($C_3$-$C_7$)-cycloalkyl, or
(q) when $R^4$ groups are on adjacent carbon atoms they may join to form a phenyl ring; and
$R^5$ is:
(a) H, or
(b) ($C_1$-$C_6$)-alkyl, which is unsubstituted or substituted with: hydroxyl, or $CO_2R^2$; and $R^{5a}$ is
(a) H,
(b) ($C_1$-$C_4$)-alkyl, or
(c) ($C_1$-$C_4$)-acyl; and
$R^6$ is:
(a) H, or
(b) ($C_1$-$C_6$)-alkyl; and
$R^{6a}$ is:
(a) H, or
(b) ($C_1$-$C_4$)-alkyl; and
$R^8$ is:
(a) H,
(b) ($C_1$-$C_6$)-alkyl,
(c) which is unsubstituted or substituted with a substituent selected from the group consisting of:
  i) hydroxy,
  iii) ($C_1$-$C_4$)-alkylthio,
  iv) amino,
  vii) carboxyl,
  viii) carboxamido,
  ix) $CO_2R^{2a}$,
  x) OC(O)$R^{2a}$, or
  xi) guanidino,
(d) phenyl,
(e) benzyl,
(f) 4-hydroxybenzyl,
(g) 4-imidazolylmethyl, or
(h) 3-indolylmethyl; and
$R^9$ and $R^{10}$ are independently:
(a) H,
(b) ($C_1$-$C_6$)-alkyl, unsubstituted or substituted with ($C_3$-$C_7$)cycloalkyl,
(c) ($C_2$-$C_6$)-alkenyl,
(d) ($C_2$-$C_6$)-alkynyl,
(e) Cl, Br, F, I,
(f) ($C_1$-$C_6$)-alkoxy, or
(g) when $R^9$ and $R^{10}$ are on adjacent carbons, they can be joined to form a phenyl ring,
(h) ($C_1$-$C_6$)-perfluoroalkyl,
(i) ($C_3$-$C_7$) cycloalkyl, which is unsubstituted or substituted with ($C_1$-$C_6$)-alkyl,
(j) aryl,
(k) ($C_1$-$C_6$)-alkyl-S(O)$_n$-($CH_2$)$_n$-,
(l) hydroxy-($C_1$-$C_6$)-alkyl,
(m) -$CF_3$,
(N) -$CO_2R^{2a}$,
(o) -OH,
(p) -$NR^2R^{21}$,
(q) -[($C_1$-$C_6$)-alkyl]$NR^2R^{21}$,
(r) -$NO_2$,
(s) -($CH_2$)$_n$-$SO_2$-N($R^2$)$_2$,
(t) -$NR^2CO$-($C_1$-$C_4$)-alkyl, or
(u) -CON($R^2$)$_2$;
X is
(a) -O-,
(b) -S(O)$_n$-,
(c) -$NR^{13}$-,
(d) -$CH_2$O-,
(e) -$CH_2$S(O)$_n$,
(f) -$CH_2NR^{13}$-,
(g) -OCH$_2$-,
(h) -$NR^{13}CH_2$-,
(i) -S(O)$_n$CH$_2$-,
(j) -CH$_2$-,
(k) -(CH$_2$)$_2$-,
(l) single bond, or (m) =(CH)-, wherein Y and $R^{12}$ are absent forming a -C≡C- bridge to the carbon bearing Z and $R^{11}$; and Y is:
(a) single bond,
(b) -O-,
(c) -$CH_2$-,
(d) -S(O)$_n$-, or
(e) -$NR^{13}$-; and except that X and Y are not defined in such a way that the carbon atom to which Z is attached also simultaneously is bonded to two heteroatoms (O, N, S, SO, $SO_2$);

$R^{11}$ and $R^{12}$ are independently:
(a) H,
(b) ($C_1$-$C_6$)-alkyl, unsubstituted or substituted with a substituent selected from the group consisting of:
  (i) aryl,
  (ii) ($C_3$-$C_7$)-cycloalkyl,
  (iii) $NR^2R^{21}$,
  (iv) morpholin-4-yl,
  (v) OH,
  (vi) $CO_2R^{2a}$, or
  (vii) CON($R^2$)$_2$.
(c) aryl or aryl-($C_1$-$C_2$)-alkyl unsubstituted or substituted with 1 to 3 substituents selected from the group consisting of:
  (i) Cl, Br, I, F,
  (ii) ($C_1$-$C_6$)-alkyl,
  (iii) [($C_1$-$C_5$)-alkenyl]$CH_2$-,
  (iv) [($C_1$-$C_5$)-alkynyl]$CH_2$-,
  (v) ($C_1$-$C_6$)-alkyl-S(O)$_n$-($CH_2$)$_n$-,
  (vi) -$CF_3$,
  (vii) -$CO_2R^{2a}$,
  (viii) -OH,
  (ix) -$NR^2R^{21}$,
  (x) -$NO_2$,
  (xi) -$NR^2COR^2$,
  (xii) -CON($R^2$)2,
  (xiii) -$G^1$-[($C_1$-$C_6$)-alkyl]-$R^{27}$,
  (xiv) -N[$CH_2CH_2$]$_2Q^1$, or
  (xv) -P(O)[O-($C_1$-$C_4$)-alkyl]$_2$.

and can additionally be substituted with 1 or 2 substituents selected from the group consisting of: Br, Cl or F,
(d) ($C_3$-$C_7$)-cycloalkyl, or
(e) when Y is single bond, $R^{11}$ and $R^{12}$ can be joined to form a ring of 5 to 7 carbon atoms, the ring can be benzo-fused and one carbon of which can be replaced with a heteroatom selected from the group consisting of: O, S(O)$_n$ and $NR^{26}$; and $G^1$ is: a single bond, O, S(O)$_n$ or $NR^{27}$; and
$Q^1$ is: O, S(O)$_n$ or $NR^{26}$; and $R^{13}$ is:
(a) H,
(b) ($C_1$-$C_6$)-alkyl,
(c) aryl,
(d) aryl-($C_1$-$C_6$)-alkyl-(C=O)-, or
(e) ($C_1$-$C_6$)-alkyl-(C=O)-; and Z is:
(a) -$CO_2H$,
(b) -$CO_2R^{28}$,
(c) -tetrazol-5-yl,
(d) -CONH(tetrazol-5-yl),
(e) -$CONHSO_2$-aryl,
(f) -$CONHSO_2$-($C_1$-$C_4$)-alkyl,
(g) -$CONHSO_2$-($C_1$-$C_4$)-perfluoroalkyl,
(h) -$CONHSO_2$-heteroaryl, wherein heteroaryl is defined as a 5 or 6 membered aromatic ring containing one or two heteroatoms selected from the group consisting of O, N, or S;
(i) -$CONHSO_2NR^{2a}R^{2a}$,
(j) -$SO_2NHCO$-aryl,
(k) -$SO_2NHCO$-($C_1$-$C_6$)-alkyl,
(l) -$SO_2NHCO$-($C_1$-$C_4$)-perfluoroalkyl,
(m) -$SO_2NHCO$-heteroaryl, wherein heteroaryl is defined as a 5 or 6 membered aromatic ring containing one or two heteroatoms selected from the group consisting of O, N, or S,
(n) -$SO_2NHCONR^{2a}R^{2a}$,
(o) -PO(OH)$_2$,
(p) -PO(O$R^2$)$_2$, or
(q) -PO(OH)(O$R^2$); and $R^{22}$ groups are independently:
(a) H,
(b) ($C_1$-$C_6$)-alkyl, ($C_2$-$C_6$)-alkenyl or ($C_2$-$C_6$)-alkynyl each of which is unsubstituted or substituted with a substituent selected from the group consisting of: ($C_3$-$C_7$)-cycloalkyl, Cl, Br, I, F, -OH, -NH[($C_1$-$C_4$)-alkyl], -N[($C_1$-$C_4$)-alkyl]$_2$, -$CO_2R^{25}$, or C(=O)NH($C_1$-$C_4$)-alkyl)],
(c) aryl or aryl-($C_1$-$C_4$)-alkyl, which is unsubstituted or substituted with a substituent selected from the group consisting of: H, Br, Cl, I, F, ($C_1$-$C_4$)-alkyl, hydroxy-($C_1$-$C_4$)-alkyl, ($C_1$-$C_4$)-alkoxy, or $CO_2R^{25}$,
(d) Cl, Br, I, F,
(e) amino,
(f) NH($C_1$-$C_4$)-alkyl],
(g) N[($C_1$-$C_4$)-alkyl]$_2$,
(h) ($C_1$-$C_6$)-alkoxy,
(i) $CO_2R^{25}$,
(j) C(=O)N($R^{25}$)$_2$, or
(k) ($C_1$-$C_4$)-alkylthio; and $R^{23}$ is:
(a) H,
(b) ($C_1$-$C_6$)-alkyl, which is unsubstituted or substituted with a substituent selected from the group consisting of: -OH, -$NH_2$, -N[($C_1$-$C_4$)-alkyl]$_2$, or -$CO_2R^{25}$,
(c) aryl or aryl-($C_1$-$C_4$)-alkyl, which is unsubstituted or substituted with: Br, Cl, F, I, ($C_1$-$C_4$)-alkyl, hydroxy-($C_1$-$C_4$)-alkyl, $CO_2R^{25}$, $COR^{25}$, or $SO_2R^{25}$, $R^{24}$ groups are independently:
(a) H,
(b) ($C_1$-$C_6$)-alkyl, which is unsubstituted or substituted with a substituent selected from the group consisting of: Cl, Br, I, F, -$CO_2R^{25}$, hydroxy-($C_1$-$C_4$)-alkyl, or ($C_1$-$C_4$)-acyl, or
(c) aryl or aryl-($C_1$-$C_4$)-alkyl; and $R^{25}$ is:
(a) H,
(b) ($C_1$-$C_6$)-alkyl,
(c) aryl, or
(d) aryl-($C_1$-$C_5$)-alkyl; and $R^{26}$ is:
(a) H,
(b) ($C_1$-$C_4$)-alkyl,
(c) ($C_1$-$C_4$)-alkoxyl,
(d) aryl,
(e) aryl-($C_1$-$C_4$)-alkyl,
(f) $CO_2R^{2a}$,
(g) CON($R^2$)$_2$,
(h) $SO_2R^{2a}$,
(i) $SO_2N(R^2)_2$,
(j) P(O)[($C_1$-$C_4$)-alkoxyl]$_2$, or (k) imidazol-2-yl or imidazol-4-yl, in which the imidazolyl can be substituted with $(C_1-C_4)$-alkyl; and $R^{27}$ is:
(a) OH,
(b) $NR^2R^{21}$,
(c) $CO_2R^{2a}$,
(d) $CON(R^2)_2$,
(e) $S(O)_n-(C_1-C_4)$-alkyl,
(f) $N(CH_2CH_2)_2Q$; and $R^{28}$ is:
(a) $(C_1-C_4)$-alkyl,
(b) $CHR^{29}$-O-$COR^{30}$,
(c) $CH_2CH_2$-$N[(C_1-C_2)$-alkyl$]_2$,
(d) $CH_2CH_2$-$N[CH_2CH_2]_2O$,
(e) $(CH_2CH_2O)_y$-O-$[(C_1-C_4)$-alkyl ], wherein y is 1 or 2,
(f) aryl or $CH_2$-aryl, where aryl is as defined above or optionally substituted with $CO2-(C_1-C_4)$-alkyl,

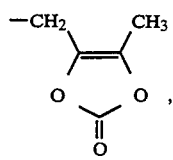 (g)

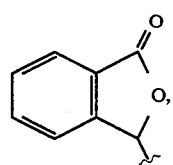 (h)

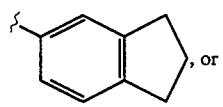 (i), or

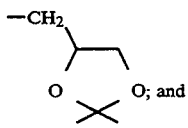 (j)

$R^{29}$ and $R^{30}$ independently are $(C_1-C_6)$-alkyl or phenyl.

Wherein a more preferred embodiment of the invention is when:

$R^1$ is:
(a) $(C_1-C_6)$-alkyl, $(C_2-C_6)$-alkenyl or $(C_2-C_6)$-alkynyl, each of which is unsubstituted or substituted with a substituent selected from the group consisting of:
 i) $(C_1-C_4)$-alkylthio,
 ii) $(C_1-C_4)$-alkoxy,
 iii) $CF_3$,
 iv) $CF_2CF_3$, or
 v) $(C_3-C_5)$-cycloalkyl, or
(b) $(C_1-C_4)$-perfluoroalkyl; and -$A^1$-$A^2$-$A^3$-$A^4$-$A^5$- is:

when $A^4$ and $A^5$ are absent, then -$A^1$-$A^2$-$A^3$- is:

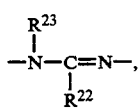 (a)

-continued

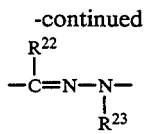 (b)

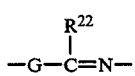 (c)

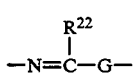 (d)

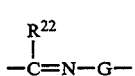 (e)

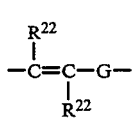 (f)

when $A^4$ is present and $A^5$ is absent, then -$A^1$-$A^2$-$A^3$-$A^4$- represents:

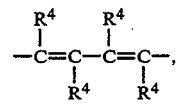 (g)

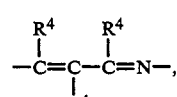 (h)

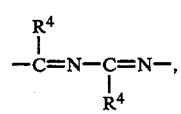 (i)

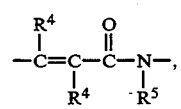 (j)

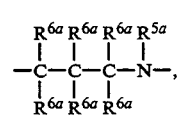 (k)

When $A^1$-$A^2$-$A^3$-$A^4$-$A^5$ are all present:

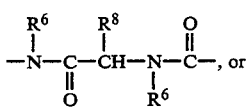 (l)

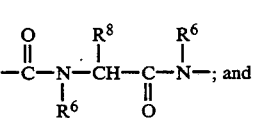 (m)

E is a single bond; and
G is -O-, or -S-; and $R^2$ is:
(a) H,
(b) $(C_1-C_6)$-alkyl; and $R^{2a}$ is:
(a) $R^2$,
(b) benzyl, or (c) phenyl; and
R⁴ groups are independently:
(a) H,
(b) ($C_1$–$C_6$)-alkyl, which is unsubstituted or substituted with:
  i) OH,
  ii) $CO_2R^{2a}$,
  iii) $NH_2$,
  iv) ($C_1$–$C_4$)-alkylamino,
  v) di[($C_1$–$C_4$)-alkyl]amino,
(c) Cl, Br, I, F,
(d) $CF_3$,
(e) $CO_2R^{2a}$,
(f) C(=O)NR$^{2a}$R$^{2a}$,
(g) ($C_3$–$C_7$)-cycloalkyl;
(h) -C(=O)-aryl,
(i) -OR²⁴,
(j) -N[($C_1$–$C_4$)-alkyl]$_2$,
(k) -NHC(=O)($C_1$–$C_4$)-alkyl,
(l) -NHCO$_2$($C_1$–$C_4$)-alkyl,
(m) -SO$_2$NH-($C_1$–$C_4$)-alkyl,
(n) -SO$_2$NH-aryl,
(o) -NO$_2$,
(p) -NHSO$_2$CH$_3$,
R⁵ is:
(a) H, or
(b) ($C_1$–$C_6$)-alkyl, unsubstituted or substituted with: hydroxyl, or $CO_2R^2$; and
R$^{5a}$ is
(a) H,
(b) ($C_1$–$C_4$)-alkyl, or
(c) ($C_1$–$C_4$)-acyl; and
R⁶ is:
(a) H, or
(b) ($C_1$–$C_6$)-alkyl; and
R$^{6a}$ is:
(a) H, or
(b) ($C_1$–$C_4$)-alkyl; and
R⁸ is:
(a) H,
(b) ($C_1$–$C_6$)-alkyl, which is unsubstituted or substituted with a substituent selected from the group consisting of:
  i) hydroxy,
  ii) ($C_1$–$C_4$)-alkoxyl,
  iii) amino,
  iv) carboxyl,
  v) carboxamido,
  vi) $CO_2R^{2a}$,
  vii) OC(O)R$^{2a}$, or
  viii) guanidino,
(c) phenyl,
(d) benzyl,
(e) 4-hydroxybenzyl,
(f) 4-imidazolylmethyl, or
(g) 3-indolylmethyl; and
R⁹ and R¹⁰ are independently:
(a) H,
(b) ($C_1$–$C_6$)-alkyl, unsubstituted or substituted with ($C_3$–$C_7$)cycloalkyl,
(c) ($C_2$–$C_6$)-alkenyl,
(d) ($C_2$–$C_6$)-alkynyl,
(e) Cl, Br, F, I,
(f) ($C_1$–$C_6$)-alkoxy,
(g) when R⁹ and R¹⁰ are on adjacent carbons, they can be joined to form an aryl ring,
(h) ($C_1$–$C_6$)-perfluoroalkyl,
(i) ($C_3$–$C_7$)-cycloalkyl, unsubstituted or substituted with ($C_1$–$C_6$)-alkyl, or
(j) aryl; and
X is:
(a) -O-,
(b) -S(O)$_n$-,
(c) -NR¹³-,
(d) -CH$_2$O-,
(e) -CH$_2$S(O)$_n$-,
(f) -CH$_2$NR¹³-,
(g) -OCH$_2$-,
(h) -NR¹³CH$_2$-,
(i) -S(O)$_n$CH$_2$-,
(j) -CH$_2$-,
(k) -(CH$_2$)$_2$-,
(l) single bond, or
(m) -(CH)=, wherein Y and R¹² are absent forming a -C=C- bridge to the carbon bearing Z and R¹¹; and
Y is:
(a) single bond,
(b) -O-,
(c) -CH$_2$-,
(d) -S(O)$_n$-, or
(e) -NR¹³-; and
except that X and Y are not defined in such a way that the carbon atom to which Z is attached also simultaneously is bonded to two heteroatoms (O, N, S, SO, SO$_2$);
R¹¹ and R¹² are independently:
(a) H,
(b) ($C_1$–$C_6$)-alkyl, unsubstituted or substituted with:
  (i) aryl, or
  (ii) ($C_3$–$C_7$)-cycloalkyl,
(c) aryl,
(d) aryl-($C_1$–$C_2$)-alkyl, or
(e) ($C_3$–$C_7$)-cycloalkyl; and
R¹³ is:
(a) H,
(b) ($C_1$–$C_6$)-alkyl,
(c) aryl,
(d) aryl-($C_1$–$C_6$)-alkyl-(C=O)-, or
(e) ($C_1$–$C_6$)-alkyl-(C=O)-; and
Z is:
(a) -CO$_2$H,
(b) -CO$_2$-($C_1$–$C_6$)-alkyl,
(c) -tetrazol-5-yl,
(d) -CONH(tetrazol-5-yl),
(e) -CONHSO$_2$-aryl,
(f) -CONHSO$_2$-($C_1$–$C_4$)-alkyl,
(g) -CONHSO$_2$-($C_1$–$C_4$)-perfluoroalkyl,
(h) -CONHSO$_2$-heteroaryl, where in heteroaryl is a 5 or 6 membered aromatic ring containing one or two heteroatoms selected from the group consisting of O, N, or S;
(i) -CONHSO$_2$NR$^{2a}$R$^{2a}$,
(j) -SO$_2$NHCO-aryl,
(k) -SO$_2$NHCO-($C_1$–$C_4$)-alkyl,
(l) -SO$_2$NHCO-($C_1$–$C_4$)-perfluoroalkyl,
(m) -SO$_2$NHCO-heteroaryl, where in heteroaryl is a 5 or 6 membered aromatic ring containing one or two heteroatoms selected from the group consisting of O, N, or S,
(n) -SO$_2$NHCONR$^{2a}$R$^{2a}$,
(o) -PO(OH)$_2$,
(p) -PO(OR²)$_2$, or
(q) -PO(OH)(OR²); and
R²² groups are independently:

(a) H,
(b) ($C_1$–$C_6$)-alkyl, ($C_2$–$C_6$)-alkenyl or ($C_2$–$C_6$)-alkynyl each of which is unsubstituted or substituted with a substituent selected from the group consisting of: ($C_3$–$C_7$)-cycloalkyl, Cl, Br, I, F, -OH, -NH[($C_1$–$C_4$)-alkyl], -N[($C_1$–$C_4$)-alkyl]$_2$, -$CO_2R^{25}$, or C(=O)NH[($C_1$–$C_4$)-alkyl)],
(c) aryl or aryl-($C_1$–$C_4$)-alkyl, which is unsubstituted or substituted with a substituent selected from the group consisting of: Br, Cl, I, F, ($C_1$–$C_4$)-alkyl, hydroxy-($C_1$–$C_4$)-alkyl, ($C_1$–$C_4$)-alkoxy, or $CO_2R^{25}$,
(d) Cl, Br, I, F,
(e) amino,
(f) NH[($C_1$–$C_4$)-alkyl],
(g) N[($C_1$–$C_4$)-alkyl]$_2$,
(h) ($C_1$–$C_6$)-alkoxy,
(i) $CO_2R^{25}$,
(j) C(=O)N($R^{25}$)$_2$, or
(k) ($C_1$–$C_4$)-alkylthio; and
$R^{23}$ is:
(a) H,
(b) ($C_1$–$C_6$)-alkyl, which is unsubstituted or substituted with a substituent selected from the group consisting of: -OH, -$NH_2$, -N[($C_1$–$C_4$)-alkyl]$_2$, or -$CO_2R^{25}$,
(c) aryl or aryl-($C_1$–$C_4$)-alkyl, which is unsubstituted or substituted with: Br, Cl, F, I, ($C_1$–$C_4$)-alkyl, hydroxy-($C_1$–$C_4$)-alkyl, $CO_2R^{25}$, $COR^{25}$, or $SO_2R^{25}$,
$R^{24}$ groups are independently:
(a) H,
(b) ($C_1$–$C_6$)-alkyl, which is unsubstituted or substituted with a substituent selected from the group consisting of: Cl, Br, I, F, -$CO_2R^{25}$, hydroxy-($C_1$–$C_4$)-alkyl, or ($C_1$–$C_4$)-acyl, or
(c) aryl or aryl-($C_1$–$C_4$)-alkyl; and
$R^{25}$ is:
(a) H,
(b) ($C_1$–$C_6$)-alkyl,
(c) aryl, or
(d) aryl-($C_1$–$C_5$)-alkyl.

The alkyl substitutents recited above denote straight and branched chain hydrocarbons of the length specified such as methyl, ethyl, isopropyl, isobutyl, neopentyl, isopentyl, etc.

The alkenyl and alkynyl substituents denote alkyl groups as described above which are modified so that each contains a carbon to carbon double bond or triple bond, respectively, such as vinyl, allyl and 2-butenyl.

Cycloalkyl denotes rings composed of 3 to 8 methylene groups, each which may be substituted or unsubstituted with other hydrocarbon substituents, and include for example cyclopropyl, cyclopentyl, cyclohexyl and 4-methylcyclohexyl.

The alkoxy substituent represents an alkyl group as described above attached through an oxygen bridge.

The heteroaryl substituent recited above represents any 5- or 6-membered aromatic ring containing from one to three heteroatoms selected from the group consisting of nitrogen, oxygen, and sulfur, for example, pyridyl, thienyl, furyl, imidazolyl, and thiazolyl.

Compounds of the present invention illustrative of subclasses of Formula I are:

5.5-FUSED IMIDAZOLES

2-Butyl-1-[4-(1-carboxy-1-phenyl )methoxyphenyl]methyl -1,4-dihydro-4-methylimidazo[4,5-d]imidazole 1-[4-(1-Carboxy-1-phenyl )methoxyphenyl]methyl-1,4-dihydro-2-ethyl-4-methylimidazo[4,5-d ]imidazole 1-[4-(1-Carboxy-1-(2-chlorophenyl))methoxyphenyl]-methyl-1,4-dihydro-2-ethyl-4-methylimidazo[4,5-d ]-imidazole 1-[4-((1-Carboxy-1-(2-chlorophenyl))methoxy)-3-propyl -phenyl]methyl-1,4-dihydro-2-ethyl-4-methylimidazo -[4,5-d]imidazole 1-[4-(1-Carboxy-1-(2-isopropylphenyl) )methoxyphenyl]-methyl-1,4-dihydro-2-ethyl-4-methylimidazo[4,5-d]-imidazole 1-[4-(1-Carboxy-1-( 2-trifluoromethylphenyl))methoxyphenyl ]methyl-1,4-dihydro-2-ethyl-4-methylimidazo-[4,5-d]imidazole 1-[4-((1-Carboxy-1-phenyl)methoxy )-3-propyl-phenyl]methyl-1,4-dihydro-2-ethyl-4-methylimidazo[4,5-d ]-imidazole 1-[4-(1-Carboxy-1-(1-naphthyl))methoxyphenyl]-methyl -1,4-dihydro-2-ethyl-4-methylimidazo[4,5-d ]imidazole 1-[4-N-(1-Carboxy-1-(2-chlorophenyl))methylaminophenyl]methyl-1,4-dihydro-2-ethyl-4-methylimidazo -4,5-d]imidazole 1- [4-N-(1-Carboxy-1-(2-chlorophenyl))methyl-N-ethylaminophenyl ]methyl-1,4-dihydro-2-ethyl-4-methylimidazo [4,5-d]imidazole 1-[4-(1-Carboxy-1-(2-chlorophenyl))methylthiophenyl ]methyl -1,4-dihydro-2-ethyl -4-methylimidazo[4,5-d]-imidazole 1- [4-(1-Carboxy-1-phenyl)methoxyphenyl]methyl -1,4-dihydro-5-hydroxymethyl-4-methyl-2-propyl-imidazo-[4,5-d]imidazole 2-Butyl -1-[4-(1-carboxy-1-phenyl)methoxyphenyl]-methyl -1,4-dihydro-4-ethyl-5-methylimidazo[4,5-d]imidazole 2-Butyl-1-[4-(1-carboxy-1-phenyl)methoxyphenyl]-methyl -1,6-dihydro-6-methylimidazo[4,5-d]imidazole 2-butyl -1-[4-(1-carboxy-1-phenyl)methoxyphenyl]-methyl -1H-thieno[3,4-d]imidazole 1-[4-(1-Carboxy-1-phenyl)methoxyphenyl]methyl-2-propyl-1H-furo[3,4-d]imidazole 2-Butyl-1-[4-(1-carboxy-1-phenyl)methoxyphenyl]-methyl -4-methyl-1H-thieno[3,4-d]imidazole 1-[4-(1-Carboxy-1-phenyl)methoxyphenyl]methyl-4-ethyl -2-propyl-1H-thieno[3,4-d]imidazole-5,5-dioxide 2-Butyl -1- [4-(1-carboxy-1-phenyl)methoxyphenyl]-methyl -1,5-dihydro-5-methylpyrrolo[3,4-d]imidazole 2-Butyl-1-[4-(1-carboxy-1-phenyl)methoxyphenyl]-methyl -1,5-dihydro-4,5-dimethylpyrrolo[3,4-d]imidazole 2-Butyl -1-[4-(1-carboxy-1-phenyl)methoxyphenyl]-methyl -1,5-dihydro-4-ethyl-5-methylsulfonylpyrrolo[3,4-d]imidazole 3-[4-(1-Carboxy-1-phenyl)methoxyphenyl]methyl-6-methyl -5-hydroxymethyl-2-propyl-3H-thieno[2,3-d]imidazole 2-Butyl-5-carboxy-3-[4-(1-carboxy-1-phenyl)methoxyphenyl ]methyl-6-methyl-3H-thieno[2,3-d]imidazole 2-Butyl-5-carbomethoxy-3-[4-(1-carboxy-1-phenyl)-methoxyphenyl ]methyl-6-methyl-3H-thieno[2,3-d]imidazole 5-Carbomethoxy-3-[4-(1-carboxy-1-phenyl)methoxyphenyl]methyl-2-ethyl-6-methyl-3H-thieno[2,3-d]imidazole 5-Carbomethoxy-3-[4-(1-carboxy-1-(2-chlorophenyl))-methoxyphenyl ]methyl-2-ethyl-6-methyl-3H-thieno -[2,3-d]imidazole 5-Carbomethoxy-3-[4-(1-carboxy-1-(2-isopropylphenyl))-methoxyphenyl ]methyl-2-ethyl-6-methyl-3H-thieno -[2,3-d]imidazole 5-Carbomethoxy-3-[4-(1-carboxy-1-(1-naphthyl))-methoxyphenyl ]methyl-2-ethyl-6-methyl-3H-thieno -[2,3-d]imidazole 5-Carbomethoxy-3-[4-(1-carboxy-1-(2-methoxyphenyl))-methoxyphenyl ]methyl-2-ethyl-6-methyl-3H-thieno -[2,3-d]imidazole 5-Carbomethoxy-3-[4-(1-carboxy-1-(2-methoxyphenyl))-methylthiophenyl ]methyl-2-ethyl-6-methyl-3H-thieno -2,3-d]imidazole 5-Carbomethoxy-3-[4-N-(1-carboxy-1-(2-methoxyphenyl))-methylaminophenyl ]methyl-2-ethyl-6-methyl-3H-thieno -[2,3-d]imidazole 6- [4-(1-carboxy-1-phenyl)methoxyphenyl]methyl-1,6-dihydro-1,3-dimethyl-5-propylimidazo[4,5-c]pyrazole 5-Butyl-6-[4-(1-carboxy-1-phenyl)methoxyphenyl]-methyl -2-hydroxymethyl-6H-imidazo[4,5-d]thiazole 5-Butyl-6-[4-(1-carboxy-1-phenyl)methoxyphenyl]-methyl -2-phenyl-6H-imidazo[4,5-d]thiazole 5-Butyl-6-[4-(1-carboxy-1-phenyl)methoxyphenyl]-methyl -2-(2-chloro)phenyl-6H-imidazo[4,5-d]thiazole 6-[4-(1-Carboxy-1-phenyl)methoxyphenyl]methyl-5-ethyl -2-phenyl-6H-imidazo[4,5-d ]thiazole 6- [4- (1-Carboxy-1-phenyl)methoxyphenyl]methyl -2-(2-chloro) phenyl-5-ethyl-6H-imidazo[4,5-d]thiazole 6-[4-(1-Carboxy-1-phenyl)methoxyphenyl]methyl-2-(2-chloro) phenyl-5-ethyl-6H-imidazo[4,5-d]oxazole 6-[4-(1-Carboxy-1-phenyl)methoxyphenyl]methyl-3-methyl -5-butyl-6H-imidazo[4,5-d]isothiazole 6-[4-(1-Carboxy-1-phenyl)methoxyphenyl]methyl-5-ethyl -3-methyl-6H-imidazo[4,5-d]isothiazole 6-[4- (1-Carboxy-1-(2-chlorophenyl))methoxyphenyl]-methyl-5-ethyl-3-methyl-6H-imidazo[4,5-d]isothiazole 6-[4-(1-Carboxy-1-(2-ethylphenyl))methoxyphenyl]-methyl -5-ethyl-3-methyl-6H-imidazo[4,5-d]isothiazole 6-[4-(1-Carboxy-1-(2-trifluoromethylphenyl))methoxyphen yl]methyl-5-ethyl-3-methyl-6H-imidazo[4,5-d]isothiazole 6-[4-(1-Carboxy-1-(2-nitrophenyl))methoxyphenyl]-methyl -5-ethyl-3-methyl-6H- imidazo[4,5-d]isothiazole 6-[4-N-(1-Carboxy-1-(2-chlorophenyl))methylaminophenyl]methyl-5-ethyl-3-methyl-6H- imidazo[4,5-d]isothiazole 6-[4-(1-Carboxy-1-(2-chlorophenyl))methylthiophenyl]-methyl-5-ethyl-3-methyl-6H-imidazo[4,5-d]isothiazole 6-[4-(1-Carboxy-1-(2-chlorophenyl))methylsulfonylphenyl]methyl-5-ethyl-3-methyl-6H-imidazo[4,5-d]-isothiazole 6-[4-(1-Carboxy-1-(1-naphthyl))methoxyphenyl]-methyl -5-ethyl-3-methyl-6H- imidazo[4,5-d]isothiazole 6-[4-(1-Carboxy-1-phenyl)methoxyphenyl]methyl -3,5-diethyl-6H-imidazo[4,5-d]isothiazole 2-Butyl-1,4-dihydro-4-methyl-1-[4-(1-(tetrazol-5-yl) -1-phenyl)methoxyphenyl]methylimidazo[4,5-d]imidazole 1,4-Dihydro-2-ethyl-4-methyl-1-[4-(1-(tetrazol-5-yl) -1-phenyl)methoxyphenyl]methylimidazo[4,5-d]imidazole 1,4-Dihydro-2-ethyl-4-methyl-1-[4-(1-(tetrazol-5-yl) -1-(2-chloro)phenyl)methoxyphenyl]methylimidazo[4,5-d]imidazole 1,4-Dihydro-2-ethyl-4-methyl-1-[4-(1-(tetrazol-5-yl) -1-(2-isopropyl)phenyl)methoxyphenyl]methylimidazo -[4,5-d]imidazole b 1,4-Dihydro-2-ethyl-4-methyl-1-[4-(1-(tetrazol-5-yl) -1-(2-trifluoromethyl)phenyl)methoxyphenyl]methylimidazo[4,5-d]imidazole 1,4-Dihydro-2-ethyl-4-methyl-1-[4-(1-(tetrazol-5-yl) -1-(1-naphthyl))methoxyphenyl]methylimidazo[4,5-d]imidazole 1,4-Dihydro-2-ethyl-4-methyl-1-[4-N-(1-(tetrazol-5-yl) -1-(2-chlorophenyl))methylaminophenyl]methylimidazo[4,5-d]imidazole 1,4-Dihydro-2-ethyl-4-methyl-1-[4-N-(1-(tetrazol-5-yl) -1-(2-chloro)phenyl)methyl-N-ethylaminophenyl]-methylimidazo[4,5-d]imidazole 1,4-Dihydro-2-ethyl-4-methyl-1-[4-(1-(tetrazol-5-yl) -1- (2-chlorophenyl))methylthiophenyl]methylimidazo[4,5-d]imidazole 1,4-Dihydro-5-hydroxymethyl-4-methyl-2-propyl-1-[4-(1-(tetrazol-5-yl)-1-phenyl)methoxyphenyl]methylimidazo[4,5-d]imidazole 2-Butyl-1,4-dihydro-4-ethyl-5-methyl-1-[4-(1-(tetrazol-5-yl)-1-phenyl)methoxyphenyl]methylimidazo[4,5-d]imidazole 2-Butyl -1,6-dihydro-6-methyl-1-[4-(1-(tetrazol-5-yl) -1-phenyl)methoxyphenyl]methylimidazo[4,5-d]imidazole 2-Butyl-1-[4-(1-(tetrazol-5-yl)-1-phenyl)methoxyphenyl]methyl-1H-thieno[3,4-d]imidazole 2-Propyl-1-[4-(1-(tetrazol-5-yl)-1-phenyl)methoxyphenyl]methyl-1H-furo[3,4-d]imidazole 2-Butyl-4-methyl-1-[4-(1-(tetrazol-5-yl)-1-phenyl)methoxyphenyl]methyl-1H-thieno[3,4-d]imidazole 4-Ethyl-2-propyl-1-[4-(1-(tetrazol-5-yl)-1-phenyl) -methoxyphenyl-]methyl-1H-thieno[3.4-d]imidazole-5,5-dioxide 2-Butyl-1,5-dihydro-5-methyl-1-[4-(1-(tetrazol-5-yl) -1-phenyl)methoxyphenyl]methylpyrrolo[3,4-d]imidazole 2-Butyl-1,5-dihydro-4,5-dimethyl-1-[4-(1-(tetrazol-5-yl) -1-phenyl)methoxyphenyl]methylpyrrolo[3,4-d]imidazole 2-Butyl-1,5-dihydro-4-ethyl-5-methylsulfonyl-1-[4-(1-(tetrazol-5-yl)-1-phenyl)methoxyphenyl]methylpyrrolo[3,4-d]imidazole 5-Hydroxymethyl-6-methyl-2-propyl-3-[4-(1-(tetrazol-5-yl) -1-phenyl)methoxyphenyl]methyl-3H-thieno[2,3-d]-imidazole 2-Butyl-5-carboxy-6-methyl-3-[4-(1-(tetrazol-5-yl )-1-phenyl) methoxyphenyl]methyl-3H-thieno[2,3-d]imidazole 2-Butyl-5-carbomethoxy-6-methyl-3-[4-(1-(tetrazol-5-yl) -1-phenyl)methoxyphenyl]methyl-3H-thieno[2,3-d]-imidazole 5-Carbomethoxy-2-ethyl-6-methyl-3-[4-(1-(tetrazol-5-yl) -1-phenyl)methoxyphenyl]methyl-3H-thieno[2,3-d]-imidazole 5-Carbomethoxy-2-ethyl-6-methyl-3-[4-(1-(tetrazol-5-yl) -1-(2-chloro)phenyl)methoxyphenyl]methyl-3H-thieno[2,3-d]-imidazole 5-Carbomethoxy-2-ethyl-6-methyl-3-[4-(1-(tetrazol-5-yl) -1-(2-isopropylphenyl))methoxyphenyl]methyl-3H-thieno[2,3-d]-imidazole 5-Carbomethoxy-2-ethyl-6-methyl-3-[4-(1-(tetrazol-5-yl) -1-(1-naphthyl))methoxyphenyl]methyl-3H-thieno[2,3-d]imidazole 5-Carbomethoxy-2-ethyl-6-methyl-3-[4-(1-(tetrazol-5-yl) -1-(2-methoxyphenyl))methoxyphenyl]methyl-3H-thieno[2,3-d]imidazole 5-Carbomethoxy-2-ethyl-6-methyl-3-[4-(1-(tetrazol-5-yl) -1-(2-methoxyphenyl))methylthiophenyl]methyl-3H-thieno[2,3-d]imidazole 5-Carbomethoxy-2-ethyl-6-methyl-3-[4-N-(1-(tetrazol-5-yl) -1-(2-methoxyphenyl))methylaminophenyl]methyl-3H-thieno[2,3-d]imidazole 1,6-dihydro-1,3-dimethyl-5-propyl-6-[4-(1-(tetrazol-5-yl) -1-phenyl)methoxyphenyl]methylimidazo[4,5-c]pyrazole 5-Butyl-2-hydroxymethyl-6-[4-(1-(tetrazol-5-yl)-1-phenyl) methoxyphenyl]methyl-6H-imidazo[4,5-d]thiazole 5-Butyl-2-phenyl-6-[4(1(tetrazol-5-yl)- 1-phenyl)methoxyphenyl]methyl-6H-imidazo)[4,5-d]thiazole 5-Butyl-2-(2-chloro)phenyl-6-[4-(1-(tetrazol-5-yl)-1-phenyl) methoxyphenyl]methyl-6H-imidazo[4,5-d]thiazole 5-Ethyl-2-phenyl-6-[4-(1-(tetrazol-5-yl)-1-phenyl)-methoxyphenyl ]methyl-6H-imidazo[4,5-d]thiazole 2-(2-Chloro)phenyl-5-ethyl-6-[4-(1-(tetrazol-5-yl)-1phenyl) methoxyphenyl]methyl-6H-imidazo[4,5-d]thiazole 2-(2-Chloro)]phenyl-5-ethyl-6-[4-(1-(tetrazol-5-yl)-1phenyl) methoxyphenyl]methyl-6H-imidazo[4,5-d]oxazole 3-Methyl-5-butyl-6-[4-(1-(tetrazol-5-yl)-1-phenyl)methoxyphenyl]methyl-6H-imidazo[4,5-d]isothiazole 5-Ethyl-3-methyl-6-[4-(1-(tetrazol-5-yl)-1-phenyl)methoxyphenyl ]methyl-6H- imidazo[4,5-d]isothiazole 5-Ethyl-3-methyl-6-[4-(1-(tetrazol-5-yl)-1-(2-chlorophenyl)) methoxyphenyl]methyl-6H-imidazo[4,5-d]isothiazole 5-Ethyl-3-methyl -6-[4(1(tetrazol-5-yl)-1(2-ethylphenyl)) methoxyphenyl]methyl-6H-imidazo[4,5-d]isothiazole 5-Ethyl-3-methyl-6-[4-(1-(tetrazol-5-yl)-1-(2-trifluoromethylphenyl))methoxyphenyl]methyl-6H-imidazo[4,5-d]isothiazole 5-Ethyl-3-methyl-6-[4-(1-(tetrazol-5-yl)-1-(2-nitrophenyl))methoxyphenyl]methyl-6H-imidazo -[4,5-d]isothiazole 5-Ethyl-3-methyl-6-[4-N-(1-(tetrazol-5-yl)-1-(2-chlorophenyl)) methylaminophenyl]methyl-6H-imidazo[4,5-d]isothiazole 5-Ethyl-3-methyl-6-[4-(1-(tetrazol-5-yl)-1-(2-chlorophenyl)) methylthiophenyl]methyl-6H-imidazo[4,5-d]isothiazole 5-Ethyl-3-methyl-6-[4-(1-(tetrazol-5-yl)-1-(2-chlorophenyl)) methylsulfonylphenyl]methyl-6H-imidazo[4,5-d]isothiazole 5-Ethyl-3-methyl-6-[4-(1-(tetrazol-5-yl)-1-(1-naphthyl) methoxyphenyl]methyl-6H- imidazo[4,5-d]isothiazole 3,5-Diethyl-6-[4-(1-(tetrazol-5-yl)-1-phenyl)methoxyphenyl ]methyl-6H- imidazo[4,5-d]isothiazole 2-Butyl-1-[4-(1-((N-phenylsulfonyl)carboxamido)-1-phenyl) methoxyphenyl]methyl-1,4-dihydro-4-methylimidazo[4,5-d]imidazole 2-Butyl -1-[4-(1-((N-methylsulfonyl)carboxamido )-1-phenyl) methoxyphenyl]methyl-1,4-dihydro-4-methylimidazo[4,5-d]imidazole 2-Butyl-1-[4-(1-((N-trifluoromethylsulfonyl)carboxamido) -1-phenyl)methoxyphenyl]methyl-1,4-dihydro-4-methylimidazo [4,5-d]imidazole 2-Butyl-1-[4-(1-((N-phenylsulfonyl)carboxamido)-1-phenyl) methoxyphenyl]methyl-1,5-dihydro-5-methylpyrrolo[3,4-d]imidazole 2-Butyl-1-[4-(1-((N-trifluoromethylsulfonyl)-carboxamido) -1-phenyl)methoxyphenyl]methyl-1,5-dihydro-5-methylpyrrolo[3,4-d]imidazole 2-(2-Chloro)phenyl-5-ethyl-6-[4-(1-((N-isopropylsulfonyl) carboxamido)-1-phenyl)methoxyphenyl]methyl -6H-imidazo[4,5-d]oxazole

BENZIMIDAZOLES

2-Butyl-1-[4-(1-carboxy-1-phenyl)methoxyphenyl]-methylbenzimidazole

21-Butyl -1-[4-(1-carboxy-1-phenyl)methoxyphenyl]methyl -7-methylbenzimidazole

1-[4-(1-Carboxy-1-phenyl)methoxyphenyl]methyl-7-methyl -2-propylbenzimidazole

1-[4-(1-Carboxy-1-phenyl)methoxyphenyl]methyl-5,7-dimethyl-2-ethylbenzimidazole

1-[4(1-Carboxy-1(2-chlorophenyl))methoxyphenyl]-methyl-5,7-dimethyl-2-ethylbenzimidazole 1-[4(1-Carboxy-1(2-methylphenyl))methoxyphenyl]-methyl-5,7-dimethyl-2-ethylbenzimidazole 1-[4(1-Carboxy-1(2,6-dichlorophenyl))methoxyphenyl]-methyl-5,7-dimethyl-2-ethylbenzimidazole 1-[4-(1-Carboxy-1-(2-nitrophenyl))methoxyphenyl]-methyl-5,7-dimethyl-2-ethylbenzimidazole 1-[4-(1-Carboxy-1-(2-trifluoromethylphenyl))methoxyphenyl ]methyl-5,7-dimethyl-2-ethylbenzimidazole 1-[4(1-Carboxy-1(2-ethoxyphenyl))methoxyphenyl]-methyl-5,7-dimethyl-2-ethylbenzimidazole 1-[4-(1-Carboxy-1-(1-naphthyl))methoxyphenyl]-methyl -5,7-dimethyl-2-ethylbenzimidazole 1-[4-(1-Carboxy-1-(2,6-dimethylphenyl))methoxyphenyl]-methyl-5,7-dimethyl-2-ethylbenzimidazole 1-[4-(N-(1-Carboxy-1-(2-chlorophenyl))methyl-)aminophenyl]methyl-5,7-dimethyl -2-ethylbenzimidazole 1-[4-(N-(1-Carboxy-1-(2-chlorophenyl))methyl-N-methyl) aminophenyl]methyl-5,7-dimethyl-2ethylbenzimidazole 1-[4-(N-(1-Carboxy-1-(2-chlorophenyl))methyl-N-acetyl) aminophenyl]methyl-5,7-dimethyl -2-ethylbenzimidazole 1-[4(1-Carboxy-1(2-chlorophenyl))methylthiophenyl]-methyl-5,7-dimethyl -2-ethylbenzimidazole 1-[4-(1-Carboxy-1-(2-chlorophenyl))methylsulfinylphenyl]methyl-5,7-dimethyl-2-ethylbenzimidazole 1-[4-(1-Carboxy-1-(2-chlorophenyl))methylsulfonylphenyl ]methyl-5,7-dimethyl-2-ethylbenzimidazole 1-[4-(1-Carboxy-1-(2-chlorophenyl))methoxy-3-methylphenyl ]methyl-5,7-dimethyl-2-ethylbenzimidazole 1-[4-(1-Carboxy-1-(2-chlorophenyl))methoxy-3-ethylphenyl ]methyl-5,7-dimethyl -2-ethylbenzimidazole 1-[4-(1-Carboxy-1-(2-chlorophenyl))methoxy-3-propylphenyl ]methyl-5,7-dimethyl-2-ethylbenzimidazole 1-[4-(1-Carboxy-1-(2-chlorophenyl))methoxy-3-chlorophenyl ]methyl-5,7-dimethyl-2-ethylbenzimidazole 1-[4-(1-Carboxy-1-(2-chlorophenyl))methoxy-3,5-dichlorophenyl]methyl- 5,7-dimethyl-2-ethylbenzimidazole 1-[4-(1-Carboxy-1-(2-chlorophenyl))methoxyphenyl]-methyl-2-ethyl-5-hydroxymethyl-7-methylbenzimidazole 5-Carboxy-1-[4-(1-carboxy-1-(2-chlorophenyl))methoxyphenyl]methyl-2-ethyl-7-methylbenzimidazole 5-Carbomethoxy-1-[4-(1-carboxy-1-(2-chlorophenyl))methoxyphenyl]methyl-2-ethyl-7-methylbenzimidazole 1-[4-(1-Carboxy-1-(2-chlorophenyl))methoxyphenyl]-methyl-2,5-diethyl-7-methylbenzimidazole 1-[4(1-Carboxy-1(2-chlorophenyl))methoxyphenyl]-methyl-2,5,7-triethylbenzimidazole 1-[4-(1-Carboxy-1-(2-chlorophenyl))methoxyphenyl]-methyl-2-ethyl-4,5,7-trimethylbenzimidazole 1-[4-(1-Carboxy-1-(2-chlorophenyl))methoxyphenyl]-methyl-5,7-dimethyl-2-ethyl-4-hydroxybenzimidazole 5,7-Dimethyl-2-ethyl-1-[4-(1-(tetrazol-5-yl)-1-(2-chlorophenyl))methoxyphenyl]methylbenzimidazole 5,7-Dimethyl-2-ethyl-1-[4-(1-(tetrazol-5-yl)-1-(2-methylphenyl))methoxyphenyl]methylbenzimidazole 5,7-Dimethyl-2-ethyl-1-[4-(1-(tetrazol-5-yl)-1-(2-ethoxyphenyl))methoxyphenyl]methylbenzimidazole 5,7-Dimethyl-2-ethyl-1-[4-(1-(tetrazol-5-yl)-1-(2-trifluoromethylphenyl))methoxy-3-methoxyphenyl]methylbenzimidazole 5,7-Dimethyl-2-ethyl-1-[4-N-(1-(tetrazol-5-yl)-1-(2-chlorophenyl))methylaminophenyl]methylbenzimidazole 5,7-Dimethyl-2-ethyl-1-[4-N-(1-(tetrazol-5-yl)-1-(2-chlorophenyl))methyl-N-methylaminophenyl]methylbenzimidazole 5,7-Dimethyl-2-ethyl-1-[4-(1-(tetrazol-5-yl)-1-(2-chlorophenyl)) methylthiophenyl]methylbenzimidazole 5,7-Dimethyl-2-ethyl-1-[4-(1-(tetrazol-5-yl)-1-(2-chlorophenyl))methylsulfinylphenyl]methylbenzimidazole 5,7-Dimethyl-2-ethyl-1-[4-(1-(tetrazol-5-yl)-1-(2-chlorophenyl))methylsulfonylphenyl]methylbenzimidazole 2-Ethyl-5-hydroxymethyl-7-methyl-1-[4-(1-(tetrazol-5yl) -1-(2-chlorophenyl))methoxyphenyl]methylbenzimidazole 5-Carboxy-7-methyl-2-ethyl-1-[4-(1-(tetrazol-5-yl)-1-(2-chlorophenyl))methoxyphenyl]methylbenzimidazole 5-Carbomethoxy-2-ethyl-7-methyl-1-[4-(1-(tetrazol-5yl) -1-(2-chlorophenyl))methoxyphenyl]methylbenzimidazole 2,5-Diethyl-7-methyl-1-[4-(1-(tetrazol-5-yl)-1-(2chlorophenyl)) methoxyphenyl]methylbenzimidazole 1-[4-(1-(Tetrazol-5-yl)-1-(2-chlorophenyl))methoxyphenyl ]methyl-2,5,7-triethylbenzimidazole 2-Ethyl-1-[4-(1-(tetrazol-5-yl)-1-(2-chlorophenyl)-)methoxyphenyl ]methyl-4,5,7-trimethylbenzimidazole 5,7-Dimethyl-2-ethyl -4-hydroxy-1-[4-(1-(tetrazol-5-yl) -1(2-chlorophenyl))methoxyphenyl]methylbenzimidazole 5,7-Dimethyl-2-ethyl-1-[4-(1-(N-Phenylsulfonyl) -carboxamido- 1-(2-chlorophenyl))methoxyphenyl]methylbenzimidazole 5,7-Dimethyl-2-ethyl-1-[4-(1-(N-trifluoromethylsulfonyl) carboxamido-1-(2-chlorophenyl))methoxyphenyl]methylbenzimidazole 5,7-Dimethyl-2-ethyl-1-[4-(1-(N-methylsulfonyl) -carboxamido-1(2-chlorophenyl))methoxyphenyl]methylbenzimidazole

IMIDAZOPYRIDINES

2-Butyl-1-[4-(1-carboxy-1-phenyl)methoxyphenyl]-methyl -7-methyl-3H-imidazo[4,5-b]pyridine 3-[4-(1-Carboxy-1-phenyl)methoxyphenyl]methyl-7-methyl -2-propyl-3H-imidazo[4,5-b]pyridine 3-[4-(1-Carboxy-1-phenyl)methoxyphenyl]methyl-5,7-dimethyl-2-ethyl-3H-imidazo[4,5-b ]pyridine 3-[4-(1-Carboxy-1-(2-chlorophenyl))methoxyphenyl]-methyl-7-methyl-2-propyl-3H- imidazo[4,5-b]pyridine 3-[4-(1-Carboxy-1-(2-chlorophenyl))methoxyphenyl]-methyl-5,7-dimethyl-2-ethyl-3H-imidazo[4,5-b]pyridine 3-[4(1-Carboxy-1(3-chlorophenyl))methoxyphenyl]methyl-7-methyl-2-propyl-3H-imidazo[4,5-b]pyridine 3-[4-(1-Carboxy-1-(2,6-dichlorophenyl))methoxyphenyl]-methyl-7-methyl-2-propyl-3H- imidazo[4,5-b]pyridine 3-[4-(1-Carboxy-1-(4-chlorophenyl))methoxyphenyl]-methyl-7-methyl-2-propyl-3H- imidazo[4,5-b]pyridine 3-[4(1-Carboxy-1-(2-bromophenyl))methoxyphenyl]-methyl-5,7-dimethyl-2-ethyl-3H-imidazo[4,5-b]pyridine 3-[4-(1-Carboxy-1-(2-methylphenyl))methoxyphenyl]-methyl-7-methyl-2-propyl-3H-imidazo[4,5-b]pyridine 3-[4-(1-Carboxy-1-(2-methylphenyl))methoxyphenyl]-methyl-5,7-dimethyl-2-ethyl- 3H-imidazo[4,5-b]pyridine 3-[4-(1-Carboxy-1-(2-methoxyphenyl))methoxyphenyl]-methyl-7-methyl-2-propyl- 3H-imidazo[4,5-b]pyridine 3-[4-(1-Carboxy-1-(2-methoxyphenyl))methoxyphenyl]-methyl-5,7-dimethyl-2-ethyl-3H-imidazo[4,5-b]pyridine 3-[4-(1-Carboxy-1-(2-ethoxyphenyl))methoxyphenyl]-methyl-7-methyl-2-propyl-3H-imidazo[4,5-b]pyridine 3-[4(1-Carboxy-1(2-ethoxyphenyl))methoxyphenyl]-methyl-5,7-dimethyl-2-ethyl-3H-imidazo[4,5-b]pyridine 3-[4-(1-Carboxy-1-(2-(1-hexyloxy)phenyl))methoxyphenyl]methyl-7-methyl-2-propyl-3H-imidazo[4,5-b]pyridine 3-[4-(1-Carboxy-1-(2-(1-hexyloxy)phenyl))methoxyphenyl ]methyl-5,7-dimethyl-2-ethyl-3H-imidazo[4,5-b 9 pyridine 3-[4-(1-Carboxy-1-(2,6-dichlorophenyl))methoxyphenyl ]methyl-5,7-dimethyl-2-ethyl-3H-imidazo[4,5-b]pyridine 3-[4-(1-Carboxy-1-(2-nitrophenyl))methoxyphenyl]-methyl-7-methyl-2-propyl-3H-imidazo[4,5-b]pyridine 3-[4(1-Carboxy-1(2-nitrophenyl))methoxyphenyl]-methyl-5,7-dimethyl-2-ethyl-3H-imidazo[4,5-b]pyridine 3-[4(1-Carboxy)-1(2-carboxyphenyl)methoxyphenyl]-methyl-7-methyl-2-propyl-3H-imidazo[4,5-b]pyridine 3-[4-(1-Carboxy)-1-(2-carboxyphenyl)methoxyphenyl]-methyl-5,7-dimethyl-2-ethyl- 3H-imidazo[4,5-b]pyridine 3-[4-(1-Carboxy-1-(2-trifluoromethylphenyl))methoxyphenyl ]methyl-5,7-dimethyl-2-ethyl-3H-imidazo[4,5-b]pyridine 3-[4-(1-Carboxy-1-phenyl)methoxy-3-chlorophenyl]-methyl -7-methyl-2-propyl-3H-imidazo[4,5-b]pyridine 3-[4-(1-Carboxy-1-phenyl)methoxy-3-chlorophenyl]-methyl -5,7-dimethyl-2-ethyl-3H-imidazo[4,5-b]pyridine 3-[4((1-Carboxy-1-phenyl)methoxy )-2-chlorophenyl]-methyl-5,7-dimethyl-2-ethyl-3H- imidazo[4,5-b]pyridine 3-[4-(1-Carboxy-1-(2-chlorophenyl))methoxy-3-chlorophenyl ]methyl-5,7-dimethyl-2-ethyl-3H-imidazo[4,5-b]pyridine 3-[3-Benzoyl-4-((1-carboxy-1-phenyl)methoxy)-phenyl]-methyl-5,7-dimethyl-2-ethyl-3H-imidazo[4,5-b]pyridine 3-[3-Acetyl-4((1-carboxy-1-phenyl)methoxy)phenyl]-methyl-5,7-dimethyl-2-ethyl-3H-imidazo[4,5-b]pyridine 3-[4-((1-Carboxy-1-phenyl)methoxy)-3-methoxyphenyl]-methyl-5,7-dimethyl-2-ethyl-3H- imidazo[4,5-b]pyridine 3-[4((1-Carboxy-1-phenyl)methoxy)-3-ethoxyphenyl]-methyl-5,7-dimethyl-2-ethyl-3H- imidazo[4,5-b]pyridine 3-[3-tert-Butyl-4-((1-carboxy-1-phenyl)methoxy)-phenyl]methyl-5,7-dimethyl-2-ethyl-3H-imidazo[4,5-b]pyridine 3-[4-((1-Carboxy-1-phenyl)methoxy)-3-methylphenyl]-methyl-5,7-dimethyl-2-ethyl-3H-imidazo[4,5-b]pyridine 3-[4-((1-Carboxy-1-(2-methylphenyl))methoxy)-3-chlorophenyl ]methyl-5,7-dimethyl-2-ethyl-3H- imidazo[4,5-b]pyridine 3-[4((1-Carboxy-1-phenyl)methoxy)-3,5-dichlorophenyl]methyl-5,7-dimethyl-2-ethyl-3H-imidazo[4,5-b]pyridine 3-[4-(1-Carboxy-1-(2-chlorophenyl))methoxy-3,5-dichlorophenyl]methyl-5,7-dimethyl-2-ethyl-3H-imidazo[4,5-b]pyridine 3-[4-((1-Carboxy-1-phenyl)methoxy )-3-chloro-5-methoxyphenyl ]methyl-5,7-dimethyl-2-ethyl-3H-imidazo[4,5-b]pyridine 3-[4((1-Carboxy-1-phenyl)methoxy)-3-(prop-2-enyl)-phenyl ]methyl-5,7-dimethyl-2-ethyl-3H-imidazo[4,5-b]pyridine 3-[4((1-Carboxy-1-phenyl)methoxy)-3-propylphenyl]-methyl- 5,7-dimethyl- 2-ethyl- 3H-imidazo[4,5-b]pyridine 3-[4-((1-Carboxy-1-(2-methylphenyl))methoxy)-3-propylphenyl ]methyl-5,7-dimethyl-2-ethyl-3H-imidazo[4,5-b]pyridine 3-[4-((1-Carboxy-1-(2-chlorophenyl))methoxy)-3-propylphenyl ]methyl-5,7-dimethyl-2-ethyl-3H-imidazo[4,5-b]pyridine 3-[4-((1-Carboxy-1-(4-chlorophenyl))methoxy)-3-propylphenyl ]methyl-5,7-dimethyl-2-ethyl-3H-imidazo[4,5-b]pyridine 3-[4((1-Carboxy-1(2-methoxyphenyl))methoxy )-3-propyl phenyl]methyl-5,7-dimethyl-2-ethyl-3H-imidazo[4,5-b]pyridine 3-[4-((1-Carboxy-1-(2,5-dibromo-3,4-dimethoxyphenyl))methoxy) -3-propylphenyl]methyl- 5,7-dimethyl-2-ethyl -3H-imidazo[4,5-b]pyridine 3-[4-((1-Carboxy-1-(3,4-dimethoxyphenyl))methoxy)-3propylphenyl ]methyl-5,7-dimethyl-2-ethyl-3H-imidazo[4,5-b]pyridine 3-[4-(1-Carboxy-1-phenyl)methoxy-3-propylphenyl]-methyl-5-carbomethoxy-2-ethyl-7-methyl-3H-imidazo[4,5-b]pyridine 3-[4-(1-Carboxy-1-phenyl)methoxy-3-propylphenyl]-methyl-5-carboxy-2-ethyl-7-methyl-3H-imidazo[4,5-b]pyridine 3-[4-(1-Carboxy-1-phenyl)methoxy-3-propylphenyl]-methyl-5-carbobenzyloxy-2-ethyl-7-methyl-3H-imidazo[4,5-b]pyridine 3-[4((1-Carboxy-1-phenyl)methoxy)-3(1-methylcyclohex -1-yl)phenyl]methyl-5,7-dimethyl-2-ethyl -3H-imidazo[4,5-b]pyridine 3-[4((1-Carboxy-1-phenyl)methoxy )-3,5-dipropylphenyl]-methyl- 5,7-dimethyl-2-ethyl- 3H-imidazo[4,5-b]pyridine 3-[4-((1-Carboxy-1-(2-methoxyphenyl))methoxy)-3,5-dipropylphenyl]methyl-5,7-dimethyl-2-ethyl-3H-imidazo [4,5-b]pyridine 3-[4-((1-Carboxy-1-(2,5-dibromo-3,4-dimethoxyphenyl))-methoxy) -3,5-dipropylphenyl]methyl-5,7-dimethyl -2-ethyl-3H-imidazo[4,5-b]pyridine 3-[4-(1-Carboxy-1-(2-chlorophenyl))methoxyphenyl]-methyl-2-ethyl-5-hydroxymethyl-7-methyl-3H-imidazo[4,5-b]pyridine 5-Carboxy-3-[4-(1-carboxy-1-(2-chlorophenyl))methoxyphenyl ]methyl-2-ethyl-7-methyl-3H-imidazo[4,5-b]pyridine 5-Carbomethoxy-3-[4(1-carboxy-1(2-chlorophenyl)-)methoxyphenyl ]methyl-2-ethyl-7-methyl-3H-imidazo[4,5-b]pyridine 5-Carbomethoxy-3-[4-(1-carboxy-1-(2-chlorophenyl))methoxyphenyl ]methyl-2-ethyl-7-trifluoromethyl-3H-imidazo[4,5-b]pyridine 3-[4-(1-Carboxy-1-cyclohexyl)methoxyphenyl]methyl-7-methyl-2-propyl-3H-imidazo[4,5-b]pyridine 3-[4-(1-Carboxy-1-propyl)methoxyphenyl]methyl-7-methyl-2-propyl-3H-imidazo[4,5-b]pyridine 3-[4-((1-Carboxy-1-(3-phenyl)propyloxy)phenyl]-methyl -5,7-dimethyl,2-ethyl-3H-imidazo[4,5-b]pyridine 3-[4-((1-Carboxy-1-(2-phenyl)ethoxy)phenyl]methyl-5,7-dimethyl-2-ethyl-3H-imidazo[4,5-b]pyridine 3-[4-(1-carboxy-1-phenoxy)methylphenyl]methyl-7-methyl-2-propyl-3H-imidazo[4,5-b]pyridine (Z)-3-[(4-((2-Carboxy-2-phenyl)ethylenyl)phenyl)-methyl ]-7-methyl-2-propyl-3H-imidazo[4,5-b]pyridine 3-[(4-((2-Carboxy-2-phenyl)ethyl)phenyl)methyl]-7-methyl-2-propyl-3H-imidazo[4,5-b]pyridine 3-[4(1-Carboxy-1-methyl-1-phenyl)methoxyphenyl]-methyl-7-methyl-2-propyl-3H-imidazo[4,5-b]pyridine 3-[4-(1-Carboxy-1-(naphth-1-yl))methoxyphenyl]-methyl -7-methyl-2-propyl-3H-imidazo[4,5-b]pyridine 3-[4-(1-Carboxy-1-(3-methylnaphth-2-yl))methoxyphenyl ]methyl- 7-methyl- 2-propyl- 3H-imidazo[4,5-b]pyridine 3-[4-N-(1-Carboxy-1-phenyl)methyl)-N-methylaminophenyl ]methyl-5,7-dimethyl-2-ethyl-3H-imidazo[4,5-b]pyridine 3-[4-N(1-Carboxy-1-phenyl)methyl)-N-ethylaminophenyl]-methyl-5,7-dimethyl-2-ethyl-3H-imidazo[4,5-b]pyridine 3-[4-N-(1-Carboxy-1-phenyl)methyl)-N-propylaminophenyl ]methyl-5,7-dimethyl-2-ethyl-3H-imidazo[4,5-b]pyridine 3-[4-N(1-Carboxy-1-phenyl)methyl)aminophenyl]-methyl -5,7-dimethyl- 2-ethyl-3H-imidazo[4,5-b ]pyridine 3-[4-N-(1-Carboxy-1-phenyl)methyl) -N-allylaminophenyl]-methyl- 5,7-dimethyl-2-ethyl-3H-imidazo[4,5-b]pyridine 3-[4-N-(1-Carboxy-1-phenyl)methyl)-N-iso-butylaminophenyl ]methyl-5,7-dimethyl-2-ethyl-3H-imidazo[4,5-b]pyridine 3-[4-N(1-Carboxy-1-phenyl)methyl)-N-cyclopropylmethylaminophenyl ]methyl-5,7-dimethyl-2-ethyl-3H-imidazo[4,5-b]pyridine 3-[4-N-(1-Carboxy-1-phenyl)methyl)-N-sec-butylaminophenyl ]methyl-5,7-dimethyl-2-ethyl-3H-imidazo -[4,5-b]pyridine 3-[4-N-(1-Carboxy-1-phenyl)methyl)-N-isopropylaminophenyl ]methyl-5,7-dimethyl-2-ethyl-3H-imidazo[4,5-b]pyridine 3-[4-N-(1-(Tetrazol-5-yl)-1-phenyl)methyl)-N-methylaminophenyl ]methyl-5,7-dimethyl-2-ethyl-3H-imidazo -[4,5-b]pyridine 2-Butyl-7-methyl-1-[4-(1-(tetrazol-5-yl)-1-phenyl)methoxyphenyl ]methyl-3H-imidazo[4,5-b]pyridine 7-Methyl-2-propyl-3-[4-(1-(tetrazol-5-yl)-1-phenyl)methoxyphenyl ]methyl-3H-imidazo[4,5-b]pyridine 7-Methyl-2-propyl-3-[4-(1-(tetrazol-5-yl)-1-(2-chlorophenyl) methoxyphenyl]methyl-3H-imidazo[4,5-b]pyridine 7-Methyl-2-propyl-3-[4(2-phenyl-2-(tetrazol-5-yl)ethyl) phenyl]methyl-3H-imidazo[4,5-b]pyridine 5,7-Dimethyl-2-ethyl-3-[4-(1-(tetrazol-5-yl)-1-phenyl)methoxyphenyl]methyl- 3H-imidazo[4,5-b]pyridine 5,7-Dimethyl-2-ethyl-3-[4-(1-(tetrazol-5-yl)-1-(2-chlorophenyl))methoxyphenyl]methyl-3H-imidazo[4,5-b]pyridine 5,7-Dimethyl-2-ethyl-3-[4-(1-(tetrazol-5-yl)-1-(2-methylphenyl))methoxyphenyl]methyl-3H-imidazo[4,5-b]pyridine 5,7-Dimethyl-2-ethyl-3-[4-(1-(tetrazol-5-yl)-1-(2-ethoxyphenyl)) methoxyphenyl]methyl-3H-imidazo[4,5-b]pyridine 5,7-Dimethyl-2-ethyl-3-[4-(1-(tetrazol-5-yl)-1-(2,6-dichlorophenyl))methoxyphenyl]methyl-3H-imidazo[4,5-b]pyridine 5,7-Dimethyl-2-ethyl-3-[4-(1-(tetrazol-5-yl)-1-(2-nitrophenyl))methoxyphenyl]methyl-3H-imidazo[4,5-b]pyridine 5,7-Dimethyl-2-ethyl-3-[4-(1-(tetrazol-5-yl)-1-(2-trifluoromethylphenyl)) methoxyphenyl]methyl-3H-imidazo[4,5-b]pyridine 5,7-Dimethyl-2-ethyl-3-[4-(1-(tetrazol-5-yl)-1-(2-chlorophenyl))methoxy-3-chlorophenyl]methyl-3H-imidazo[4,5-b]pyridine 5,7-Dimethyl-2-ethyl-3-[4-(1-(tetrazol-5-yl)-1-(2-chlorophenyl))methoxy-3,5-dichlorophenyl]methyl-3H -imidazo[4,5-b]pyridine 2-Ethyl-5-hydroxymethyl-7-methyl-3-[4-(1-(tetrazol-5yl) -1-(2-chlorophenyl))methoxyphenyl]methyl-3H -imidazo[4,5-b]pyridine 5-Carboxy-2-ethyl-7-methyl-3-[4-(1-(tetrazol-5-yl)-1-(2-chlorophenyl))methoxyphenyl]methyl-3H-imidazo[4,5-b]pyridine 5-Carbmethoxy-2-ethyl-7-methyl-3-[4-(1-(tetrazol-5-yl) -1(2-chlorophenyl))methoxyphenyl]methyl-3H-imidazo[4,5-b]pyridine 5-Carbmethoxy-2-ethyl-3-[4-(1-(tetrazol-5-yl)-1-(2-chlorophenyl)) methoxyphenyl]methyl-7-trifluoromethyl -3H-imidazo[4,5-b]pyridine 5,7-Dimethyl-2-ethyl-3-[4-(1-((N-phenylsulfonyl) -carboxamido)-1-(2-chloro)phenyl)methoxyphenyl]-methyl -3H-imidazo[4,5-b]pyridine 5,7-Dimethyl-2-ethyl-3-[4-(1-((N-methylsulfonyl) -carboxamido)-1-(2-chloro )phenyl)methoxyphenyl]-methyl -3H-imidazo[4,5-b]pyridine 5,7-Dimethyl-2-ethyl-3-[4-(1-((N-trifluoromethylsulfonyl) carboxamido )-1-(2-chloro)phenyl)methoxyphenyl ]methyl-3H-imidazo[4,5-b]pyridine 3-[4-(1-(Hydroxymethoxyphosphoryl)-1-(2-methylphenyl)) methoxyphenyl]methyl-5,7-dimethyl-2-ethyl-3H-imidazo[4,5-b ]pyridine

PURINES

9-[4-(1-Carboxy-1-phenyl)methoxyphenyl]methyl-6-methyl-8-propylpurine

9-[4-(1-Carboxy-1-(2-chlorophenyl))methoxyphenyl]-methyl-6-methyl-8-propylpurine 4,6-Dimethyl-8-ethyl-9-[4-(1-carboxy-1-(2-chlorophenyl)) methoxyphenyl]methylpurine 9-[4-(1-Carboxy-1-(2-chlorophenyl))methoxyphenyl]-methyl-8-ethyl-6-methylpurine 9-[4-(1-Carboxy-1-(2-chlorophenyl))methoxy-3-propylphenyl ]methyl-8-ethyl-6-methylpurine 9-[4-(1-Carboxy-1-phenyl)methoxy-3-propylphenyl]-methyl-8-ethyl-6-methylpurine 9-[4-(1-Carboxy-1-(2-chlorophenyl))methoxyphenyl]-methyl-4-dimethylamino-8-ethyl-6-methylpurine 9-[4-(1-Carboxy-1-(2-chlorophenyl))methoxyphenyl]-methyl -8-ethyl -6-methyl -4-(morpholin-4-yl)purine 9-[4-(1-Carboxy-1-(2-chlorophenyl))methoxyphenyl]-methyl-8-ethyl-6-methyl-4-methylaminopurine 9-[4-(1-Carboxy-1-(2-chlorophenyl))methoxyphenyl]-methyl-4,8-diethyl-6-methylpurine 9-[4-(1-Carboethoxy-1-(2-chlorophenyl))methoxyphenyl]-methyl-4,8-diethyl-6-methylpurine 9-[4-(1-Carboxy-1-(2-chlorophenyl))methoxyphenyl]-methyl-4,8-diethyl-6-trifluoromethylpurine 9-[4-(1-Carboxy-1-(2-trifluoromethylphenyl))methoxyphenyl ]methyl-8-ethyl-6-methyl-4-methylaminopurine 6-Methyl-8-propyl-9-[4-(1-(tetrazol-5-yl)-1-phenyl)-methoxyphenyl ]methylpurine 6-Methyl-8-propyl-9-[4-(1-(tetrazol-5-yl)-1-(2-chlorophenyl)) methoxyphenyl]methylpurine 4,6-Dimethyl-8-ethyl-9-[4-(1-(tetrazol-5-yl)-1-(2-chlorophenyl))methoxyphenyl]methylpurine 8-Ethyl-6-methyl-9-[4-(1-(tetrazol-5-yl)-1-(2-chlorophenyl)) methoxyphenyl]methylpurine 4-Dimethylamino-8-ethyl-6-methyl-9-[4-(1-(tetrazol-5-yl) -1-(2-chlorophenyl))methoxyphenyl]methylpurine 8-Ethyl-6-methyl -4-(morpholin-4-yl)-9-[4-(1-(tetrazol -5-yl)-1-(2-chlorophenyl))methoxyphenyl]methylpurine 8-Ethyl-6-methyl-4-methylamino-9-[4-(1-(tetrazol-5-yl) -1-(2-chlorophenyl))methoxyphenyl]methylpurine 4,8-Diethyl-6-methyl-9-[4-(1-(tetrazol-5-yl)-1-(2chlorophenyl)) methoxyphenyl]methylpurine 4,8-Diethyl-6-methyl-9-[4-(1-(tetrazol-5-yl)-1-(2-chlorophenyl))methoxyphenyl]methylpurine 4,8-Diethyl-9-[4-(1-(tetrazol-5-yl)-1-(2-chlorophenyl)) methoxyphenyl]methyl-6-trifluoromethylpurine 8-Ethyl-6-methyl-4-methylamino-9-[4-(1-(tetrazol-5-yl) -1-(2-trifluoromethylphenyl))methoxyphenyl]methylpurine 4,6-Dimethyl-8-ethyl-9-[4-(1-(N-phenylsulfonyl) -carboxamido-1-(2-chlorophenyl))methoxyphenyl]methylpurine 4,6-Dimethyl-8-ethyl-9-[4-(1-(N-methylsulfonyl) -carboxamido- 1(2-chlorophenyl))methoxyphenyl]methylpurine 4,6-Dimethyl-8-ethyl-9-[4-(1-(N-trifluoromethylsulfonyl) carboxamido-1-(2-chlorolphenyl))methoxyphenyl ]methylpurine 4,6-Dimethyl-8-ethyl-9-[4-(I-(N-acetyl)sulfonamido-1-(2-chlorophenyl))methoxyphenyl]methylpurine 4,6-Dimethyl-8-ethyl-9-[4-(1-(N-benzoyl)sulfonamido-1-(2-chlorophenyl))methoxyphenyl]methylpurine 4,6-Dimethyl-8-ethyl-9-[4-(1-(N-pyzimidin-2-yl) -sulfonamido-]-(2-chlorophenyl))methoxyphenyl]methylpurine

5,7-FUSED IMIDAZOLES

2-Butyl-1-[4-(1-carboxy-1-phenyl)methoxyphenyl]-methyl -1,4,6,7-tetrahydroimidazo[4,5-e][1,4]diazepine-5,8-dione 2-Butyl -1-[4-(1-carboxy-1-(2-chlorophenyl))methoxyphenyl ]methyl-1,4,6,7-tetrahydroimidazo[4,5-e][1,4]-diazepine-5,8-dione 2-Butyl-1-[4-((1-carboxy-1-phenyl)methoxy )-3-propylphenyl ]methyl-1,4,6,7-tetrahydroimidazo[4,5-e][1,4 ]-diazepine-5,8-dione 2-Butyl-1-[4-((1-carboxy-1-(2-chlorophenyl))methox) -3-pzopylphenyl]methyl-1,4,6,7-tetrahydroimidazo[4,5-e][1,4]diazepine-5,8-dione

GENERAL METHODS FOR PREPARATION OF COMPOUNDS OF GENERAL FORMULA I

The methods described in PAKT I AND PART II below illustrate the preparation of angiotensin II antagonists of Formula I. There are several general approaches to the synthesis of antagonists of Formula I, and it is taken as a general principle that one or another method may be more readily applicable for the preparation of a given antagonist; some of the approaches illustrated below may not be readily applicable for the preparation of certain antagonists of Formula I.

It should be recognized that antagonists of Formula I consist of a heterocyclic component designated above by formula I and a substituted benzyl substitutent which is attached to the heterocyclic component at a nitrogen atom. Thus, two generally applicable approaches to antagonists of formula I are these:

1. A heterocycle, designated above with Formula I is prepared as described in PART I below. Then the heterocycle is alkylated at a nitrogen atom with a substituted benzyl halide or pseudohalide giving an alkylated heterocycle. In the Schemes below, this alkylating agent is often designated as "Ar-CH$_2$Q" where Q is a halide (-Cl, Br, I) or pseudohalide (-OMs, OTs, OTf). In some cases, alkylation may take place at more than one nitrogen atom of the heterocycle, and in these cases, separation by fractional crystallization or by chromatographic methods may be necessary for isolation of the desired product. In some cases, the alkylation step produces a fully-assembled antagonist of Formula I, except that functional groups in the alkylating agent or in the heterocycle may be present in protected form and require deprotection steps to be carried out to complete the synthesis. In other cases, the alkylation is carried out with a substituted benzylic halide or pseudohalide ("Ar-CH$_2$Q"), but here the alkylation step is followed by subsequent steps which are required to assemble the substituted benzyl element of the antagonist of Formula I. The alkylation steps and subsequent steps used to prepare antagonists of Formula I, are described in PART II below.

2. In another approach to antagonists of Formula I, a substituted benzyl element is introduced at the beginning of, or during the preparation of the heterocyclic element. Routes of this type are illustrated in PART II below. In most cases where this general approach is used, the substituted benzyl component which is introduced during the synthesis of the heterocycle must be subjected to further synthetic transformations in order to complete the synthesis of the antagonist of Formula I. In the Schemes shown below in PART II, this substituted benzyl component is designated as "-CH$_2$Ar," and is usually introduced by an alkylation step with a substituted benzyl halide or pseudohalide designated ArCH$_2$-Q (where Q is, for example, Cl, Br, I, F, OTs, or OMs). Substituted benzyl halides or pseudohalides which are useful in the preparation of alkylated heterocycles described in PART I are illustrated by those listed below in Table 1. In cases where these benzylic halides, or pseudohalides are not commercially available, they are prepared as described in Part II below or by standard methods of organic synthesis. Subsequent steps which may be required to complete the synthesis of antagonists of Formula I are described in PART II below.

The compounds of this invention maybe resolved using techniques known in the art. The diastereomeric salts or esters of the enantiomers are separated and the desired compound is the more active stereoisomer. The compounds of this invention, their pharmaceutically acceptable salts and their prodrug forms are included within the scope of this invention.

TABLE 1

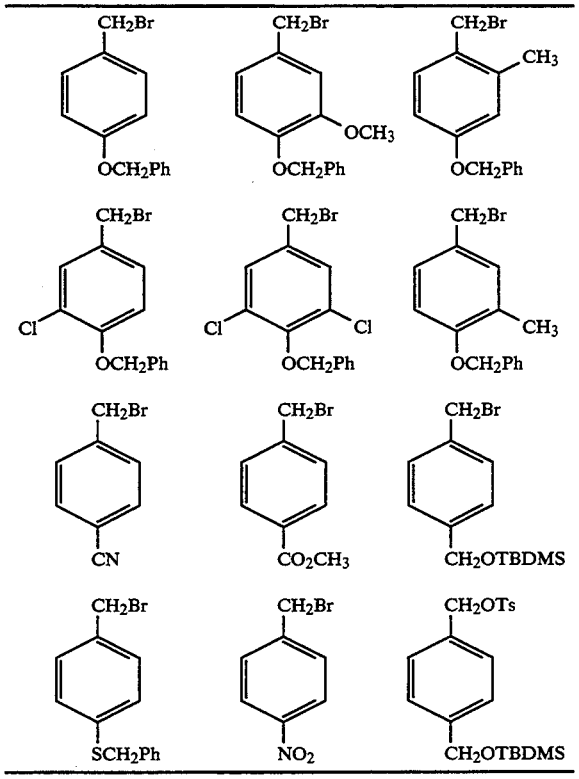

Abbreviations used in the schemes and examples are listed in Table 3.

TABLE 3

| Reagents | |
|---|---|
| NBS | N-bromosuccinimide, |
| AIBN | Azo(bis) isobutyronitrile |
| DDQ | Dichlorodicyanoquinone |
| Ac$_2$O | acetic anhydride |
| TEA | triethylamine |
| DMAP | 4-dimethylaminopyridine |
| PPh$_3$ | triphenylphosphine |
| TFA | trifluroacetic acid |
| TMS-Cl | trimethylsilyl chloride |

TABLE 3-continued

| | |
|---|---|
| Im | imidazole |
| AcSK | potassium thioacetate |
| p-TsOH | p-toluenesulfonic acid |
| FMOC-Cl | 9-Fluorenylmethyloxycarbonyl chloride |
| Solvents: | |
| DMF | dimethylformamide |
| HOAc (AcOH) | acetic acid |
| EtOAc (EtAc) | ethyl acetate |
| Hex | hexane |
| THF | tetrahydrofuran |
| DMSO | dimethylsulfoxide |
| MeOH | methanol |
| iPrOH | isopropanol |
| Others: | |
| rt | room temperature |
| TBDMS | t-butyldimethylsilyl |
| OTf | $OSO_2CF_3$ |
| Ph | phenyl |
| FAB-MS | Fast atom bombardment mass spectroscopy |
| NOE | Nuclear Overhauser Effect |
| $SiO_2$ | silica gel |
| trityl | triphenylmethyl |
| Bn | benzyl |

PART I: Preparation of the heterocycles shown in Formula

A. Preparation of the imidazo-5,6-and 7-membered fused heterocycles

The preparations of the imidazo-5-, 6-, 7-membered heterocycles are described in the Schemes below. There are several routes which have been used to prepare these systems. The first route involves, in the final steps, the closure of the imidazole ring. In other cases it has been advantageous to do the imidazole ring closure early in the synthesis and generate the fused 5-, 6-, or 7- membered ring in the final steps.

IMIDAZO-5-MEMBERED FUSED HETEROCYCLES

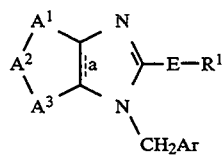

The compounds of Formula I, wherein $-A^1-A^2-A^3-$ represents a 3 atom sequence defined by (a)–(dd) in the Detailed Description of the Invention to generate the imidazo-5-fused system, can be synthesized using the reactions and techniques described herein below. The reactions are performed in a solvent appropriate to the reagents and materials employed and suitable for the transformation being effected. It is understood by those skilled in the art of organic synthesis that the functionality present on the heterocycle and other parts of the structure should be consistent with the chemical transformations proposed. Depending upon the reactions and techniques employed, this may involve changing the order of synthetic steps, the use of required protecting groups followed by deprotection, and, depending upon the particular imidazo-fused 5-membered heterocycle being formed, the use of different strategies may be employed regarding the cyclization steps and the particular starting material utilized.

The starting materials for preparing the compounds of this invention are dependent upon the nature of the heterocycle being formed. In many cases the heterocycles can be prepared either from a suitably functionalized 5-membered heterocycle by a ring closure step which gives an imidazo fused bicyclic ring system (see Reaction Schemes I-1 to I-4) or by starting with a suitably functionalized substituted imidazole and ring closing to give an imidazo-fused 5-membered ring heterocycle (see Reaction Schemes 5-7). The particular route chosen depends upon the nature of the bicyclic ring system being formed and the availability of starting materials.

One approach (Reaction Scheme I-1) starts with monocyclic derivatives bearing vicinal carbon-bound nitro and amino functions, such as 2 which are often readily available, or can be prepared from the mono nitro derivatives 9 by reaction with hydroxylamine. Compounds 2 may be reduced by any one of several methods, including catalytic hydrogenation or reaction with $SnCl_2$ to give the diamino derivative 3. Such derivatives are often unstable and can be ring-closed to the imidazo fused heterocycle 4 (E=single bond) by reaction with an appropriate carboxylic acid, nitrile, imidate ester, thioimidate ester, amidine, or orthoformate, either neat, or in a solvent appropriate and compatible with the starting materials and reagents, such as polyphosphoric acid, ethanol, methanol, hydrocarbon solvents and with a catalytic amount of acid if required.

Another possible approach, not shown in Reaction Scheme I-1. to compounds having the general structure 4 (E=single bond) from 3 involves the reaction of 3 with an appropriate aldehyde in the presence of an oxidizing agent such as $Cu^{II}$. nitrobenzene, or dicyanodichloroquinone (DDQ) to give heterocycles such as 4.

Ring closure of the vicinal diamino heterocycles 3, to give derivatives such as 5 can be effected by treatment with reagents such as $CS_2$, $CSCl_2$, $COCl_2$, $NH_2CONH_2$, alkyl chloroformates, dialkyl carbonates, or potassium cyanate in the presence of bases such as KOH or $K_2CO_3$. Another potential route to 5 (E=O) involves the use of a vicinal amino carboxylate such as 6a or 6b which can be converted to 5 via a Curtius or Hofmann rearrangement on suitable derivatives of 6a/6b such as acyl azides, hydroxyamides or N-haloamides. The bicyclic derivatives 5 can be alkylated under the appropriate conditions with alkyl halides, alkyl mesylates, alkyl tosylates, trialkyloxonium salts or with diazomethane to afford compounds of type 4 (E=O or S).

Another approach to 4 (E=single bond) which has been used for example when $A^1-A^2-A^3-$ together are $-N=C(CH_3)-N(CH_3)-$starts from 2 and utilizes acylation of the amino function with an acyl chloride or anhydride to give the nitro amido compound 7.

REACTION SCHEME I-1

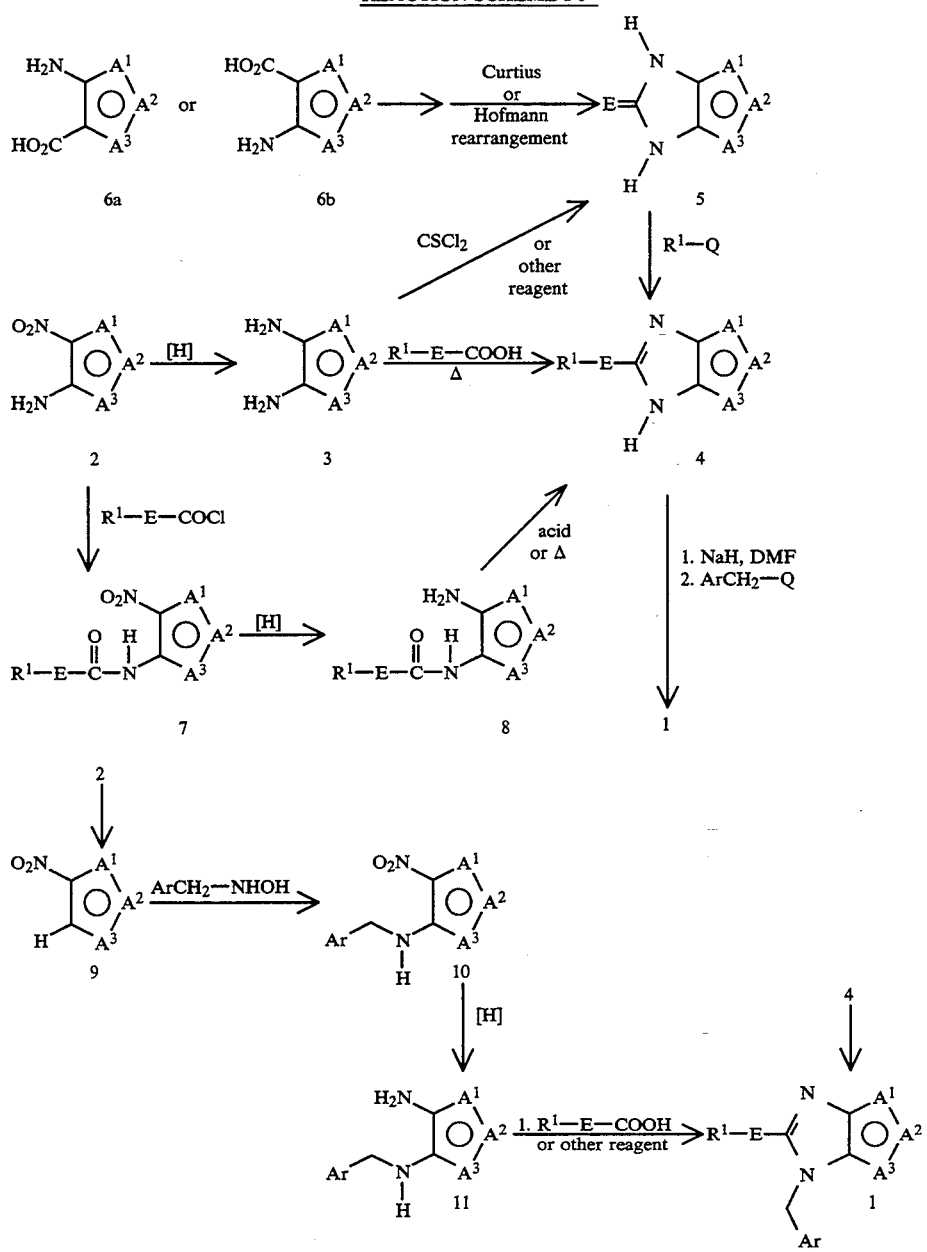

Q=a suitable leaving group such as Cl, Br, I, O-mesyl or O-tosyl Reduction of the nitro group leads to 8 and this can be ring closed to 4 via cyclodehydration, by heating and/or acid catalysis.

The imidazo fused heterocycle 4 can then be alkylated with ArCH$_2$-Q (where Q is a suitable leaving group such as Cl, Br, I, O-mesyl, or O-tosyl) in one of several ways. One way is initially to form the alkali metal salt of 4 by using MH (where M is Li, Na or K) in anhydrous dimethylformamide (DMF) or by treating 4 with a metal alkoxide such as sodium or potassium methoxide, ethoxide or t-butoxide in an appropriate alcohol such as methanol, ethanol or t-butanol as solvent. The alkylation is then carried out by dissolving the above-mentioned salt of 4 in an anhydrous aprotic solvent such as DMF, dimethylsulfoxide (DMSO) or tetrahydrofuran (THF) and reacting it with the alkylating agent ArCH$_2$-Q (preparation of ArCH$_2$-Q is described hereinbelow) at 20° C. to reflux temperature of the solvent for 1 to 24 hours.

If the substituents on the heterocyclic ring system result in an unsymmetrical heterocycle, then the alkylation may produce a mixture of regioisomers. These regioisomers possess distinct physico-chemical and biological properties and in most cases can be separated and purified using conventional separation techniques such as chromatography and/or crystallization. In those cases where the separation of regiosomers is difficult by conventional methods, the mixture can be transformed into suitable derivatives that are more amenable to the usual separation methods. The identification of the individual regioisomers can be made using Nuclear Overhauser Effect (NOE) NMR methods, $^{13}$C NMR methods (e.g. vicinal $^{13}$C-$^1$H coupling constants) or by single crystal X-ray crystallography.

It should be noted that the relative amounts of the regioisomers formed in the alkylation reaction can be influenced by several factors including the nature of the base used (while the alkali metal salt of the heterocycle is generally used, the regioisomeric ratio can be altered in some instances by using the heterocycle in the presence of a weaker base such as triethylamine, diisopropylethylamine, potassium carbonate or sodium bicarbonate) and the nature of the solvent used in the reaction.

An alternative approach, also shown in Reaction Scheme I-1, starts with the mono nitro derivative 9. This can be reacted with a substituted hydroxylamine bearing the ArCH$_2$ side chain, to give 10. Reduction of the nitro function gives the vicinal substituted diamine 11 which can be ring closed in the usual fashion. This allows for regioselective introduction of the Ar-CH$_2$ side chain into the bicyclic system.

Another approach to the compounds of this invention is shown in Reaction Scheme I-2. In this instance, a monoamino heterocycle such as 12 can be acylated under standard conditions to give the amido derivative 13. This amido compound can be reduced with LiAlH$_4$ in a anhydrous solvent such as THF or Et$_2$O to the alkylamino derivative 14 which can then be nitrosated with isoamyl nitrite to give 15. Such alkylamino nitroso derivatives particularly, for example, when A$^1$-A$^2$-A$^3$- together are -C(CH$_3$)=N-N(CH$_3$)-, undergo cyclodehydration when heated in pyridine to give the imidazo fused bicyclic heterocycle 4. The conversion of 4 to 1 can be carried out as described in Reaction Scheme I-1. Alternatively, it should be possible to alkylate 15 prior to ring closure to give the bis-N-alkylated derivative 16 which can then be subjected to cyclodehydration in hot pyridine to give the blocked 1. Separation of any regioisomers that may be formed can be effected by using conventional chromatographic methods.

An alternative approach to the synthesis of 16 might utilize alkylation of the monoalkylated side-chain 14 with ArCH$_2$-Q. This would provide the bis-N-alkylated derivative 17 which can be nitrosated with isoamyl nitrite to give 16.

An additional approach to the compounds of this invention is shown in Reaction Scheme I-3. In this approach the starting material is a vicinal bromo nitro heterocycle 18 which is reacted with an appropriate mono alkylamine to give 19. Ring closure can be effected using MeOH/NaOH with heating to give the N-oxide derivative 20 which can be reduced with either triethylphosphine, TiCl$_2$ or Si$_2$Cl$_6$ to give the imidazo-fused bicyclic heterocycle 4. This can be converted to 1 in the usual fashion as described above in Reaction Scheme I-1.

Alternatively, 18 can be reacted with the appropriate dialkylamine to give 21 (which can also be prepared by alkylation of 19 with ArCH$_2$-Q under the appropriate conditions). Ring closure of 21 in a fashion similar to that described above in the conversion of 19 to 20 is followed by reduction and separation of the products to give 1.

Another approach to compounds of the Formula 1 (particularly where -A$^1$-A$^2$-A$^3$- together are -C(R$^{7a}$)=C(R$^{7b}$)-S- is shown in Reaction Scheme I-4. In these instances, the starting material is the substituted heterocycle which can be alkylated with ARCH$_2$-Q to give 24. Treatment with hydrazine/nitrous acid and a refluxing alcohol (HOR$^1$) gives rise to 25 via a Curtius rearrangement of the intermediate acyl azide. The cyclization of 25 can be accomplished with polyphosphoric acid or other acidic catalyst to provide 1.

REACTION SCHEME I-2

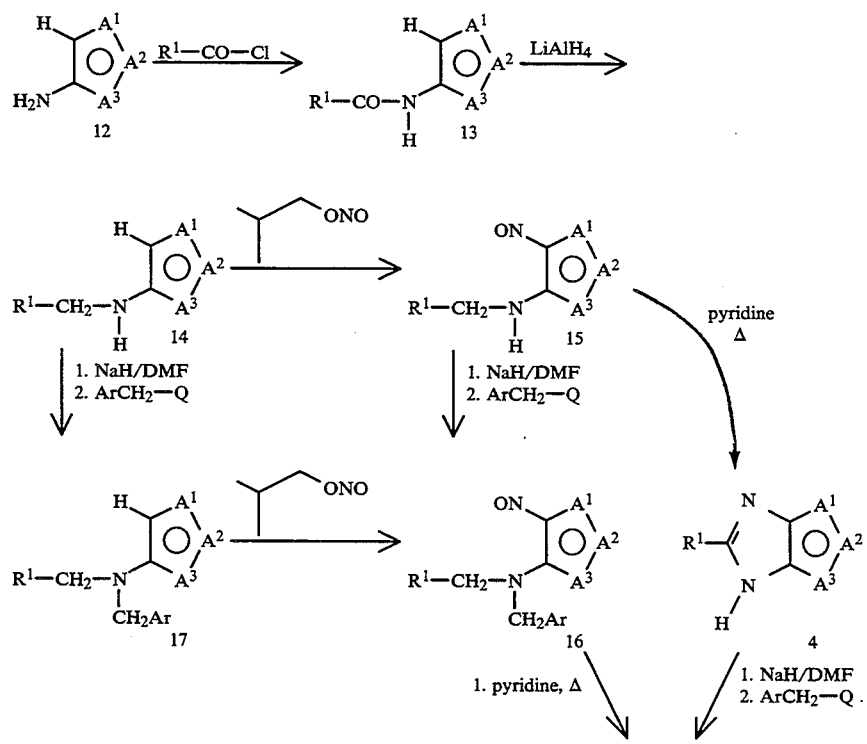

-continued
REACTION SCHEME I-2

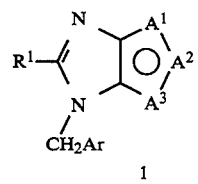

REACTION SCHEME I-3

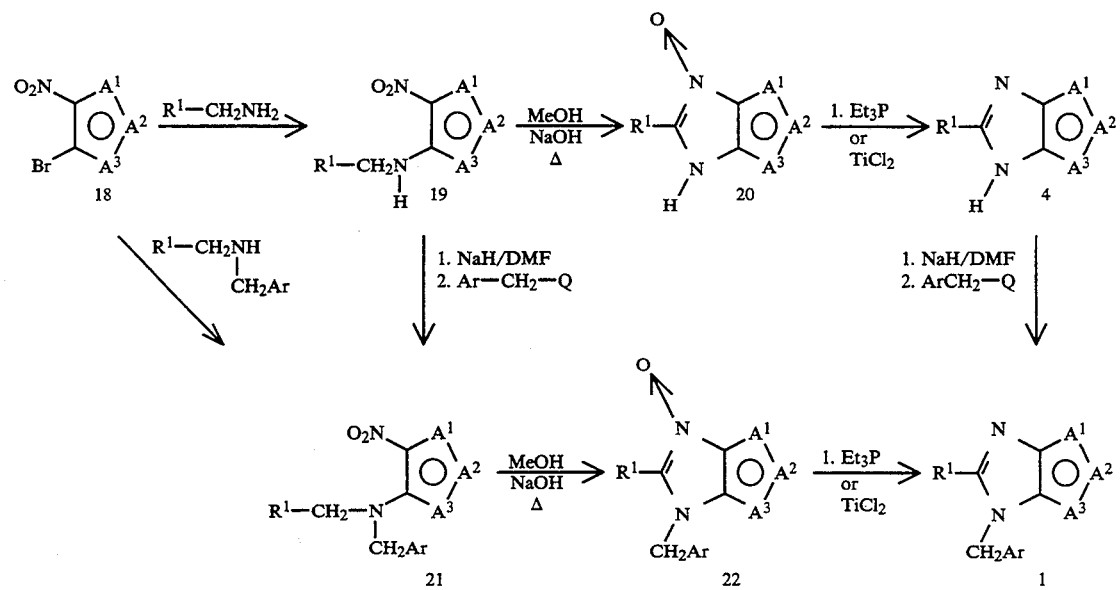

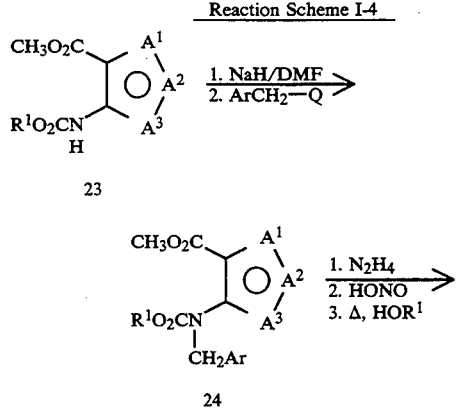

The required heterocyclic precursors for these transformations which are shown in Reaction Schemes 1–4 may be prepared by adaptations of literature procedures. A listing of representative precursors to these imidazo fused bicyclic heterocycles, along with literature references to their preparations is shown below in Table 4.

TABLE 4

| Structure | Name | Reference |
|---|---|---|
| 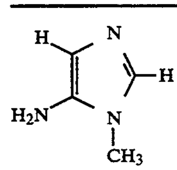 | 5-amino-1-methyl-imidazole | J. Chem. Soc., 2028 (1948) |

TABLE 4-continued

| Structure | Name | Reference |
|---|---|---|
| 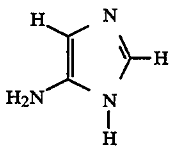 | 5-amino-imidazole | Can. J. Res., 19B 296 (1941) |
| 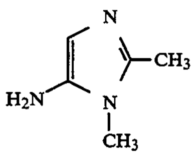 | 5-amino-1,2-dimethyl-imidazole | J. Chem. Soc, 164B (1954) |
| 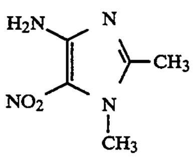 | 4-amino-5-nitro-1,2-dimethyl-imidazole | J. Het. Chem. 6, 53 (1969) |
| 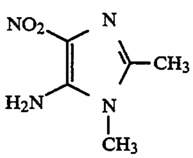 | 5-amino-4-4-nitro-1,2-dimethyl-imidazole | J. Het. Chem. 6, 53 (1969) |
| 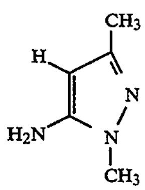 | 5-amino-1,3-dimethyl-pyrazole | U.S. Pat. No. 3,646,059 |
| 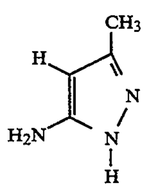 | 5-amino-3-methyl-pyrazole | U.S. Pat. No. 3,646,059 |
| 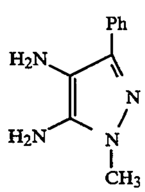 | 4,5-diamino-1-methyl-3-phenyl-pyrazole | J. Gen. Chem. (USSR) 32, 1898 (1962) |
| 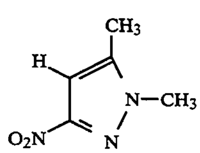 | 3-nitro-1,5-dimethyl-pyrazole | J. Gen. Chem. (USSR) 50, 2106 (1980) |
| 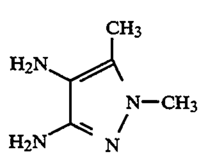 | 3,4-diamino-1,5-dimethyl-pyrazole | J. Gen. Chem. (USSR) 50, 2106 (1980) |

TABLE 4-continued

| Structure | Name | Reference |
|---|---|---|
| (structure) | 4-nitro-1,3-dimethyl-pyrazole | J. Gen. Chem. (USSR) 50, 2106 (1980) |
| (structure) | 5-amino-3-methyl-isoxazole | J. Het. Chem, 10, 181 (1973) |
| (structure) | 4,5-diamino-3-methyl-isoxazole | J. Het. Chem, 10, 181 (1973) |
| (structure) | 4-butyr-amido-thiazole | Eur. J. Med. Chem. 14 105 (1979) |
| (structure) | 5-nitro-2-methyl-thiazole | J. Org. Chem, 33 2545 (1968) |
| (structure) | 4-nitro-2-methyl-thiazole | J. Org. Chem, 33 2545 (1968) |
| (structure) | 4-aminoiso-thiazole | J. Chem. Soc., 306 (1959) |
| (structure) | 4-amino-3-methyl-isothiazole | J. Chem. Soc., 306 (1959) |
| (structure) | 5-amino-3-methyl-isothiazole | J. Chem. Soc., 306 (1959) |
| (structure) | 5-amino-4-nitro-3-methyl-isothiazole | J. Chem. Soc., 306 (1959) |
| (structure) | 3,4-diamino-1,2,5-thiadiazole 1,1- | Liebigs Ann. Chem. 4. 337 (1988) |

TABLE 4-continued

| Structure | Name | Reference |
|---|---|---|
| (4,5-diamino-1H-1-benzyl-1,2,3-triazole structure) | 4,5-diamino-1H-1-benzyl-1,2,3-triazole | Izv. Akad. Nauk SSRR, Ser Khim 11, 2633 (1985) |
| (2,3-diaminothiophene structure) | 2,3-diaminothiophene | Arch, Pharm (Weinheim), 314, 567 (1981) |
| (1-benzyl-3,4-diamino-2H-pyrrol-2-one structure) | 1-benzyl-3,4-diamino-2H-pyrrol-2-one | Liebeigs Ann. Chem. 183, 1424 (1978) |
| (4,5-diamino-3-[(phenylmethylene)amino]-2H-pyrrol-2-one structure) | 4,5-diamino-3-[(phenylmethylene)amino]-2H-pyrrol-2-one | Japanese Patent 53/109527 |
| (2,3-diaminomaleimide structure) | 2,3-diaminomaleimide | Chem. Ber., 116, 2591 (1983) |
| (3,4-diaminothiophene structure) | 3,4-diaminothiophene | Bull Soc. Chem. Fr., 5-6, pt. 2, 153 (1983) |
| (3,4-diamino-1,2,5-thiadiazole structure) | 3,4-diamino-1,2,5-thiadiazole | J. Het. Chem., 13, 13 (1976) |

In certain cases due to the nature of the heterocycle being prepared and to the availability of starting materials, it may be advantageous to prepare some of the compounds of this invention from a suitably functionalized imidazole ring by ring closing to give compounds of Formula 1. Some specific examples are shown in Reaction Schemes I-5 to I-7. Thus, Reaction Scheme 6 shows an approach to the preparation of the substituted regioisomers of 1H- and 3H- thieno[2,3-d]imidazoles. The substituted imidazole 26 can be readily alkylated in the fashion described earlier by using NaH in DMF, followed by treatment of the anion so formed with the alkylating agent ArCH$_2$-Q to give a separable mixture of the regioisomers 27a and 27b. These can be independently converted to ketones 28a and 28b, respectively, via oxidation with a suitable oxidizing agent such as MnO$_2$ to the aldehyde, followed by reaction with an appropriate Grignard reagent to give the secondary alcohol which is further oxidized with MnO$_2$ to 28a, b. These isomers can then be independently converted to the corresponding thieno[2,3-d]imidazoles 29 by treatment with a thioglycolic acid ester and the appropriate alkoxide in the appropriate refluxing alcohol (i.e., 28a gives the 3H-thieno -[2,3-d]imidazole 29a and 28b gives the 1H-thieno -[2,3-d]imidazole regioisomer 29b). Saponification of 29a, gives the carboxylic acid 33a. Other conversions possible with the 29a,b regioisomers include reduction with LiAlH$_4$ to the alcohol 30a,b, saponification followed by decarboxylation to give 31a,b, and conversion of the alkyl carboxylate to a ketone with an alkyl lithium reagent to give 32a,b. In addition, the intermediate 28a can be utilized as a precursor to the 1,6-dihydro-imidazo -[4,5-c]pyrazole, series by cyclization with a substituted hydrazine derivative, to give 34a. Similarly, 28b can be converted to the imidazo[4,5-c]pyrazole 1,4-dihydro series 34b.

REACTION SCHEME I-5

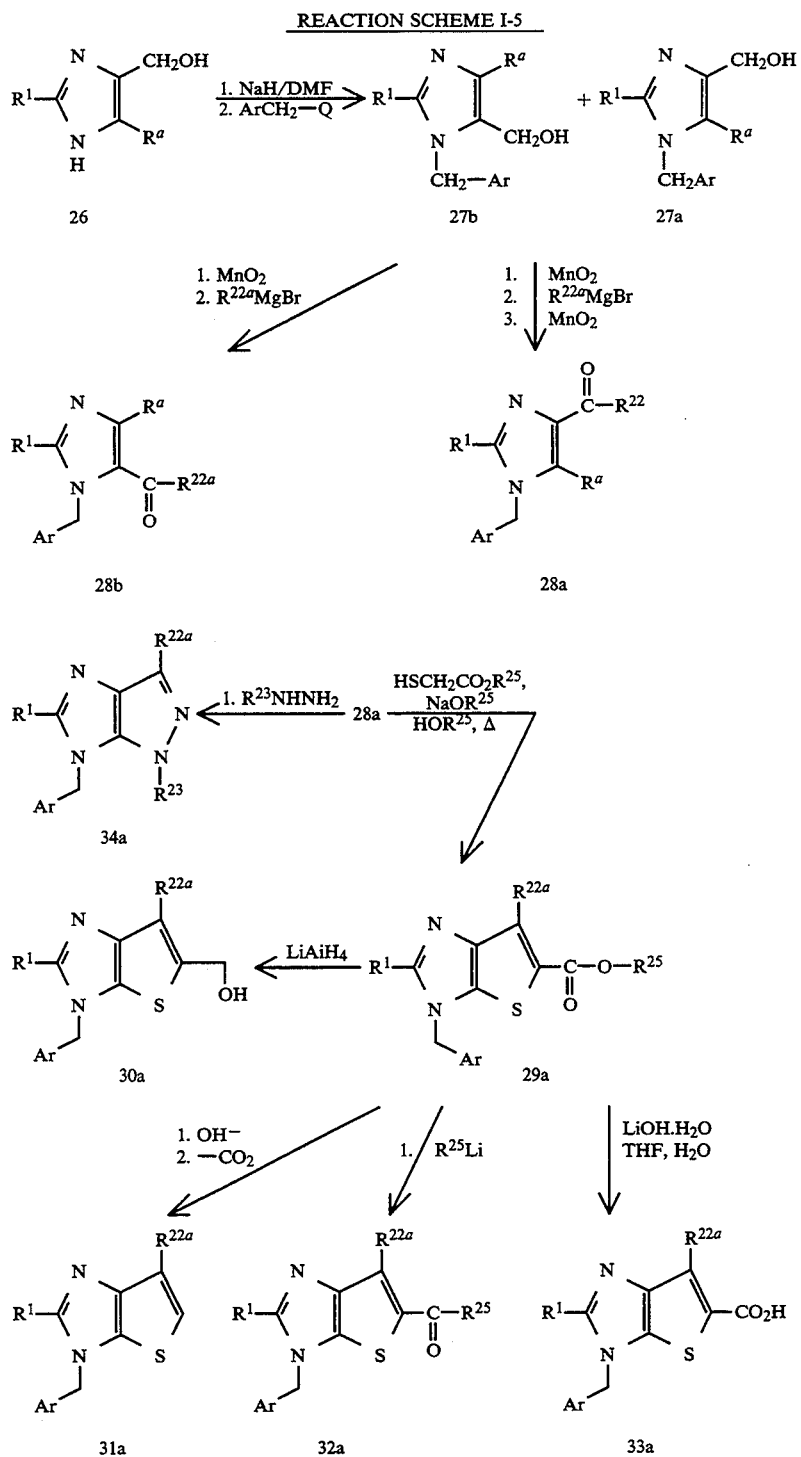

Similarly, 28b can be converted into the regioisomeric 29b, 30b, 31b, 32b, 33b, and 34b.

$R^a$ = halogen (Cl, Br, F, I)
$R^{22a}$ = H, alkyl, substituted alkyl, aryl or substituted aryl
$R^{23}$ = alkyl or substituted alkyl.
$R^{25}$ = alkyl or substituted alkyl.

A similar cyclization using hydroxylamine can be used to give the 6H-imidazo[4,5-d]isoxazole series (starting from 28a) or the 4H-imidazo[4,5-d]-isoxazole series (starting from 28b).

Preparation of the lactone derivatives 36a,b can probably he accomplished from the regioisomers 35a,b as shown in Reaction Scheme I-6. These tertiary alcohol starting materials can be obtained from respective ketones such as 28a,b (see Reaction Scheme I-5) by reaction with an appropriate Grignard reagent, followed by protection of the alcohol with t-butyldimethylsilylchloride. Thus, lithiation of 35a,b can be carried out with t-BuLi and the lithio derivative reacted with methyl chloroformate. The intermediate so formed can be treated with acid to remove the t-butyldimethylsilyl protecting group and to effect cyclization to the lactone. Deblocking can be effected as described earlier in Reaction Scheme 1.

A possible route to the substituted 1,5-dihydropyrrolo[3,4-d]imidazole 41 is shown in Reaction Scheme I-7. Thus, the functionalized imidazole 37 (or its regioisomer) prepared as described in European Patent Application 253,310 can be treated with tosyl chloride in pyridine to give the O-tosylate which can then be converted to the aminomethyl derivative via a Gabriel synthesis (displacement of tosylate with potassium phthalimide, followed by de-phthaloylation with hydrazine). This intermediate can be blocked by treatment with 1,2-bis(chlorodimethylsilyl)ethane to give the intermediate 38. Lithiation and subsequent formylation is accomplished by treatment with butyllithium and DMF to give the intermediate 39 which can cyclize under acid catalysis to the pyrrolo[3,4-d]imidazole derivative 40. Compound 40 is then treated with an alkyl, acyl or sulphonyl halide to block the pyrrole fine nitrogen. Deblocking with acid under the conditions described earlier gives rise to the required 41.

With regard to the preparation of derivatives containing the furo[2,3-d]imidazole heterocycle (i.e., compounds of Formula 1 where $A^1$-$A^2$-$A^3$- together are -C($R^{22}$)=C($R^{22}$)-O- and -O-C($R^{22}$)=C($R^{22}$)- these can be prepared by alkylation of the appropriate furo[2,3-d]imidazole [prepared as described in Chem. Pap., 40, 675(1986)] using the general procedures shown in Reaction Scheme I-1 for the conversion of 4 to 1.

$R^{24a}$ = aryl, substituted aryl, alkyl or substituted alkyl
Ar = subs phenyl Ar* = deprotected Ar
TBDMS = t-butyldimethylsilyl.

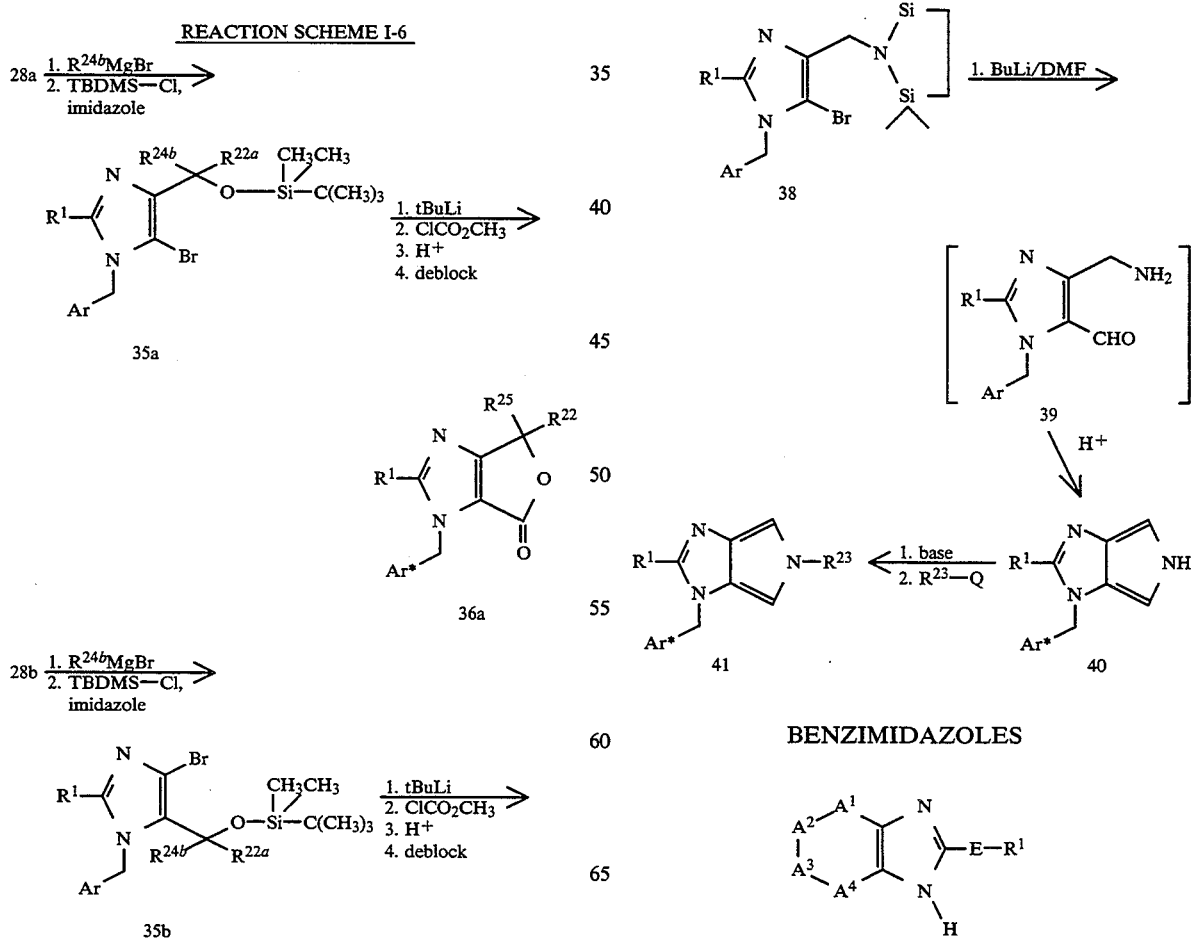

BENZIMIDAZOLES (Formula I, wherein $A^5$ is a single bond and -$A^1$-$A^2$-$A^3$-$A^4$- is as defined by (r) above)

The compounds of Formula I wherein (-$A^1$-$A^2$-$A^3$-$A^4$-) is a 4-atom sequence as defined in the General Description of the invention can be synthesized using the reactions and techniques described herein below. The reactions are performed in a solvent appropriate to the reagents and materials employed and suitable for the transformation being effected. It is understood by those skilled in the art of organic synthesis that the functionality present on the benzimidazole and other parts of the structure should be consistent with the chemical transformations proposed. Depending upon the reactions and techniques employed, this may involve changing the order of synthetic steps, use of required protecting groups followed by deprotection, and activation of the benzylic position of the alkylating agents used to enable alkylation at the nitrogen on the imidazole part of benzimidazoles.

REACTION SCHEME I-8

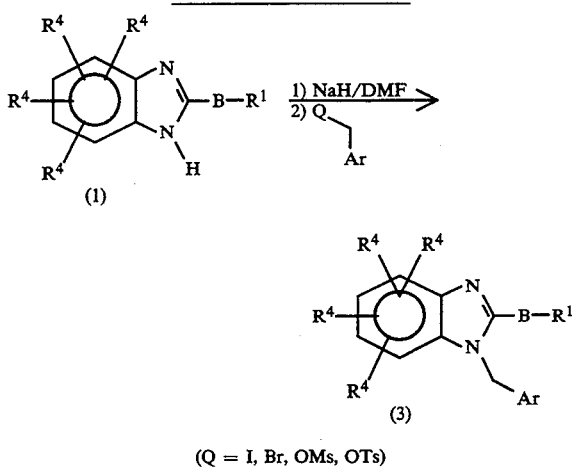

(Q = I, Br, OMs, OTs)

-continued
REACTION SCHEME I-8

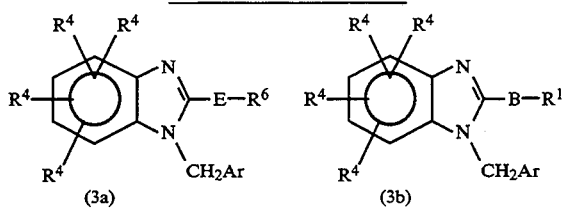

As shown in Reaction Scheme I-8, compounds of Formula (3) can be prepared by carrying out direct alkylation of alkali-metal salt of benzimidazole (1) (preparation of benzimidazoles are described in Reaction Schemes I-9 to I-12) using appropriately protected benzyl halide, tosylate (OTs) or mesylate (OMs) derivatives (2). The salt is prepared preferably using MH (where M is lithium, sodium or potassium) in anhydrous dimethylformamide (DMF), or by treating it with metal alkoxide such as sodium or potassium methoxide, ethoxide or t-butoxide in an appropriate alcohol such as methanol, ethanol or t-butanol as the solvent. The alkylation is generally carried-out by dissolving the metal salt of benzimidazole in a dipolar aprotic solvent such as DMF or dimethylsulfoxide (DMSO) and reacting it with the alkylating agent at 20° C. to reflux temperature of the solvent for 1-24 hours.

If substituents on the benzene ring result in an unsymmetrical benzimidazole, the alkylation may produce a mixture of two regioisomers as products, which may be represented by formulas 3a and 3b. These regioisomers possess distinct physico-chemical and biological properties and in most cases can be separated and purified by using conventional separation techniques such as chromatography (flash column chromatography, medium-pressure liquid chromatography, high pressure liquid chromatography (HPLC) and/or crystallization. In those cases where separation of regioisomers is difficult by conventional techniques, the mixture can be transformed into suitable derivatives that can be separated by usual separation methods. The structural assignments of the isomers can be made using proton NMR, Nuclear Overhauser Effect (NOE) experiments or X-ray crystallography.

REACTION SCHEME I-9

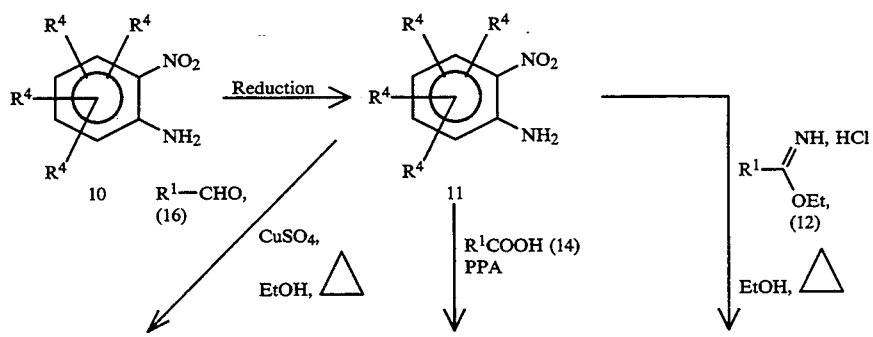

REACTION SCHEME I-9

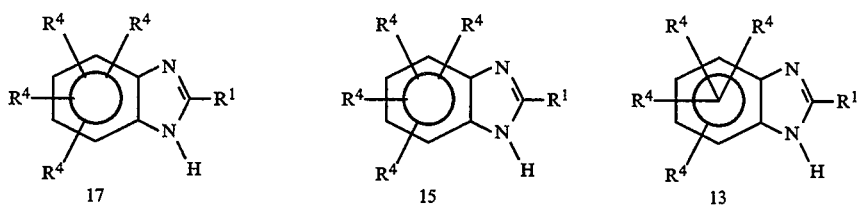

The starting benzimidazoles can be readily prepared by any of the standard procedures described in the literature [P. N. Preston, *Chemistry of Heterocyclic Compounds*, Vol. 40, part I, pp. 1–286 (1981) and references cited therein]. Several alternative routes to obtain benzimidazoles are outlined in Reaction Scheme I-9. The most widely used starting material, o-phenylenediamines (11), can be readily prepared from the corresponding o-nitroaniline (10) using standard reductive procedures such as metal-acid reduction or catalytic reduction. The substituted or unsubstituted 11 can then be treated with an appropriate imidate hydrochloride (12) to form corresponding benzimidazoles (13). Alternatively, the reaction of carboxylic acids (14) with o-phenylenediamines in the presence of polyphosphoric acid (PPA) is also effective in producing benzimidazoles (15). Benzimidazoles (17) can also be prepared from o-phenylenediamines and aldehyde (16) using cupric salt as an oxidant [R. Weidenhagen, *Chem. Ber.*, 69, 2263 (1936)].

REACTION SCHEME I-10

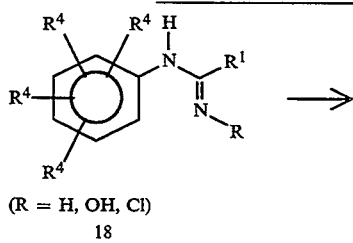

(R = H, OH, Cl)
18

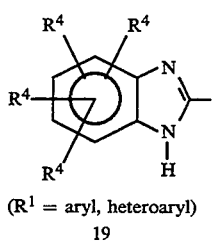

($R^1$ = aryl, heteroaryl)
19

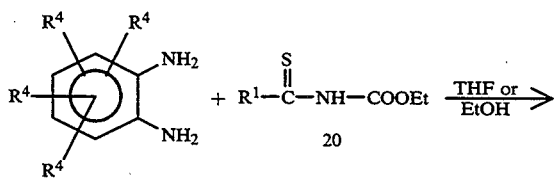

-continued
REACTION SCHEME I-10

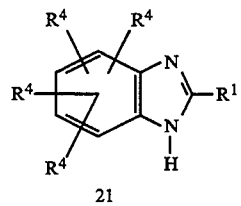

21

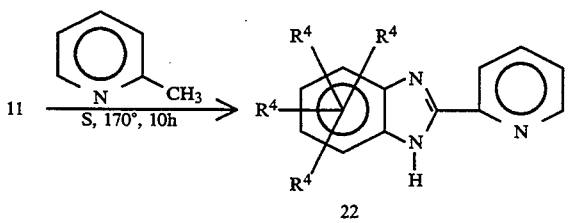

22

Although some benzimidazoles having aryl and heteroaryl groups at the 2 position can be prepared using the methods described in Reaction Scheme I-9, Reaction Scheme I-10 outlines methods which are more suitable for the synthesis of this class of compounds. N'-aryl-N-hydroxyamidines (18; R=OH) are cyclized under mild conditions using benzenesulfonyl chloride in pyridine or triethylamine to give 19 in good yield [M. W. Partridge and H. A. Turner, *J. Chem. Soc.*, 2086 (1958)]. Parent amidines (18; R=H) can also be oxidized with sodium hypochlorite under basic conditions to form19 [V. J. Grenda, R. E. Jones, G. Gal and M. Sletzinger, *J. Org. Chem.*, 30, 259, (1965)].

Alternatively, as shown in Reaction Scheme I-10, o-phenylenediamines (11) can be reacted with N-ethoxycarbonylthioamides (20) to give 2-substituted benzimidazoles (21) in excellent yields. This method avoids the use of acidic catalysts. The reagents (20) are easily obtained in one step from ethoxycarbonyl isothiocyanate and simple aromatic or heterocyclic compounds or alkylmagnesium halides [B. George and E. P. Papadopoulos., *J. Org. Chem.*, 41, 3233(1976); E. P, Papadopoulos., *J. Org. Chem.*, 41, 962(1976)]. Heterocyclic compounds containing reactive methyl groups (e.g., 2-picoline) can also be reacted with o-phenylenediamines in the presence of sulfur at elevated temperatures to give 2-heteroaryl benzimidazoles (22).

REACTION SCHEME I-11

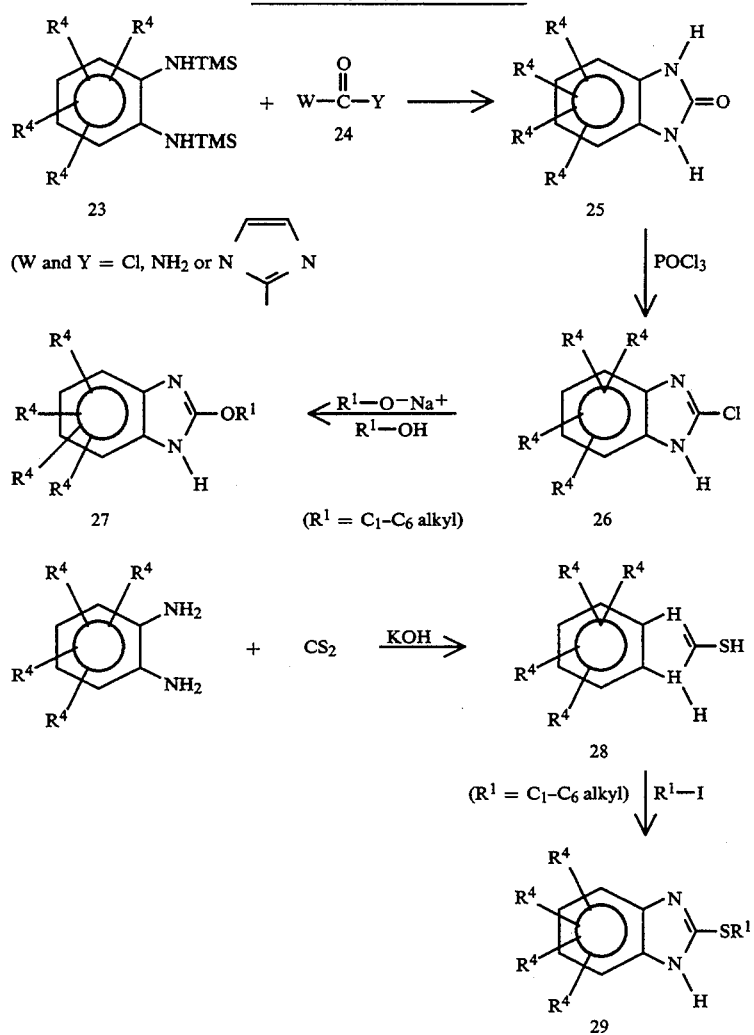

(W and Y = Cl, NH₂ or N⌒N imidazole)

($R^1$ = $C_1$-$C_6$ alkyl)

($R^1$ = $C_1$-$C_6$ alkyl)

As outlined in Reaction Scheme I-11, benzimidazoles containing 2-alkoxy and thioalkyl substituents (27 and 29) can be prepared from the corresponding benzimidazolones (25) or benzimidazolethiones (28). Benzimidazolones are conveniently prepared from o-phenylenediamines and phosgene or urea [K. Hofmann, "Imidazole and its Derivatives, Part 1," Wiley-Interscience, New York, 1953, pp. 285-291]. Carbonate esters, diethylpyrocarbonate, N,N-carbonyldiimidazole and N,N-diethylcarbamyl chloride may also be used in this reaction. The reaction of phosgene is apparently facilitated by the use of N,N'-]bis-trimethylsilyl (TMS) derivative (23) instead of the parent diamine [L. Birkhofer, H. P. Kuhlthau, and A. Ritter, *Chem. Ber.*, 93, 2810 (1960)].

REACTION SCHEME I-12

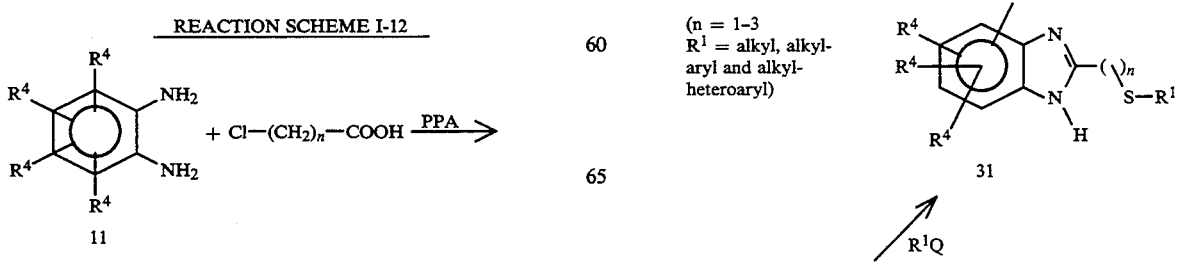

(n = 1-3
$R^1$ = alkyl, alkylaryl and alkylheteroaryl)

-continued
REACTION SCHEME I-12

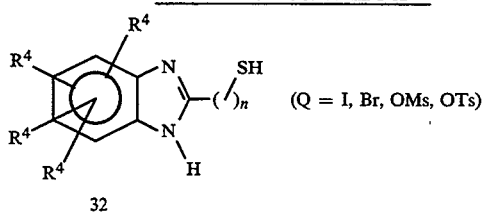

(Q = I, Br, OMs, OTs)

32

As described in Reaction Scheme I-12, 2-alkylthioalkyl substituted benzimidazoles (31) can be prepared from the reaction of RS-M (where M is sodium, potassium or lithium) with 2-chloroalkyl benzimidazoles (30). 2-Chloroalkyl benzimidazoles (30) can be conveniently prepared from the diamines and the chloroalkyl carboxylic acids using PPA [W. Knobloch, *Chem. Ber.*, 91, 2557 (1958)]. Alternatively, compound 31 can also be prepared from the readily available 2-thioalkyl derivative (32) [E. S. Milner, S. Snyder, and M. M. Joullie, *J, Chem. Soc.*, 4151 (1964)].

IMIDAZO-6-FUSED HETEROCYCLES

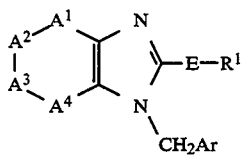

(FORMULA I, wherein $A^5$ is a single bond and $-A^1-A^2-A^3-A^4-$ is a 4-atom sequence as defined in the Detailed Description of the Invention)

The compounds of Formula I, wherein $-A^1-A^2-A^3-A^4-$ are defined by (ak) to (bw) in the Detailed Description of the invention can be synthesized using the reactions and techniques described herein below. The reactions are performed in a solvent appropriate to the reagents and materials employed and suitable for the transformation being effected. It is understood by those skilled in the art of organic synthesis that the functionality present on the heterocycle and in the reactants being employed should be consistent with the chemical transformations being conducted. Depending upon the reactions and techniques employed, optimal yields may require changing the order of synthetic steps or use of protecting groups followed by deprotection.

As shown in Reaction Scheme 1, compounds of Formula I can be prepared by carrying-out direct alkylation of alkali-metal salts of heterocycles (1) (preparation of heterocycles are described in Reaction Schemes 3-6) using appropriately protected benzyl halide, tosylate (OTs) or mesylate (OMs) derivatives (2). The salt is prepared preferably using MH (where M is lithium, sodium or potassium) in anhydrous dimethylformamide (DMF), or by treating it with a metal alkoxide such as sodium or potassium methoxide, ethoxide or t-butoxide in an appropriate alcohol such as methanol, ethanol or t-butanol as the solvent. The alkylation is generally carried-out by dissolving the metal salt of the heterocycle in a dipolar aprotic solvent such as DMF or dimethylsulfoxide (DMSO) and reacting it with the alkylating agent at 20° C. to reflux temperature of the solvent for 1-24 hours.

If substituents and/or the heteroatom positions in the six membered ring are not symmetrically disposed, the alkylation on the imidazole nitrogen(s) generally produces a mixture of two regioisomers as products arising from $N^1$ and $N^3$ alkylation. These regioisomers I and Ia possess distinct physico-chemical and biological properties and in most cases can be separated and purified by using conventional separation techniques such as chromatography (flash column chromatography, medium-pressure liquid chromatography, high performance liquid chromatography) and/or crystallization. In those cases where separation of regioisomers is difficult by conventional techniques, the mixture can be transformed into suitable derivatives that can be separated by the above separation methods. The structural assignments of the isomers can be made using Nuclear Overhauser Effect (NOE), $^1H$-$^{13}C$ coupled NMR experiments or X-ray crystallography.

When there is potential for alkylation of the 6-membered heterocyclic ring, this can be avoided by the use of suitable protecting groups.

The heterocycles of type (1) can be prepared by any of the standard procedures described in the literature [J. A. Montgomery and J. A. Secrist III in "Comprehensive Heterocyclic Chemistry," Vol. 5, A. R. Katritsky add C. W. Rees Eds., Pergamon Press 1984; pp 567–597 and 631–656 and references cited therein]. As shown in Reaction Scheme I-13, the most widely used starting materials are six member heterocyclic vicinal diamines (9). Fused imidazoles (10) can be prepared by condensation of (9) with an appropriate carboxylic acid, nitrile, imidate ester, or orthoester, either neat, or in a solvent appropriate and compatible with the starting materials and reagents, such as polyphosphoric acid, ethanol, methanol, hydrocarbon solvents, and with a catalytic amount of acid if required. Oxidation of an imine formed by reaction of diamine (9) with an appropriate aldehyde using oxidants such as Cu (II), nitrobenzene, or 2,3-dichloro-5,6-dicyano-1,4-benzoquinone (DDQ) also affords heterocycles (10). Aminoamides (11, W=H) or diamides (11, W=$R^6$CO) can be converted to fused imidazoles (10) by heating neat, or at an elevated temperature in a solvent such as xylene under acidic or neutral conditions.

Halogenation of the imidazo[4,5-b]pyridine ring at the 6-position can be accomplished using $Br_2$, or N-bromosuccinimide. Halogenation of the 7-position can be accomplished by reaction of the corresponding imidazopyridine-4-oxide (prepared by reaction of the imidazopyridine with peracids such as m-chloroperbenzoic acid) with $POCl_3$. When the 7-position is substituted other than hydrogen halogenation at the 5-position of the 4(N)-oxide precursor occurs on treatment with $POCl_3$. Chlorides may be substituted by bromides or iodides by treatment with either HBr or HI, respectively, in a solvent such as HOAc.

2-Alkyl-imidazo[4,5-b]pyridines can be substituted at the 5, 6, or 7 positions by displacement of a halogen at that position by nucleophiles such as cyanide (followed by hydrolysis to obtain carboxylic acids), amines, copper alkoxides, trialkylphosphites, and thiolates. Also, substitution of the halogens, in particular bromides or iodides, can be accomplished by reaction with a coupling partner such as alkylzinc or arylzinc halides, or monoalkylarylphosphonites in the presence of an appropriate metal catalyst such as nickel, palladium, ruthenium, or platinum. In cases where the displacement of a halogen is sluggish or otherwise complicated due to an acidic proton, the imidazopyridine may be protected at the 1, 3, or 4 positions by benzyl or other arylmethyl groups.

7-Methyl-2-propylimidazo[4,5-b]pyridine-5-carboxylic acid or the 2-ethyl analog is prepared from 7-methyl-2-propylimidazo[4,5-b]pyridine or the 2-ethyl analog by treatment with m-chloroperoxybenzoic acid to obtain the N-oxide which is then treated with POCl₃ to give 5-chloro-7-methyl-2-propylimidazo-[4,5-b]pyridine or 2-ethyl analog. The chloride is then exchanged for a bromide by reaction of 5-chloro-7-methyl -2- propylimidazo[4,5-b]pyridine or the 2-ethyl analog with HBr in acetic acid. The resulting 5-bromo-7-methyl-2-propylimidazo[4,5-b]- pyridine or 2-ethyl analog is treated with NaH in DMF followed by benzyl bromide to obtain 3-benzyl-5-bromo -7-methyl-2-propylimidazo[4,5-b]pyridine or its corresponding 2-ethyl analog which is in turn treated with CuCN in hot pyridine to obtain 3-benzyl -5-cyano-7-methyl-2-propylimidazo[4,5-b]pyridine or the corresponding 2-ethyl analog. The cyano compound is hydrolyzed to 3-benzyl-7-methyl-2-propylimidazo -[4,5-b]pyridine-5-carboxylic acid or the corresponding 2-ethyl analog by treatment with H₂SO₄-H₂O. This acid is esterified by reaction with MeOH-HCl. The benzyl group is removed by hydrogenation at 1 arm in MeOH-HCl solution using Pd(OH)₂ as catalyst. This compound can be alkylated as described earlier and the product methyl ester is converted to the carboxylic acid by treatment with hydroxide.

As shown in Reaction Scheme I-14, methods of preparing heterocycles of types 12 and 13 involve treatment of diamines (9) with reagents such as urea, phosgene, potassium cyanate, alkyl chloroformates, dialkylcarbonates, or carbon disulfide in the presence of bases such as potassium hydroxide or potassium carbonate. Amino acids 14 or 15 can be converted to 13 via Curtius or Hoffman rearrangement of suitable derivatives such as acyl azides, hydroxyamides, or N-haloamides. Bicyclic compounds of type (16, E=sulfur or oxygen) are formed from 12 by reaction under neutral or basic conditions with alkyl halides, alkyl mesylates, alkyl tosylates, trialkyloxonium salts, or with an appropriate diazoalkane. Compounds of type (16; B=oxygen or sulfur) are prepared by displacement reactions using alkoxides or alkyl mecaprides with chloro intermediates as indicated.

Diamines of type 9 can be prepared by a wide variety of methods such as hydrolysis of bis-amides or amino amides, reduction of dinitro or aminonitro or hydrazino or azido groups, displacement of heteroaromatic halides or alkoxy or thio or alkylthio or hydroxy or alkyl sulfonyl groups with ammonia or amines, or rearrangement of acyl azides or amides or acids (Curtius, Hoffman, or Schmidt rearrangements). [A. S. Tomcufcik, L. N. Starker in "Heterocyclic Compounds, Pyridine and it's Derivatives" Pt 3, E. Klingsberg Ed., Wiley Interscience, 1962, pp 59–62, and references cited therein; T. Nakagome in "Heterocyclic Compounds, Pyridazines" Vol. 28, R. N. Castle, Ed., Wiley Interscience, 1973, pp 597–601, and references cited therein; "Heterocyclic Compounds, The Pyrimidines" Vol. 16, D. J. Brown Ed., Wiley Interscience 1985, pp 299–325; E. Schipper, and A. R. Day *J. Am. Chem. Soc.* (1952) 74, 350; "Comprehensive Heterocyclic Chemistry," Vol. 5, A. R. Katritsky and C. W. Rees Eds., Pergamon Press 1984; pp 567–597 and 631–656 and references cited therein].

In cases wherein heterocycles of type 10 or 16 are not easily prepared from their corresponding diamines, or when these diamines cannot be prepared then alternative routes involving fusion of the six member heterocycle onto an appropriately substituted imidazole, are used. Two of these routes are illustrated in Reaction Scheme I-15. For example, imidazo[4,5-d][1,2,3]triazines (18) are preferentially prepared by treatment of amino carboxamido imidazoles (17) with sodium nitrite in aqueous acid. Precursor imidazoles (17) are prepared by degradation of an appropriately substituted xanthine or by condensation of an appropriate imidate ester with aminocyanoacetamide. Imidazo[4,5-b]-pyridazines (20) can be prepared from imidazodicarboxylate esters (19) by treatment with hydrazine. Oxidation of (20) gives pyridazinediones (21). The oxygen(s) in (20) or (21) can be converted to other functionalities such as halides or thiones, which are themselves precursors for the synthesis of more elaborate systems ["Comprehensive Heterocyclic Chemistry," Vol 5 A R Katritsky and C. W. Rees Eds., Pergamon Press 1984; pp 567–597 and 631–656 and references cited therein].

REACTION SCHEME I-13

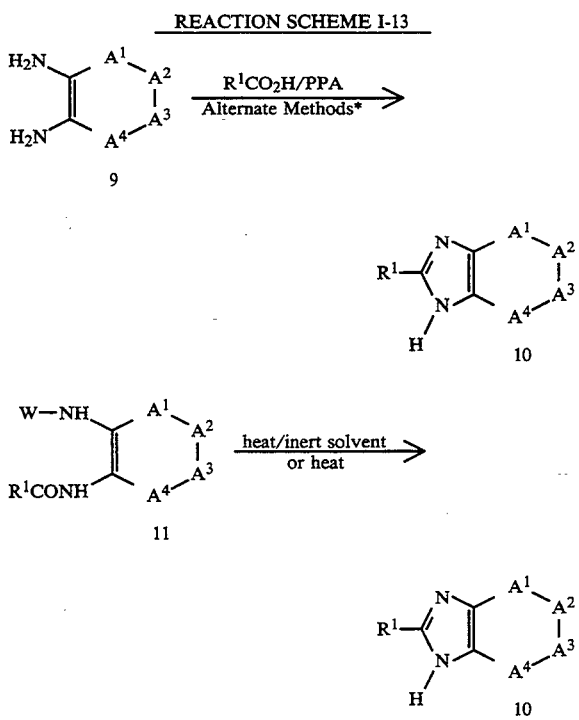

*Alternate reagents and reaction conditions:

R¹—CN, PPA
R¹—C(=NHHCl)—(OC₂H₅), C₂H₅OH,
R¹C(OCH₃)₃, toluene, H⁺, Δ
R¹CHO, C₂H₅OH, Cu(OCH₃)₂

REACTION SCHEME I-14

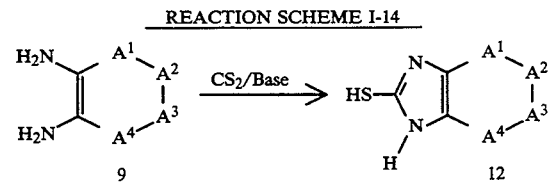

REACTION SCHEME I-14
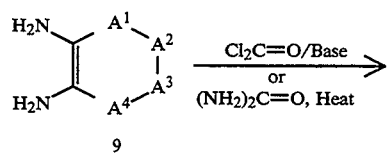
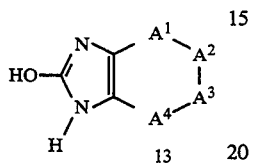
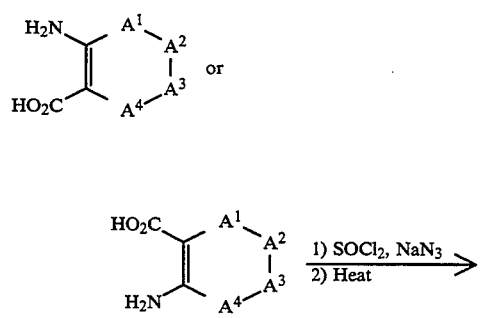
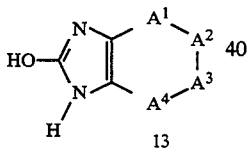
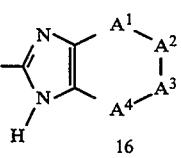
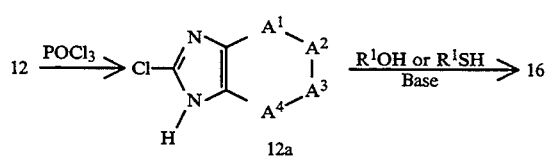
(E = O or S)
REACTION SCHEME I-15
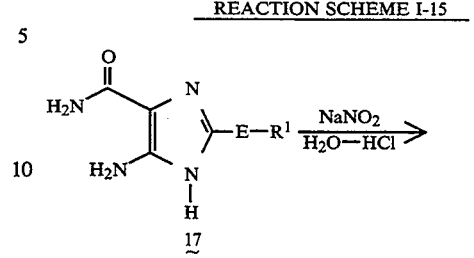
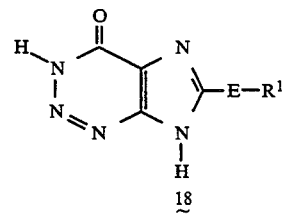
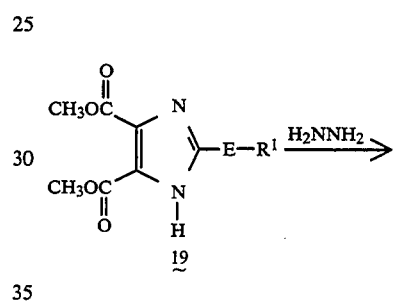
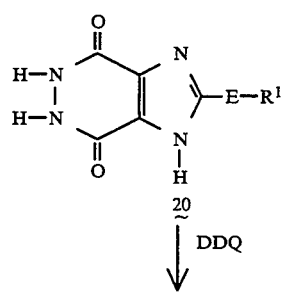
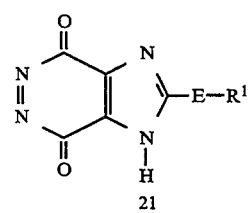
As shown in Reaction Scheme I-16 amino imidazole esters and amides are versatile intermediates for the preparation of purines. This scheme also illustrates the synthesis of the 6-membered heterocyclic ring after the alkylating agent 2 has been reacted with a suitably substituted imidazole to afford 22 or 24.

REACTION SCHEME I-16

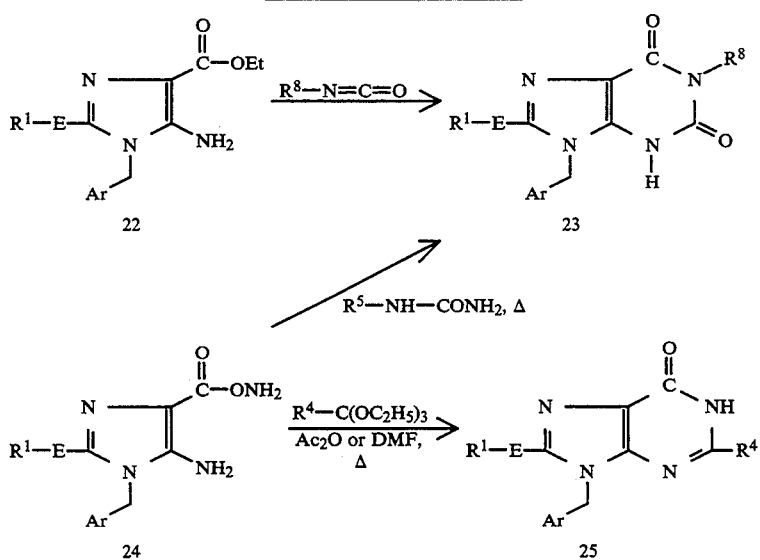

The preparation of reduced forms of heterocycles can be achieved by catalytic reduction, or by synthesis from a suitable imidazole precursor. For example, histidine and derivatives thereof react with formaldehyde to afford partially saturated imidazo(4,5-c) pyridines [cf. Neuberger, A. Biochem. J., (1944), 38, 309].

IMIDAZO-7-MEMBERED FUSED HETEROCYCLES

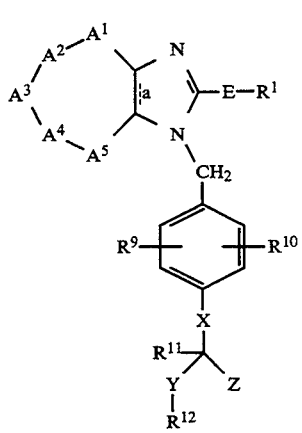

Compounds of FORMULA I, wherein $-A^1-A^2-A^3-A^4-A^5-$ represents a 5-atom sequence as defined in the Detailed Description of the Invention are prepared as described below in Schemes I-17 to I-23.

SCHEME I-17

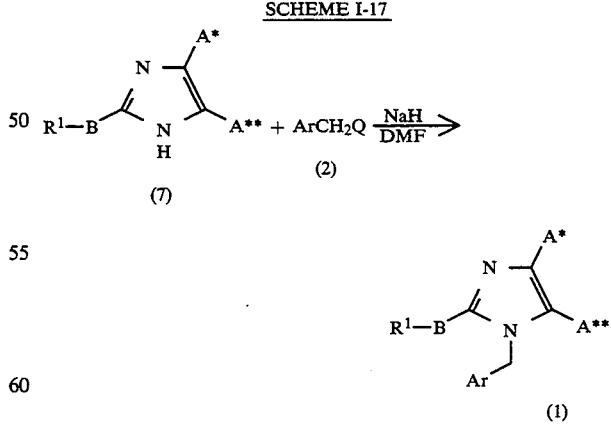

The imidazoles (7) required in alkylation Scheme I-17 can be prepared by a number of methods well known in the literature including those described in EPO publication 253,310. A useful method of generating compound (7) wherein A* and A** are $NH_2$ and $CONHR^6$ or $CO_2R^7$ is illustrated in Scheme I-18.

Scheme I-18

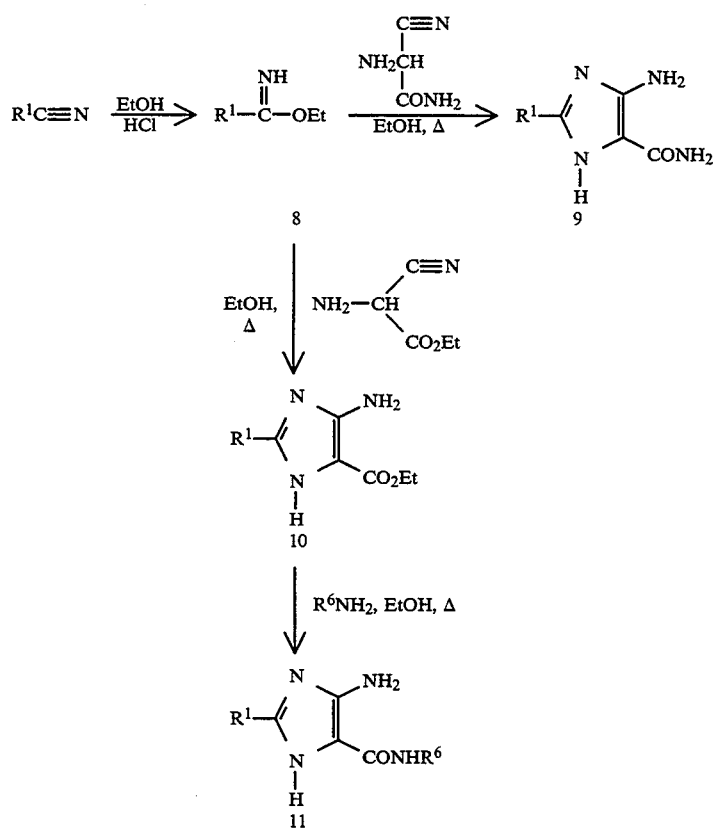

The synthesis of intermediate (1) wherein A* is NHR$^6$ and A** is CONHR$^6$ or CO$_2$R$^7$ (R$^7$=ethyl) and E is a single bond can be accomplished by the alkylation of the cyanoamidine (13) with a benzylic halide or pseudohalide represented as "ArCH$_2$-Q" where Q is a leaving group as outlined in Scheme I-19.

Scheme I-19

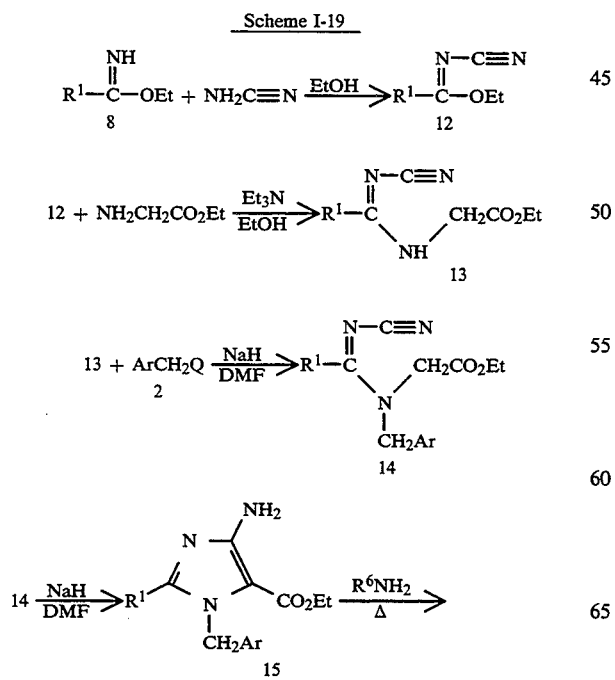

-continued
Scheme I-19

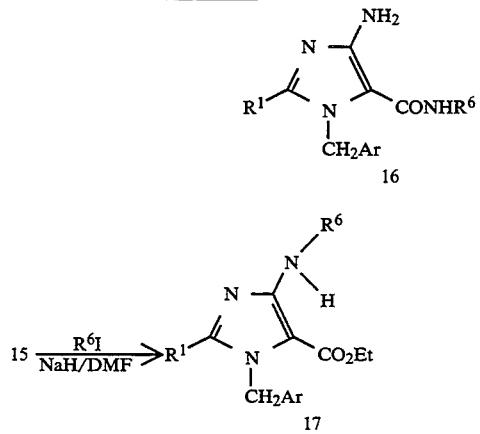

Cyanoamidine (13) is prepared according to the methods described by Edenhofer, Helv. Chim Acta, 58, 2192(1975).

Alkylation of cyanoamidine 13 may require an alkylating reagent which incorporates functional groups. In such cases, protecting groups may be required for these functional groups during the alkylation step. For example, a carboxyl group can be conviently protected as a t-butyl ester and a tetrazole group as an N-trityl derivative. The alkylated cyanomidine (14) is purified by silica gel chromatography as is the ring-closed product (15). Conversion of (15) to amide (16) is accomplished by heating the ester with R$^6$NH$_2$ in an inert solvent such as ethanol. Compound (15) can be alkylated on the amino moiety using a small excess of $R^1$-I in DMF in the presence of NaH.

Compounds of Formula (7) wherein A, and A** are either Cl and $CH_2OH$ or $CH_2OH$ and Cl respectively are also useful intermediates, and their preparations are described in EPO publication 253,310. The primary alcohol ($CH_2OH$) moiety in their alkylation products (18) can be oxidized directly to the corresponding $-CO_2CH_3$ ester groups using $MnO_2$ in the presence of NaCN and acetic acid in methanol as illustrated in Scheme I-20.

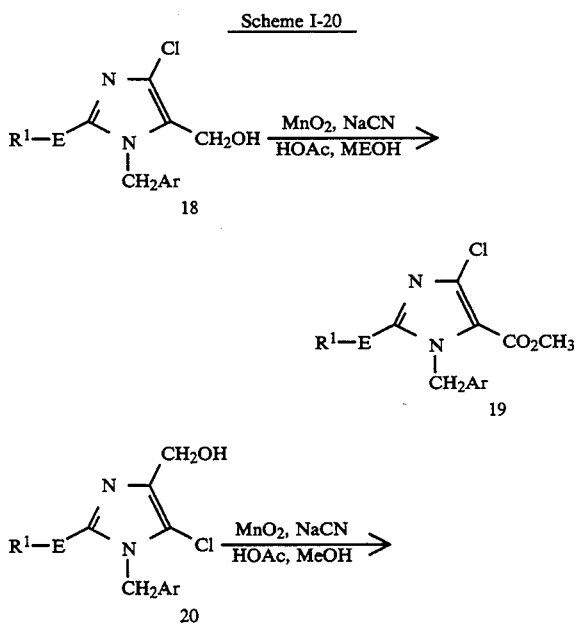

Compounds (19) and (21) from Scheme I-20 can be further converted to thiol compounds as illustrated by the methodology of Scheme I-21. Scheme I-21 also illustrates an alternate route to amino compounds (22) which involves azide displacement of Cl followed by hydrogenation.

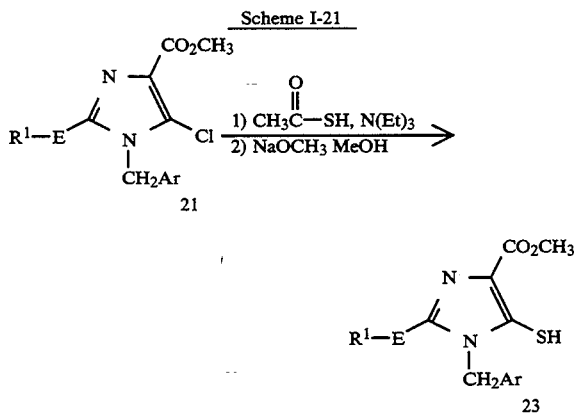

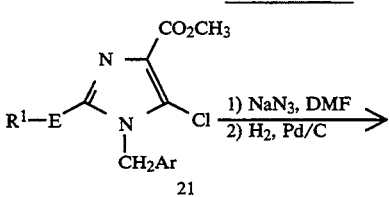

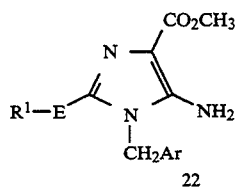

Formation of the products (I) wherein the fused ring A represented by $A^1$-$A^2$-$A^3$-$A^4$-$A^5$ contains D =$NR^6$ is carried out from intermediates (1) wherein A* and A** are ($NHR^6$, $CONHR^6$) or ($CONHR^6$, $NHR^6$) respectively by treating (1) in DMF with Q-C(O)-C($R^7$)($R^8$)-Q in the presence of a tertiary amine such as triethylamine. Q is a leaving group which preferably is a halo group. When A* or A** is $CO_2R^7$ and $R^7$=H then Y in the resultant products is oxygen. The transformations illustrated in Scheme I-22 with intermediate (16) are analogous to transformations which can be employed to synthesize similarly substituted benzodiazepines.

Scheme I-22

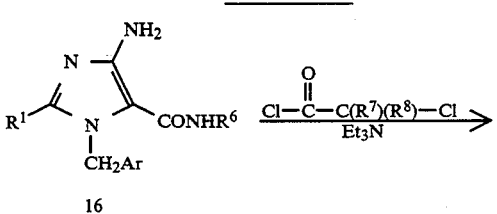

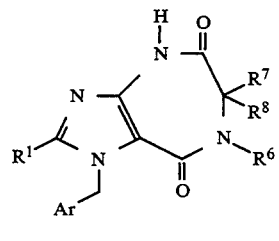

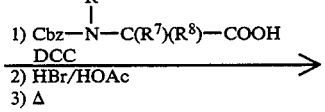

-continued
Scheme I-22

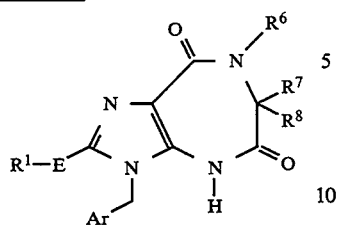

25

Scheme I-22 also provides an alternate route to generate products (I) wherein Y is $NR^6$. In this sequence N-protected amino acids are used to acylate intermediate (1) wherein A* or A** is $NR^6$, by employing either an acyl halide or a standard carboxyl activating reagent such as dicyclohexylcarbodiimide (DCC) or (benzotriazol-1-yl)oxytris(dimethylamino) phosphonium hexafluorophosphate (BOP). The N-protecting group of the amino acid such as the carbobenzyloxy (Cbz), t-butoxycarbonyl (t-BOC) or the fluorenylethylmethoxyloxycarbonyl (FMOC) group is removed according to standard peptide synthetic conditions. The final ring forming step is made by heating this intermediate in an alcoholic solvent or by saponifying the imidazole $CO_2R^7$ group to yield a carboxylic acid which is treated with a carboxyl activating reagent such as DCC or polyphosphoric acid.

Following the methodology of the above described transformation of Scheme I-22, if A* and A** are SH and $CO_2R^7$, as illustrated by intermediate (23), and the ring forming reagent is $HNR^6C(R^7)(R^8)CH_2Cl$, it is possible to form products of formula (I) wherein the $A^1-A^2-A^3-A^4-A^5$ element is $-CON(R^6)-C(R^7)(R^8)-CH_2S$ $-SCH_2C(R^7)(R^8)-N(R^6)-CO-$ $-CON(R^6)-C(R^{14})(R^{15})-CH_2S-SCH_2C(R^{14})(R^{15})-N(R^{16})CO-$ The preparation of products of Formula I, wherein $-A^1-A^2-A^3-A^4-A^5$ is $-CON(R^6)-C(R^7)(R^8)-C(R^9)=N-$ is carried out in Scheme I-23. The final ring closure, which involves a dehydration to yield an amine, can be assisted by heating in the presence of molecular sieves and acetic acid in an inert solvent such as dioxane, or by employing polyphosphoric acid as the dehydrating agent.

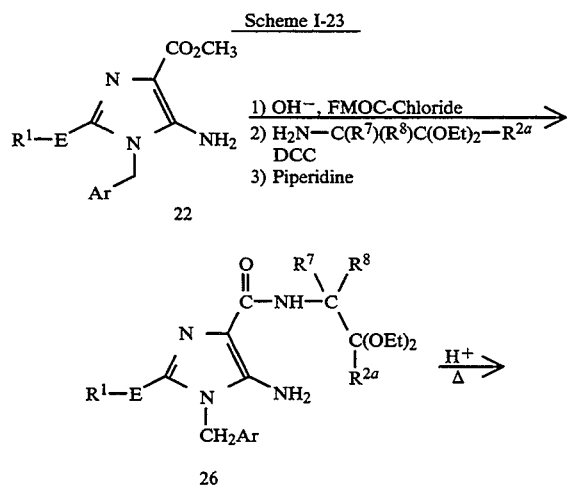

-continued
Scheme I-23

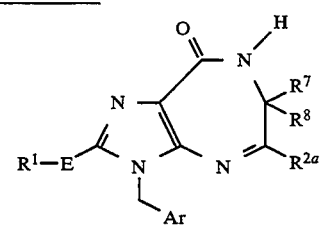

27

PART II

Preparation of substituted benzyl derivatives of the general Formula I. Preparation of compounds of Formula I starting from the heterocycles or benzyl-substituted heterocycles described in Part I is illustrated in the following schemes and descriptions.

The synthesis of Angiotensin II Antagonists incorporating a substituted benzyl group as shown in Formula I may be accomplished by reactions in the presence of a base of a heterocyclic compound (as described in Part I) with a benzylic compound bearing a good leaving group, and the appropriate substituents $R^9$, $R^{10}$, $R^{11}$, $R^{12}$, X, Y and Z as shown in Formula I. Alternatively, compounds with structures according to Formula I may also be synthesized in stages from a benzyl-substituted heterocycle which contains the substituents $R^9$, $R^{10}$ and X, followed by reaction with an intermediate (such as a substituted alpha-bromophenylacetic ester) which introduces the substituents at $R^{11}$, $R^{12}$ and Z. Examples of this latter methodology in which a benzyl-substituted heterocyclic intermediate is prepared first, and then elaborated to afford compounds with structures described by Formula I, are shown in the Schemes II-1, II-2 and II-3. The preparation of compound 5 of Formula I wherein: $-A^1-A^2-A^3-A^4-$ =$-CH=CH-CH=CH-$, E=a single bond, $R^1$=butyl, $R^9$, $R^{10}$ and $R^{11}$ are H, X=0, Y=a single bond, Z=$CO_2H$ and $R^{12}$=phenyl appears in Scheme II-1 and in Example 1 of the experimental section. Deprotonation of 2-butylbenzimidazole with strong bases such as sodium hydride or potassium tert-butoxide in DMF for a period of 1–24 hours at temperatures of 20°–100° C., followed by alkylation with 4-benzyloxybenzyl chloride affords the protected ether 2. The benzyl ether is next removed by hydrogenolysis using hydrogen and an appropriate catalyst such as Pd/C, $Pd(OH)_2/C$ or Pt/C which affords the intermediate phenol 3. The phenolic proton is then abstracted, and the phenolate is alkylated with methyl 2-bromophenylacetate to furnish ester 4. Finally, the ester is hydrolyzed and the free acid 5 is obtained.

SCHEME II-1

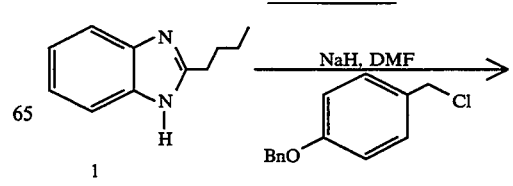

-continued
SCHEME II-1

SCHEME II-2

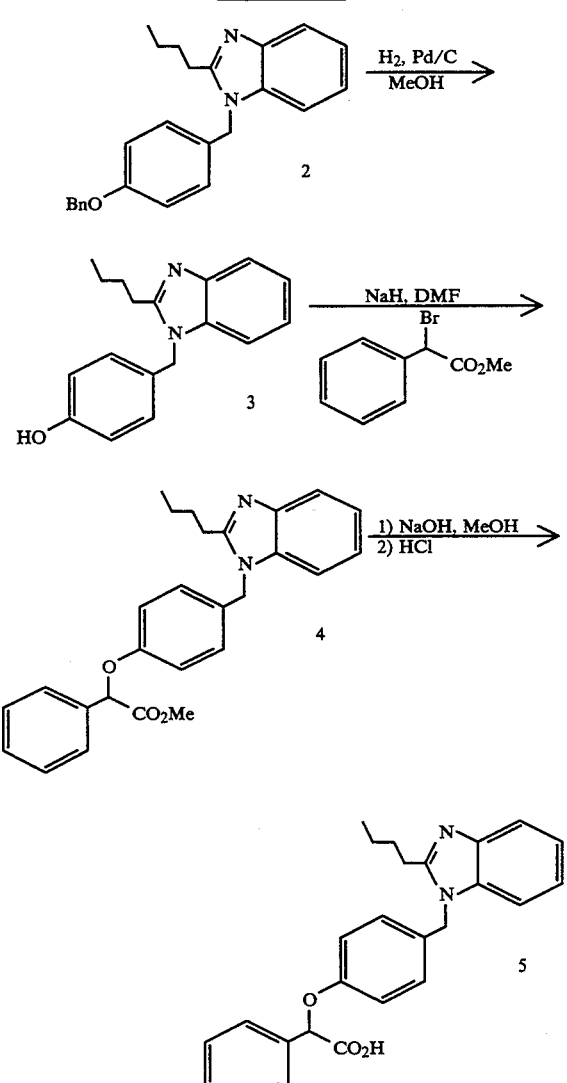

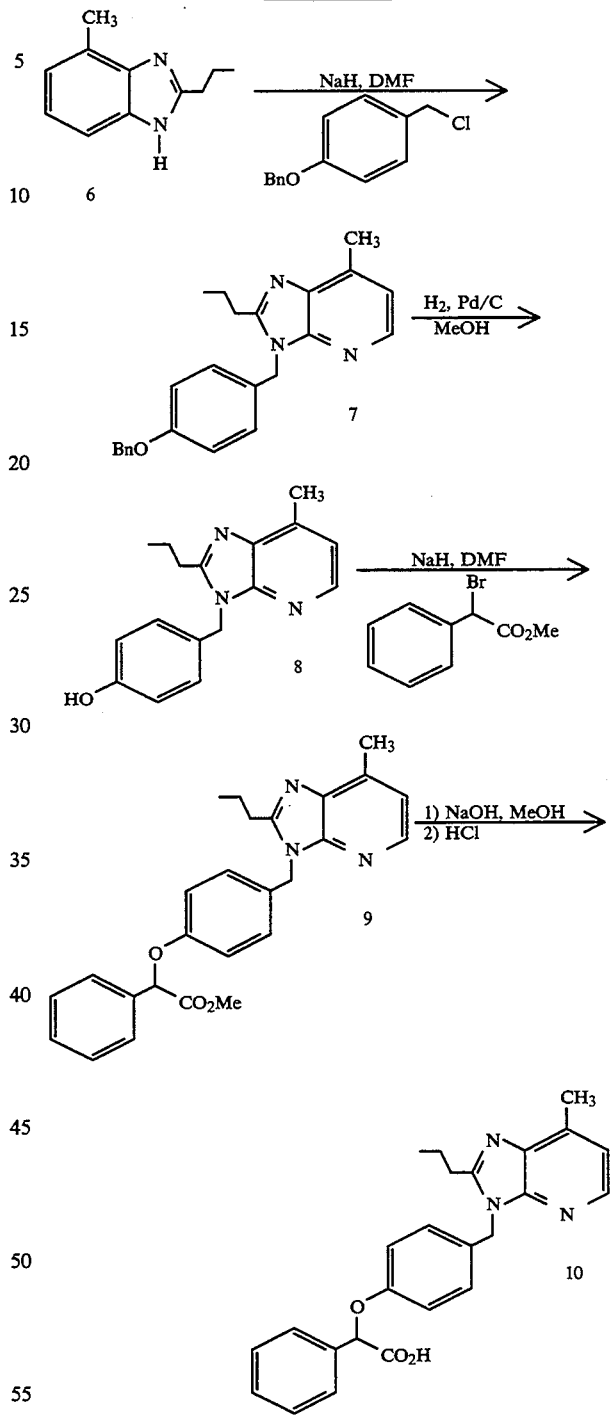

The synthesis of compound 10 of Formula I wherein: -A$^1$-A$^2$-A$^3$-A$^4$-=-C(CH$_3$)=CH—CH=N-, E=a single bond, R$^1$=n-propyl, R$^9$, R$^{10}$ and R$^{11}$ are H, X=O, Y=a single bond, Z=CO$_2$H and R$^{12}$=phenyl is presented in Scheme II-2 and in Example 2 of the experimental section. Deprotonation of 7-methyl-2 propylimidazo[4,5-b]pyridine (6) with sodium hydride in DMF followed by treatment with 4-benzyloxybenzyl chloride gives compound 7. The benzyl ether is removed by hydrogenolysis to give the phenol 8. which is then deprotonated with potassium hydride and 18-crown-6 in DMF and alkylated with methyl 2-bromophenylacetate to give the ester 9. Basic hydrolysis of 9 gives the free acid 10. Alkylation of the phenol 8 with substituted 2-bromophenylacetic esters followed by ester hydrolysis leads to compounds of Formula I where R$^{12}$ is a substituted phenyl group such as those show in Examples 6 (R$^{12}$=2,6-dichlorophenyl), 7 (R$^{12}$=2-nitrophenyl), 8 (R$^{12}$=cyclohexyl), 9 (R$^{12}$=n-propyl), and 10 (R$^{12}$=o-carboxyphenyl) in the experimental section.

The synthesis of compound 15 of Formula I wherein: -A$^1$-A$^2$-A$^3$-A$^4$- =-C(CH$_3$)=CH-C(CH$_3$)=N-, E=a single bond, E$^1$=ethyl, R$^9$, R$^{10}$ and R$^{11}$ are H, X=O, Y=a single bond, Z=CO$_2$H and R$^{12}$=2-methylphenyl is shown in Scheme II-3 and in Example 24 of the experimental section. Deprotonation of 5,7-dimethyl-2-ethylimidazo[4,5-b]pyridine (11) with a strong base such as sodium hydride in DMF, followed by treatment with 4-benzyloxybenzyl chloride produces the ether 12. The benzyl ether is removed by hydrogenolysis to give the phenol 13, which is then deprotonated with potassium hydride and 18-crown-6 in DMF and alkylated with methyl 2-bromo-2'-methylphenylacetate to give the ester 14. Alkaline hydrolysis of 14 gives the free acid 15. Reaction of the phenol 13 with other substituted alpha-bromophenylacetic esters followed by alkaline hydrolysis leads to additional derivatives in this heterocycle series, such as Examples 25 ($R^{12}$=2-chlorophenyl), 26 ($R^{12}$=2-bromophenyl) and 40 ($R^{12}$=2-phenylethyl) in the experimental section.

SCHEME II-3

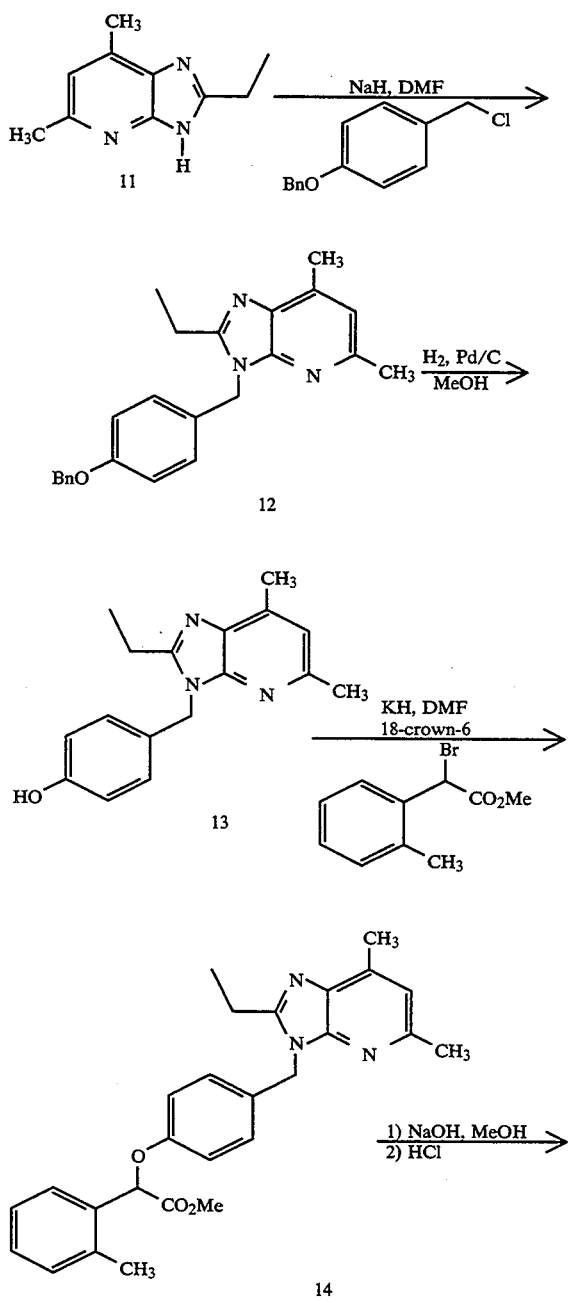

-continued
SCHEME II-3

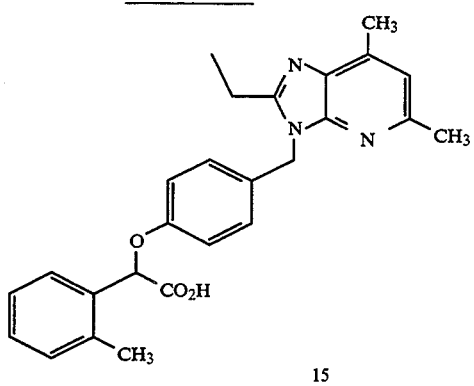

Substituted 2-bromophenylacetic esters are typically employed in the synthesis of compounds of general Formula I when it is desired that $R^{12}$ be a substituted phenyl group, $R^{11}$ is hydrogen, Y is a single bond and Z is a carboxylic acid. These substituted 2-bromophenylacetic esters are readily prepared from substituted phenyl acetic acids (16) by a Hell-Volhard-Zelinsky reaction as shown in Scheme II-4. Alternatively, substituted 2-bromophenylacetic esters may also be obtained from benzaldehydes (18) as shown in Scheme II-5. Reaction of the substituted benzaldehydes (18) with trimethylsilyl cyanide affords the trimethylsilyl-cyanohydrins 19. Treatment of 19 with acidic ethanol produces the hydroxy esters 20, and subsequent reaction with carbon tetrabromide and triphenylphosphine provides the substituted 2-bromophenylacetic esters 17.

Scheme II-4

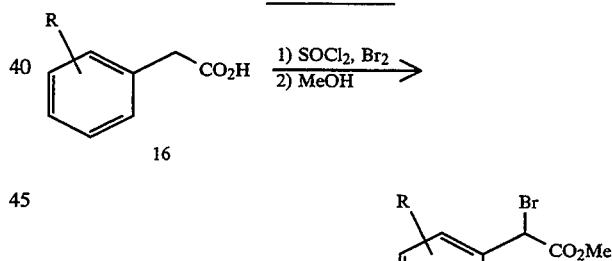

Scheme II-5

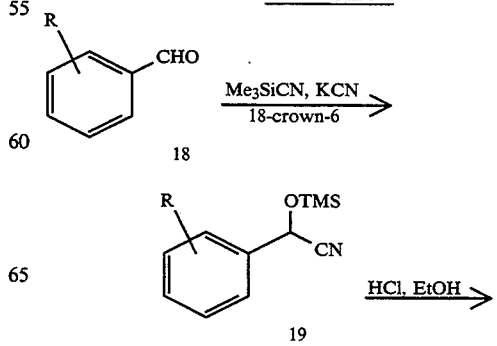

Scheme II-5 (continued)

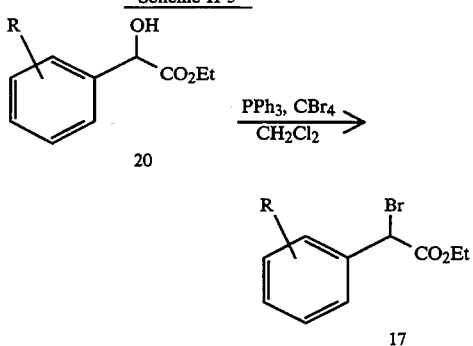

The synthesis of Angiotensin II Antagonists incorporating a substituted benzyl element defined by Formula I may also be accomplished by the alkylation reaction of a heterocycle (as described in Part I) with a benzylic intermediate bearing a good leaving group, and with all of the appropriate substituents $R^9$, $R^{10}$, $R^{11}$, $R^{12}$, X, Y and Z in place. This approach which is generally preferred when either $R^9$ or $R^{10}$ are non-hydrogen, is illustrated in Scheme II-6 and in Examples 3, 4, 27-31, 33, and 46 of the experimental section. Deprotonation of p-cresol (21) with strong bases such as potassium hydride or potassium tert-butoxide in DMF and alkylation with methyl 2-bromo-2-phenylacetate gives the ether 22. Bromination of 22 at the benzylic methyl group with N-bromosuccinimide gives the alkylating agent 23. Deprotonation of 5,7-dimethyl-2-ethylimidazo[4,5-b]pyridine (11) with sodium hydride in DMF, followed by reaction with bromide 23, and subsequent ester hydrolysis provides the acid 24.

SCHEME II-6

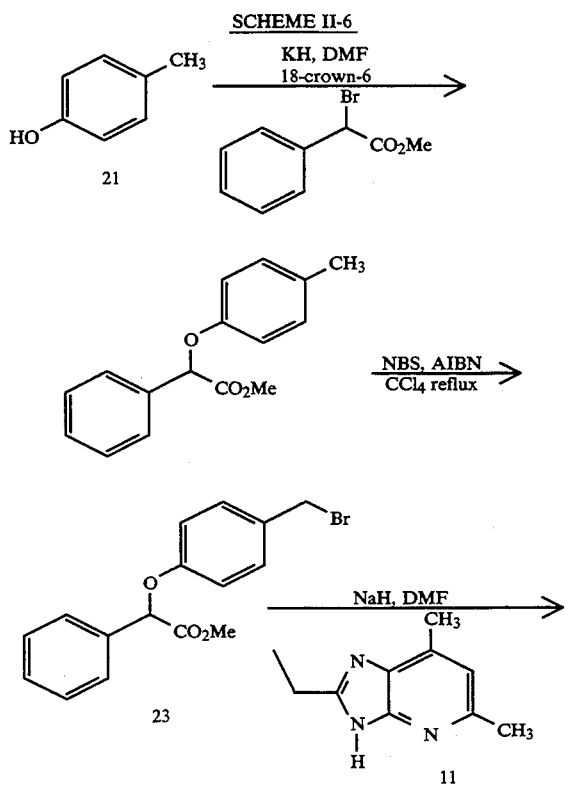

SCHEME II-6 (continued)

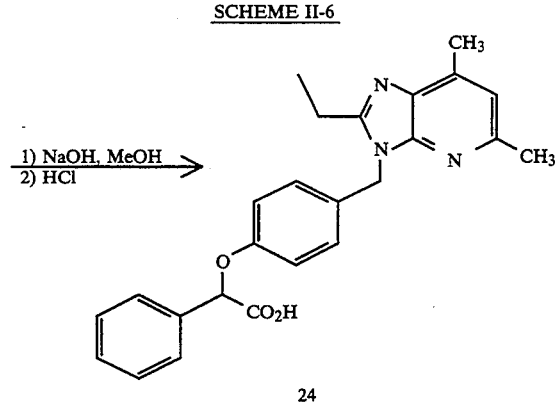

A strategy similar to that of Scheme II-6 is applied when substitution at $R^{11}$ is desired as shown in Scheme II-7. Intermediate ethers such as 22 in Scheme II-6 are deprotonated with strong bases such as lithium bis(trimethylsilyl)amide in THF and can then be reacted with an alkylating agent such as an alkyl halide or mesylate. In this case, reaction of the anion derived from ether 22 with methyl iodide affords the alkylated product 25. Reaction of 25 with N-bromosuccinimide gives bromide 26, which is in turn used for alkylation of a heterocyclic compound from Part I. Scheme II-7 illustrates the alkylation of heterocycle 6 with bromide 26 which after ester hydrolysis affords acid 27.

SCHEME II-7

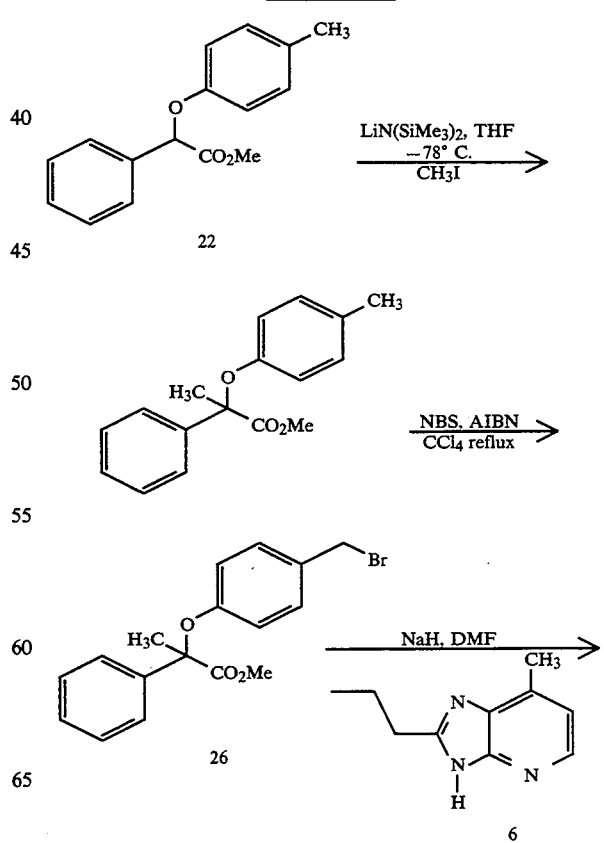

-continued
SCHEME II-7

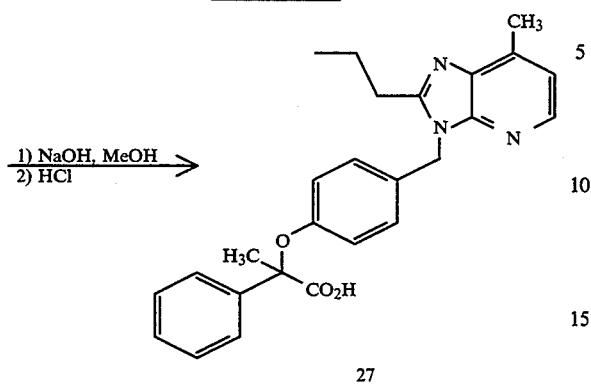

27

The synthesis of compound 32 of Formula I wherein: $-A^1-A^2-A^3-A^4-$ =-C(CH$_3$)=CH-C(CH$_3$)=N-, E=a single bond, R$^1$=ethyl, R$^9$, R$^{10}$, and R$^{11}$ are H, X=0, Y=CH$_2$, Z=CO$_2$H and R$^{12}$=phenyl is shown in Scheme II-8. In this example, p-hydroxybenzyl alcohol (28) is selectively alkylated at the phenolic hydroxyl group with methyl bromoacetate when they are refluxed with potassium carbonate in acetone. After the remaining hydroxyl group is protected as a tert-butyldimethylsilylether, this ether (29) may then be deprotonated with a strong base such as potassium bis(trimethylsilyl)amide and reacted with an alkylating agent in a manner similar to that shown for intermediate 22 in Scheme II-7. Alkylation of ether 29 with benzyl bromide provides 30. Silylether hydrolysis of 30 and bromination of the resulting alcohol affords an alkylating agent (31) which is then used to alkylate a heterocyclic compound from Part I. Alkylation of the anion derived from heterocycle 11, followed by ester hydrolysis affords the acid 32 shown in Scheme II-8 and described in Example 41 of the experimental section.

Scheme II-8

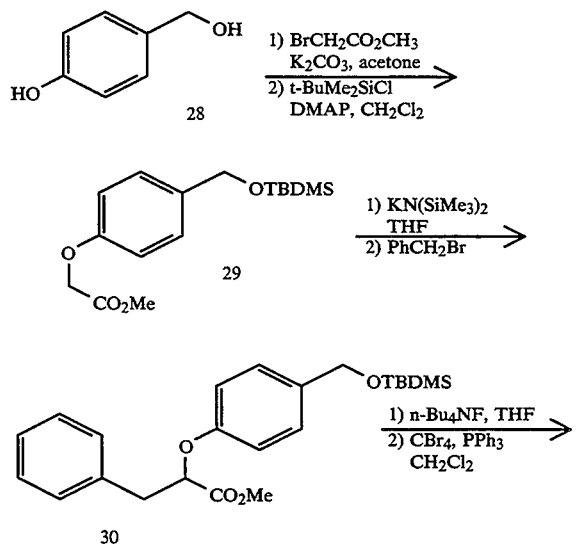

-continued
Scheme II-8

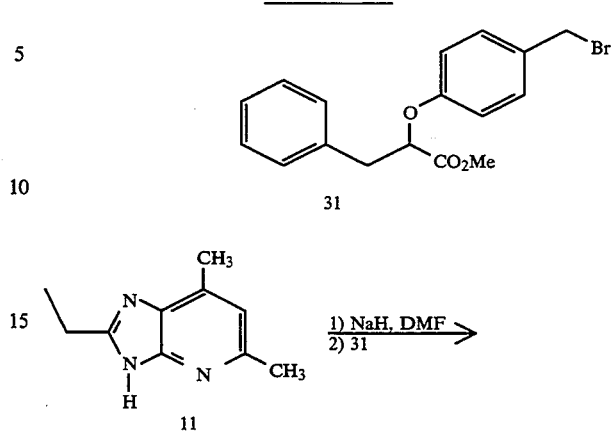

Scheme II-9 illustrates the preparation of an antagonist of Formula I wherein: $-A^1-A^2-A^3-A^4-$=-C(CH$_3$)=CH-CH-N-, E=a single bond, R1=propyl, R$^9$, R$^{10}$ and R$^{11}$ are H, X is a single bond. Y=0, Z=CO$_2$H and, R$^{12}$=phenyl. In this example, the Hell-Volhard-Zelinsky reaction converts 4'-methylphenylacetic acid (33) to the alpha-bromoester 34. which is in turn reacted with the potassium salt of phenol to yield 35. Benzylic bromination of 35 provides alkylating agent 36 which is then reacted with a heterocyclic species described in Part I. When the sodium salt of heterocycle 6 is alkylated with the bromide 36 in DMF, ester 37 is obtained. Alkaline hydrolysis of ester 37 then provides acid 38, which is also the product of Example 17 in the experimental section.

SCHEME II-9

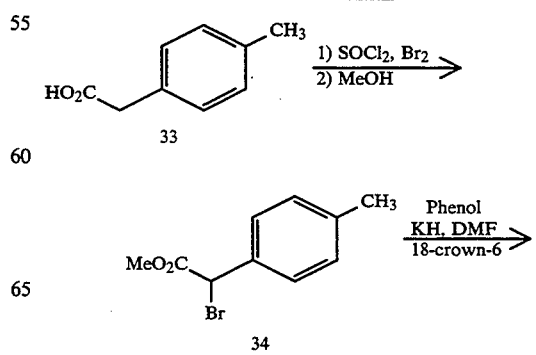

SCHEME II-9 (continued)

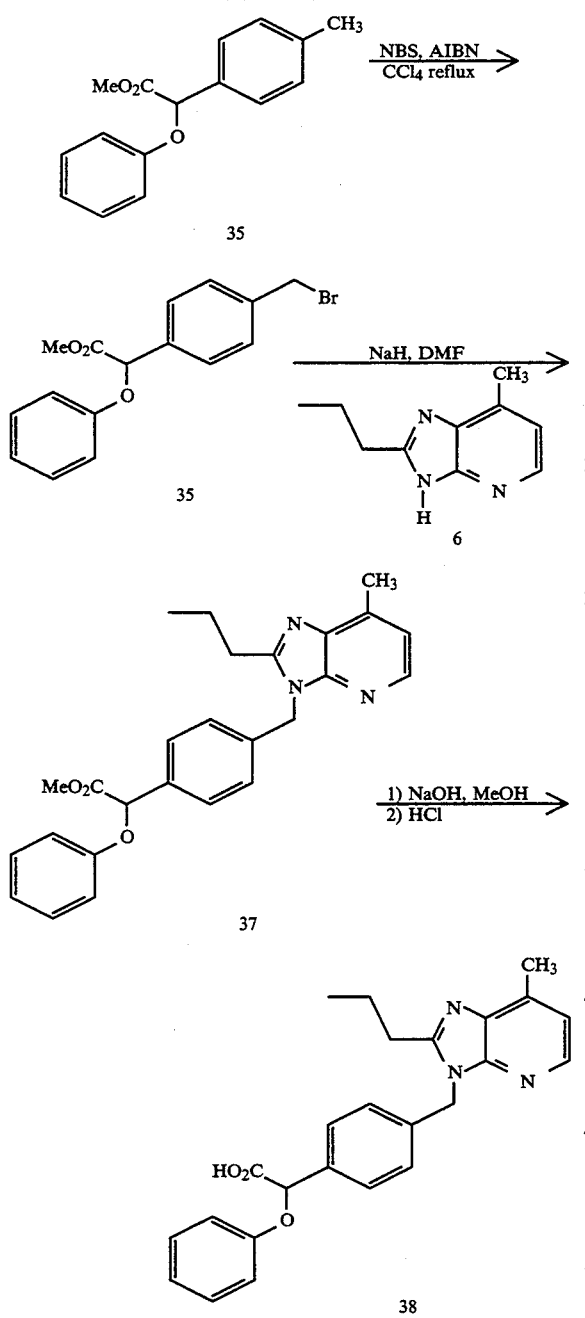

Schemes II-10 and II-11 illustrate the preparation of analogs where -A$^1$-A$^2$-A$^3$-A$^4$- =-C(CH$_3$)=CH-CH=N-, E=a single bond, R$^1$=n-propyl, R$^9$ and R10 are H, Y=a single bond, R$^{12}$ is phenyl, Z=CO2H and X is either methyne or methylene. A Reformatsky reaction is first employed to prepare methyl 3-hydroxy-3-(4-methylphenyl)-2-phenylpropanoate (39) from the starting materials shown in Scheme II-10. When heated in the presence of p-toluenesulfonic acid in benzene 39 is dehydrated to the trans-stilbene derivative 40, and then benzylic bromination of 40 gives the alkylating agent 41. Deprotonation of heterocycle 6 with sodium hydride in DMF and treatment with 41 gives ester 42. Alkaline hydrolysis of 42 affords the product 43, in which X is a methyne group (R$^{11}$ is absent) doubly bonded to the carbon atom bearing substituents R$^{12}$ and Z as shown in Scheme II-11 and in Example 11. Catalytic hydrogenation of 43 gives the derivative 44 where X is a methylene group and R$^{11}$ is a hydrogen atom (Scheme II-11; Example 12 in the experimental section).

SCHEME II-10

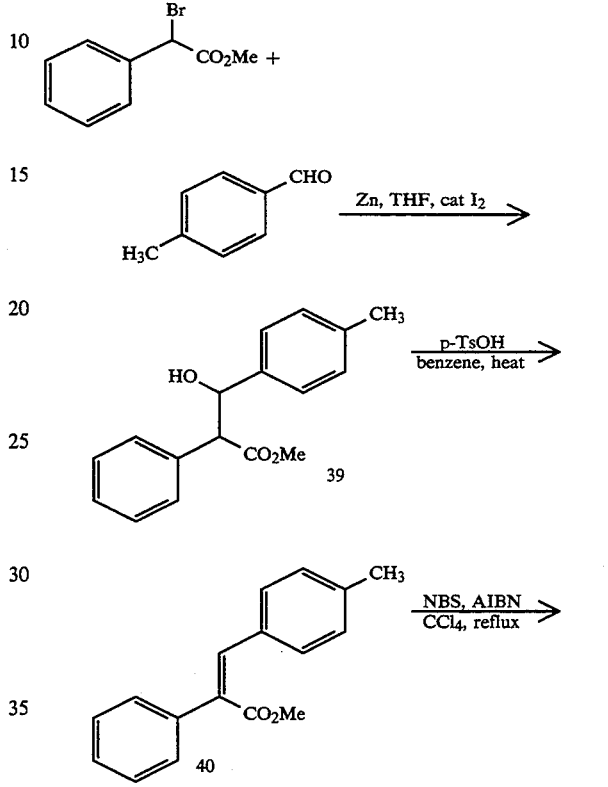

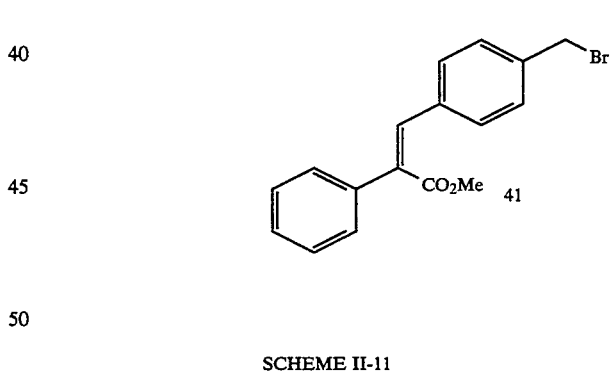

SCHEME II-11

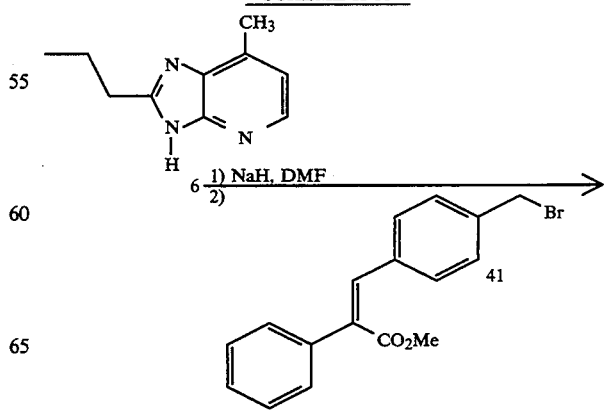

SCHEME II-11

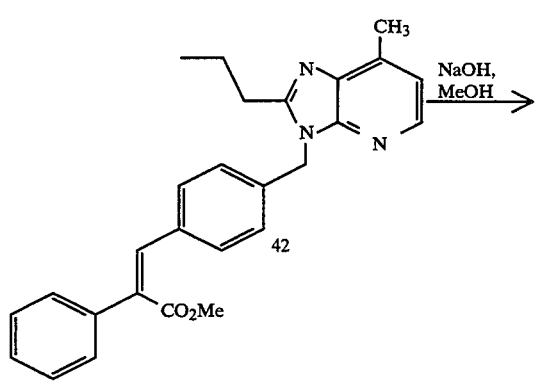

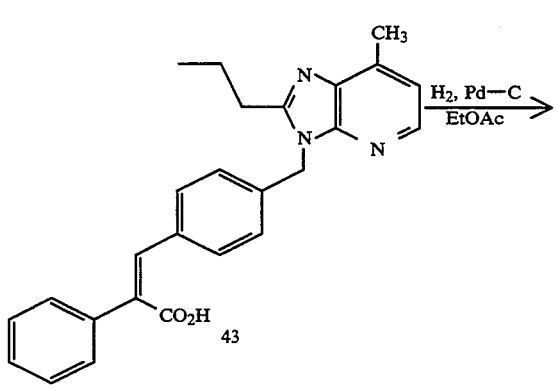

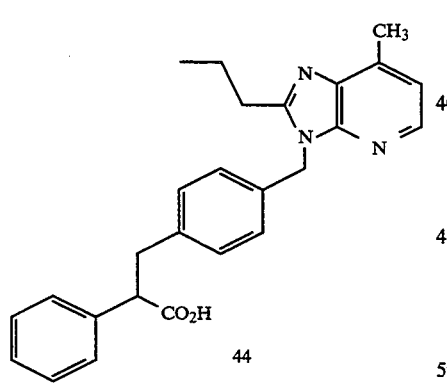

The synthesis of compound 47 of Formula I which has the same substituents as compound 10 (Scheme II-2) with the exception that Z is a tetrazol-5-yl group, is illustrated in Scheme II-12. Exposure of ester 9 to excess ammonia in methanol produces the corresponding amide which is then dehydrated with phosphorous oxychloride and triethylamine to give the nitrile 45. Reaction of the nitrile 45 with trimethylstannyl azide in refluxing toluene provides the tetrazole derivative 46.

Scheme II-12

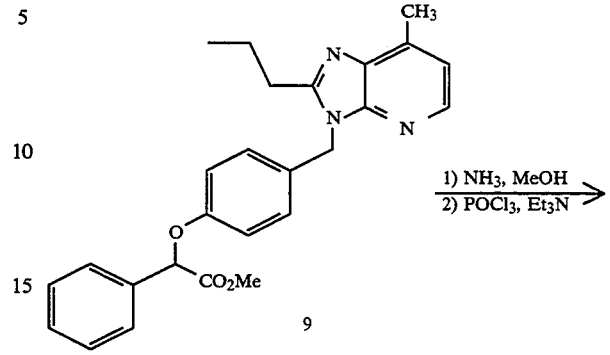

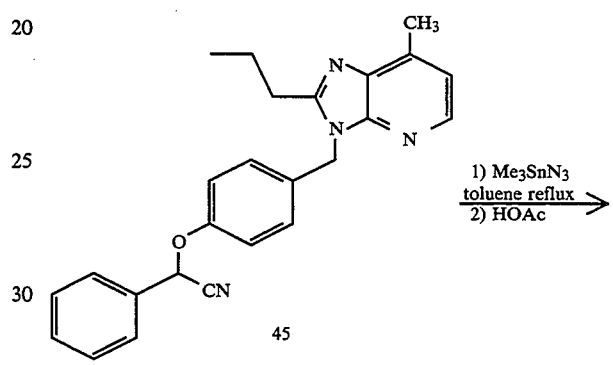

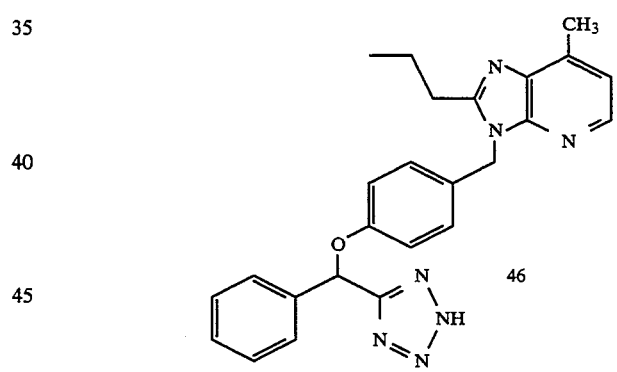

Scheme II-13 illustrates the preparation of a tetrazole analog (52) similar to structure 46 wherein $R^{12}$ is a 2-chlorophenyl group. In this synthesis, the ester group of intermediate 47 is converted to a nitrile prior to alkylating a heterocycle (Part I) with this substituted benzyl element. Thus, reaction of ester 47 with ammonia in methanol, followed by dehydration of amide 48 produces nitrile 49. Benzylic bromination affords 50, which is then reacted with the sodium salt of heterocycle 6 in DMF to give intermediate 51. Finally, reaction of nitrile 51 with trimethylstannyl azide in refluxing toluene gives the tetrazole 52 show in Scheme II-13 (Example 15).

SCHEME II-13

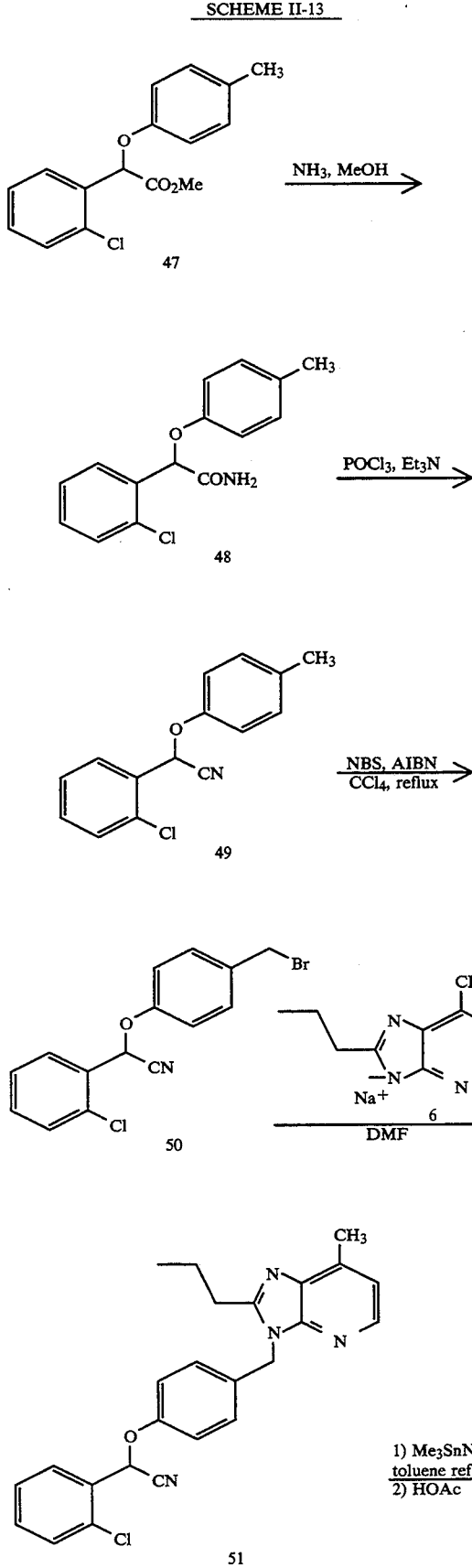

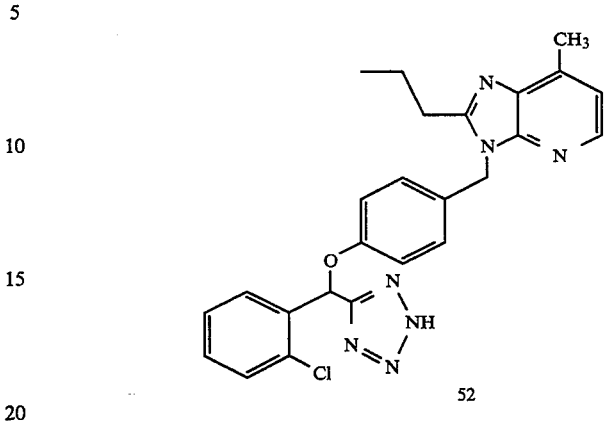

The preparation of a derivative of Formula I analogous to tetrazole 47 (Scheme II-12) which has a methylene group for the X substituent, is shown in Scheme II-15 and in Example 16 of the experimental section. In this synthesis, phenylacetonitrile is deprotonated with lithium bis(trimethylsilyl)amide and then alkylated with the tert-butyldimethylsilylether of p-hydroxymethylbenzyl bromide (preparation of bromide 53 is shown in Scheme II-14 and Example 16 of the experimental section) to yield nitrile 54. The silylether group in compound 54 is directly converted to the bromide 55 with carbon tetrabromide, triphenylphosphine and acetone in dichloromethane (Mattes, H.; Benezra, C. Tetrahedron Lett., 1987, 1697). Alkylation of the sodium salt of heterocycle 6 with bromide 55, followed by reaction of 56 with trimethylstannyl azide in refluxing toluene yields the tetrazole 57.

SCHEME II-14

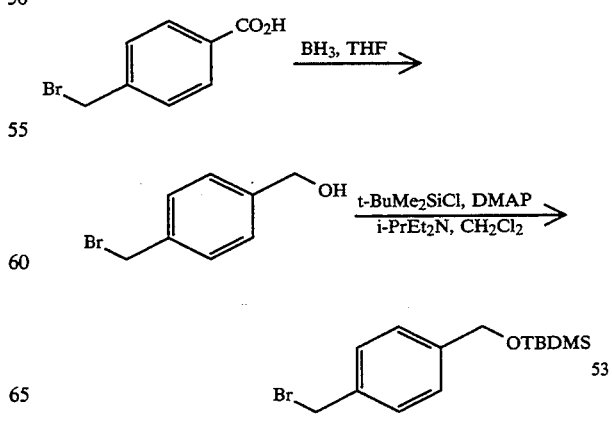

SCHEME II-15

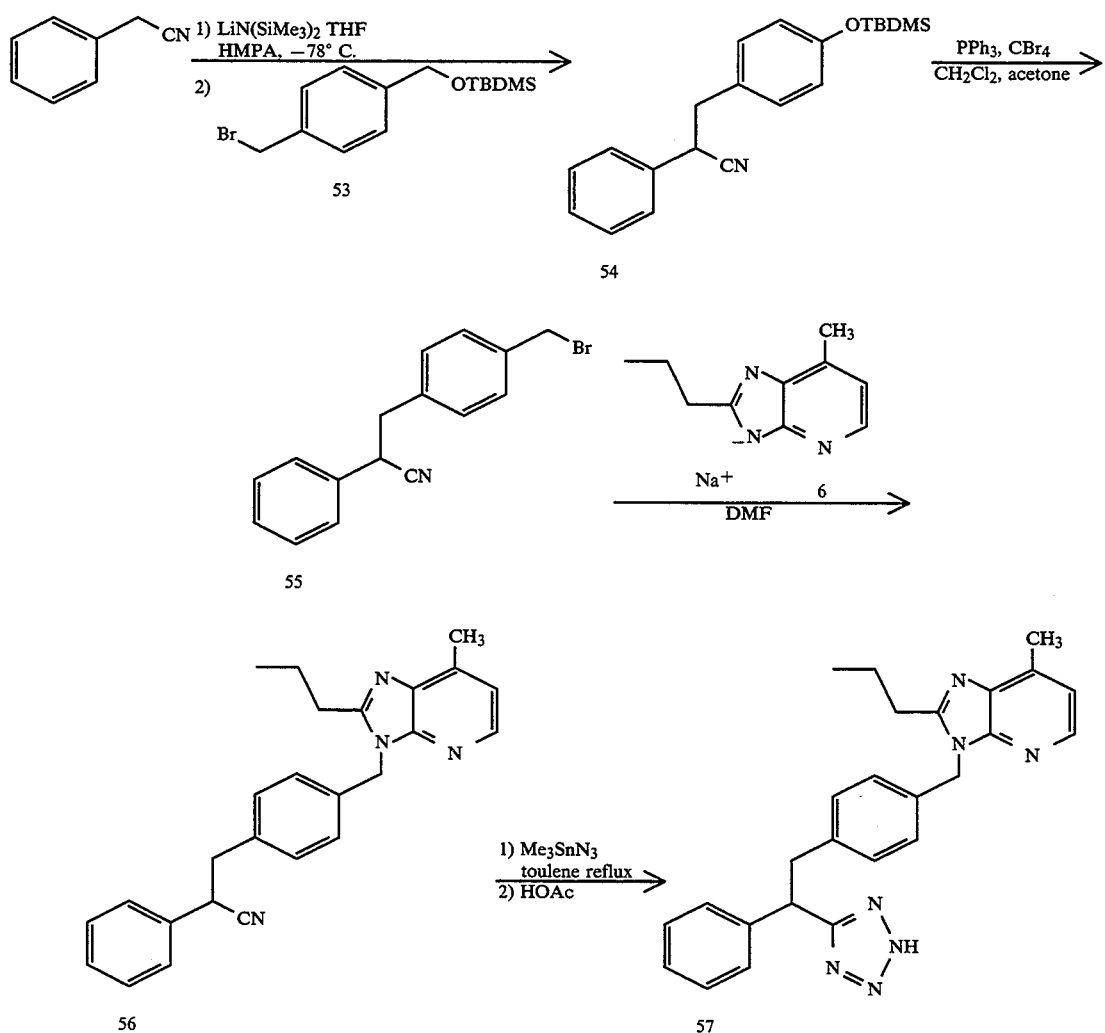

Scheme II-16 illustrates the preparation of a derivative of Formula I where -A$^1$-A$^2$-A$^3$-A$^4$- =-C(CB$_3$)=CH-C(CH$_3$)=N-, R$^1$ is ethyl, E is a single bond R$^9$ R$^{10}$ and R$^{11}$ are H, X=0, Y=a single bond, R$^{12}$ is 2-methylphenyl, and Z is a phosphonic acid group. Reaction of o-tolualdehyde (58) with dimethylphosphite in the presence of triethylamine affords the phosphonate ester 59. Bromination of the hydroxyl group of 59 with carbon tetrabromide and triphenylphosphine in dichloromethane gives bromide 60. Deprotonation of p-hydroxybenzyl alcohol with sodium hydride in DMF followed by addition of bromide 60 affords intermediate 61. A second bromination reaction (CBr$_4$, PPh$_3$, CH$_2$Cl$_2$) converts alcohol 61 to the bromide 62 which is then used to alkylate a heterocyclic compound described in Part I. Scheme II-16 illustrates the case where the anion of heterocycle 11 is reacted with bromide 62 to give upon workup, the phosphonate mono-ester 63 (Example 67). Phosphonic acid 64 may be obtained by treatment of ester 63 with trimethylsilyl bromide.

SCHEME II-16

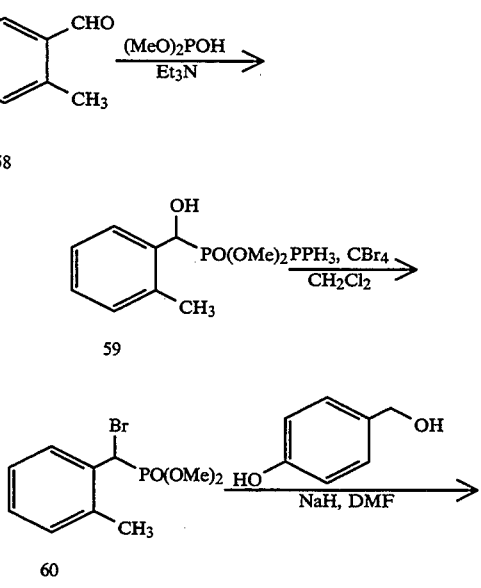

-continued
SCHEME II-16

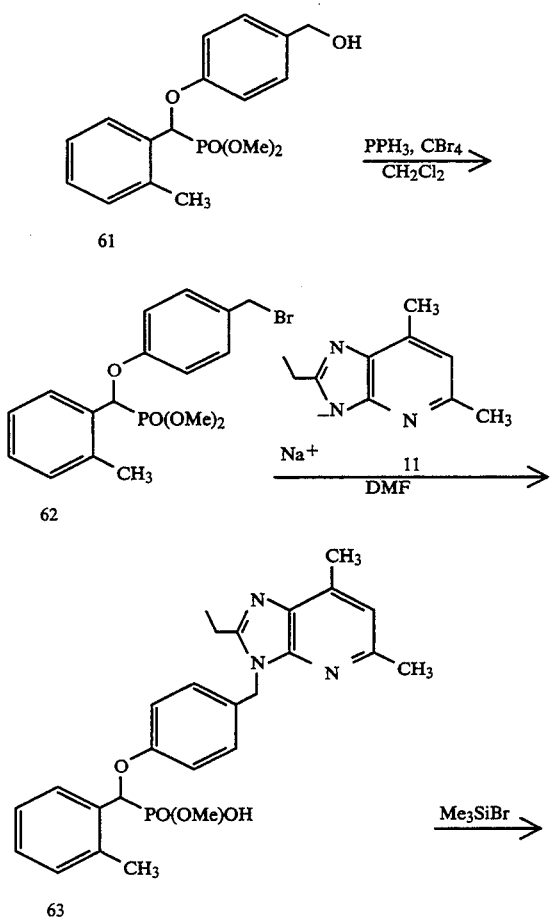

-continued
SCHEME II-16

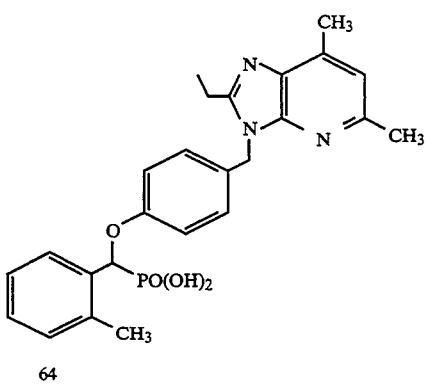

The synthesis of a derivative of Formula I where Z is an acyl-sulfonamide group is illustrated in Scheme II-17. Alkylation of the anion derived from heterocycle 11 with bromide 65 (synthesis described in Example 28 of the experimental section) and alkaline hydrolysis of the resulting ester (66) affords the acid 67 (Example 29). Reaction of acid 67 with 1,1′-carbonyldiimidazole in THF at elevated temperatures gives an acylimidazolide which may be reacted with a sulfonamide (benzenesulfonamide in this example) and DBU in THF to provide the target compound (68) where Z is the acyl-sulfonamide group.

SCHEME II-17

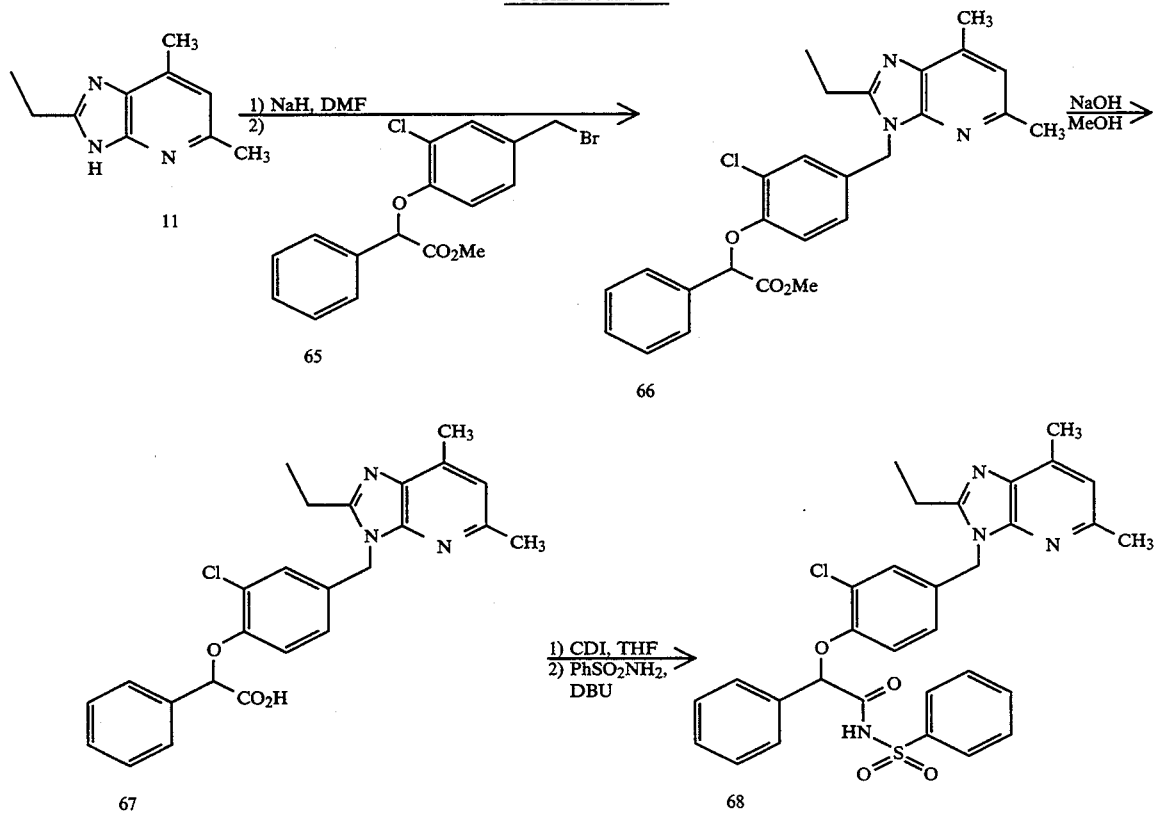

Precursors for the synthesis of AII Antagonists incorporating a substituted benzyl element wherein either substituents $R^9$ or $R^{10}$ are non-hydrogen include substituted p-cresols (Scheme II-6), 4-hydroxybenzyl alcohols, 4-hydroxybenzaldehydes, 4-hydroxybenzoic acids and their esters as shown in Schemes II-18–20.

Commercially available benzyl alcohols such as 3-chloro-4-hydroxy-5-methoxybenzyl alcohol may be selectively alkylated by alpha-bromophenylacetic esters when they are refluxed together in the presence of bases such as anhydrous potassium carbonate, giving 2-phenoxyesters like 69 shown in Scheme II-18. Conversion of the benzyl alcohol group in 69 to a bromide ($CBr_4$, $PPh_3$, $CH_2Cl_2$) affords an alkylating agent (70). A heterocyclic compound from Part I (11) is then alkylated with bromide 70; hydrolysis of the intermediate ester affords 71, the product of Example 37 in the experimental section. Alternatively, a heterocyclic compound from Part I may be directly coupled with benzyl alcohols like 69 using Mitsunobu reaction conditions (diethyl azodicarboxylate, $PPh_3$, THF). Again, hydrolysis of the resulting ester completes the synthesis.

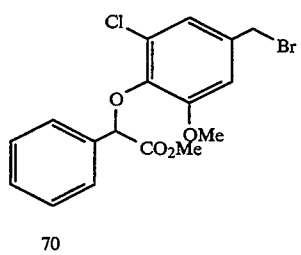

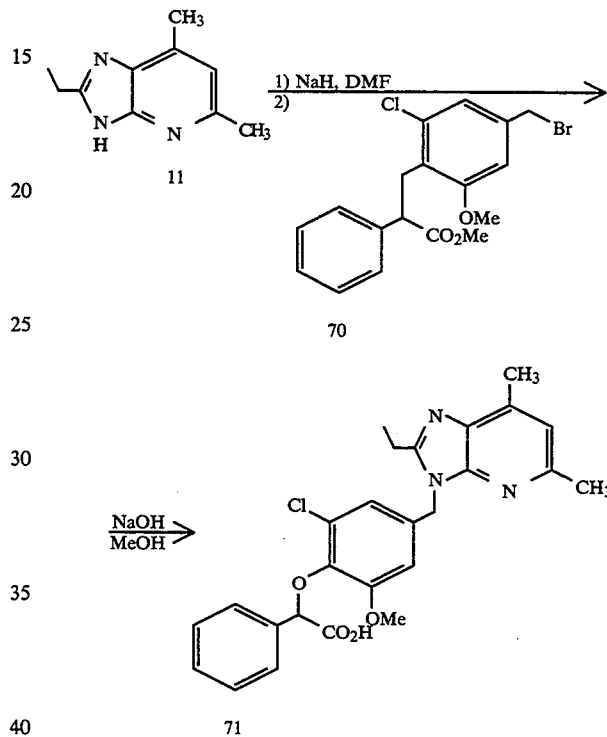

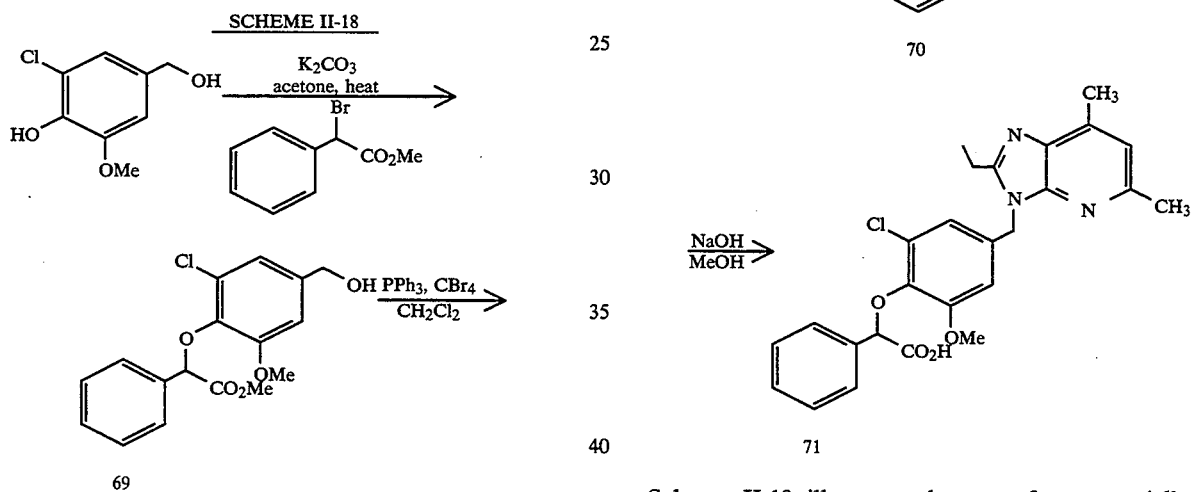

Scheme II-19 illustrates the use of commercially available 3-ethoxy-4-hydroxybenzaldehyde (72) to prepare an AII Antagonist of Formula I bearing a 3-ethoxy group ($R^9$) on the substituted benzyl element. Alkylation of the phenolic group of 72 with methyl 2-bromophenylacetate gives the aldehyde: 73 which is then reduced to a benzyl alcohol with sodium borohydride in methanol or ethanol. The alcohol is converted to the bromide 74, and the synthesis of product 75 (Example 34) is completed as previously described.

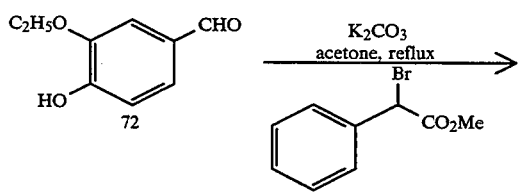

SCHEME II-19

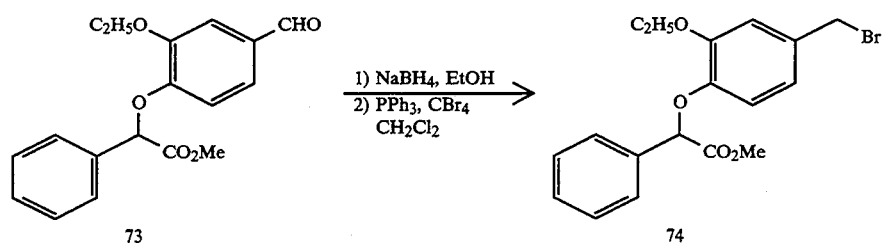

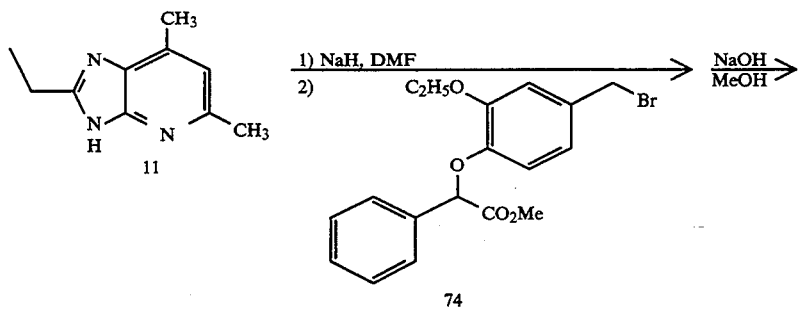

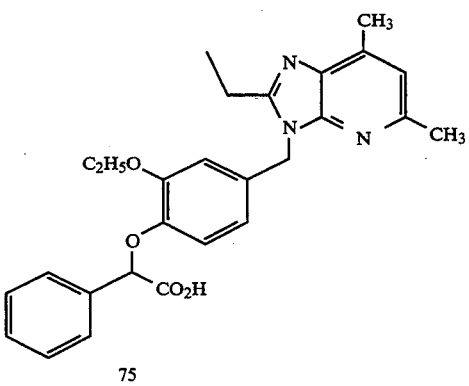

Substituted 4-hydroxybenzoic esters are also convenient precursors for the synthesis of the substituted benzyl element defined in AII Antagonists of Formula I. In this approach, the phenolic hydroxyl group is usually first protected with a suitable protecting group, the ester is then reduced to a hydroxymethyl group, and deprotection affords a 4-hydroxybenzyl alcohol derivative. Scheme II-20 illustrates the preparation of derivative 80 using this sequence starting from methyl 3,5-dichloro-4-hydroxybenzoate (76). Silylation of phenol 76 followed in turn by lithium aluminum hydride reduction of the ester and silylether deprotection affords 3,5-dichloro-4-hydroxybenzyl alcohol 77. Phenol 77 was then selectively alkylated with methyl 2-bromophenylacetate, and the synthesis of derivative 80 (Example 38) was completed using the previously described methods.

SCHEME II-20

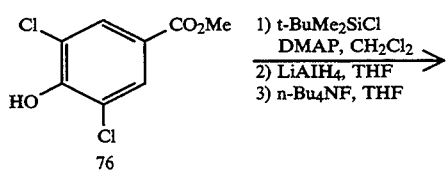

-continued
SCHEME II-20

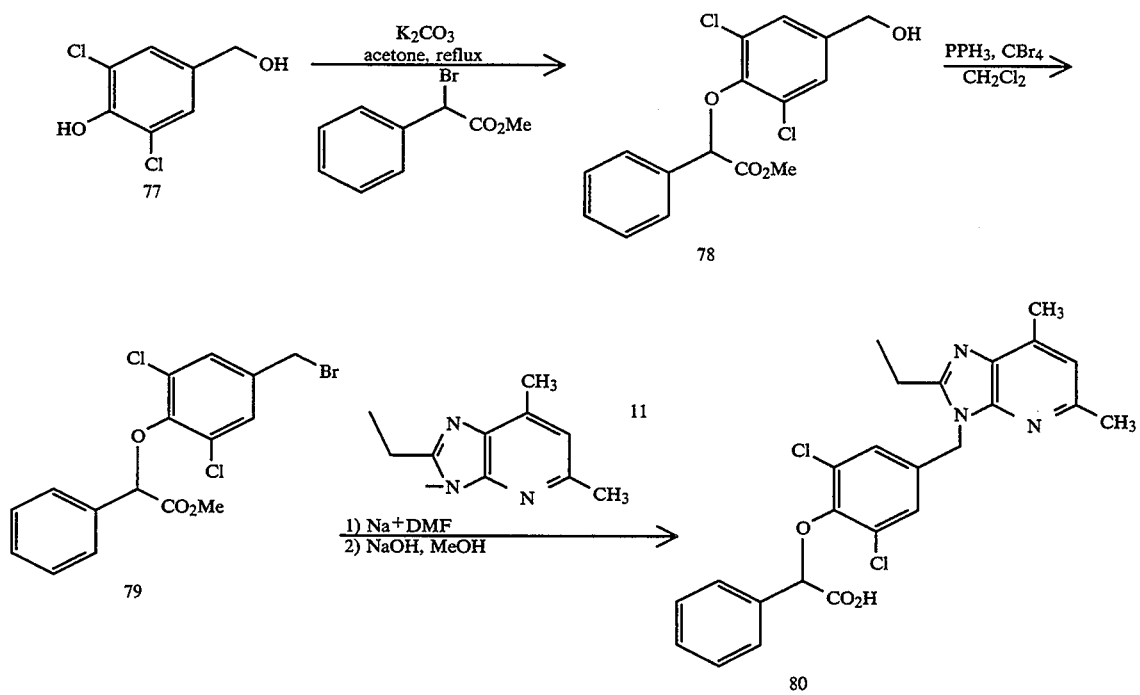

A variety of 2-substituted phenols are selectively-carboxylated when refluxed with carbon tetrachloride, 50% aqueous sodium hydroxide and powdered copper (European Patent Application #193,853, Sept. 10, 1986) to afford the corresponding substituted 4-hydroxybenzoic acids. This reaction may be added to the synthetic sequence when it is convenient to derive the desired substituent on the benzyl portion of the target AII Antagonist from a readily available 2-substituted phenol.

This strategy is illustrated for the preparation of derivative 84 shorn in Scheme II-21. Carboxylation of 2-ethylphenol provides 3-ethyl-4-hydroxybenzoic acid (81). Acid 81 is then esterified, silylated, reduced and desilylated to give the 3-ethyl-4-hydroxybenzyl alcohol 82. Alcohol 82 may then be used to complete the synthesis Of AII Antagonist 84 shown in Scheme II-21 using the previously discussed methodology.

SCHEME II-21

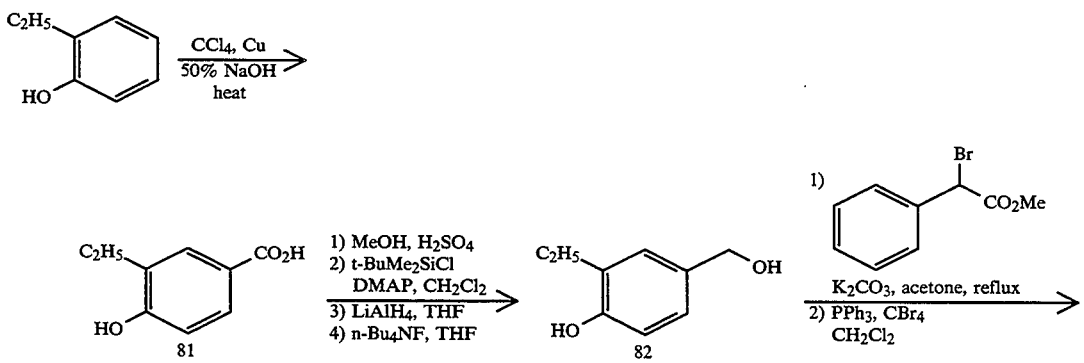

-continued
SCHEME II-21

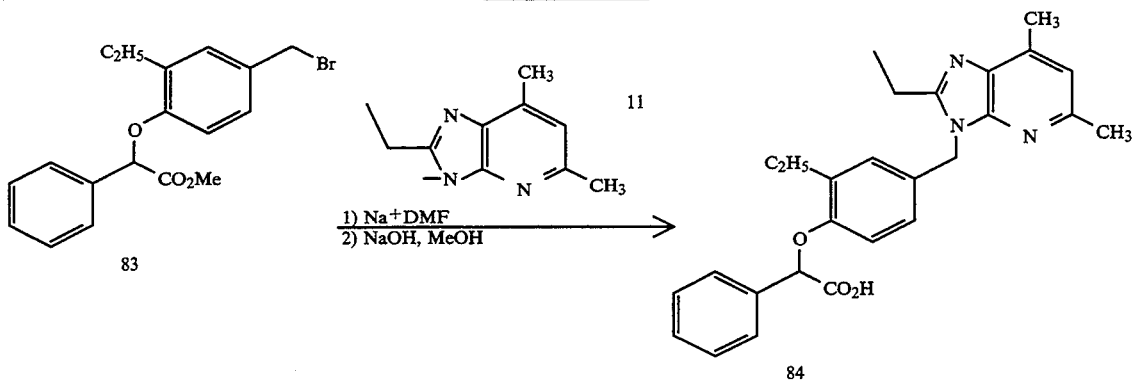

The Claisen rearrangement of phenyl-allylethers offers another useful technique for the introduction of alkyl substitutents (R⁹ or R¹⁰) at the meta position of the substituted benzyl element. In Scheme II-22, Claisen rearrangement at 185° C. of allyl ether 85 provides the allylphenol 86. Silylation of this phenol (86), followed by reduction of the ester group and bromination leads to the benzyl bromide 87. Alkylation of a heterocyclic species from Part I, such as imidazopyridine 11, followed by silylether removal gives intermediates related to 88. Alkylation of 88 with methyl 2-bromophenylacetate followed by alkaline hydrolysis gives a derivative of Formula I (89) wherein R⁹ is a meta-allyl group (Example 42). Hydrogenation of intermediate 88 followed by the same sequence provides derivative 90 where R⁹ is the meta-propyl group as shown in Scheme II-22 and described in Example 43 of the experimental section.

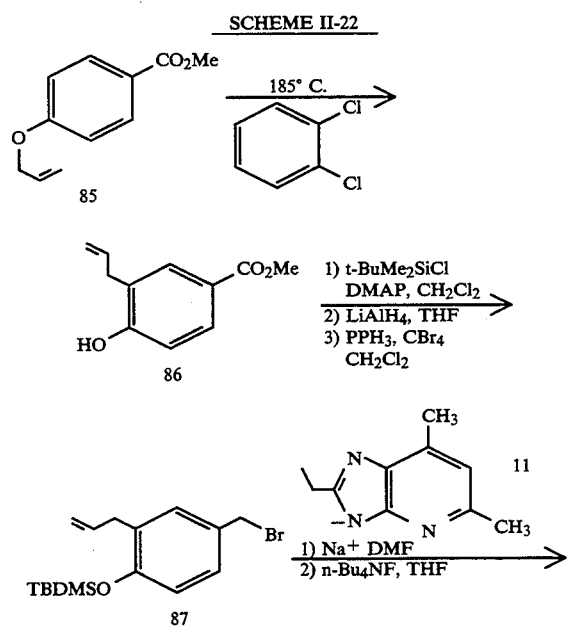

-continued
SCHEME II-22

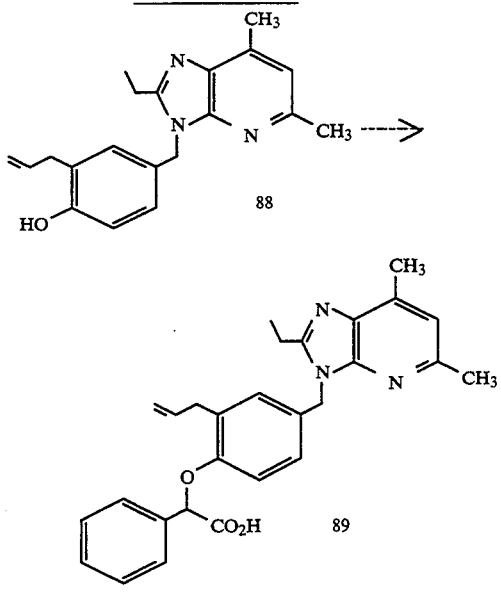

The Claisen rearrangement strategy for the introduction of a meta-alkyl substituent onto the substituted benzyl element of an AII Antagonist of Formula I may be exercised twice when it is desired that both R⁹ and R¹⁰ be meta-alkyl substituents. Thus, allyl phenol 86 may be converted to its O-allylether and subjected to a second Claisen rearrangement to provide the phenol (91) shown in Scheme II-23. Silylation of phenol 91, followed by catalytic hydrogenation and reduction of the ester group with lithium aluminum hydride gives the benzyl alcohol 92. A Mitsunobu reaction of the benzyl alcohol 92 with a heterocyle (11) described in Part I, followed by silylether deprotection gives an intermediate related to 93. The phenolic hydroxyl group of 93 may then be alkylated with a substituted alpha-bromoester and the ester hydrolyzed to yield the acid 94 in which $R^9$ and $R^{10}$ are meta-propyl groups as shown in Scheme II-23 and Example 52.

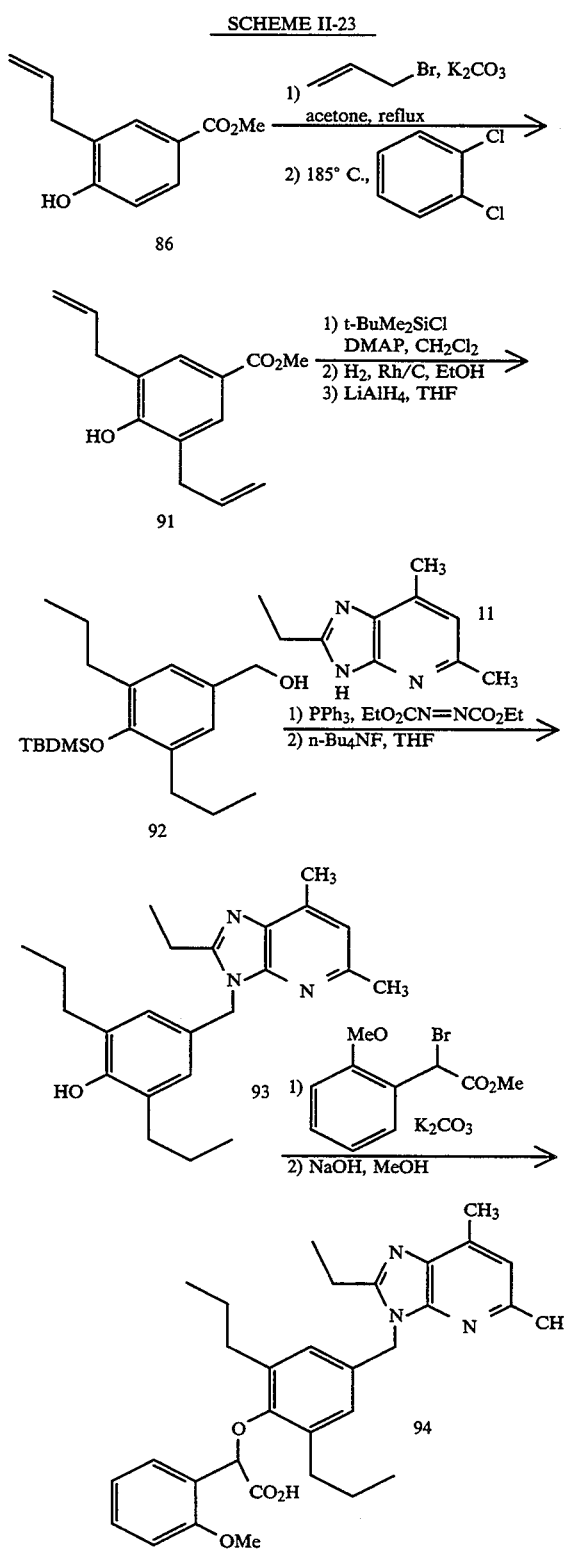

The synthesis of compounds of Formula I wherein: $-A^1-A^2-A^3-A^4-$ =$-C(CH_3)$=$CH-C(CH_3)$=$N-$, E=a single bond, $R^1$=ethyl, $R^9$, $R^{10}$ and $R^{11}$ are H, Y=a single bond, Z=$CO_2H$ $R^{12}$=phenyl, and X=NR, are presented in the following two Schemes. To access these analogs, a heterocycle (ie. 11) defined in Part I is alkylated with p-nitrobenzyl bromide to yield nitro compounds such as 95 in Scheme II-24. Catalytic hydrogenation of the nitro group provides an aniline derivative (96) which is then alkylated by an alpha-bromoester. The ester 97 is subsequently hydrolyzed to afford a derivative of Formula I (98) where X=NH (Example 57).

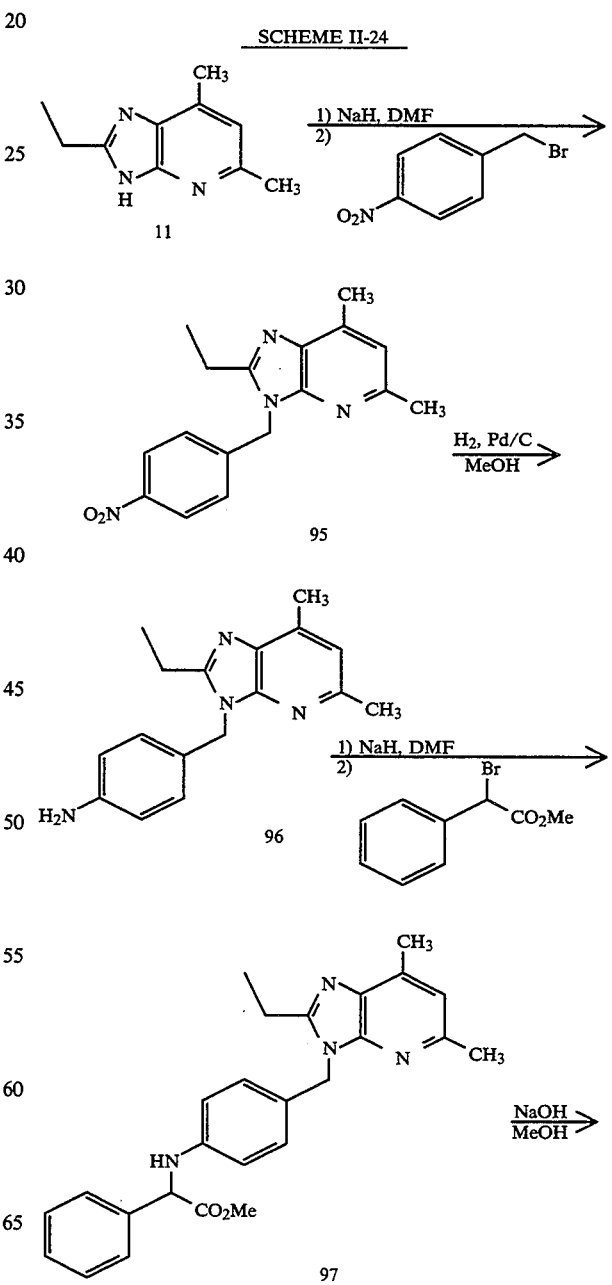

SCHEME II-24 -continued

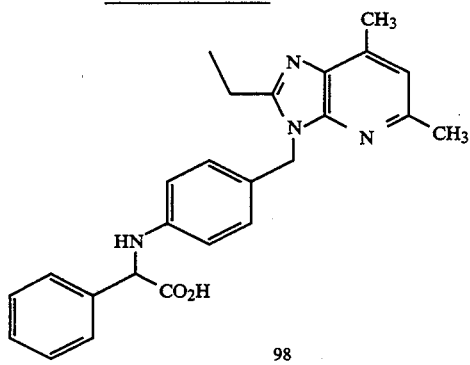

The preparation of AII Antagonists of Formula I similar to 98 in Scheme II-24 but having X=NR may be accomplished by methodology shown in Scheme II-25. The substituted aniline (96) presented above, is readily converted to the N-tert-butylcarbamate (BOC) 99. Carbamates such as 99 may be deprotonated at the amide nitrogen atom when reacted with bases such as sodium hydride in DMF, and then reacted with an alkyl halide. Subsequent treatment of the intermediate with trifluoroacetic acid removes the BOC group providing the mono-alkylated aniline derivative 100. The aniline nitrogen in 100 may be deprotonated again with sodium hydride in DMF and alkylated a second time with a substituted alpha-bromoester to provide esters such as 101. Alternatively, the order of introduction of the substituents on the nitrogen atom may be reversed. Intermediate 97 (Scheme II-24) may also be deprotonated by strong bases such as lithium bis(trimethylsilyl)amide in THF and then reacted with an alkyl halide to yield similar products (101). Ester 101 prepared by either synthetic route, is then hydrolyzed to afford the targeted AII Antagonists (102) of Formula I where X=NR.

SCHEME II-25

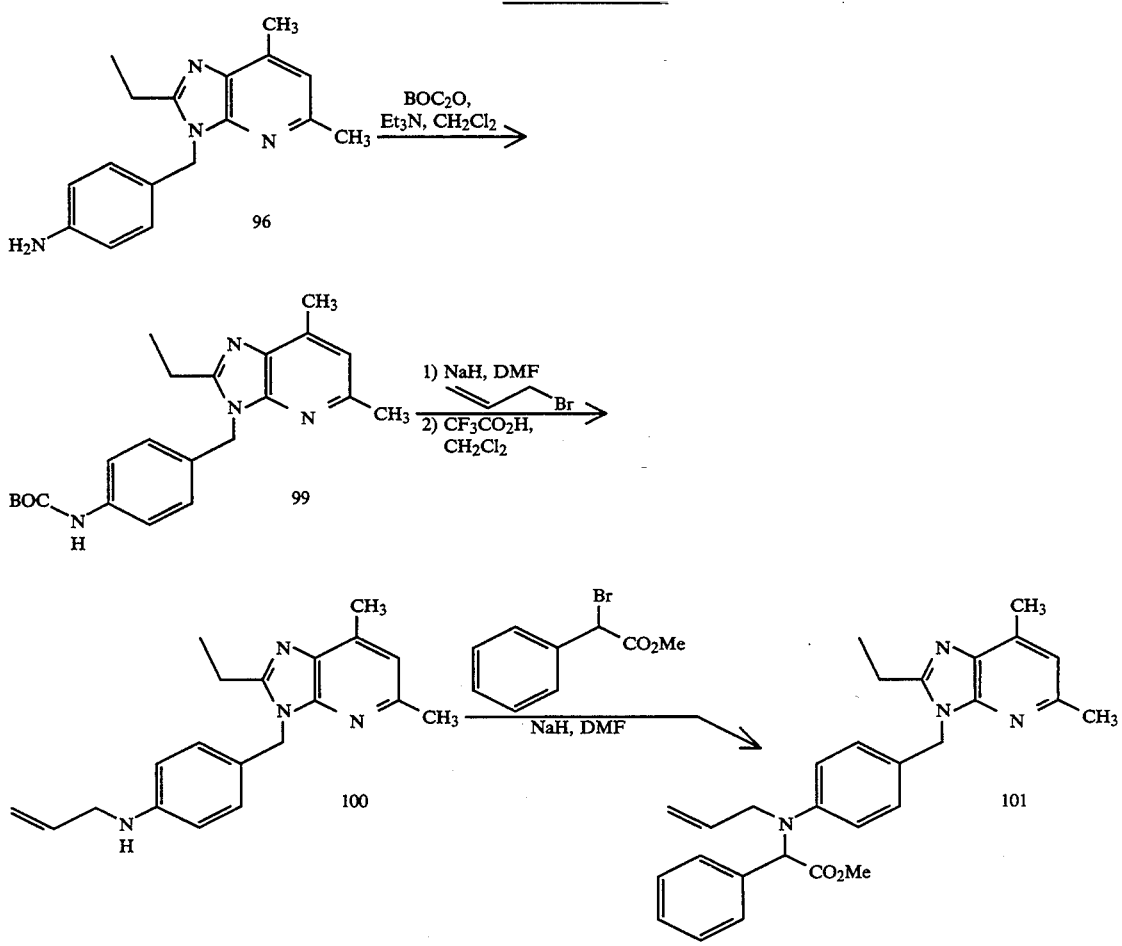

-continued
SCHEME II-25

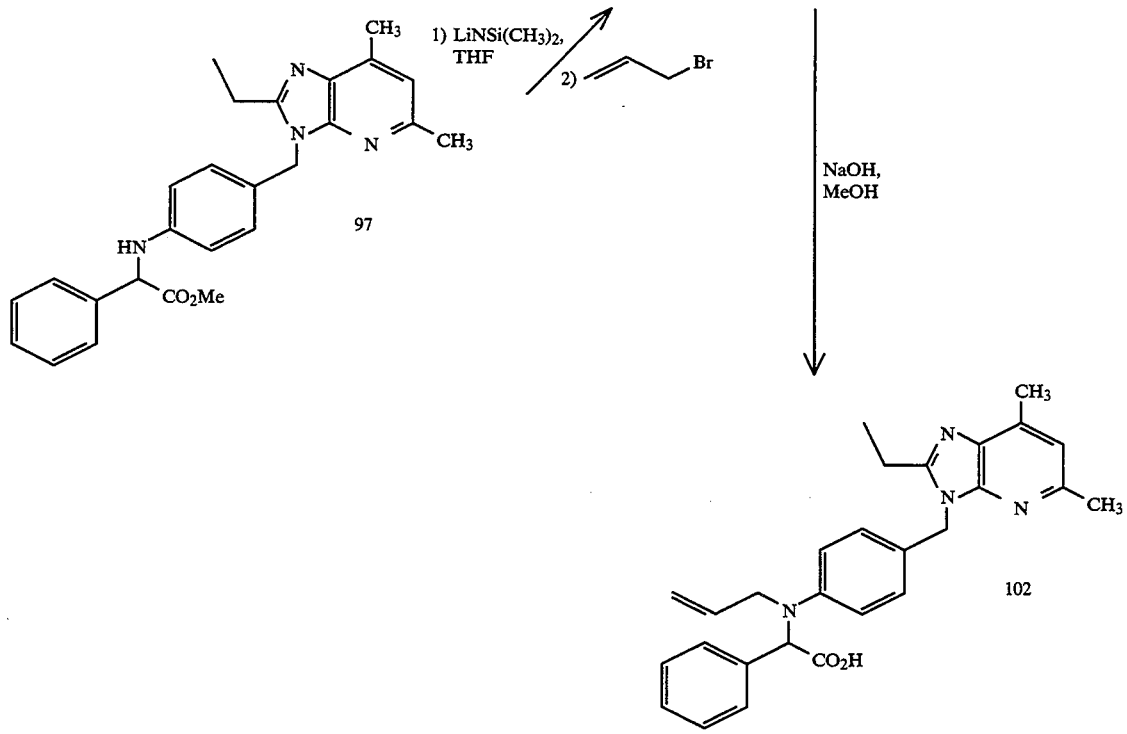

It will be appreciated by those skilled in the art that functional group transformations can be conducted on aryl and heterocyclic rings to afford desired analogs. For example, esters may be converted to amides by heating them with amines and an amide nitrogen if present in the heterocycle may be alkylated using bases such as sodium hydride in DMF with the appropriate alkyl halide. Functional group protection throughout these syntheses will be chosen to be compatible with subsequent reaction conditions. Ultimately such protecting groups will be removed to generate the desired optimally active compounds of Formula I.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methanesulfonic, toluenesulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

It will be further appreciated that the compounds of general Formula I in this invention may be derivatised at functional groups to provide prodrug derivatives which are capable of conversion back to the parent compounds in vivo. The concept of prodrug administration has been extensively reviewed (e.g. A. A. Sinkula in Annual Reports in Medicinal Chemistry, Vol 10, R. V. Heinzelman, Ed., Academic Press, New York London, 1975, Ch. 31, pp. 306–326), H. Ferres, Drugs of Today, Vol.19, 499–538 (1983) and J. Med. Chem., 18, 172 (1975). Examples of such prodrugs include the physiologically acceptable and metabolically labile ester derivatives, such as lower alkyl (e.g. methyl or ethyl esters), aryl (e.g. 5-indanyl esters), alkenyl (e.g. vinyl esters), alkoxyalkyl (e.g. methoxymethyl esters), alkylthioalkyl (e.g. methylthiomethyl esters), alkanoyloxyalkyl (e.g. pivaloyloxymethyl esters), and substituted or unsubstituted aminoethyl esters (e.g. 2-dimethylaminoethyl esters). Additionally, any physiologically acceptable equivalents of the compounds of general Formula I, similar to the metabolically labile esters, which are capable of producing the parent compounds of general Formula I in vivo, are within the scope of this invention.

Angiotensin II (AII) is a powerful arterial vasoconstrictor, and it exerts its action by interacting with specific receptors present on cell membranes. The compounds described in the present invention act as competitive antagonists of AII at the receptors, In order to identify AII antagonists and determine their efficacy in vitro, the following two ligand-receptor binding assays were established.

Receptor binding assay using rabbit aortae membrane preparation:

Three frozen rabbit aortas (obtained from Pel-Freeze Biologicals) were suspended in 5 mM Tris-0.25M Sucrose, pH 7.4 buffer (50 ml) homogenized, and then centifuged. The mixture was filtered through a cheesecloth and the supernatant was centrifuged for 30 minutes at 20,000 rpm at 4° C. The pellet thus obtained was resuspended in 30 ml of 50mM Tris-5 mM MgCl$_2$ buffer containing 0.2% Bovine Serum Albumin and 0.2 mg/ml Bacitration and the suspension was used for 100 assay tubes. Samples tested for screening were done in duplicate. To the membrane preparation (0.25 ml) there was added $^{125}$I-Sar$^1$Ile$^8$-angiotensin II [obtained from New England Nuclear] (10 ml; 20,000 cpm) with or without the test sample and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration (IC$_{50}$) of potential AII antagonist which gives 50% displacement of the total specifically bound $^{125}$I-Sar$^1$Ile$^8$-angiotensin II was presented as a measure of the efficacy of such compounds as AII antagonists.

Receptor assay using Bovine adrenal cortex preparation

Bovine adrenal cortex was selected as the source of AII receptor. Weighed tissue (0.1 g is needed for 100 assay tubes) was suspended in Tris.HCl (50mM), pH 7.7 buffer and homogenized. The homogenate was centrifuged at 20,000 rpm for 15 minutes. Supernatant was discarded and pellets resuspended in buffer [Na$_2$HPO$_4$ (10 mM)-NaCl (120 mM)-disodium EDTA (5 mM) containing phenylmethane sulfonyl fluoride (PMSF)(0.1 mM)]. (For screening of compounds, generally duplicates of tubes are used). To the membrane preparation (0.5 ml) there was added 3H-angiotensin II (50mM) (10ml) with or without the test sample and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration (IC$_{50}$) of potential AII antagonist which gives 50% displacement of the total specifically bound $^3$H-angiotensin II was presented as a measure of the efficacy of such compounds as AII antagonists.

Using the methodology described above, representative compounds of the invention were evaluated and were found to exhibit an activity of at least IC$_{50}$<50 mM thereby demonstrating and confirming the utility of the compounds of the invention as effective AII antagonists.

The potential antihypertensive effects of the compounds described in the present invention may be evaluated using the methodology described below:

Male Charles River Sprague-Dawley rats (300–375 gm) were anesthetized with methohexital (Brevital; 50 mg/kg i.p.). The trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate - 60 strokes per minute, volumn - 1.1 cc per 100 grams body weight). The right carotid artery was ligated, both left and right vagal nerves were cut, the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered and 15 minutes later propranolol (1 mg/kg i.v.). Thirty minutes later antagonists of formula I were administered intravenously or orally. Angiotensin II was then typically given at 5, 10, 15, 30, 45 and 60 minute intervals and every half-hour thereafter for as long as the test compound showed activity. The change in the mean arterial blood pressure was recorded for each angiotensin II challenge and the percent inhibition of the angiotensin II response was calculated.

Thus, the compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinapathy and in the management of vascular disorders such as migraine, Raynaud's disease, luminal hyperclasia, and to minimize the atherosclerotic process. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Preferably, the dosage range will be about 2.5 to 250 mg. per patient per day; more preferably about 2.5 to 75 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, rauwolfia serpentina, rescinnamine, resetpine, sodium nitroprusside, spironolactone, timolol maleate, trichlormethiazide, trimethophan camsylate, benzthiazide, guinethazone, ticrynafan, triamterene, acetazolamide, aminophylline, cyclothiazide, ethacrynic acid, furosemide, merethoxylline procains, sodium ethacrynate, captopril, delapril hydrochloride, enalapril, enalaprilat, fosinopril sodium, lisinopril, pentopril, quinapril hydrochloride, ramapril, reprotide, zofenopril calcium, diflusinal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5–250 milligrams per day range can be effectively combined at levels at the 0.5–250 milligrams per day range with the following compounds at the indicated per day dose range: hydrochlorothiazide (15–200 mg) chlorothiazide (125–2000 mg), ethacrynic acid (15–200 mg), amiloride (5–20 mg), furosemide (5–80 mg), propranolol (20–480 mg), timolol maleate (5–60 mg.), methyldopa (65–2000 mg), felodipine (5–60 mg), nifedipine (5–60 mg), and nitrendipine <5–60 mg). In addition, triple drug combinations of hydrochlorothiazide (15–200 mg) plus amiloride (5–20 mg) plus angiotensin II antagonist of this invention (3–200 mg) or hydrochlorothiazide (15–200 mg) plus timolol maleate (5–60) plus an angiotensin IX antagonist of this invention (0.5–250 mg) or hydrochlorothiazide (15–200 mg) and nifedipine (5–60 mg) plus an angiotensin II antagonist of this invention (0.5–250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage uniform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The compounds of this invention are also useful to treat elevated intraocular pressure and can be administered to patients in need of such treatment with typical pharmaceutical formulations such as tablets, capsules, injectables, as well as topical ocular formulations in the form of solutions, ointments, inserts, gels and the like. Pharmaceutical formulations prepared to treat intraocular pressure would typically contain about 0.1% to 15% by weight, and preferably 0.5% to 2.0% by weight of a compound of this invention.

Thus, the compounds of the invention are useful in treating hypertension. They are also of value in the management of acute and chronic congestive heart failure, in the treatment of secondary hyperaldosteronism, primary and secondary pulmonary hypertension, renal failure such as diabetic nephropathy, glomerulonephritis, scleroderma, and the like, renal vascular hypertension, left ventricular dysfunction, diabetic retinopathy, and in the management of vascular disorders such as migraine or Raynaud's disease. The application of the compounds of this invention for these and similar disorders will be apparent to those skilled in the art.

The useful central nervous system (CNS) activities of the compounds of this invention are demonstrated and exemplified by the ensuing assays.

COGNITIVE FUNCTION ASSAY

The efficacy of these compounds to enhance cognitive function can be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

ANXIOLYTIC ASSAY

The anxiolytic activity of the invention compounds can be demonstrated in a conditioned emotional response (CER) assay. Diazepam is a clinically useful anxiolytic which is active in this assay. In the CER protocol, male Sprague-Dawley rats (250–350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), lever presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

DEPRESSION ASSAY

The antidepressant activity of the compounds Of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

SCHIZOPHRENIA ASSAY

The antidopaminergic activity of the compounds of this invention can be demonstrated in an apomorphine-induced stereotypy model. A clinically useful antipsychotic drug that is used as a positive control in this assay is haloperidol. The assay method is based upon the observation that stimulation of the dopaminergic system in rats produces stereo-typed motor behavior. There is a strong correlation between the effectiveness of classical neuroleptic drugs to block apomorphine-induced stereotypy and to prevent schizophrenic symptoms. Stereotyped behavior induced by apomorphine, with and without pretreatment with test compounds, is recorded using a keypad linked to a microcomputer. Compounds of the invention should be efficacious in this assay in the range of from about 0.1 mg/kg to about 100 mg/kg.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 6000 mg. per patient per day which can be administered in single or multiple doses. Perferably, the dosage range will be about 10 to 4000 mg. per patient per day; more preferably about 20 to 2000 mg. per patient per day.

In order to obtain maximal enhancement of cognitive function, the compounds of this invention may be combined with other cognition-enhancing agents. These include acetylcholinesterase inhibitors such as heptyl-physostigmine and tetrahydroacridine (THA; tactine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers such as nimodipine, and nootropic agents such as piracetam.

In order to achieve optimal anxiolytic activity, the compounds of this invention may be combined with other anxiolytic agents such as alprazolam, lorazepam diazepam, and busipirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promethazine, fluphenazine and haloperidol.

The following examples illustrate the preparation of the compounds of Formula I and their incorporation into pharmaceutical compositions and as such are not to be considered as limiting the invention set forth in the claims appended hereto.

EXAMPLE 1

2-Butyl-1-[4-(1-carboxy-1-phenyl)methoxyphenyl]methylbenzimidazole

Step A: Preparation of 1-(4-benzyloxyphenyl)-methyl-2-butylbenzimidazole

A suspension of 1.50 g (8.62 mmol) of 2-butylbenzimidazole (described in European Patent Application #400,835, May 12, 1990) and NaH (272 mg, 1.05 eq) in DMF (20 mL) was stirred 25 minutes. Next, 4-benzyloxybenzyl chloride (2.10 g, 1.05 eq) was added to the reaction mixture. After stirring overnight, the reaction mixture was concentrated in vacuo and the residue was chromatographed on a medium pressure liquid chromatograph eluted with 30% ethyl acetate/hexane to yield 3.08 g (96%) of the title compound.

$^1$H NMR (300 MHz, CDCl$_3$, ppm): δ0.9–1.0 (t, 3H), 1.35 (m, 2H), 1.75–1-9 (m, 2H), 2.8–2.9 (t, 2H), 5.0 (s, 2H), 6.85–6.95 (d, 2H), 6.95–7.05 (d, 2H), 7.15–7.45 (m, 8H),7.75–7.80 (d, 1H). FAB-MS: m/e 371 (M+H).

Step B: Preparation of 2-butyl-1-(4-hydroxyphenyl)-methylbenzimidazole

A solution of the product of Step A (1.00 g, 2.70 mmol) dissolved in 20 mL of MeOH, was added 0.100 g of a 10% Pd/C catalyst and the reaction mixture was stirred under an $H_2$ atmosphere (1 atm) for 6.5 hours. The reaction mixture was filtered through $MgSO_4$ and the filtrate concentrated in vacuo to yield 0.628 g (83%) of the title compound.

$^1$H NMR (300 MHz, $CD_3OD$, ppm): δ0.9–1.0 (t, 3H), 1.35–1.50 (m, 2H), 1.65–1.8 (m, 2H), 2.9–3.0 (t, 2H), 5.4 (s,2H),6.7–6.8 (d, 2H), 6.9–7.0 (d, 2H), 7.25–7.35 (m, 2H), 7.4–7.5 (m, 1H), 7.6–7.7 (m, 1H; FAB-MS: m/e 281 (M+H).

Step C: Preparation of 2-butyl-1-[4-(1-carbomethoxy-1-phenyl)methoxyphenyl]methylbenzimidazole To a solution of the product of Step B (100 mg, 0.357 mmol) in DMF (1 mL) was added NaH (11 mg, 1.0 eq). After stirring the reaction mixture for 15 minutes, a solution of methyl 2-bromophenylacetate (82 mg, 1.0 eq) in DMF (500 mL) was added and the reaction mixture was stirred for 60 hours. The reaction mixture was quenched with saturated ammonium chloride solution and the organic layer was concentrated in vacuo. The residue was dissolved ethyl acetate and washed with water and then brine. The organic layer was dried ($MgSO_4$), filtered and concentrated in vacuo and the residue was purified on a silica gel flash chromatography column (120×40 mm) eluted with 50% ethyl acetate/hexane to yield 26 mg (17%) of the title compound.

$^1$H NMR (300 MHz, $CDCl_3$, ppm): δ0.9–1.0 (t, 3H), 1.35–1.50 (m, 2H), 1.65–1.75 (m, 2H), 2.75–2.85 (t, 2H), 3.7 (s, 3H), 5.25 (s, 2H), 5.6 (s, 1H), 6.8–6.9 (d, 2H), 6.9–7.0 (d, 2H), 7.15–7.25 (m, 3H), 7.35–7.45 (m, 3H), 7.5–7.6 (m, 2H), 7.7–7.8 (d, 2H). FAB-MS: m/e 429 (M+H).

Step D: Preparation of 2-butyl-1-[4-(1-carboxy-1-phenyl)methoxyphenyl]methylbenzimidazole To a solution of the product of Step C (25 mg, 0.058 mmol) in 2.0 mL of MeOH was added 1N KOH (0.5 mL). The reaction mixture was stirred for 1 hour and then concentrated in vacuo. The residue was dissolved in water, acidified to pH 4 with 1N HCl, and the resulting precipitate was extracted into chloroform. The organic extracts were dried ($MgSO_4$), filtered and evaporated in vacuo, and then precipitated from HCl/EtOAc to yield 7.1 mg (30%) of the title compound.

$^1$H NMR (300 MHz, $CDCl_3$, ppm): δ0.55–0.65. (t, 3H), 1.05–1.2 (m, 2H), 1.40–1.50 (m, 2H), 2.75–2.85 (t, 2H), 5.15–5.30 (q, 2H), 5.6 (s, 1H), 6.85–7.00 (m, 4H), 7.2–7.4 (m, 6H), 7.65–7.75 (m, 2H), 7.75–7.85 (m, 1H). FAB-MS: m/e 4.15 (M+H).

EXAMPLE 2

3-[4-(1-carboxy-1-phenyl)methoxyphenyl]methyl-7-methyl-2-propyl-3H-imidazo[4,5-b]pyridine Step A: Preparation of 2,3-diamino-4-picoline (cf. Lappin, G. R.; Slezak, F. B. J. Am. Chem. Soc., 1950, 72, 2806–7)

To a slurry of 2-amino-4-methyl-3-nitropyridine (10.0 g, 65.3 mmol) in 350 mL of 95% EtOH was added 500 mg of a 10% Pd/C catalyst. The mixture was stirred under a $H_2$ atmosphere (1 atm) for 36 hours. Filtration and evaporation gave 8.05 g of a black solid which was used directly in the next step.

Step B: Preparation of 7-methyl-2-propylimidazo[4,5-b]pyridine (cf. Lappin, G. R.; Slezak, F. B. J Am. Chem. Soc., 1950, 72, 2806–7)

A mixture of burytic acid (6.57 mL, 71.9 mmol), 2,3-diamino-4-picoline (8.05 g, 65.4 mmol), and polyphosphoric acid (50 g) was heated to 100° C. with stirring for 3 hours, and monitored by tlc of $NH_4OH$ neutralized aliquots. Basification ($NH_4OH$), extraction ($CH_2Cl_2$, 4×50 mL), drying ($K_2CO_3$), purification (by filtering through 100 g silica gel, EtOAc solution), and concentration gave 10.0 g (87%) of the title compound as an amorphous tan solid which was judged pure by $^1$H NMR and tlc: mp 110°–112° C. (without recrystallization).

$^1$H NMR (300 MHz, $CDCl_3$, ppm): δ8.13 (d, 1H, J=5 Hz), 7.01 (d, 1H, J=5 Hz), 3.01 (t, 2H, J=7.8 Hz), 2.67 (s, 3H), 2.07.–1.93 (m, 2H), 1.06 (t, 3H, J=7.5 Hz).

Step C: Preparation of 3-(4-benzyloxyphenyl)methyl-7-methyl-2-propyl-3H-imidazo[4,5-b]pyridine A suspension of 7-methyl-2-propylimidazo[4,5-b]pyridine (1.00 g, 5.71 mmol) and NaH (189 mg, 1.1 eq) in DMF (25 mL) was stirred for 1 hour and then cooled to 0° C. 4-Benzyloxybenzyl chloride (1.46 g; 1.1 eq) was then added and the ice bath removed. The reaction mixture was stirred for 2.5 hours and was then concentrated in vacuo. The residue was chromatographed on a silica gel flash chromatography column (30×200 mm) eluted with 30% ethyl acetate/hexane to yield 1.07 g (50%) of product.

$^1$H NMR (300 MHz, $CDCl_3$, ppm): δ0.9–105 (m, 3H), 1.7–1.85 (m, 2H), 2.65–2.85 (m, 5H), 5.0–5.1 (m, 2H), 5.4–5.5 (m, 2H), 6.8–6.95 (m, 2H), 6.95–7.15 (m, 3H), 7.2–7.5 (m, 5H), 8.15–8.25 (m, 1H).

Step D: Preparation of 3-(4-hydroxyphenyl)methyl-7-methyl-2-propyl-3H-imidazo[4,5-b]pyridine To a solution of the product of Step C (0.60 g, 1.62 mmol) in 10 mL of MeOH was added 60 mg of a 10% Pd/C catalyst and was stirred under a $H_2$ atmosphere (1 atm) for 7 hours. The reaction mixture was then filtered through magnesium sulfate and the filtrate was concentrated in vacuo to yield 0.372 g (82%) of the title compound.

$^1$H NMR (300 MHz, $CD_3OD$, ppm): δ0.95–1.05 (t, 3H), 2.65–2.8 (m, 2H), 2.7 (s, 3H), 2.9–3.0 (t, 2H), 5.5 (s, 2H), 6.7–6.8 (d, 2H), 7.0–7.1 (d, 2H), 7.2–7.5 (d, 1H), 8.25–8.3 (d, 1H).

Step E: Preparation of 3-[4-(1-carbomethoxy-1-phenyl)-methoxyphenyl]methyl-7-methyl-2-propyl-3H-imidazo[4,5-b]pyridine To a suspension of KH (45 mg, 1.1 eq) in DMF (0.5 mL) was added the product of Step D (100 mg, 0.365 mmol) followed by 18-crown-6 (20 mg, 0.2 eq). After stirring the reaction mixture for 0.5 hour until the foaming subsided, a solution of methyl 2-bromophenylacetate (81 mg, 1.0 eq) in DMF (0.5 mL) was added and the reaction mixture was stirred 2 hours and was then concentrated in vacuo. The residue was purified on a silica gel flash chromatography column, (120×20 mm) eluted with 50% ethyl acetate/hexane to yield 67 mg (44%) of the title compound.

$^1$H NMR (300 MHz, $CDCl_3$, ppm): δ0.9–1.0 (t, 3H) 1.65–1.80 (m, 2H), 2.65 (s, 3H), 2.7–2.8 (t, 2H), 3.7 (s, 3H), 5.4 (s, 2H), 5.6 (s, 1H), 6.8–6.9 (d, 2H), 6.95–7.1 (m, 3H), 7.35–7.45 (m, 3H), 7.5–7.6 (m, 2H), 8.2 (d, 1H).

Step F: Preparation of 3-[4-(1-carbomethoxy-1-phenyl)methoxyphenyl]methyl-7-methyl-2-propyl-3H-imidazo[4,5-b]pyridine To a solution of the product of Step E (21 mg, 0.0490 mmol) in MeOH (1 mL) was added 1N NaOH (1 mL). The reaction mixture was stirred for 1.5 hours, and was then concentrated in vacuo. The residue was partitioned between brine and THF. The organic layer was separated from the aqueous layer, dried (MgSO$_4$), filtered, and evaporated in vacuo. The residue was purified on a silica gel flash chromatography column (15×130 mm) eluted first with 20% methanol/ethyl acetate, and later with 50% methanol/ethyl acetate. The product fractions were concentrated in vacuo, redissolved in ethyl acetate and filtered to yield 16 mg (76%) of the title compound.

$^1$H NMR (300 MHz, CDCl$_3$, ppm): δ0.8–0.9 (t, 3H), 1.5–1.7 (m, 2H), 2.2–2.3 (m, 5H), 5.1 (s, 1H), 5.25 (s, 2H), 6.6–6.6 (d, 2H), 6.7–6.8 (d, 2H), 6.9–7.0 (m, 4H), 7.15–7.25 (m, 2H), 8.1 (d, 1H). FAB-MS: m/e 438 (M+H).

EXAMPLE 3

3-[4-(1-Carboxy-1-(4-chlorophenyl)methoxyphenyl]-methyl-7-methyl-2-propyl-3H-imidazo[4,5-b]pyridine Step A: Preparation of methyl 2-bromo-2-(4-chlorophenyl)acetate A mixture of 4-chlorophenylacetic acid (5.00 g, 29.3 mmol) and thionyl chloride (2.67 mL, 1.25 were heated at reflux while bromine (1.51 mL, 1.0 was added from a dropping funnel over 15 minutes. The reaction mixture was heated at reflux 19.5 hours, and then cooled to room temperature. Methanol (30 mL, 25 eq) was then added slowly, as an exotherm and violent bubbling resulted. The reaction mixture was then concentrated in vacuo. The residue was partitioned between water and ether and the aqueous phase was then extracted twice with ether. The combined ether portions were washed with 5% NaHSO$_3$, dried (MgSO$_4$), filtered, and concentrated in vacuo. The residue was purified on a silica gel flash chromatography column (170×45 mm) eluted with 15% ethyl acetate/hexane to yield 2.89 g (37%) of the title compound.

$^1$H NMR (300 MHz, CDCl$_3$, ppm): δ3.8 (s, 3H), 5.35 (s, 1H), 7.2–7.3 (d, 2H), 7.45–7.55 (d, 2H). EI-MS: m/e 262, 264, 266 (M+, 10:13:3 ratio).

Step B: Preparation of methyl 2-(4-methylphenoxy)-4-chlorophenylacetate

To a 0° C. suspension of KH (530 mg, 1.0 eq) in DMF (10 mL) was quickly added p-cresol (500 mg, 4.63 mmol), and the reaction mixture was stirred at room temperature. After stirring 10 minutes hydrogen evolution had subsided, and 50 mg of 18-crown-6 was added followed by the product of Step A (1.22 g, 1.0 eq). The reaction mixture was stirred 2.5 hours and was then concentrated in vacuo. The residue was purified on a silica gel flash chromatography column (140×30 mm) eluted with 5% ethyl acetate/hexane to yield 0.744 g (55%) of the title compound.

$^1$H NMR (300 MHz, CDCl$_3$, ppm): δ2.3 (s, 3H), 3.75 (s, 3H), 5.6 (s, 1H), 6.8–6.9 (d, 2H), 6.9–7.1 (d, 2H), 7.3–7.4 (d, 2H), 7.5–7.6 (d, 2H). EI-MS: m/e 290, 292 (M+, 3:1 ratio).

Step C: Preparation of methyl 2-(4-bromomethylphenoxy)-4-chlorophenylacetate

A solution of the product of Step B (200 mg, 0.690 mmol), NBS (117 mg, 0.95 eq) and AIBN (10 mg, catalytic amount) in CCl$_4$ (5 mL) was heated at reflux for 2 hours and then cooled and concentrated in vacuo. The residue was purified on a silica gel flash chromatography column (30×130 mm) eluted with 5% ethyl acetate/hexane to yield 128 mg (50%) of the title compound.

$^1$H NMR (300 MHz, CDCl$_3$, ppm): δ3.75 (s, 3H), 4.5 (s, 2H), 5.6 (s, 1H), 6.8–6.9 (d, 2H), 7.25–7.35 (d, 2H), 7.35–7.45 (d, 2H), 7.5–7.6 (d, 2H).

Step D: Preparation of 1-[4-(1-carbomethoxy-1-(4-chlorophenyl))methoxyphenyl]methyl-7-methyl-2-propyl-3H-imidazo[4,5-b]pyridine To a suspension of NaH (4.3 mg, 1.0 eq) in DMF (1 mL) was added 7-methyl-2-propylimidazo[4,5-b]pyridine (25 mg, 0.143 mmol). Next a solution of product from Step C (53 mg, 1.0 eq) in DMF (1 mL) was added. The reaction mixture was stirred for 2 hours and then concentrated in vacuo. The residue was purified on a silica gel flash chromatography column (20×230 mm) eluted with 50% ethyl acetate/hexane to yield 17 mg (26%) of the title compound.

$^1$H NMR (300 MHz, CDCl$_3$, ppm): δ0.9–1.0 (t, 3H), 1.65–1.8 (m, 2H), 2.65 (s, 3H), 2.7–2.8 (t, 2H), 3.7 (s, 3H), 5.4 (s, 2H), 5.55 (s, 1H), 6.8–6.9 (d, 2H), 7.0–7.1 (m, 3H), 7.3–7.4 (d, 2H), 7.45–7.5 (d, 2H), 8.2 (d, 1H). FAB-MS: m/e 464, 466 (M+1, 3:1 ratio).

Step E: Preparation of 1-[4-(1-carboxy-1-(4-chlorophenyl))methoxyphenyl]methyl-7-methyl-2-propyl-3H-imidazo[4,5-b]pyridine To a solution of product from Step D (16 mg, 0.035 mmol) in MeOH (1 mL) was added 1N NaOH (1 mL). The reaction mixture was stirred 10 minutes, and then concentrated in vacuo. Water was added to the residue and the mixture was acidified to pH 2 with 1N HCl. The aqueous layer was then extracted 3 times with chloroform, the combined organic layers were dried (MgSO$_4$), filtered and concentrated in vacuo to yield 12 mg (70%) of the titled product.

$^1$H NMR (300 MHz, CDCl$_3$, ppm): δ0.75–0.85 (t, 3H), 1.55–1.7 (m, 2H), 2.65 (S, 3H), 2.9–3.0 (t, 2H), 5.4 (s, 2H), 5.55 (s, 1H), 6.85–6.95 (d, 2H), 7.05–7.1 (d, 2H), 7.15 (d, 1H) 7.3–7.4 (d, 2H), 7.5–7.6 (d, 2H), 8.3 (d, 1H). FAB-MS: m/e 450, 452 (M+1, 3:1 ratio).

EXAMPLE 4

3-[4-(1-Carboxy-1-(2-chlorophenyl))methoxyphenyl]-methyl-7-methyl-2-propyl-3H-imidazo[4.5-b]pyridine Step A: Preparation of methyl 2-bromo-(2'-chloro)-phenylacetate Commercially available 2-chlorophenylacetic acid (5.00 g, 29,3 mmol) was converted to 2.13 g (28%) of the title compound in a procedure similar to that described in Step A of Example 3.

$^1$H NMR (300 MHz, CDCl$_3$, ppm): δ3.8 (s, 3H), 5.95 (s, 1H), 7.25–7.45 (m, 3H), 7.7–7.8 (m, 1H).

Step B: Preparation of methyl 2-(2-chlorophenyl)-2-(4-methylphenoxy)acetate

The product of Step A (1.22 g. 4.63 mmol) was used to alkylate p-cresol (0.5 g, 4.63 mmol) using the procedure described in Step B of Example 3, and afforded 1.03 g (77%) of the title compound.

$^1$H NMR: (300 MHz, CDCl$_3$, ppm): δ2.25 (s, 3H), 3.8 (s, 3H), 6.12. (s, 1H), 6.85 (d, 2H), 7.05 (d, 2H), 7.28–7.35 (m, 2H), 7.40–7.45 (m, 1H), 7.63–7.70 (m, 1H). EI-MS: m/e 290, 292 (M+).

Step C: Preparation of methyl 2-(4-bromomethylphenoxy)-2-(2-chlorophenyl)acetate The product of Step B (0.200 g, 0.69 mmol) was brominated with NBS (117 mg, 0.66 mmol) and purified using the procedure described in Step C of Example 3, and afforded 0.186 g (73%) of the title compound.

$^1$H NMR (300 MHz, CDCl$_3$, ppm): δ3.8 (s, 3H), 4.5 (s, 2H), 6.15 (s, 1H), 6.85–6.95 (d, 2H), 7.25–7.35 (m, 4H); 7.4–7.5 (m, 1H), 7.6–7.7 (m, 1H). EI-MS: m/e 368, 370, 372 (M+1, 10:13:3 ratio).

Step D: Preparation of 3-[4-(1-carbomethoxy-1-(2-chlorophenyl))methoxyphenyl]methyl-7-methyl-2-propyl-3H-imidazo[4,5-b]pyridine The product of Step C (0.100 g, 0.27 mmol) was used to alkylate 0.047 g of 7-methyl-2-propylimidazo[4,5-b]pyridine (Example 2, Step B) according to the procedure described for Step D of Example 3, which after purification afforded 0.040 g (32%) of the title compound.

$^1$H NMR (300 MHz, CDCl$_3$, ppm): δ0.9–1.0 (t, 3H), 1.65–1.8 (m, 2H), 2.65 (s, 3H), 2.7–2.8 (t 2H), 3.75 (s, 3H), 5.4 (s, 2H), 6.1 (s, 1H), 6.8–6.9 (d, 2H), 7.0–7.1 (m, 3H), 7.25–7.35 (m, 2H), 7.35–7.45 (m, 1H), 7.55–7.65 (m, 1H), 8.2 (d, 1H). FAB-MS: m/e 464, 466 (M+1, 3:1 ratio).

Step E: Preparation of 3-[4-(1-carboxy-1-(2-chlorophenyl))methoxyphenyl]methyl-7-methyl-2-propyl-3H-imidazo[4,5-b]pyridine The product of Step D (0.040 g, 0.086 mmol) was dissolved in 1.0 mL of methanol and 1.0 mL of 1N NaOH was added. The hydrolysis was complete in 5 minutes, and the solution was then concentrated in vacuo. The residue was chromatographed on silica gel (130×20 mm) eluted with ethyl acetate/hexane/acetic acid (19:5:1 ) to afford 33 mg (85%) of the title compound.

$^1$H NMR (300 MHz, CD$_3$OD, ppm): δ0.85–0.95 (t, 3H), 1.55–1.75 (m, 2H), 2.65 (s, 3H), 2.8–2.9 (t, 2H), 5.5 (s, 2H), 6.05 (s, 1H), 6.85–6.95 (d, 2H), 7.05–7.20 (m, 3H), 7.25.–7.35 (m, 2H), 7.35–7.45 (m, 1H), 7.55–7.65 (m 1H), 8.2 (d, 1H). FAB-MS: m/e 4.50,452 (M+1).

EXAMPLE 5

3-[4-(1-Carboxy-1-(3-chlorophenyl))methoxyphenyl]-methyl-7-methyl-2-propyl-3H-imidazo[4,5-b]pyridine Step A: Preparation of methyl 2-bromo-2-(3-chlorophenyl)acetate Commercially available 3-chlorophenylacetic acid (5.00 g, 29.3 mmol) was converted to 1.70 g (22%) of the title compound in a procedure similar to that described in Step A of Example 3.

$^1$H NMR (300 MHz, CDCl$_3$, ppm): δ3.80 (s, 3H) 5.30 (s, 1H) 7.25–7.60 (m, 4H).

Step B: Preparation of 3-[4-(1-carbomethoxy-1-(3-chlorophenyl))methoxyphenyl]methyl-7-methyl-2-propyl-3H-imidazo[4,5-b]pyridine To a solution of 0.150 g (0.54 mmol) of the product of Step D of Example 2 dissolved in 1.0 mL of DMF was added 61 mg of KH, and 0.141 g of 18-crown-6. The reaction was stirred under an N$_2$ atmosphere for 20 minutes, and then 0.155 g of the product of Step A dissolved in 0.5 mL of DMF was added. The reaction was stirred all additional 30 minutes, then partitioned between water and ethyl acetate. The organic layer was washed with water, dried (MgSO$_4$), filtered and evaporated in vacuo. The residue was purified on a silica gel flash chromatography column eluted first with 30% ethyl acetate/hexane then with 50% ethyl acetate/hexane to afford 0.087 g (35%) of the title compound.

$^1$H NMR (300 MHz, CDCl$_3$, ppm): δ0.90–1.00 (t, 3H), 1.65–1.85 (m, 2H), 2.65 (s, 3H), 2.70–2.85 (t, 2H), 3.75 (s, 3H), 5.45 (s, 2H), 5.55 (s, 1H), 6.80–6.90 (d, 2H), 7.00–7.10 (m, 3H), 7.25–7.35 (m, 2H), 7.30–7.35 (m, 1H), 7.55 (br s, 1H), 8.15–8.25 (d, 1H).

Step C: Preparation of 3-[4-(1-carboxy-1-(3-chlorophenyl))methoxyphenyl]methyl-7-methyl-2-propyl-3H-imidazo[4,5-b]pyridine To a solution of 0.087 g (0.19 mmol) of the product of Step B dissolved in 2 mL of methanol was added 1 mL of 2N NaOH and the reaction was stirred for 2 hours at room temperature. The reaction mixture was concentrated in vacuo and applied to a silica gel flash chromatography column eluted with CHCl$_3$/MeOH/HOAc (100:3:1) to afford 0.049 g (58%) of the title compound.

$^1$H NMR (300 MHz, CD$_3$OD, ppm): δ0.90–1.00 (t, 3H), 1.60–1.75 (m, 2H), 2.65 (s, 3H), 2.80–2.90 (t, 2H), 5.50 (s, 2H), 5.70 (s, 1H), 6.90–6.95 (d, 2H), 7.05–7.20 (m, 3H), 7.30–7.35 (m, 2H), 7.45–6.50 (m, 2H), 7.45–7.50 (m, 1H), 7.55 (br s, 1H), 8.15–8.25 (d, 1H). FAB-MS: m/e 450,452 (M+1).

EXAMPLE 6

3-[4-(1-carboxy-1-(2.6-dichlorophenyl))methoxyphenyl]methyl-7-methyl-2-propyl-3H-imidazo[4,5-b]pyridine Step A: Preparation of methyl 2-bromo-2',6'-dichlorophenylacetate Commercially available 2,6-dichlorophenylacetic acid (5.00 g, 24.4 mmol) was converted to 2.60 g (35%) of the title compound in a procedure similar to that described in Step A of Example 3.

$^1$H NMR (300 MHz, CDCl$_3$, ppm): δ3.80 (s, 3H), 6.70 (s, 1H), 7.20–7.30 (m. 1H), 7.35–7.40 (d, 2H).

Step B: Preparation of 3-[4-(1-carbomethoxy-1-(2,6-dichlorophenyl))methoxyphenyl]methyl-7-methyl-2-propyl-3H-imidazo[4,5-b]pyridine The product of Step D of Example 2 (0.100 g, 0.36 mmol) was deprotonated (41 mg KH, 94 mg 18-crown-6, 1.0 mL DMF) and alkylated with 0.117 g (0.39 mmol) of the product of Step A according to the procedure described in Step B of Example 5. Purification on a silica gel flash chromatography column eluted with 40% ethyl acetate/hexane afforded 0.085 g (48%) of the title compound.

$^1$H NMR (300 MHz, CDCl$_3$, ppm): δ0.90–1.00 (t, 3H), 1.60–1.80 (m, 2H), 2.65 (s, 3H), 2.70–2.80 (t, 2H), 3.80 (s, 3H), 5.40 (s, 2H), 6.40 (s, 1H), 6.60–6.65 (d, 1H), 6.85–6.90 (d, 1H), 6.90–7.05 (m, 5H), 7.15–7.35 (m, 2H), 8.15–8.35 (d, 1H).

Step C: Preparation of 3-[4-(1-carboxy-1-(2,6-dichlorophenyl))methoxyphenyl]methyl-7-methyl-2-propyl-3H-imidazo[4,5-b]pyridine To a solution of 0.085 g (0.17 mmol) of the product of Step B dissolved in 1.0 mL of methanol was added 1.0 mL of 1N NaOH and the reaction was stirred for 3 hours at room temperature. The reaction mixture was concentrated in vacuo and applied to a silica gel flash chromatography column eluted with CHCl$_3$/MeOH/NH$_4$OH (80:15:1) to afford 0.070 g (84%) of the title compound.

$^1$H NMR (300 MHz, CD$_3$OD, ppm): δ0.90–1.00 (t, 3H), 1.55–1.75 (m, 2H), 2.65 (s, 3H), 2.80–2.90 (t, 2H), 5.50 (s, 2H), 6.30 (s, 1H), 6.95–7.10 (m, 2H), 7.30–7.40 (d, 2H), 8.20 (d, 1H). FAB-MS: m/e 484 (M+1).

EXAMPLE 7

3-[4-(1-carboxy-1-(2-nitrophenyl))methoxyphenyl]-methyl-7-methyl-2-propyl-3H-imidazo[4,5-b]pyridine Step A: Preparation of methyl 2'-nitrophenylacetate To a flask charged with 5 mL of methanol was introduced a fine stream of hydrogen chloride gas until the solution was saturated. The hydrogen chloride was stopped, and 0.50 g (2.7 mmol) of 2'-nitrophenylacetic acid was added and the reaction mixture was stirred for 1.5 hours. The reaction mixture was then partitioned between ethyl acetate and water, the organic layer was washed with saturated NaHCO$_3$, brine, dried (MgSO$_4$), filtered and evaporated to afford 0.529 g (98%) of the title compound.

$^1$H NMR (300 MHz, CDCl$_3$, ppm): δ3.75 (s, 3H), 4.05 (s, 2H), 7.25–7.30 (d, 1H), 7.45–7.55 (m, 1H), 7.55–7.65 (m, 1H), 8.20–8.25 (d, 1H). FAB-MS: m/e 196 (M+1).

Step B: Preparation of methyl 2-bromo-2'-nitrophenylacetate

To a solution of the product of Step A dissolved in 10 mL of carbon tetrachloride was added 0.441 g of N-bromosuccinimide and 25 mg of AIBN and the reaction was heated at reflux for 14 hours. The mixture was then cooled and evaporated and the residual oil was purified on a silica gel flash chromatography column eluted with 5% ethyl acetate. Evaporation of the purified fractions afforded 0.335 g (50%) of the title compound.

$^1$H NMR (300 MHz, CDCl$_3$, ppm): δ3.80 (s, 3H), 6.10 (s, 1H), 7.50–7.60 (m, 1H), 7.70–7.80 (m, 1H), 8.00–8.10 (m, 2H).

Step C: Preparation of 3-[4-(1-carbomethoxy-1-(2-nitrophenyl))methoxyphenyl]methyl-7-methyl-2-propylimidazo[4,5-b]pyridine A solution of 0.364 g (1.30 mmol) of 3-(4-hydroxyphenyl)methyl-7-methyl-2-propyl-3H-imidazo [4,5-b]pyridine (Step D, Example 2) dissolved in 5 mL of DMF was deprotonated (0.163 g KH, 0.376 g 18-crown-6) and alkylated with 0.355 g (1.30 mmol) of the product of the previous step similarly to the procedure described in Example 2, Step E. Purification on a silica gel flash chromatography column eluted with 40% ethyl acetate/hexane afforded 0.296 g (48%) of the title compound.

$^1$H NMR (300 MHz, CDCl$_3$, ppm): δ0.95–1.05 (t, 3H), 1.70–1.80 (m, 3H), 2.65 (s, 3H), 2.70–2.80 (t, 2H), 3.75 (s, 3H), 5.40 (s, 2H), 6.65 (s, 1H), 6.85–6.95 (d, 2H), 7.00–7.10 (m,3H), 7.50–7.55 (t, 1H), 7.60–7.65 (t, 1H), 7.80–7.85 (d, 1H), 8.05–8.10 (d, 1H), 8.20–8.25 (d, 1H).

Step D: Preparation of 3-[4-(1-carboxy-1-(2-nitrophenyl))methoxyphenyl]methyl-7-methyl-2-propyl-3H-imidazo[4,5-b]pyridine Hydrolysis of 0.030 g (0.063 mmol) of the ester prepared in the previous step was performed in a manner similar to that described in Example 2, Step F. Purification on a silica gel flash chromatography column eluted with CHCl$_3$/MeOH/HOAc (100:3:1) afforded 0.023 g (74%) of the title compound.

$^1$H NMR (300 MHz, CD$_3$OD, ppm): δ0.90–1.00 (t, 3H), 1.60–1.75 (m, 2H), 2.65 (s, 3H), 2.80–2.90 (t, 2H), 5.50 (s, 2H), 6.45–6.60 (br s, 1H), 6.90–7.00 (d, 2H), 7.05–7.15 (d, 2H), 7.15–7.20 (d, 2H), 7.50–7.60 (t, 1H), 7.60–7.70 (t, 1H), 7.75–7.80 (t, 1H), 8.00–8.05 (d, 1H), 8.20–8.25 (d, 1H). FAB-MS: m/e 461 (M+1).

EXAMPLE 8

3-[4-(1-Carboxy-1-cyclohexyl)methoxyphenyl]methyl-7-methyl-2-propyl-3H-imidazo[4,5-b]pyridine Step A: Preparation of 3-[4-(1-carbomethoxy-1-cyclohexyl)methoxyphenyl]methyl-7-methyl-2-propyl-3H-imidazo[4,5-b]pyridine A solution of 0.200 g (0.71 mmol) of 3-(4-hydroxyphenyl)methyl-7-methyl-2-propyl-3H-imidazo [4,5-b]pyridine (Step D, Example 2) dissolved in 0.5 mL of DMF was deprotonated (82 mg KH, 0.188 g 18-crown-6) and alkylated with 0.184 g (0.78 mmol) of commercially available methyl 2-bromo-2-cyclohexylacetate similarly to the procedure described in Example 2, Step E. Purification on a silica gel flash chromatography column eluted with 30% ethyl acetate/hexane afforded 0.029 g (10%) of the title compound.

$^1$H NMR (300 MHz, CDCl$_3$, ppm): δ0.97 (t, J=8 Hz, 3H), 1.10–1.90 (m, 13H), 2.66 (s, 3H), 2.78 (t, J=8 Hz, 2H), 3.70 (s, 3H), 4.31 (d, J=6 Hz, 1H), 5.40 (s, 2H), 6.77 (d, J=10 Hz, 2H), 7.02–7.10 (m, 3H), 8.10 (d, J=6 Hz, 1H).

Step B: Preparation of 3-[4-(1-carboxy-1-cyclohexyl)methoxyphenyl]methyl-7-methyl-2-propyl-3H-imidazo[4,5-b]pyridine Hydrolysis of 0.029 g (0.066 mmol) of the ester prepared in Step A was performed in a manner similar to that described in Example 2, Step F. Purification on a silica gel flash chromatography column eluted with CHCl$_3$/MeOH/HOAc (100:3:1) afforded 0.017 g (61%) of the title compound.

$^1$H NMR (300 MHz, CD$_3$OD, ppm): δ0.95 (t, J=8 Hz, 3H), 1.10–1.90 (m, 13H), 2.65 (s, 3H), 2.85 (t, J=8 Hz, 2H), 4.38 (d, J=6 Hz, 1H), 5.48 (s, 2H), 6.84 (d, J=10 Hz, 2H), 7.06 (d, J=10 Hz, 2H), 7.15 (d, J=6 Hz, 1H), 8.20 (d, J=6 Hz, 1H). FAB-MS: m/e 422 (M+1).

EXAMPLE 9

3-[4-(1-Carboxy-1-propyl)methoxyphenyl]methyl-7-methyl-2-propyl-3H-imidazo[4,5-b]pyridine Step A: Preparation of 3-[4-(1-carbomethoxy-1-propyl)methoxyphenyl]methyl-7-methyl-2-propyl-3H-imidazo[4,5-b]pyridine To a suspension of KH (22 mg, 1.1 eq) in 0.25 mL of DMF under N$_2$ was added 0.050 g (0.18 mmol) of the product of Step D in Example 2, and the reaction mixture was stirred for 15 minutes. When the KH had dissolved, 18-crown-6 (10 mg, 0.2 eq) was added, followed by ethyl 2-bromopentanoate (30 uL, 1.0 eq). After 5 minutes, tlc showed that the bromide had disappeared, but that some of the starting phenolic intermediate remained. The reaction mixture was quenched with saturated ammonium chloride and concentrated in vacuo. The residue was chromatographed on silica gel (120×20 mm) eluted with 30% ethyl acetate/hexane. The product was isolated in a 19% yield (14 mg).

$^1$H NMR (300 MHz, CDCl$_3$ ppm): δ0.9–1.0 (m, 6H), 1.15–1.25 (t, 3H), 1.4–1.6 (m, 2H), 1.7–2.0 (m, 4H), 2.65 (s, 3H), 2.7–2.8 (t, 2H), 4.1–4.2 (m, 2H), 4.5–4.6 (m, 1H), 5.4 (s, 2H), 6.7–6.8 (d, 2H), 7.0–7.1 (m, 3H), 8.2 (d, 1H). FAB-MS: m/e 410 (M+1).

Step B: Preparation of 3-[4-(1-carboxy-1-propyl)methoxyphenyl]methyl-7-methyl-2-propyl-3H-imidazo[4,5-b]pyridine To a solution of 21 mg (0.049 mmol) of the product of Step B dissolved in 1 mL of ethanol was added 0.25 mL of 1N NaOH. The reaction mixture was stirred overnight, after which time tlc indicated the consumption of the starting material. The reaction mixture was neutralized with 1N HCl and concentrated in vacuo. The residue was purified on a silica gel flash chromatography column (90×10) eluted with ethyl acetate/hexane/acetic acid (76:20:4). The product fractions were combined and evaporated, redissolved in ethyl acetate and reconcentrated in vacuo several times to remove residual acetic acid. Drying in vacuo afforded 13 mg (93%) of the title compound.

$^1$H NMR (300 MHz, CD$_3$OD, ppm): δ0.9–1.0 (m, 6H), 1.4–1.6 (m, 2H), 1.6–1.8 (m, 2H), 1.8–1.9 (m, 2H), 2.65 (s, 3H), 2.8–2.9 (t, 2H), 4.5–4.6 (t, 1H), 5.5 (s, 2H), 6.8–6.9 (d, 2H), 7.0–7.1 (d, 2H), 7.15 (d, 1H), 8.2 (d, 1H). FAB-MS: m/e 382 (M+1).

EXAMPLE 10

3-[4-(1-Carboxy)-1-(2-carboxyphenyl)methoxyphenyl]-methyl-7-methyl-2-propyl-3H-imidazo[4,5-b]pyridine Step A: Preparation of dimethyl homophthalate To homophthalic acid (500 mg, 2.78 mmol) cooled to 0° C. was added a saturated solution of HCl/CH$_3$OH (20 mL). The solution was gradually warmed to room temperature and stirred for 3 days. The reaction was concentrated in vacuo, the residue was partitioned between ethyl acetate and water, and the organic layer washed with saturated NaHCO$_3$ and brine. The organic layer was concentrated in vacuo, then redissolved in ethyl acetate, dried (MgSO$_4$), filtered and evaporated to afford 0.470 g (81%) of the title compound.

$_1$H NMR (300 MHz, CDCl$_3$, ppm): δ3.7 (s, 3H), 3.9 (s, 3H), 4.0 (s, 2H), 7.2–7.2 (m, 1H), 7.25–7.35 (m, 1H), 7.45–7.55 (m, 1H), 8.0–8.1 (m, 1H). EI-MS: m/e 208 (M+).

Step B: Preparation of methyl 2-bromo-(2'-carbomethoxy)phenylacetate

To a solution of the product of Step A (464 mg, 223 mmol) in 10 mL CCl$_4$ were added NBS (377 mg, 0.95 eq) and a catalytic amount of AIBN. The reaction mixture was refluxed overnight, and then concentrated in vacuo. The residue was chromatographed on silica gel (140×40 mm) eluted with 8% ethyl acetate/hexane. The product was isolated in a 65% yield (398 mg).

$^1$H NMR (300 MHz, CDCl$_3$, ppm): δ3.8 (s, 3H), 3.9 (s, 3H), 6.6 (s, 1H), 7.35–7.45 (t, 1H), 7.55–7.65 (t, 1H), 7.8–7.9 (d, 1H), 7.95–8.0 (d, 1H).

Step C: Preparation of 3-[4-(1-carbomethoxy-1-(2-carboethoxyphenyl))methoxyphenyl]methyl-7-methyl-2-propyl-3H-imidazo[4,5-b]pyridine To a suspension of KH (22 mg, 1.1 eq) in 250 uL DMF under N$_2$ was added 50 mg (0.178 mmol) of 3-(4-hydroxyphenyl)methyl-7-methyl-2-propyl-3H-imidazo[4,5-b]pyridine (Example 2, Step D), and the reaction mixture was stirred for 1 hour. To this solution were added 18-crown-6 (47 mg, 1.1 eq) and the product of Step B (56 mg, 1.1 eq). The reaction mixture was stirred at room temperature overnight. The reaction mixture was then quenched with saturated ammonium chloride and concentrated in vacuo. The residue was partitioned between ethyl acetate and water, the organic layer extracted with saturated NaHCO$_3$ and concentrated in vacuo. The product was purified on a silica gel flash chromatography column (130×20 mm) eluted with 40% ethyl acetate/hexane to afford 33 mg (38%) of the title compound.

$^1$H NMR (300 MHz, CDCl$_3$, ppm): δ0.9–1.0 (t, 3H), 1.65–1.8 (m, 2H), 2.65 (s, 3H), 2.7–2.8 (t, 2H), 3.7 (s, 3H), 3.9 (s, 3H), 5.2 (s, 2H), 6.8–6.95 (m, 3H), 7.0–7.1 (m, 3H), 7.35–7.45 (m, 1H), 7.45–7.55 (m, 1H), 7.7 (m, 1H), 7.9–8.0 (m, 1H), 8.2 (d, 1H). FAB-MS: m/e 488 (M+1).

Step D: Preparation of 3-[4-(1-carboxy)-1-(2-carboxyphenyl)methoxyphenyl]methyl-7-methyl-2-propyl-3H-imidazo[4,5-b]pyridine To a methanol solution (1.5 mL) of the product of Step C (33 mg, 0.068 mmol) was added 1.5 mL of 1N NaOH. The reaction mixture was stirred at room temperature for 4.5 hours, and was then neutralized with 1N HCl and concentrated in vacuo. The residue was chromatographed on silica gel (120×20 mm) eluted with CHCl$_3$/MeOH/HOAc (100:10:2) to afford 32 mg (94%) of the title compound.

$^1$H NMR (300 MHz, CD$_3$OD, ppm): δ0.85–0.95 (t, 3H), 1.5–1.7 (m, 2H), 2.6 (s, 3H), 2.7–2.8 (t, 2H), 5.35 (s, 2H), 6.3 (s, 1H), 6.8–7.0 (m, 4H), 7.05–7.30 (m, 3H), 7.55–7.7 (m, 2H), 8.15 (d, 2H).

EXAMPLE 11

(Z)-3-[(4-((2-Carboxy-2-phenyl)ethenyl)phenyl)methyl]-7-methyl-2-propyl-3H-imidazo[4,5-b]pyridine Step A: Preparation of methyl 3-hydroxy-3-(4-methylphenyl)-2-phenylpropionate To a solution of methyl 2-bromophenylacetate (473 mg; 2.065 mmol) and 4-methylbenzaldehyde (188 mg, 1.57 mmol) in dry THF (5 mL) under N$_2$ was added powdered zinc (201 mg, 3.09 mmol). After stirring at reflux for 10 min, a few crystals of iodine were added. The mixture was refluxed under N$_2$ for 4 hours, then allowed to stand at room temperature overnight. The next day the mixture was diluted in Et$_2$O and 1N HCl was added. The biphasic mixture was stirred until the zinc had completely dissolved in the aqueous layer. The organic layer was separated, washed with brine, dried (MgSO$_4$), filtered, and concentrated in vacuo. The residue which contained two diastereomers (Rf=0.22, 0.17 in 15% EtOAc/hexane), was purified on a silica gel flash chromatography column eluted with 15% ethyl acetate/hexane. A total of 283 mg (67%) of both diastereomers was isolated. The 300 MHz $^1$H NMR spectra of each diastereomer was consistent with its structure.

Step B: Preparation of methyl (Z)-3-(4-methylphenyl)-2-phenylpropenoate

To a solution of a mixture of the diastereoisomers from Step A (34 mg, 0.126 mmol) in dry benzene (3 mL) was added a-few crystals of p-TsOH and the mixture was heated to reflux. After several minutes tlc analysis indicated complete reaction. The mixture was diluted with Et$_2$O, washed with saturated NaHCO$_3$, brine, dried (MgSO$_4$), filtered and concentrated in vacuo to provide 31 mg (98%) of the title compound.

$^1$H NMR (300 MHz, CDCl$_3$, ppm): δ2.27 (s, 3H), 3.79 (s, 3H), 6.92 (q, 4H), 7.25 (m, 2H), 7.40 (m, 3H), 7.82 (s, 1H).

Step C: Preparation of methyl (Z)-3-(4-bromomethylphenyl)-2-phenylpropenoate

To a solution of the product of Step B (31 mg, 0.123 mmol) in dry CCl$_4$ (1 mL) under N$_2$ were added NBS (20 mg, 0.9 eq) and a catalytic amount of AIBN. The mixture was stirred at reflux under N$_2$ for 1.5 hours. The mixture was cooled to room temperature, diluted with EtO$_2$ and filtered to remove the precipitated succinimide. The filtrate was concentrated in vacuo and the residue was purified on a silica gel flash chromatography column eluted with 15:1 hexane/EtOAc to afford 27.4 mg (67%) of the title compound.

¹H NMR (300 MHz, CDCl₃, ppm): δ3.80 (s, 3H), 4.49 (s, 2H), 7.02 (d, 2H), 7.18 (d, 2H), 7.24 (d, 1H), 7.39 (m, 4H), 7.82 (s, 1H).

Step D: Preparation of (Z)-3-[(4-(2-carbomethoxy-2-phenylethen-1-yl)phenyl)methyl]-7-methyl-2-propyl-3H-imidazo[4,5-b]pyridine To a solution of 30 mg (0.171 mmol) of 2-propyl-7-methylimidazo[4,5-b]pyridine (Example 2, Step D) dissolved in 1 mL of dry DMF was added 11 mg of a 60% oil dispersion of NaH (1.5 eq) and the reaction mixture was stirred under an N₂ atmosphere. After stirring at room temperature for 30 minutes the product from Step C (27.4 mg, 0.082 mmol) dissolved in 0.5 mL DMF was added via syringe. The reaction mixture was quenched with saturated NH₄Cl solution, and the solvent was removed under in vacuo. The residue was dissolved in EtOAc and washed with H₂O and brine. The organic layer was dried (MgSO₄), filtered, and concentrated in vacuo. The residue was purified on a silica gel flash chromatography column eluted with 50% ethyl acetate/hexane to provide 13.2 mg (38%) of the title compound.

¹H NMR (300 MHz, CDCl₃, ppm): δ0.95 (t, 3H), 1.72 (q, 2H), 2.68 (s, 3H), 2.71 (g, 2H), 3.78 (s, 3H), 5.40 (s, 2H), 6.91 (q, 4H), 7.02 (d, 1H), 7.19 (dd, 1H), 7.32 (m, 3H), 7.79 (s, 1H), 8.16 (d, 1H).

Step E: Preparation of (Z)-3-[(4-((2-carboxy-2-phenyl)ethen-1-yl)phenyl)methyl]-7-methyl-2-propyl-3H, imidazo[4,5-b]pyridine To a solution of the product of Step D (13.2 mg, 0.031 mmol) in MeOH (1 mL) was added 1N NaOH (0.138 mL, 4.5 eq). After stirring overnight the mixture was quenched with 0.5 mL of acetic acid and concentrated in vacuo. The product was purified on a silica gel flash chromatography column eluted with hexane/EtOAc/HOAc (75:50:1) to afford 10.8 mg (85%) of the title compound.

¹H NMR (300 MHz, CD₃OD, ppm): δ0.91 (t, 3H), 1.63 (q, 2H), 2.62 (s, 3H), 2.79 (t, 2H), 5.47 (s, 2H), 6.87 (d, 2H), 6.96 (d, 2H), 7.12 (m, 3H), 7.31 (m, 3H), 7.79 (s, 1H), 8.12 (d, 1H).

EXAMPLE 12

3-[(4-((2-Carboxy-2-phenyl)ethyl)phenyl)methyl]-7-methyl-2-propyl-3H-imidazo[4,5-b]3-pyridine Step A: Preparation of 3-[(4-((2-carboxy-2-phenyl)ethylphenyl)methyl]-7-methyl-2-propyl-3H-imidazo[4,5-b]pyridine To a solution of 2.2 mg (0.0054 mmol) of the product of Step E of Example 11 in 1 mL of EtOAc was added a catalytic amount of 10% Pd on carbon. A hydrogen atmosphere was secured with a balloon and the mixture was stirred for 1 hour. The catalyst was removed by filtering the mixture through a pad of celite, and the filtrate was concentrated in vacuo to provide 1.3 mg (59%) of the title compound.

¹H NMR (300 MHz, CDCl₃, ppm): δ0.87 (t, 3H), 1.63 (q, 2H), 2.62 (s, 3H), 2.67 (t, 2H), 5.30 (s, 2H), 6.80 (s, 4H), 6.92 (d, 1H), 7.01 (m, 5H), 8.12 (d, 1H).

EXAMPLE 13

3-[4-(1-carboxy-1-methyl-1-phenyl)methoxyphenyl]-methyl-7-methyl-2-propyl-3H-imidazo[4,5-b]pyridine Preparation of methyl 2-(4-methylphenoxy)phenylacetate To a cooled (0° C.) suspension of KH (2.12 g, 1.0 eq) in DMF (30 mL) was added a solution of p-cresol (2.00 g, 18.5 mmol) in 20 let of DMF. The reaction mixture was stirred 15 minutes, then 18-crown-6 (200 mg) was added followed by a solution of 4.24 g (18.5 mmol) of methyl 2-bromophenylacetate dissolved in 10 mL of DMF. The reaction mixture was stirred 45 minutes, then partitioned between ethyl acetate and water. The organic layer was washed with water, brine, dried (MgSO₄), filtered and evaporated in vacuo. The residue was purified on a silica gel flash chromatography column (150×40 mm) eluted with 5% ethyl acetate/hexane to yield 2.63 g (58%) of the title compound.

¹H NMR (300 MHz, CDCl₃): δ2.3 (s, 3H), 3.75 (s, 3H), 5.6 (s, 1H), 6.8–6.9 (d, 2H), 7.0–7.1 (d, 2H), 7.3–7.45 (m, 3H), 7.5–7.6 (d, 2H). FAB-MS: m/e 257 (M+1).

Step B: Preparation of methyl 2-(4-methylphenoxy)-2-phenylpropanoate

A solution of the product of Step A (50 mg, 0.195 mmol) in 500 uL of THF was cooled to −78° C. A solution of lithium bis(trimethylsilyl)amide (195 uL, 1.0M in THF) was added and the reaction was stirred for 15 minutes. Methyl iodide (12 uL, 1.0 eq) was added and the cooling bath removed. After 8 minutes, the reaction mixture was quenched with saturated NH₄Cl and concentrated in vacuo. The residue was purified on a on a silica gel flash chromatography column (140×20 mm) eluted with 2.5% ethyl acetate/hexane to yield 26 mg (49%) of the title compound.

¹H NMR (300 MHz, CDCl₃, ppm): δ1.9 (s, 3H), 2.3 (s, 3H), 3.75 (s, 3H), 6.7–6–8 (d, 2H), 7.0–7.1 (d, 2H), 7.3–7.45 (m, 3H), 7.6–7.7 (d, 2H). FAB-MS: m/e : 271 (M+1).

Step C: Preparation of methyl 2-(4-bromomethylphenoxy)-2-phenylpropanoate

A solution of the product of Step B (26 mg, 0.096 mmol) NBS (16 mg, 0.95 eq) and AIBN (2 mg, catalytic amount) in CCl₄ (2 mL) was heated to reflux for 1 hour and then concentrated in vacuo. The residue was purified on a silica gel flash chromatography column (125×20 mm) eluted with 5% ethyl acetate/hexane to yield 21 mg (62%) of the title compound.

¹H NMR (300 MHz, CDCl₃, ppm): δ1.9 (s, 3H), 3.75 (s, 3H), 4.5 (s, 2H), 6.9–6.9 (d, 2H), 7.2–7.3 (d, 2H), 7.3–7.5 (m, 3H), 7.6–7.7 (d, 2H).

Step D: Preparation of 1-[4-(1-carbomethoxy-1-methyl-1-phenyl)methoxyphenyl]methyl-7-methyl-2-propyl-3H-imidazo[4,5-b]pyridine To a suspension of NaH (2.0 mg, 1 eq) in DMF (0.25 mL) was added 10 mg (1.0 eq) of 7-methyl-2-propylimidazo[4,5-b]pyridine (Example 2, Step B), and the reaction mixture was stirred 15 minutes. Next, a solution of the product of Step C (20 mg, 0.057 mmol) in DMF (0.5 mL) was added. After stirring 1.5 hours, the reaction mixture was concentrated in vacuo. The residue was purified on a silica gel flash chromatography column (140×15 mm) eluted with 50% ethyl acetate/hexane to yield 12 mg (48%) of the titled product.

¹H NMR (300 MHz, CDCl₃, ppm): δ0.9–1.0 (t, 3H), 1.65–1.8 (m, 2H), 1.85 (s, 3H), 2.7 (s, 3H), 2.75–2.85 (t, 2H), 3.7 (s, 3H), 7.55–7.65 (m, 2H),8.2 (d 1H). FAB-MS: m/e 444 (M+1).

Step E: Preparation of 3-[4-(1-carboxy-1-methyl-1-phenyl)methoxyphenyl]methyl-7-methyl-2-propyl-3H-imidazo[4,5-b]pyridine To a solution of the product of Step D (12 mg, 0.027 mmol) in MeOH (2 mL) was added 2 mL of a 1N NaOH solution. The reaction mixture was stirred for 45 minutes, and was then concentrated in vacuo. The residue was taken up in water and acidified to pH 2 with 1N HCl. Next, the aqueous layer was diluted with water and extracted 3 times with chloroform. The combined organic layers were dried (MgSO$_4$), filtered, and concentrated in vacuo to yield 8.3 mg (70%) of the title compound.

$^1$H NMR (300 MHz, CDCl$_3$, ppm): δ0.9–1.0 (t, 3H), 1.7–1.85 (m, 2H), 1.8 (s, 3H), 2.8 (s, 3H), 3.1–3.2 (t, 2H), 5.5 (s, 2H), 6.75–6.85 (d, 2H), 7.0–7.1 (d, 2H), 7.25–7.4 (m, 4H), 7.5–7.6 (m, 2H), 8.45 (d, 1H). FAB-MS: m/e 450, 452 (M+1, 3:1 ratio).

EXAMPLE 14

7-Methyl-2-propyl-3-[4-(1-(tetrazol-5-yl)-1-phenyl)methoxyphenyl]methyl-3H-imidazo[4,5-b]pyridine Step A: Preparation of 3-[4-(1-carboxamido-1-phenyl)methoxyphenyl]methyl-7-methyl-2-propyl-3H-imidazo[4,5-b]pyridine A solution of the product of Example 2, Step E (125 mg, 0.291 mmol) in MeOH (10 mL) was cooled to 0° C. and ammonia was bubbled through the mixture for 1.5 hours. The flask was stoppered and stirred for 6 hours, during which time the product precipitated. The reaction mixture was concentrated in vacuo to yield 105 mg (88%) of product (Rf=0.50 5% methanol/ethyl acetate) which was used in the next step without further purification.

$^1$H NMR (300 MHz, CDCl$_3$, ppm): δ0.9–1.0 (t, 3H), 1.7–1.8 (m, 2H), 2.65 (s, 3H), 2.7–2.8 (t, 2H), (s, 2H), 5.45 (s, 1H), 5.5–5.6 (s, 1H), 6.55–6.65 (s, 1H), 6.8–6.9 ( d, 2H), 7.0–7.1 (m, 3H), 7.3–7.4 (m, 3H), 7.45–7.55 (m, 2H), 8.2 (d, 1H).

Step B: Preparation of 3-[4-(1-cyano-1-phenyl)methoxyphenyl]methyl-7-methyl-2-propyl-3H-imidazo[4,5-b]pyridine To a 0° C. suspension of the product of Step A (83 mg, 0.20 mmol) in phosphorous oxychloride (0.51 mL, 27 eq) was added Et$_3$N (61 uL, 2.2 eq) over 55 minutes. After the addition was complete, the reaction mixture was warmed to room temperature over 2 hours and then heated to reflux for 45 minutes. Next, the reaction mixture was concentrated in vacuo, and the residue was partitioned between ice water and toluene. The aqueous layer was extracted three times with toluene. The combined extracts were washed with 0.5N NaOH and then with water. The organic layer was separated and concentrated in vacuo to yield 59 mg (74%) of crude product (Rf=0.35 in 50% ethyl acetate/hexane), which was used in the next step without purification.

Step C: Preparation of 7-methyl-2-propyl-3-[4-(1-(tetrazol-5-yl)methoxyphenyl]methyl-3H-imidazo-[4,5-b]pyridine To a solution of the product of Step B (29 mg, 0.073 mmol) dissolved in 0.5 mL of toluene was added 15 mg (1.2 eq) of Me$_3$SnN$_3$ and the reaction mixture was refluxed for 22 hours. An additional 15 mg (1.2 eq) of Me$_3$SnN$_3$ was then added, and the refluxing continued for another hour. The reaction mixture was then poured into ethyl acetate/ether and washed with saturated NH$_4$Cl and brine. The organic layer was separated and concentrated in vacuo. The residue was purified on a silica gel flash chromatography column (120×30 mm) eluted with chloroform/methanol/acetic acid (100:5:1) to yield 5 mg (16%) of the title compound.

$^1$H NMR (300 MHz, CD$_3$OD, ppm): δ0.9–1.0 (t, 3H), 1.6–1.7 (m, 2H), 2.65 (s, 3H), 2.8–2.9 (t, 2H), 5.5 (s, 2H), 6.8 (s, 1H), 6.95–7.1 (m, 5H), 7.1–7.2 (d, H), 7.3–7.4 (m, 2H), 7.45–7.55 (m, 2H), 8.2 (d, 1H). FAB-MS: m/e 440 (M+1).

EXAMPLE 15

7-Methyl-2-propyl-3-[4-(1-(tetrazol-5-yl)-1-(2-chlorophenyl)methoxyphenyl]methyl-3H-imidazo[4,5-b]pyridine Preparation of 2-(4-methylphenoxy)-2-(2-chlorophenyl)acetamide To a solution of 0.700 g (2.41 mmol) of methyl 2-(2-chlorophenyl)-2-(4-methylphenoxy)acetate (Example 4, Step B) in 10 mL of methanol, stirred at 0° C. (ice-bath) was added anhydrous NH$_3$ for 45 minutes. The reaction mixture was warmed to room temperature and stirred overnight. The reaction mixture was then concentrated in vacuo and afforded 0.658 g (99%) of title compound.

$^1$H NMR (300 MHz, CD$_3$OD, ppm): δ2.25 (s, 3H), 6.0 (s, 1H), 6.8–6.9(d, 2H), 7.0–7.1 (d, 2H), 7.25–7.35 (m, 2H), 7.4–7.5 (m, 1H), 7.55–7.6 (m, 1H) FAB-MS: m/e 276, 278 (M+1, 3:1 ratio).

Step B: Preparation of 2-(4-methylphenoxy)-2-(2'-chlorophenyl)acetonitrile

The product of Step A (0.650 g, 2.36 mmol) was added to phosphorous oxychloride (5.95 mL, 27 at 0° C. followed by slow addition of 0.73 mL (2.2 eq) of triethylamine. The reaction mixture was warmed to room temperature for 10 minutes, refluxed for 50 minutes and then cooled to room temperature. The reaction mixture was concentrated in vacuo, and partitioned between ice water and toluene. The aqueous layer was extracted 3 times with toluene, and the combined toluene extracts were washed with 0.5N NaOH and H$_2$O. The crude product was concentrated in vacuo and purified on a silica gel flash chromatography column (140×30 mm) eluted with 2% ethyl acetate/hexane to afford 0.555 g (91%) of the title compound.

$^1$H NMR (300 MHz, CD$_3$OD, ppm): δ2.35 (s, 3H), 6.15 (s, 1H), 6.95–7.05 (d, 2H), 7.1–7.2 (d, 2H), 7.4–7.6 (m, 3H), 7.8–7.9 (m, 1H). EI-MS: m/e 257,259 (M+, 3:1 ratio).

Step C: Preparation of 2-(4-bromomethylphenoxy)-2-(2-chlorophenyl)acetonitrile

To a CCl$_4$ solution (5 mL) of the product (0.200 g) of Step B was added NBS (0.132 g, 0.95 eq) and a catalytic amount of AIBN. The reaction mixture was refluxed overnight. TLC indicated clean conversion to product, and the reaction mixture was cooled to room temperature and concentrated in vacuo. The crude product was purified on a silica gel flash chromatography column (120×30 mm) eluted with 5% ethyl acetate in hexane to afford 0.178 g (72%) of the title compound.

$^1$H NMR (300 MHz, CDCl$_3$ ppm): δ4.5 (s, 2H), 6.2 (s, 1H), 7.05–7.15 (d, 2H), 7.35–7.55 (m, 5H), 7.8–7.9 (m, 1H).

Step D: Preparation of 3-[4-(1-cyano-1-(2-chlorophenyl)methoxyphenyl]methyl-7-methyl-2-propyl-3H-imidazo[4,5-b]pyridine To a DMF suspension (0.5 mL) of NaH (7.5 mg, 0.252 mmol) under N$_2$ was added 0.040 g (0.23 mmol) of 7-methyl-2-propylimidazo[4,5-b]pyridine (Example 2, Step B) and the reaction mixture was stirred at room temperature for 1.5 hours. To the resulting sodium salt was added the product of Step C (84 mg, 1.1 eq) and the reaction mixture was stirred for 5 hours. The reaction mixture was then quenched with saturated NH$_4$Cl and concentrated in vacuo. The crude product was purified on a silica gel flash chromatography column (130×20 mm) eluted with 30% ethyl acetate/hexane to afford 24 mg (24%) of the title compound.

¹H NMR (300 MHz, CDCl₃, ppm): d 0.9–1.0 (t, 3H), 1.7–1.85 (m, 2H), 2.7 (s, 3H), 2.75–2.85 (t, 2H), 5.45 (s, 2H), 6.15 (s, 1H), 6.95–7.05 (m, 3H), 7.1–7.2 (d, 2H), 7.35–7.5 (m, 3H), 7.75–7.85 (m, 1H), 8.2 (d, 1H). FAB-MS: m/e 431 (M+1).

Step E: Preparation of 7-methyl-2-propyl-3-[4-(1-(tetrazol-5-yl)-1-(2-chlorophenyl)methoxyphenyl]methyl-3H-imidazo[4,5-b]pyridine To a toluene solution (1 mL) of the product of Step D (24 mg, 0.056 mmol) was added trimethylstannyl azide (14 mg, 1.2 eq) and the mixture was refluxed for 48 hours. The reaction mixture was then concentrated in vacuo and purified on a silica gel flash chromatography column (130×15 mm) eluted with CHCl₃/MeOH/HOAc (100:3:1) to afford 13 mg (50%) of the title compound.

¹H NMR (300 MHz, CD₃OD, ppm): δ0.85–0.95 (t, 3H), 2.55–2.7 (m, 2H), 2.65 (s, 3H), 2.8–2.9 (t, 2H), 5.5 (s, 2H), 6.9–7.0 (d, 2H), 7.05–7.2 (m, 4H), 7.3–7.5 (m, 3H), 7.55–7.65 (m, 1H), 8.2 (d, 1H). FAB-MS: m/e 474, 476 (M+1).

EXAMPLE 16

7-Methyl-2-propyl-3-[4-(2-phenyl-2-(tetrazol-5-yl)ethyl)phenyl]methyl-3H-imidazo[4,5-b]pyridine Step A: Preparation of 4-(bromomethyl)benzyl alcohol A suspension of 4-bromomethylbenzoic acid (5.04 g, 23.3 mmol) in THF (30 mL) was cooled to 0° C. and treated with borane/THF (35 mmol). The ice bath was removed and the mixture was allowed to warm to room temperature and stirred for 1.5 hours. The excess borane was quenched first with MeOH, then with water. The reaction mixture was then concentrated in vacuo and redissolved in ethyl acetate. The ethyl acetate layer was washed with 5% HCl, water, NaHCO₃, brine, dried (MgSO₄), filtered, and evaporated in vacuo to afford 4.44 g (94%) of the titled product.

¹H NMR: (300 MHz, CDCl₃, ppm): d 7.38 (q, 4H), 4.70 (s, 2H), 4.51 (s, 2H). FAB MS: m/e 2,02 (M+1).

Step B: Preparation of 4-(bromomethyl)-1-(tert-butyldimethylsilyloxymethyl)benzene To a solution of the product of Step A (4.44 g, 22.1 mmol) in CH₂Cl₂ were added N,N-diisopropylethylamine (1.2 sq.), 4-dimethylaminopyridine (0.1 eq), and tert-butyldimethylsilyl chloride (1.2 eq). The reaction mixture was stirred for 1.5 hours at room temperature, then concentrated in vacuo. The residue was dissolved in ethyl acetate and washed with water, brine, dried (MgSO₄), filtered, and concentrated in vacuo. The residue was chromatographed on silica gel eluted with 2.5% ethyl acetate/hexane to afford 5.0 g (71%) of the titled product.

¹H NMR (300 MHz, CDCl₃, ppm): δ7.34 (q, 4H), 4.74 (s, 2H), 4.59 (s, 2H), 0.95 (s, 9H), 0.11 (s, 6H).

Step C: Preparation of 3-[4-(tert-butyldimethylsilyloxymethyl)phenyl]-2-phenylpropanonitrile A solution of phenylacetonitrile (1.5 mL, 12.7 mmol) in THF (40 mL) containing HMPA (11 mL, 63.4 mmol) was cooled to −78° C. and treated with 16 mL (16 mmol) of a 1.0M THF solution of lithium bis(trimethylsilyl)amide dropwise while the temperature was maintained at −78° C. The reaction was stirred at −78° C. for 1.5 hours, and a solution of the product of Step B (2.00 g, 6.34 mmol) in THF (8 mL) was added dropwise with the temperature maintained below −70° C. The reaction temperature was maintained below −68° C. for 3 hours. The reaction was quenched at this temperature by addition of 1N Na₂HSO₄. After warming to room temperature, the mixture was partitioned between EtOAc and water, and the combined organic layers were washed with water, saturated NaHCO₃, brine, dried (MgSO₄), filtered, then concentrated in vacuo. The residue was chromatographed on a silica gel flash chromatography column eluted with 5% ethyl acetate/hexane to afford 1.5 g (67%) of the title compound.

¹H NMR (300 MHz, CDCl₃, ppm): δ7.40–7.30 (m, 3H), 7.30–7.22 (m, 4H), 7.10 (d, 2H), 4.73 (s, 2H), 3.98 (t, 1H), 3,23–3.08 (m, 2H), 0.94 (s, 9H), 0.10 (s, FAB MS: m/e 294 (M+ less tert-Bu).

Step D: Preparation of 3-[4-(bromomethyl)phenyl]-2-phenylpropanonitrile

To a cooled (0° C.) solution of 1.5 g (4.27 mmol) of the product of Step C dissolved in 20 mL of acetonitrile, was added 2.12 g (6.4 mmol) of carbon tetrabromide, and 1.68 g (6.40 mmol) of triphenylphosphine. The reaction mixture was stirred 30 minutes at 0° C., then allowed to warm to room temperature and 0.5 mL (6.4 mmol) of acetone was added. The reaction mixture was stirred an additional 16 hours at room temperature, then filtered and evaporated in vacuo. The residue was purified on a silica gel flash chromatography column eluted with 5% ethyl acetate/hexane to afford 0.575 g (45%) of the title compound.

¹H NMR (300 MHz, CDCl₃, ppm): δ7.48–7.10 (m, 9H), 4.50 (s, 2H), 4.00 (t, 1H), 3.26–3.10 (m, 2H). FAB MS: m/e 299,301 (M+1).

Step E: Preparation of 3-[4-(2-cyano-2-phenylethyl)phenyl]methyl-7-methyl-2-propyl-3H-imidazo [4,5-b]pyridine To a solution of 7-methyl-2-propylimidazo [4,5-b]pyridine (106 mg, 0.61 mmol) in DMF (3 mL) was added NaH (0.91 mmol). The suspension was stirred at room temperature for 30 minutes, at which time a solution of the product of Step D (200 mg, 0.667 mmol) in DMF (2 mL) was added. The mixture was stirred for 2 hours at room temperature, quenched with water, and then concentrated in vacuo. The residue was partitioned between water and EtOAc, and the combined organic layers were washed with brine, dried (K₂CO₃), filtered, and evaporated in vacuo. The residue was chromatographed on a silica gel flash chromatography column eluted with 50% ethyl acetate/hexane to afford 46 mg (19%) of the title compound.

¹H NMR (300 MHz, CD₃OD, ppm): δ consistent with structure. FAB MS: m/e 395 (M+1).

Step F: Preparation of 7-Methyl-2-propyl-3-[4-(2-phenyl-2-(tetrazol-5-yl)ethyl)phenyl]methyl-3H-imidazo[4,5-b]pyridine To a solution of the product of the product of Step E (46 mg, 0.12 mmol) in toluene (2 mL) was added 29 mg (0.14 mmol) of trimethylstannyl azide and the reaction mixture was refluxed for 24 hours. The reaction mixture was concentrated in vacuo. The residue was dissolved in THF and treated with 12N HCl (5 drops) for 5 minutes at room temperature. The mixture was concentrated in vacuo and purified on a silica gel flash chromatography column eluted with CHCl₃/MeOH/NH₄OH (80:20:2) to afford 19.6 mg (38%) of the title compound.

¹H NMR (300 MHz, CD₃OD, ppm): δ8.18 (d, 1H), 7.28–7.12 (m, 6H), 7.05 (d, 2H), 6.93 (d, 2H), 5.48 (s, 2H), 4.58 (t, 1H), 3.59–3.49 (m, 1H), 3.38–3.30 (m, 1H), 2.78 (t, 2H), 2.65 (s, 3H), 1.68–1.52 (m, 2H), 0.89 (t, 3H). FAB MS: m/e 4.38 (M+1).

EXAMPLE 17

3-[4-(1-carboxy-1-phenoxy)methylphenyl]methyl-7-methyl-2-propyl-3H-imidazo[4,5-b]pyridine Step A: Preparation of methyl 2-bromo-4'-methylphenylacetate A mixture of 4-methylphenylacetic acid (5.00 g, 33.3 mmol) and thionyl chloride (2.67 mL, 36.6 mmol) were heated to reflux. Bromine (1.51 mL, 29.3 mmol) was added dropwise to the reaction mixture over 10 minutes and then the mixture was refluxed overnight (17 hours). The reaction mixture was cooled to room temperature and 34 mL of methanol was added slowly. The reaction mixture was concentrated in vacuo and chromatographed on silica gel (45×120 mm) eluted with 2% ethyl acetate/hexane to afford 3.18 g (37%) of the titled compound.

$^1$H NMR (300 MHz, CDCl$_3$, ppm): d 2.35 (s, 3H), 3.8 (s, 3H), 5.35 (s, 1H), 7.1–7.2 (d, 2H), 7.4–7.5 (d, 2H). FAB-MS: m/e 243,241 (M+1, 1:1 ratio).

Step B: Preparation of methyl 2-phenoxy-2-(4-methylphenyl)acetate

To a suspension of KH (244 mg, 2.13 mmol) in 2 mL of DMF at room temperature under N$_2$ was added a DMF solution (1 mg) of phenol (200 mg, 2.13 mmol). When the KH had completely dissolved, the reaction mixture was cooled to 0° C. A DMF solution (1 mL) of the product of Step A (517 mg, 2.13 mmol) was then added by syringe. After the addition was complete, the reaction mixture was allowed to warm to room temperature, and was then stirred for 2 hours. The reaction mixture was quenched with saturated NH$_4$Cl and concentrated in vacuo. The residue was purified on a silica gel flash chromatography column (130×40 mm) eluted with 5% ethyl acetate/hexane to afford 0.126 g (23%) of the title compound.

$^1$H NMR (300 MHz, CDCl$_3$, ppm): δ2.35 (s, 3H), 3.75 (s, 3H), 5.65 (s, 1H), 6.9–7.0 (m, 3H), 7.1–7.3 (m, 4H), 7.4–7.5 (d, 2H). EI-MS: m/e 256 (M+).

Step C: Preparation of methyl 2-phenoxy-2-(4-bromomethylphenyl)acetate

To a CCl$_4$ solution (1 mL) of the product of Step B (126 mg, 0.495 mmol) was added N-bromosuccinimide (44 mg, 246 mmol) and a catalytic amount of AIBN. The solution was refluxed for 30 minutes and then concentrated in vacuo. The residue was purified on a silica gel flash chromatography column (150×30 mm) eluted with 5% ethyl acetate/hexane to afford 27 mg (33%) of the title compound.

$^1$H NMR (300 MHz, CDCl$_3$ ppm): δ3.75 (s, 3H), 4.5 (s, 2H), 5.65 (s, 1H), 6.9–7.0 (m, 3H), 7.25–7.35 (m, 2H), 7.4–7.5 (d, 2H), 7.55–7.6 (d, 2H). EI-MS: m/e 33,6, 336 (M+, 1:1 ratio).

Step D: Preparation of 3-[4-(1-carbomethoxy-1-phenoxy)methylphenyl]methyl-7-methyl-2-propyl-3H-imidazo[4,5-b]pyridine To a DMF suspension (0.1 mL) of NaH (2.4 mg; 0.081 mmol) under N$_2$ was added 1.0 sq. of 7-methyl-2-propylimidazo[4,5-b]pyridine (14 mg). After 15 minutes, the NaH had completely reacted. The reaction mixture was then treated with a DMF solution (0.4 mL) of the product of Example 9, Step C (27 mg, 0.081 mmol). The reaction mixture was stirred for 5 hours, and then concentrated in vacuo. The crude product was chromatographed on silica gel (140×20 mm) eluted first with 300 mL of 30% ethyl acetate/hexane, then with 50% ethyl acetate/hexane to afford 5.2 mg (15%) of the titled compound.

$^1$H NMR (300 MHz, CDCl$_3$, ppm): δ0.9–1.0 (t, 3H), 1.65–1.85 (m, 2H), 2.7 (s, 3H), 2.75–2.85 (t, 2H), 3.7 (s, 3H), 5.5 (s, 2H), 5.65 (s, 1H), 6.9–7.1 (m, 4H), 7.1–7.2 (m, 2H), 7.2–7.3 (m, 2H), 7.5 (d, 2H), 8.2 (d, 1H).

Step E: Preparation of 3-[4-(1-carboxy-1-phenoxy)methylphenyl]methyl-7-methyl-2-propyl-3H-imidazo-[4,5-b]pyridine To a methanol solution (50 uL) of the product of Example 9, Step D (5.2 mg, 0.012 mmol) was added 1N NaOH (12.1 uL, 1.0 eq). The hydrolysis was complete after stirring for 4 days. The reaction mixture was chromatographed on silica gel (140×10 mm) eluted with ethyl acetate/hexane/acetic acid (30:20:1) to afford 3.0 mg (57%) of the title compound.

$^1$H NMR (300 MHz, CD$_3$OD, ppm): δ0.9–1.0 (t, 3H), 1.6–1.8 (m, 2H), 2.65 (s, 3H), 2.8–2.9 (t, 2H), 5.4 (s, 1H), 5.6 (s, 2H), 6.8–7.0 (m, 3H), 7.1–7.3 (m, 5H), 7.55–7.65 (d, 2H), 8.2 (d, 1H). FAB-MS: m/e 416 (M+1).

EXAMPLE 18

3-[4-(1-Carboxy-1-(2-methylphenyl))methoxyphenyl]-methyl-7-methyl-2-propyl-3H-imidazo[4,5-b]pyridine General procedure for the synthesis of 2-bromophenylacetic esters from benzaldehydes (Steps A–C):

Step A: Preparation of 2-trimethylsilyloxy-2-(2-methylphenyl)acetonitrile

To a solution of 1.00 g (8.33 mmol) of 2-methylbenzaldehyde dissolved in 20 mL of dichloromethane was added 1.33 mL (10.0 mmol) trimethylsilylcyanide, 1–2 mg of potassium cyanide, 1–2 mg of 18-crown-6, and the reaction mixture was stirred at room temperature for 3 hours. The reaction mixture was then diluted into diethyl ether, washed with 5% NaHCO$_3$, brine, dried (MgSO$_4$), filtered and evaporated. The residual oil was used directly in the next step.

Step B: Preparation of ethyl 2-hydroxy-2-(2-methylphenyl)acetate

To a stirred 0° C. (ice-water bath) solution of 1.83 g (8.35 mmol) of the product of Step A dissolved in 10 mL of ethanol was introduced a slow stream of anhydrous hydrogen chloride gas. After 5 minutes the hydrogen chloride was turned off and the reaction mixture was stoppered and stirred at room temperature 14 hours. The reaction was then poured into ice-water and extracted into chloroform. The chloroform solution was filtered through a 60 mL sintered funnel filled with silica gel and the silica gel was washed with additional chloroform. The combined filtrate was evaporated in vacuo to afford 0.437 g (27%) of the title compound.

$^1$H NMR (300 MHz, CDCl$_3$, ppm): δ1.15–1.25 (t, 3H), 2.40 (s, 3H), 3.35–3.45 (d, 1H), 4.05–4.30 (m, 2H), 5.30–5.35 (d, 1H), 7.05–7.20 (m, 4H).

Step C: Preparation of ethyl 2-bromo-2-(2-methylphenyl)acetate

To a cooled (0° C.) solution of 0.425 g (2.19 mmol) of the product of Step B dissolved in 10 mL of dichloromethane was added 0.717 g (2.74 mmol) of triphenylphosphine followed by 0.908 g (2.74 mmol) of carbon tetrabromide. After 30 minutes the reaction was allowed to warm to room temperature and stirring was continued for 2 hours. The raction mixture was evaporated in vacuo and the residue was purified on a silica gel flash chromatography column eluted with 5% ethyl acetate/hexane to afford 0.373 g (66%) of the title compound.

¹H NMR (300 MHz, CDCl₃, ppm): δ1.20–1.30 (t, 3H), 2.40 (s, 3H), 4.15–4.30 (m, 2H), 5.60 (s, 1H), 7.10–7.25 (m, 3H), 7.55–7.65 (m, 1H).

General procedure for the alkylation of imidazo[4,5-b]pyridines with 2-bromophenylacetic esters:

Step D: Preparation of 3-[4-(1-carbomethoxy)-1-(2-methylphenyl)methoxyphenyl]methyl-7-methyl-2-propyl-3H-imidazo[4,5-b]pyridine To a suspension of 37 mg (0.32 mmol) of a 35% oil dispersion of potassium hydride in 0.5 mL of DMF was added 0.090 g (0.32 mmol) of 3-(4-hydroxyphenyl)-methyl-7-methyl-2-propyl-3H-imidazo[4,5-b]pyridine (Example 2, Step D) and the reaction was stirred under an N₂ atmosphere. After stirring for 15 minutes, 0.085 g of 18-crown-6 was added followed by addition of a solution of 0.090 g (0.35 mmol) of the product of Step C dissolved in 0.75 mL of DMF. The reaction mixture was stirred for 4 hours, then concentrated in vacuo. The residue was purified on a silica gel flash chromatography column eluted with 40% ethyl acetate/hexane to afford 0.099 g (68%) of the title compound.

¹H NMR (300 MHz, CDCl₃, ppm): δ0.90–1.00 (t, 3H), 1.15–1.25 (t, 3H), 1.65–1.80 (m, 2H), 2.45 (s, 3H), 2.65 (s, 3H) 2.70–2.80 (t, 2H), 4.05–4.25 (m, 2H), 5.35 (s, 2H), 5.75 (s, 1H), 6.75–6.85 (d, 2H), 6.95–7.05 (m, 3H), 7.10–7.25 (m, 3H), 7.45–7.55 (m, 1H), 8.15–8.20 (d, 1H). FAB-MS: m/e 458 (M+1).

General procedure for ester hydrolysis:

Step E: Preparation of 3-[4-(1-carboxy)-1-(2-methylphenyl)methoxyphenyl]methyl-7-methyl-2-propyl-3H-imidazo[4,5-b]pyridine To a solution of 0.097 g (0.21 mmol) of the product of Step D dissolved in 3 mL of ethanol was added 1 mL of a 1N NaOH solution. The reaction mixture was stirred at room temperature for 1.5 hours, neutralized to pH 7 with 1N HCl and then concentrated in vacuo. The residue was purified on a silica gel flash chromatography column eluted with CHCl₃/MeOH/NH₄OH (80:15:1) to afford 0.076 g (84%) of the title compound.

₁H NMR (300 MHz, CDCl₃, ppm): δ0.90–1.00 (t, 3H), 1.65–1.75 (m, 2H), 2.50 (s, 3H), 2.70 (s, 3H), 2.85–2.95 (t, 2H), 5.50 (s, 2H), 5.85 (s, 1H), 6.85–6.95 (d, 2H), 7.05–7.15 (d, 2H), 7.15–7.25 (m, 4H), 7.45–7.55 (d, 1H), 8.20–8.25 (d, 1H). FAB-MS: m/e 430 (M+1).

EXAMPLE 19

3-[4-(1-Carboxy-1-(2-ethoxyphenyl))methoxyphenyl]-methyl-7-methyl-2-propyl-3H-imidazo[4,5-b]pyridine Preparation of ethyl 2-bromo-2-(2-ethoxyphenyl)acetate Using the general procedure for the synthesis of 2-bromophenylacetic esters from benzaldehydes (Steps A-C, Example 18), 1.00 g (6.67 mmol) of 2-ethoxybenzaldehyde was converted to 0.291 g (1.01 mmol) of the title compound in 15% overall yield.

¹H NMR (300 MHz, CDCl₃, ppm): d 1.30–1.40 (t, 3H), 1.45–1.55 (t, 3H), 4.00–4.10 (m, 2H), 4.15–4.30 (m, 2H), 5.85 (s, 1H), 6.80–6.85 (d, 1H), 6.90–7.00 (t, 1H), 7.00–7.30 (t, 1H), 7.55–7.65 (d, 1H).

Step B: Preparation of 3-[4-(1-carbomethoxy)-1-(2-ethoxyphenyl)methoxyphenyl]methyl-7-methyl-2-propyl-3H-imidazo[4,5-b]pyridine Using the general procedure for the alkylation reaction described in Step D of Example 18, 0,089 g (0.32 mmol) of 3-(4-hydroxyphenyl)methyl-7-methyl-2-propyl-3H-imidazo[4,5-b]pyridine (Example 2, Step D) was alkylated with 0.100 g (0.35 mmol) of the product of Step A, to afford 0.107 g (69%) of the title compound.

¹H NMR (300 MHz, CDCl₃, ppm): δ0.85–0.95 (t, 3H), 1.10–1.20 (t, 3H), 1.30–1.40 (t, 3H), 1.60–1.76 (m, 2H), 2.65 (s, 3H), 2.70–2.80 (t, 2H), 4.00–4.25 (m, 4H), 5.35 (s, 2H), 6.05 (s, 1H), 6.80–7.05 (m, 6H), 7.20–7.30 (m, 2H), 7.40–7.50 ( d, 1H), 8.15–8.20 ( d, 1H).

Step C: Preparation of 3-[4-(1-carboxy)-1-(2-ethoxyphenyl)methoxyphenyl]methyl-7-methyl-2-propyl-3H-imidazo[4,5-b]pyridine Using the general procedure for ester hydrolysis described in Step E of Example 19, 0.107 g (0.22 mmol) of the product of Step B was converted to 0.087 g (86%) of the title compound.

¹H NMR (300 MHz, CD₃OD, ppm): δ0.90–1.00 (t, 3H), 1.35–1.45 (t, 3H), 1.50–1.65 (m, 2H), 2.70 (s, 3H), 2.80–2.90 (t, 2H), 4.05–4.20 (m, 2H), 5.50 (s, 2H), 6.05 (s, 1H), 6.90–7.05 (m, 3H), 7.05–7.10 (m, 3H), 7.15–7.20 (d, 1H), 7.25–7.35 (t, 1H), 7.45–7.50 (d, 1H), 8.20–8.25 (d, 1H). FAB-MS: m/e 460 (M+1).

EXAMPLE 20

3-[4-(1-Carboxy-1-(2-(1-hexyloxy)phenyl))methoxyphenyl]methyl-7-methyl-2-propyl-3H-imidazo[4,5-b]pyridine Step A: Preparation of ethyl 2-bromo-2-(2-(1-hexyloxy)phenyl)acetate Using the general procedure for the synthesis of 2-bromophenylacetic esters from benzaldehydes (Steps A-C, Example 18), 0.50 g (2.43 mmol) of -hexyloxybenzaldehyde was converted to 0.088 g (0.26 retool) Of the title compound in 11% overall yield.

¹H NMR(300 MHz, CDCl₃, ppm): δ0.85–0.95 (t, 3H), 1.20–1.5 5 (m, 9H), 1.75–1.85 (m, 2H), 3.95–4.05 (t, 2H), 4.1 5–4.30 (m, 2H), 5.85 (s, 1H), 6.80–6.85 (d, 1H), 6.9 0–7.00 (t, 3H), 7.20–7.30 (t, 1H), 7.55–7.65 (d, 1H).

Step B: Preparation of 3-[4-(1-carbomethoxy)-1-(2-(1-hexyloxy)phenyl)methoxyphenyl]methyl-7-methyl-2-propyl-3H-imidazo[4,5-b]pyridine Using the general procedure for the alkylation reaction described in Step D of Example 18, 0.065 g (0.23 mmol) of 3-(4-hydroxyphenyl)methyl-7-methyl-2-propyl-3H-imidazo[4,5-b]pyridine (Example 2, Step D) was alkylated with 0.088 g (0.25 mmol) of the product of Step A, to afford 0.090 g (71%) of the title compound.

¹H NMR (300 MHz, CDCl₃, ppm): d 0.80–0.90 (t, 3H), 0.90–1.00 ( t, 3H), 1.15–1.50 (m, 9H), 1.65–1.80 (m, 4H), 2.65 (s, 3H), 2.70–2.80 (t, 2H), 3.95–4.05 (t, 2H), 4.05–4.25 (m, 2H), 5.35 (s, 2H), 6.05 (s, 1H), 6.80–7.05 (m, 6H), 7.20–7.30 (m, 2H), 7.40–7.45 (d, 1H), 8.15–8.20 (d, 1H).

Step C: Preparation of 3-[4-(1-carboxy)-1-(2-(1-hexyloxy)phenyl)methoxyphenyl]methyl-7-methyl-2-propyl-3H-imidazo[4,5-b]pyridine Using the general procedure for ester hydrolysis described in Step E of Example 19, 0.090 g (0.17 mmol) of the product of Step B was converted to 0.072 g (85%) of the title compound.

¹H NMR (300 MHz, CDCl₃, ppm): δ0.80–0.90 (t, 3H), 0.90–1.00 (t, 3H), 1.20–1.35 (m, 4H), 1.50–1.60 (m, 2H), 1.60–1.8.5 (m, 2H), 2.65 (s, 3H), 2.80–2.90 (t, 2H), 3.95–4.05 (m, 2H), 5.50 (s, 2H), 6.05 (s, 1H), 6.90–7.05 (m, 4H), 7.05–7.15 (d, 2H), 7.15–7.20 (d, 1H), 7.25–7.35

(t, 1H), 7.40–7.45 (d, 1H), 8.20–8.25 (d, 1H). FAB-MS: m/e 516 (M+1).

EXAMPLE 21

3-[4-(1-Carboxy-1-(2-methoxyphenyl))methoxyphenyl]-methyl-7-methyl-2-propyl-3H-imidazo[4,5-b]pyridine Step A: Preparation of ethyl 2-bromo-2-(2-methoxyphenyl)acetate Using the general procedure for the synthesis of 2-bromophenylacetic esters from benzaldehydes (Steps A–C, Example 18), 1.00 g (7.35 mmol) of 2-methoxybenzaldehyde was converted to 0.736 g (2.69 mmol) of the title compound in 37% overall yield.

$^1$H NMR (300 MHz, CDCl$_3$, ppm): δ1.20–1.30 (t, 3H), 3.85 (s, 3H), 4.15–4.30 (m, 2H), 5.85 (s, 1H), 6.80–6.90 (d, 1H), 6.90–7.00 (t, 1H), 7.25–7.35 (t, 1H), 7.55–7.65 (d, 1H).

Step B: Preparation of 3-[4-(1-carbomethoxy)-1-(2-methoxyphenyl)methoxyphenyl]methyl-7-methyl-2-propyl-3H-imidazo[4,5-b]pyridine Using the general procedure for the alkylation reaction described in Step D of Example 18, 0.090 g (0.32 mmol) of 3-(4-hydroxyphenyl)methyl-7-methyl-2-propyl-3H-imidazo[4,5-b]pyridine (Example 2, Step D) was alkylated with 0.096 g (0.35 mmol) of the product of Step A, to afford 0.126 g (83%) of the title compound.

$^1$H NMR (300 MHz, CDCl$_3$, ppm): δ0.90–1.00 (t, 3H), 1.15–1.25 (m, 3H), 1.65–1.80 (m, 2H), 2.65 (s, 3H), 2.70–2.80 (t, 2H), 4.05–4.25 (m, 2H), 5.35 (s, 2H), 6.05 (s, 1H), 6.80–7.05 (m, 7H), 7.25–7.35 (m, 1H), 7.45–7.50 (d, 1H), 8.15–8.20 (d, 1H). FAB-MS: m/e 474 (M+1).

Step C: Preparation of 3-[4-(1-carboxy)-1-(2-methoxyphenyl)methoxyphenyl]methyl-7-methyl-2-propyl-3H-imidazo[4,5-b]pyridine Using the general procedure for ester hydrolysis described in Step E of Example 19, 0.123 g (0.26 mmol) of the product of Step E was converted to 0.095 g (82%) of the title compound.

$^1$H NMR (3.00 MHz, CD$_3$OD, ppm): δ0.90–1.00 (t, 3H), 1.60–1.80 (m, 2H), 2.60 (s, 3H), 2.80–2.90 (t, 2H), 3.90 (s, 3H), 5.50 (s, 2H), 6.00 (s, 1H), 5.90–7.15 (m, 6H), 7.15–7.20 (d, 1H), 7.20–7.25 (t, 1H), 7.45–7.55 (d, 1H), 8.20–8.25 (d, 1H). FAB-MS: m/e 446 (M+1).

EXAMPLE 22

3-[4-(1-Carboxy-1-(naphth-1-yl))methoxyphenyl]methyl-7-methyl-2-propyl-3H-imidazo[4,5-b]pyridine Step A: Preparation of ethyl 2-bromo-2-(naphth-1-yl)acetate Using the general procedure for the synthesis of 2-bromophenylacetic esters from benzaldehydes (Steps A–C, Example 18), 1.00 g (6.40 mmol) of 1-naphthaldehyde was converted to 0.694 g (2.69 mmol) of the title compound in 37% overall yield.

$^1$H NMR (300 MHz, CDCl$_3$, ppm) δ1.20–1.30 (t, 3H), 4.15–4.35 (m, 2H), 6.15 (s, 1H), 7.40–7.65 (m, 3H), 7.75–7.95 (m, 3H), 8.05–8.15 (d, 1H). EI-MS: m/e 292, 294 (M+, 1:1 ratio).

Step B: Preparation of 3-[4-(1-carbomethoxy-1-(naphth-1-yl))methoxyphenyl]methyl-7-methyl-2-propyl-3H-imidazo[4,5-b]pyridine Using the general procedure for the alkylation reaction described in Step D of Example 18, 0.090 g (0.32 mmol) of 3-(4-hydroxyphenyl)methyl-7-methyl-2-propyl-3H-imidazo[4,5-b]pyridine (Example 2, Step D) was alkylated with 0.103 g (0.35 mmol) of the product of Step A, to afford 0.132 g (84%) of the title compound.

$^1$H NMR (300 MHz, CDCl$_3$, ppm) δ 0.85–0.95 (t, 3H), 1.05–1.15 (t, 3H), 1.60–1.80 (m, 2H), 3.65 (s, 3H), 3.70–3.80 (t, 2H), 4.05–4.25 (m, 2H), 5.35 (s, 2H), 6.20 (s, 1H), 6.80–6.90 (d, 2H), 6.95–7.05 (m, 3H), 7.40–7.60 (m, 3H), 7.65–7.75 (d, 1H), 7.80–7.90 (m, 2H), 8.15–8.20 (d, 2H), 8.20–8.30 (d, 1H). FAB-MS: m/e 494 (M+1).

Step C: Preparation of 3-[4-(1-carboxy-1-(naphth-1-yl))methoxyphenyl]methyl-7-methyl-2-propyl-3H-imidazo[4,5-b]pyridine Using the general procedure for ester hydrolysis described in Step E of Example 19, 0.125 g (0.25 mmol) of the product of Step B was converted to 0.108 g (91%) of the title compound.

$^1$H NMR (300 MHz, CD$_3$OD, ppm): δ0.90–1.00 (t, 3H), 1.50–1.75 (m, 2H), 2.70 (s, 3H), 2.80–2.90 (t, 2H), 6.50 (s, 2H), 6.20 (s, 1H), 6.95–7.05 (d, 2H), 7.05–7.15 (d, 2H), 7.15–7.20 (d, 1H), 7.45–7.55 (m, 3H), 7.80–7.95 (m, 2H), 8.15–8.25 (d, 1H), 8.35–8.45 (d, 1H). FAB-MS: m/e 466 (M+1).

EXAMPLE 23

3-[4-(1-Carboxy-1-(3-methylnaphth-2-yl))methoxyphenyl]methyl-7-methyl-2-propyl-3H-imidazo[4,5-b]pyridine Step A: Preparation of ethyl 2-bromo-2-(3-methylnaphth-2-yl)acetate Using the general procedure for the synthesis of 2-bromophenylacetic esters from benzaldehydes (Steps A–C. Example 18), 1.00 g (5.88 mmol) of 3-methyl-2-naphthaldehyde was converted to 0.953 g (3.10 mmol) of the title compound in 53% overall yield.

$_1$H NMR (300 MHz, CDCl$_3$, ppm): δ1.20–1.30 (t, 3H), 2.55 (s. 3H), 4.20–4.40 (m, 2H), 5.60 (s, 1H), 7.40–7.50 (m, 2H), 7.65 (s, 1H), 7.70–7.75 (d, 2H), 7.75–7.85 (d, 1H), 8.10 (s, 1H). EI-MS: m/e 306, 308 (M+, 1:1 ratio).

Step B: Preparation of 3-[4-(1-carbomethoxy-1-(3-methylnaphth-2-yl))methoxyphenyl]methyl-7-methyl-2-propyl-3H-imidazo[4,5-b]pyridine Using the general procedure for the alkylation reaction described in Step D of Example 18, 0. 090 g (0.32 mmol) of 3-(4-hydroxyphenyl)methyl-7-methyl-2-propyl-3H-imidazo[4,5-b]pyridine (Example 2, Step D) was alkylated with 0.108 g (0.35 mmol) of the product of Step A, to afford 0.121 g (75%) of the title compound.

$^1$H NMR (300 MHz, CDCl$_3$, ppm): δ0.85–0.95 (t, 3H), 1.15–1.25 (m, 2H), 1.65–1.75 (m, 2It), 2.60 (s, 3H), 2.65 (s, 3H), 2.70–2.80 (t, 2H), 4.05–4.30 (m, 2H), 5.40 (s, 2H), 5.85 (s, 1H), 6.80–6.90 (d, 2H), 6.95–7.05 (m, 3H), 7.35–7.45 (m, 2H), 7.65 (s, 1H), 7.70–7.80 (m, 2H), 8.00 (s, 1H), 8.15–8.20 (d, 1H). FAB-MS: m/e 508 (M+1).

Step C: Preparation of 3-[4-(1-carboxy-1-(3-methylnaphth-2-yl))methoxyphenyl]methyl-7-methyl-2-propyl-3H-imidazo[4,5-b]pyridine Using the general procedure for ester hydrolysis described in Step E of Example 19, 0,090 g (0.32 mmol) of the product of Step B was converted to 121 g (75%) of the title compound $^1$H NMR (300 MHz, CD$_3$OD, ppm): δ0.85–0.95 (t, 3H), 1.60–1.75 (m, 2H), 2.60 (s, 3H), 2.54 (s, 3H), 2.80–2.90 (t, 2H), 5.50 (s, 2H), 5.85 (s, 1H), 6.95–7.05 (d, 2H), 7.05–7.15 (d, 2H), 7.35–7.50 (m, 2H), 7.65 (s, 1H), 7.75–7.85 (t, 2H), 8.00 (s, 1H), 8.15–8.25 (d, 1H). FAB-MS: m/e

EXAMPLE 24

3-[4-(1-Carboxy-1-(2-methylphenyl))methoxyphenyl]-methyl-5,7-dimethyl-2-ethyl-3H-imidazo[4,5-b]pyridine Step A: Preparation of 2-nitramino-4,6-dimethylpyridine 2-Amino-4,6-dimethylpyridine (10.0 g, 81.8 mmol) was added portion-wise to 65 mL of $H_2SO_4$ (conc. d=1.84) which was stirred (mechanical) at 0° C. After complete addition, the mixture was warmed to room temperature until the mixture became homogeneous. The solution was then cooled to −10° C. and a precooled (0° C.) mixture of conc $HNO_3$ (11.5 mL, d=1.40) and $H_2SO_4$ (8.2 mL, d=1.84) was added at such a rate as not to raise the internal reaction temperature above −9° C. Ten minutes after the addition was complete this cooled (−10° C.) mixture was poured onto 400 g of crushed ice. The resulting slurry was neutralized by the addition of conc $NH_4OH$ (to pH 5.5) while cooling (ice bath). The solid was isolated by filtration, and dried at room temperature to give 13.3 g of the title compound as a white solid.

Step B: Preparation of 2-amino-3-nitro-4,6-dimethylpyridine

To 75 mL of stirred conc $H_2SO_4$ cooled to −5° C. (ice-salt bath) was added 4,6-dimethyl-2-nitraminopyridine (13.2 g, 79 mmol) portion-wise at such a rate as to maintain the internal temperature below −3° C. The mixture was warmed to 0° C. until homogeneous (30 minutes) at which time tlc ($SiO_2$, 1:1 EtOAc/hexanes on a $NH_4OH$ neutralized aliquot) indicated that the rearrangement was complete. The mixture was poured onto 400 g of crushed ice and the pH was adjusted to 5.5 by the addition of conc $NH_4OH$. The resulting yellow slurry was cooled to 0° C., filtered, washed with cold water (50 mL), and dried at room temperature to give 10.32 g of a mixture of the title compound and the 5-nitro isomer in a 55:45 ratio (determined by $^1H$ NMR). This mixture was used directly in the next step.

Step C: Preparation of 5,7-dimethyl-2-ethylimidazo [4,5-b]pyridine

To a mixture of 8.44 g of a 55:45 mixture of 2-amino-3-nitro-4,6-dimethylpyridine and 2-amino-5-nitro-4,6-dimethylpyridine in MeOH (1.2 L) was added 10% Pd/C (2.4 g). The reaction vessel was evacuated then purged with $H_2$ at 1 atm. and stirred vigorously for 18 h. Filtration through a celite pad, and concentration gave 6.65 g of a mixture of 2,3-diamino-4,6-dimethylpyridine and 2,5-diamino-4,6-dimethylpyridine as a dark solid. To 5.40 g (39.4 mmol) of this mixture was added propionic acid (8.80 mL, 118 mmol) followed by polyphosphoric acid (100 mL). This stirred mixture was heated to 90° C. for 3 h then to 100° C. for 1 hour. The inside walls of the flask were scraped with a spatula to assist dissolution of the solids. After the reaction was complete, the warm mixture was poured onto 300 g of ice and the mixture was made basic. with $NH_4OH$. The mixture was extracted (4×50 mL $CH_2Cl_2$), dried ($K_2CO_3$) and concentrated to give a mixture of the title compound and 4,6-dimethyl-2,5-bis(propionamido)pyridine. Purification ($SiO_2$, 5% MeOH/EtOAc) gave 1.66 g of the title compound as the slower eluting component.

$^1H$ NMR ($CD_3OD$, 300 MHz, ppm): δ6.95 (s, 1H), 2.92 (q, J=7.8 Hz, 2H), 2.54 (apparent s, 6H), 1.40 (t, J=7.8 Hz, 3H).

Step D: Preparation of 3-(4-(benzyloxy)phenyl)methyl-5,7-dimethyl-2-ethyl-3H-imidazo [4,5-b]pyridine To a suspension of 0.503 g (12.5 mmol) of a 60% oil dispersion of sodium hydride in 20 mL of DMF was added 2.0 g (11.4 mmol) of the product of Step C and the mixture was stirred at room temperature. After 25 minutes, 2.92 g (12.5 mmol) of 4-benzyloxybenzyl chloride and a catalytic amount of sodium iodide were added and the reaction was stirred for an additional 4 hours. The reaction mixture was then partitioned between ethyl acetate and water. The organic layer was separated, washed with water, brine, dried ($MgSO_4$), filtered and evaporated. The residual oil was purified on a silica gel flash chromatography column eluted with 30% ethyl acetate/hexane to afford 3.33 g (79%) of the title compound.

$^1H$ NMR (300 MHz, $CDCl_3$, ppm): δ1.20–1.30 (t, 3H), 2.55 (s, 3H), 2.60 (s, 3H), 2.70–2.80 (m, 2H), 5.00 (s, 2H), 5.35 (s, 2H), 6.80–6.90 (m, 3H), 7.00–7.10 (d, 2H), 7.21–7.45 (m, 5H). FAB-MS: m/e 372 (M+1).

Step E: Preparation of 5,7-dimethyl-2-ethyl-3-(4-hydroxyphenyl)methyl-3H-imidazo[4,5-b]pyridine A solution of 1.40 g (3.77 mmol) of the product of Step D dissolved in 38 mL of methanol was placed in a Parr hydrogenation flask and 0.140 g of 10% Pd/C catalyst was added. The reaction mixture was placed in a Parr apparatus and rocked under a hydrogen atmosphere (32 psig) for 2 hours. The reaction mixture was then filtered through a plug of silica gel eluted with 20% methanol/chloroform to remove the catalyst. Evaporation of the filtrate and drying in vacuo afforded 0.650 g (61%) of the title compound.

$^1H$ NMR (300 MHz, $CDCl_3$, ppm): δ1.20–1.30 (t, 3H), 3.64 (s, 3H), 3.66 (s, 3H), 2.85–2.95 (m, 2H), 5.45 (s, 2H), 6.70–6.80 (d, 2H), 6.95–7.05 (m, 3H). FAB-MS: m/e 282 (M+1).

Step F: Preparation of 3-[4-(1-carboethoxy-1-(2-methylphenyl)methoxyphenyl]methyl-5,7-dimethyl-2-ethyl-3H-imidazo[4,5-b]pyridine To a suspension of 0.108 g (0.94 mmol) of potassium hydride in 2 mL of DMF was added 0.264 g (0.94 mmol) of the product of Step E and the reaction mixture was stirred under an $N_2$ atmosphere. After 10 minutes, 0.248 g (0.94 mmol) of 18-crown-6 and a solution of 0.266 g (1.03 mmol) of ethyl 2-bromo-2-(2-methylphenyl)acetate (Example 18, Step C) dissolved in 1 mL DMF were added and the reaction was then stirred an additional 15 minutes. The reaction mixture was then partitioned between ethyl acetate and water. The organic layer was separated, washed with water, brine, dried ($MgSO_4$), filtered and evaporated. The residual oil was purified on a silica gel flash chromatography column eluted with 40% ethyl acetate/hexane to afford 0.338 g (79%) of the title compound.

$^1H$ NMR (300 MHz, $CDCl_3$, ppm): δ1.10–1.20 (t, 3H), 1.20–1.30 (t, 3H), 2.45 (s, 3H), 2.55 (s, 3H), 2.60 (s, 3H), 2.70–2.80 (m, 2H), 4.05–4.25 (m, 2H), 5.35 (s, 2H), 5.70 (s, 1H), 6.75–6.85 (d, 2H), 6.88 (s, 1H), 6.95–7.05 (d, 2H) 7.15–7.25 (m, 3H), 7.45–7.55 (d, 1H). FAB-MS: m/e 458 (M+1).

Step G: Preparation of 3-[4-(1-carboxy-1-(2-methylphenyl)methoxyphenyl]methyl-5,7-dimethyl-2-ethyl-3H-imidazo[4,5-b]pyridine Using the general procedure for ester hydrolysis described in Step E of Example 19, 0.060 g (0.13 mmol) of the product of Step F was converted to 0.054 g (96%) of the title compound.

$^1$H NMR (300 MHz, CD$_3$OD, ppm): δ1.20–1.30 (t, 3H), 2.50 (s, 3H), 2.60 (s, 3H), 2.65 (s, 3H), 2.85–2.95 (m, 2H), 5.50 (s, 2H), 5.85 (s, 1H), 6.90–7.00 (d, 2H), 7.05–7.15 (m, 3H), 7.15–7.25 (m, 3H), 7.50–7.55 (d, 1H). FAB-MS: m/e 430 (M+1).

EXAMPLE 25

3-[4-(1-Carboxy-1-(2-chlorophenyl))methoxyphenyl]-methyl-5,7-dimethyl-2-ethyl-3H-imidazo[4,5-b]pyridine Step A: Preparation of 3-[4-(1-carboethoxy-1-(2-chlorophenyl)methoxyphenyl]methyl-5,7-dimethyl-2-ethyl-3H-imidazo[4,5-b]pyridine Using the procedure described in Step F of Example 24, 0.050 g (0.18 mmol) of 5,7-dimethyl-2-ethyl-3-(4-hydroxyphenyl)methyl-3H-imidazo[4,5-b]pyridine (Example 24, Step E) was alkylated with 0.052 g (0.20 mmol) of methyl 2-bromo-(2'-chloro)phenylacetate (Example 4, Step A) to afford 0.053 g (64%) of the title compound.

Step B: Preparation of 3-[4-(1-carboxy-1-(2-chlorophenyl)methoxyphenyl]methyl-5,7-dimethyl-2-ethyl-3H-imidazo[4,5-b]pyridine Using the general procedure for ester hydrolysis described in Step E of Example 19, 0.048 g (0.10 mmol) of the product of Step A was converted to 0.036 g (78%) of the title compound.

$^1$H NMR (300 MHz, CD$_3$OD, ppm): δ1.20–1.30 (t, 3H), 2.60 (s, 3H), 2.63 (s, 3H), 2.85–2.95 (m, 2H), 5.50 (s, 2H), 6.05 (s, 1H), 6.90–7.00 (d, 2H), 7.05–7.15 (m, 3H), 7.30–7.40 (m, 2H), 7.40–7.50 (m, 1H), 7.60–7.65 (m, 1H). FAB-MS: m/e 4.50, 452 (M+1, 3:1 ratio).

EXAMPLE 26

3-[4-(1-Carboxy-1-(2-bromophenyl))methoxyphenyl]-methyl-5,7-dimethyl-2-ethyl-3H-imidazo[4,5-b]pyridine Step A: Preparation of methyl 2-bromo-2-(2-bromophenyl)acetate Commercially available 2-bromophenylacetic acid (5.00 g, 23.3 mmol) was converted to 4.89 g (68%) of the title compound in a procedure similar to that described in Step A of Example 3.

$^1$H NMR (300 MHz, CDCl$_3$, ppm): δ3.80 (s, 3H), 5.90 (s, 1H), 7.15–7.20 (t, 1H), 7.20–7.25 (t, 1H), 7.50–7.55 (d, 1H), 7.70–7.75 (d, 1H). FAB-MS: m/e 306, 308,310 (M+1, 1:2:1 ratio).

Step B: Preparation of 3-[4-(1-carbomethoxy-1-(2-bromophenyl)methoxyphenyl]methyl-5,7-dimethyl-2-ethyl-3H-imidazo[4,5-b]pyridine Using the procedure described in Step F of Example 24, 0.050 g (0.18 mmol) of 5,7-dimethyl-2-ethyl-3-(4-hydroxyphenyl)methyl-3H-imidazo[4,5-b]pyridine (Example 24, Step E) was alkylated with 0.060 g (0.20 mmol) of the product of Step A to afford 0.077 g (85%) of the title compound.

$^1$H NMR (300 MHz, CDCl$_3$, ppm): δ1.20–1.30 (t, 3H), 2.55 (s, 3H), 2.60 (s, 3H), 2.65–2.75 (m, 2H), 3.75 (s, 3H), 5.35 (s, 2H), 6.05 (s, 1H), 6.80–6.90 (m, 3H), 6.95–7.05 (d, 2H), 7.15–7.35 (m, 2H), 7.50–7.60 (d, 2H). FAB-MS: m/e 508, 510 (M+1, 1:1 ratio).

Step C: Preparation of 3-[4-(1-carboxy-1-(2-bromophenyl)methoxyphenyl]methyl-5,7-dimethyl-2-ethyl-3H-imidazo[4,5-b]pyridine Using the general procedure for ester hydrolysis described in Step E of Example 19, 0.077 g (0.15 mmol) of the product of Step B was converted to 0.065 g (86%) of the title compound.

$^1$H NMR (300 MHz, CD$_3$OD, ppm): δ1.20–1.30 (t, 3H), 2.64 (s, 3H), 2.66 (s, 3H), 2.85–2.95 (m, 2H), 5.50 (s, 2H), 5.95 (s, 1H), 6.90–7.00 (d, 2H), 7.05–7.15 (m, 3H), 7.20–7.30 (t, 1H), 7.30–7.40 (t, 1H), 7.60–7.70 (m, 2H). FAB-MS: m/e 494, 496 (M+1, 1:1 ratio).

EXAMPLE 27

3-[4-(1-Carboxy-1-phenyl)methoxyphenyl]methyl-5,7-dimethyl-2-ethyl-3H-imidazo[4,5-b]pyridine Step A: Preparation of methyl 2-(4-bromomethylphenoxy)-2-phenylacetate To a solution of 0.710 g (2.77 mmol) of methyl 2-(4-methylphenoxy)phenylacetate (Step A of Example 13) dissolved in 10 mL of CCl$_4$, was added 0.494 g (2.77 mmol) of N-bromosuccinimide, and 25 mg of AIBN (catalytic amount). The mixture was stirred and heated to reflux for 4 hours, then cooled to room temperature and concentrated in vacuo. The residue was purified on a silica gel flash chromatography column (25×170 mm) eluted with 5% ethyl acetate/hexane to afford 0.509 g (55%) of the title compound.

$^1$H NMR (300 MHz, CDCl$_3$, ppm): δ3.75 (s, 3H), 4.5 (s, 2H), 5.65 (s, 1H), 6.9–7.0 (d, 2H), 7.3–7.35 (d, 2H), 7.35–7.5 (m, 3H), 7.5–7.6 (d, 2H). EI-MS: m/e 334, 336 (M+, 1:1 ratio).

Step B: Preparation of 3-[4-(1-carbomethoxy-1-phenyl)methoxyphenyl]methyl-5,7-dimethyl-2-ethyl-3H-imidazo[4,5-b]pyridine To a suspension of 12 mg of a 60% oil dispersion of sodium hydride in 1 mL of DMF was added 0.050 g (0.29 mmol) of 5,7-dimethyl-2-ethylimidazo [4,5-b]pyridine (Example 24, Step C) and the mixture was stirred at room temperature under an N$_2$ atmosphere. After 15 minutes, a solution of 0.105 g (0.32 mmol) of the product of Step A dissolved in 1 mL of DMF was added and the reaction was stirred an additional 75 minutes. The mixture was then concentrated in vacuo and purified on a silica gel flash chromatography column eluted with 50% ethyl acetate/hexane to afford 0.068 g (55%) of the title compound.

$^1$H NMR (300 MHz, CDCl$_3$, ppm): δ1.20–1.30 (t, 3H), 2.55 (s, 3H), 2.60 (s, 3H), 2.70–2.80 (m, 2H), 3.70 (s, 3H), 5.35 (s, 2H), 5.55 (s, 1H), 6.80–6.90 (m, 3H), 7.00–7.05 (d, 2H), 7.25–7.45 (m, 3H), 7.45–7.55 (m, 2H). FAB-MS: m/e 430 (M+1).

Step C: Preparation of 3-[4-(1-carboxy-1-phenyl)methoxyphenyl]methyl-5,7-dimethyl-2-ethyl-3H-imidazo[4,5-b]pyridine Using the general procedure for ester hydrolysis described in Step E of Example 19, 0.065 g (0.15 mmol) of the product of Step B was converted to 0.044 g (70%) of the title compound.

$^1$H NMR (300 MHz, CD$_3$OD, ppm): δ1.20–1.30 (t, 3H), 3.60 (s, 3H), 3.65 (s, 3H), 2.85–2.95 (m, 2H), 5.50 (s, 2H), 5.65 (s, 1H), 6.90–7.00 (d, 2H), 7.05–7.15 (m, 3H), 7.35–7.45 (m, 3H), 7.55–7.65 (m, 2H). FAB-MS: m/e 416 (M+1).

EXAMPLE 28

3-[3-Chloro-4-((1-carboxy-1-phenyl)methoxy)phenyl]-methyl-7-methyl-2-propyl-3H-imidazo[4,5-b]pyridine Step A: Preparation of methyl 2-(2-chloro-4-methylphenoxy)-2-phenylacetate To a suspension of 0.282 g (7.04 mmol) of a 60% oil dispersion of sodium hydride in DMF was added 1.00 g (7.04 mmol) of 2-chloro-4-methylphenol and the mixture was stirred under an N$_2$ atmosphere at room temperature. After 10 minutes, a solution of 1.94 g (8.45 mmol) of methyl 2-bromophenylacetate dissolved in 10 mL of DMF was added and the reaction was stirred an additional 1.5 hours. The reaction was then diluted into ethyl acetate, washed with water, dried (MgSO$_4$), filtered and evaporated. The residue was purified on a silica gel flash chromatography column eluted with 4% ethyl acetate/hexane to afford 1.70 g (83%) of the title compound.

$^1$H NMR (300 MHz, CDCl$_3$, ppm): δ2.20 (s, 3H), 3.70 (s, 3H), 5.60 (s, 1H), 6.70–6.80 (d, 1H), 6.85–6.95 (d, 1H), 7.20 (br s, 1H), 7.20–7.30 (m, 3H), 7.55–7.65 (m, 2H). EI-MS: m/e 290 (M+).

Step B: Preparation of methyl 2-(2-chloro-4-bromomethylphenoxy)-2-phenylacetate

To a solution of 1.70 g (5.86 mmol) of the product from Step A dissolved in 20 mL of CCl$_4$ was added 1.04 g (5.86 mmol) of N-bromosuccinimide and 50 mg (catalytic amount) of AIBN. The reaction mixture was stirred and heated at reflux for 7 hours, then an additional 0.20 g of NBS was added. The reaction was refluxed for 48 hours, then cooled and concentrated in vacuo. The residue was purified on a silica flash chromatography column eluted with 10% ethyl acetate/hexane to afford 0.730 g (34%) of the title compound.

$^1$H NMR (300 MHz, CDCl$_3$, ppm): δ3.70 (s, 3H), 4.40 (s, 2H), 5.65 (s, 1H), 6.75–6.85 (d, 1H), 7.10–7.20 (d, 1H), 7.30–7.45 (m, 4H), 7.55–7.65 (m, 2H). FAB-MS: m/e 3.69 (M+1).

Step C: Preparation of 3-[3-chloro-4-((1-carbomethoxy-1-phenyl)methoxy)phenyl]methyl-7-methyl-2-propyl-3H-imidazo[4,5-b]pyridine The product of Step B (0.127 g, 0.34 mmol) was used to alkylate 0.050 g (0.29 mmol) of 7-methyl-2-propylimidazo[4,5-b]pyridine (Example 2, Step H) according to the procedure described for Step D of Example 3, which after purification afforded 0.059 (45%) of the title compound.

$^1$H NMR (300 MHz, CDCl$_3$, ppm): δ0.90–1.00 (t, 3H), 1.65–1.80 (m, 2H), 2.65 (s, 3H), 2.65–2.80 (t, 2H), 3.70 (s, 3H), 5.35 (s, 2H), 5.60 (s, 1H), 6.70–6.75 (d, 1H), 6.85–6.95 (d, 1H), 7.00–7.05 (d, 1H), 7.20 (br s, 1H), 7.30–7.45 (m, 3H), 7.50–7.60 (m, 2H), 8.15–8.20 (d, 1H). FAB-MS: m/e 464 (M+1).

Step D: Preparation of 3-[3-chloro-4-((1-carboxy-1-phenyl)methoxy)phenyl]methyl-7-methyl-2-propyl-3H-imidazo[4,5,b]pyridine Using the general procedure for ester hydrolysis described in Step E of Example 19, 0.059 g (0.13 mmol) of the product of Step C was converted to 0.040 g (70%) of the title compound.

$^1$H NMR (300 MHz, CD$_3$OD, ppm): δ0.90–1.00 (t, 3H), 1.65–1.80 (m, 2H), 2.70 (s, 3H), 2.85–2.95 (t, 2H), 5.50 (s, 2H), 5.75 (s, 1H), 6.95–7.10 (m, 2H), 7.15–7.20 (d, 1H), 7.25 (br s, 1H), 7.35–7.45 (m, 3H), 7.60–7.70 (m, 2H), 8.20–8.25 (d, 1H). FAB-MS: m/e 450 (M+1).

EXAMPLE 29

3-[3-Chloro-4-((1-carboxy-1-phenyl)methoxy)phenyl]methyl-5,7-dimethyl-2-ethyl-3H-imidazo[4,5-b]pyridine Preparation of 3-[3-chloro-4-((1-carbomethoxy-1-phenyl)methoxy )phenyl]methyl-5,7-dimethyl-2-ethyl-3H-imidazo[4,5-b ]pyridine The product of Example 28, Step B (0.127 g, 0.34 mmol) was used to alkylate 0. 050 g (0.29 mmol) of 5,7-dimethyl-2-ethylimidazo[4,5-b]pyridine (Example 24, Step C) according to the procedure described for Step B of Example 27, which after purification afforded 0.080 g (61%) of the title compound.

$^1$H NMR (300 MHz, CDCl$_3$, ppm): δ1.20–1.30 (t, 3H), 2.55 (s, 3H), 2.60 (s, 3H), 2.65–2.80 (m, 2H), 3.70 (s, 3H), 5.35 (s, 2H), 5.60 (s, 1H), 6.80–6.85 (d, 1H), 6.85–6.95 (m, 2H), 7.20–7.25 (d, 1H), 7.30–7.45 (m, 3H), 7.50–7.60 (m, 2H). FAB-MS: m/e 464 (M+1).

Step B: Preparation of 3-[3-chloro-4-((1-carboxy-1-phenyl)methoxy)phenyl]methyl-5,7-dimethyl-2-ethyl-3H-imidazo[4,5-b]pyridine Using the general procedure for ester hydrolysis described in Step E of Example 19, 0.080 (0.17 mmol) of the product of Step A was converted to 0.047 g (60%) of the title compound.

$^1$H NMR (300 MHz, CD$_3$OD, ppm): δ1.25–1.35 (t, 3H), 2.60 (s, 3H), 2.65 (s, 3H), 2.85–2.95 (m, 2H), 5.50 (s, 2H), 5.75 (s, 1H), 6.95–7.10 (m, 3H), 7.25 (s, 1H), 7.35–7.4.5 (m, 3H), 7.60–7.70 (m, 2H), FAB-MS: m/e 450 (M+1).

EXAMPLE 30

3-[3-Benzoyl-4-((1-carboxy-1-phenyl)methoxy )phenyl]methyl-5,7-dimethyl-2-ethyl-3H-imidazo[4,5-b]pyridine Step A: Preparation of methyl 2-(2-benzoyl-4-methylphenoxy)-2-phenylacetate To a solution of 1.00 g (4.72 mmol) of 2-hydroxy-5-methylbenzophenone and 1.19 g (5.19 mmol) of methyl 2-bromophenylacetate in 10 mL of acetone was added 1.30 g (9.44 mmol) of K$_2$CO$_3$ and the mixture was stirred and refluxed for 14 hours. The mixture was cooled, filtered and evaporated in vacuo and the residue was purified on a silica gel flash chromatography column eluted with 5% ethyl acetate/hexane to afford 0.320 g (19%) of the title compound.

$^1$H NMR (300 MHz, CDCl$_3$, ppm): δ2.30 (s, 3H), 3.60 (s, 3H), 5.50 (s, 1H), 6.65–6.75 (d, 1H), 6.90–7.00 (d, 2H), 7.10–7.25 (m, 4H), 7.30 (s, 1H), 7.40–7.50 (m, 2H), 7.50–7.55 (m, 1H), 7.80–7.90 (m, 2H). FAB-MS: m/e 361 (M+1).

Step B: Preparation of methyl 2-(2-benzoyl-4-bromomethylphenoxy)-2-phenylacetate To a solution of 0.314 g (0.87 mmol) of the product of Step A dissolved in 10 mL of CCl$_4$ was added 0.155 g (0.87 mmol) of N-bromosuccinimide and 15 mg (catalytic amount) of AIBN. The mixture was stirred at reflux for 7 hours, then cooled filtered and evaporated in vacuo. The residue was purified on a silica gel flash chromatography column eluted with 15% ethyl acetate/hexane to afford 0.136 g (36%) of the title compound.

$^1$H NMR (300 MHz, CDCl$_3$, ppm): δ3.65 (s, 3H), 4.50 (s, 2H), 5.55 (s, 1H), 6.75–6.85 (d, 1H) 6.90–7.00 (d, 2H), 7.10–7.25 (m, 4H), 7.40–7.60 (m, 4H), 7.80–7.90 (d, 2H). FAB-MS: m/e 440 (M+1).

Step C: Preparation of 3-[3-benzoyl-4-((1-carbomethoxy-1-phenyl)methoxy)phenyl]methyl-5,7-dimethyl-2-ethyl-3H-imidazo[4,5-b]pyridine The product of Step B (0.136 g, 0.31 mmol) was used to alkylate 0.049 g (0.28 mmol) of 5,7-dimethyl-2-ethylimidazo[4,5-b]pyridine (Example 4, Step C) according to the procedure described for Step B of Example 27, which after purification afforded 0.066 g (44%) of the title compound.

$^1$H NMR (300 MHz, CDCl$_3$, ppm): δ1.20–1.30 (t, 3H), 2.50 (s, 3H), 2.55 (s, 3H), 2.65–2.80 (m, 2H), 3.80 (s, 3H), 5.30 (s, 3H), 6.80–7.30 (m, 14H). FAB-MS: m/e 534 (M+1).

Step D: Preparation of 3-[3-benzoyl-4-((1-carboxy-1-phenyl)methoxy)phenyl]methyl-5,7-dimethyl-2-ethyl-3H-imidazo[4,5-b]pyridine Using the general procedure for ester hydrolysis described in Step E of Example 19, 0.060 g (0.11 mmol) of the product of Step C was converted to 0.031 g (53%) of the title compound.

$^1$H NMR (300 MHz, CD$_3$OD, ppm): δ1.20–1.30 (t, 3H), 2.55 (s, 3H), 2.60 (s, 3H), 2.70–2.80 (m, 2H), 5.50 (s, 3H), 6.85–7.35 (m, 14H). FAB-MS: m/e 520 (M+1).

EXAMPLE 31

3-[3-Acetyl-4-((1-carboxy-1-phenyl)methoxy)phenyl]-methyl-5,7-dimethyl-2-ethyl-3H-imidazo[4,5-b]pyridine Step A: Preparation of methyl 2-(2-acetyl-4-methylphenoxy)-2-phenylacetate Using the K$_2$CO$_3$/acetone conditions for phenol alkylation described in Step A of Example 30, 1.00 g (6.67 mmol) of 2'-hydroxy-5'-methylacetophenone was alkylated with 1.68 g (7.34 mmol) of methyl 2-bromophenylacetate to afford 1.25 g (63%) of the title compound.

$^1$H NMR (400 MHz, CDCl$_3$, ppm): δ2.25 (s, 3H), 2.70 (s, 3H), 3.70 (s, 3H), 5.70 (d, 1H), 6.65–6.75 (d, 1H), 7.10–7.20 (d, 1H), 7.30–7.45 (m, 4H), 7.50–7.60 (m, 2H). FAB-MS: m/e 299 (M+1).

Step D: Preparation of methyl 2-(2-acetyl-4-bromomethylphenoxy)-2-phenylacetate

To a solution of 1.25 g (4.19 mmol) of the product of Step A dissolved in 15 mL of CCl$_4$ was added 0.821 g (4.61 mmol) of N-bromosuccinimide and 20 mg (catalytic amount) of AIBN. The mixture was stirred at reflux for 3.5 hours, then cooled, filtered and evaporated in vacuo. The residue was purified on a silica gel flash chromatography column eluted with 15% ethyl acetate/hexane to afford 0.431 g (27%) yield of the title compound.

$^1$H NMR (400 MHz, CDCl$_3$, ppm): δ2.75 (s, 3H), 3.75 (s, 3H), 4.45 (s, 2H), 5.70 (s, 1H), 6.75–6.80 (d, 2H), 7.35–7.45 (m, 4H), 7.50–7.60 (m, 2H), 7.75 (s, 1H).

Step C: Preparation of 3-[3-acetyl-4-((1-carbomethoxy-1-phenyl)methoxy)phenyl]methyl-5,7-dimethyl-2-ethyl-3H-imidazo[4,5-b]pyridine The product of Step B (0.119 g, 0.31 mmol) was used to alkylate 0.050 g (0.28 mmol) of 5,7-dimethyl-2-ethylimidazo[4,5-b]pyridine (Example 24, Step C) according to the procedure described for Step B of Example 27, which after purification afforded 0.040 g (30%) of the title compound.

$^1$H NMR (400 MHz, CDCl$_3$, ppm): δ1.20 (s, 3H), 1.20–1.30 (t, 3H), 2.55 (s, 3H), 2.60 (s, 3H), 2.70–2.80 (m, 2H), 3.75 (s, 3H), 5.35 (s, 3H), 6.85 (s, 1H), 6.95–7.00 (d, 1H), 7.05–7.10 (s, 1H), 7.15 (s, 1H), 7.20–7.30 (m, 3H), 7.50–7.55 (m, 2H). FAB-MS: m/e 472 (M+1).

Step D: Preparation of 3-[3-acetyl-4-((1-carboxy-1-phenyl)methoxy)phenyl]methyl-5,7-dimethyl-2-ethyl-3H-imidazo[4,5-b]pyridine Using the general procedure for ester hydrolysis described in Step E of Example 19, 0.038 g (0.08 mmol) of the product of Step C was converted to 0.016 g (43%) of the title compound.

$^1$H NMR (400 MHz, CD$_3$OD, ppm): δ1.15 (s, 3H), 1.20–1.30 (t, 3H), 2.55 (s, 3H), 2.60 (s, 3H), 2.85–2.95 (m, 2H), 5.50 (s, 3H), 6.95–7.05 (m, 2H), 7.05 (s, 1H), 7.10 (s, 1H), 7.25–7.35 (m, 3H), 7.60–7.70 (m, 2H). FAB-MS: m/e 458 (M+1).

EXAMPLE 32

3-[4-((1-Carboxy-1-phenyl)methoxy)-3-methoxyphenyl]methyl-5,7-dimethyl-2-ethyl-3H-imidazo[4,5-b]pyridine Step A: Preparation of methyl 2-(4-hydroxymethyl-2-methoxyphenoxy)-2-phenylacetate Using the K$_2$CO$_3$/acetone conditions for phenol alkylation described in Step A of Example 30, 1.00 g (6.49 mmol) of 4-hydroxy-3-methoxybenzyl alcohol was alkylated with 1.64 g (7.14 mmol) of methyl 2-bromophenylacetate to afford 0.495 g (25%) of the title compound.

$^1$H NMR (300 MHz, CDCl$_3$, ppm): δ1.20–1.30 (t, 1H), 3.70 (s, 3H), 3.85 (s, 3H), 4.60 (d, 2H), 5.65 (s, 1H), 6.75–6.85 (m, 2H), 6.95 (s, 1H), 7.30–7.40 (m, 3H), 7.50–7.60 (m, 2H). FAB-MS: m/e 303 (M+1).

Step B: Preparation of methyl 2-(4-bromomethyl-2-methoxyphenoxy)-2-phenylacetate To a cooled (0° C.) solution of 0.490 g (1.62 mmol) of the product of Step A dissolved in 8 mL of CH$_2$Cl$_2$ was added 0.673 g (2.03 mmol) of carbon tetrabromide and 0.531 g (2.03 mmol) of triphenylphosphine. The reaction mixture was stirred for 1.5 hours and was allowed to slowly warm to room temperature. The reaction mixture was then concentrated in vacuo, and purified on a silica gel flash chromatography column eluted with 15% ethyl acetate/hexane to afford 0.478 g (81%) of the title compound.

$^1$H NMR (300 MHz, CDCl$_3$, ppm): δ3.75 (s, 3H), 3.85 (s, 3H), 4.40 (s, 2H), 5.60 (s, 1H), 6.75–6.85 (m, 2H), 6.90 (s, 1H), 7.30–7.40 (m, 3H), 7.50–7.60 (m, Step C: Preparation of 3-[4-((1-carbomethoxy-1-phenyl)methoxy)-3-methoxyphenyl]methyl-5,7-dimethyl-2-ethyl-3H-imidazo[4,5-b]pyridine The product of Step B (0. 115 g, 0.31 mmol) was used to alkylate 0.050 g (0.28 mmol) of 5,7-dimethyl-2-ethylimidazo[4,5-b]pyridine (Example 24, Step C) according to the procedure described for Step B of Example 27, which after purification afforded 0.084 g (64%) of the title compound.

$^1$H NMR (300MHz, CDCl$_3$, ppm): 5 1.20–1.30 (t, 3H), 2.55 (s, 3H)., 2.60 (s, 3H), 2.70–2.80 (m, 2H), 3.70 (s, 3H), 3.75 (s, 3H), 5.35 (s, 2H), 5.55 (s, 1H), 6.50–6.60 (d,, 1H), 6.70–6.75 (d, 1H), 6.80 (s, 1H), 6.85 (s, 1H), 7.30–7.40 (m, 3H), 7.45–7.55 (m, 2H). FAB-MS: m/e 460 (M+1).

Step D: Preparation of 3-[4-((1-carboxy-1-phenyl)methoxy)-3-methoxyphenyl]methyl-5,7-dimethyl-2-ethyl-3H-imidazo[4,5-b]pyridine Using the general procedure for ester hydrolysis de;-scribed in Step E of Example 19, 0.080 g (0.17 mmol) of the product of Step C was converted to 0.064 g (82%) of the title compound.

$^1$H NMR (300 MHz, CD$_3$OD, ppm): δ1.20–1.30 (t, 3H), 2.60 (s, 3H), 2.62 (s, 3H), 2.85–2.95 (m, 2H), 3.80 (s, 3H), 5.50 (s, 3H), 6.50–6.60 (d, 1H), 6.80–6.90 (d, 1H), 6.95 (s, 1H), 7.05 (s, 1H), 7.30–7.40 (m, 3H), 7.55–7.65 (m, 2H). FAB-MS: m/e 446 (M+1).

EXAMPLE 33

3-[3-tert-Butyl-4-((1-carboxy-1-phenyl)methoxy)-phenyl]methyl-5,7-dimethyl-2-ethyl-3H-imidazo[4,5-b]pyridine Preparation of methyl 2-(2-tert-butyl-4-methylphenoxy)-2-phenylacetate To a suspension of 1.05 g (9.15 mmol) of a 35% oil dispersion of KH in 15 mL of DMF was added 1.50 g (9.15 mmol) of 2-tert-butyl-4-methylphenol and the mixture was stirred under $N_2$ at room temperature. After 10 minutes, 2.41g (91.5 mmol) of 18-crown-6 and then a solution of 2.30 g (10.1 mmol) of methyl 2-bromophenylacetate dissolved in 10 mL of DMF were added. The reaction mixture was stirred 17 hours, then partitioned between ethyl acetate and water. The organic layer was separated, washed with water, dried ($MgSO_4$), filtered and evaporated. The residue was purified on a silica gel flash chromatography column eluted with 5% ethyl acetate/hexane to afford 0.750 g (26%) of the title compound.

$^1$H NMR (300 MHz, $CDCl_3$, ppm): δ1.43 (s, 9H), 2.24 (s, 3H), 3.68 (s, 3H), 5.64 (s, 1H), 6.56 (d, J=10 Hz, 1H), 6.86 (dd, J=2, 10 Hz, 1H), 7.12 (d, J=2 Hz, 1H), 7.30–7.44 (m, 3H), 7.54–7.62 (m, 2H).

Preparation of methyl 2-(2-tert-butyl-4-bromomethylphenoxy)-2-phenylacetate

To a solution of 0.494 g (1.58 mmol) of the product of Step A dissolved in 10 mL of $CCl_4$ was added 0.310 g (1.74 mmol) of N-bromosuccinimide and 15 mg (catalytic amount) of AIBN and the mixture was heated at reflux for 3.5 hours. The reaction was cooled, filtered and evaporated in vacuo. The residue was purified on a silica gel flash chromatography column eluted with 3% ethyl acetate/hexane to afford 0.134 g (22%) of the title compound.

$^1$H NMR (300 MHz, $CDCl_3$, ppm): δ1.44 (s, 3H), 3.70 (s, 3H), 4.45 (s, 2H), 5.64 (s, 1H), 6.70 (d, J=10 Hz, 1H), 7.12 (dd, J=2, 10 Hz, 1H), 7.22 (d, J=2 Hz, 1H), 7.32–7.42 (m, 3H), 7.53–7.60 (m, 2H).

Step C: Preparation of 3-[3-tert-butyl-4-((1-carbomethoxy-1-phenyl)methoxy)phenyl]methyl-5,7-dimethyl-2-ethyl-3H-imidazo[4,5-b]pyridine The product of Step B (0.128 g, 0.33 mmol) was used to alkylate 0.052 g (0.30 mmol) of 5,7-dimethyl-2-ethylimidazo[4,5-b]pyridine (Example 24, Step C) according to the procedure described for Step B of Example 27, which after purification afforded 0.088 g (62%) of the title compound.

$^1$H NMR (300 MHz, $CDCl_3$, ppm): δ1.20–1.30 (t, 3H), 1.40 (s, 9H), 2.55 (s, 3H), 2.60 (s, 3H), 2.75–2.85 (m, 2H), 3.65 (s, 3H), 5.30 (s, 2H), 5.60 (s, 1H), 6.45–6.55 (d, 1H), 6.70–6.80 (d, 1H), 6.85 (br s, 1H), 7.25–7.40 (m, 4H), 7.50–7.55 (m, 2H). FAB-MS: m/e 486 (M+1).

Step D: Preparation of 3-[3-tert-butyl-4-((1-carboxy-1-phenyl)methoxy)phenyl]methyl-5,7-dimethyl-2-ethyl-3H-imidazo[4,5-b]pyridine Using the general procedure for ester hydrolysis described in Step E of Example 19, 0.080 g (0.16 mmol) of the product of Step C was converted to 0.056 g (73%) of the title compound.

$^1$H NMR (300 MHz, $CD_3OD$, ppm): δ1.25–1.35 (t, 3H), 1.40 (s, 9H), 2.63 (s, 3H), 2.65 (s, 3H), 2.85–2.95 (m, 2H), 5.50 (s, 2H), 5.65 (s, 1H), 6.75–6.85 (d, 1H), 6.90–6.95 (d, 1H), 7.05 (s, 1H), 7.30 (s, 1H), 7.35–7.45 (m, 3H), 7.60–7.70 (m, 2H). FAB-MS: m/e 472 (M+1).

EXAMPLE 34

3-[4-((1-carboxy-1-phenyl)methoxy)-3-ethoxyphenyl]-methyl-5,7-dimethyl-2-ethyl-3H-imidazo[4,5-b]pyridine Step A: Preparation of methyl 2-(2-ethoxy-4-formylphenoxy)phenylacetate Using the $K_2CO_3$/acetone conditions for phenol alkylation described in Step A of Example 30, 1.00 g (6.02 mmol) of 3-ethoxy-4-hydroxybenzaldehyde was alkylated with 1.52 g (6.62 mmol) of methyl 2-bromophenylacetate to afford 1.74 g (92%) of the title compound.

$^1$H NMR (300 MHz, $CDCl_3$, ppm): δ1.40–1.50 (t, 3H), 3.85 (s, 3H), 4.10–4.20 (m, 2H), 5.75 (s, 1H), 6.95 (s, 1H), 7.20–7.35 (m, 5H), 7.50–7.60 (m, 2H), 9.85 (s, 1H). FAB-MS: m/e 315 (M+1).

Step B: Preparation of methyl 2-(2-ethoxy-4-hydroxymethylphenoxy)phenylacetate

A stirred solution of 1.74 g (5.54 mmol) of the product of Step A dissolved in 22 mL of methanol was treated with 0.105 g (2.8 mmol) of sodium borohydride at room temperature. After 5 minutes the reaction mixture was partitioned between ethyl acetate and 1N hydrochloric acid, and the organic layer was separated. The product was washed with water, brine, dried ($MgSO_4$), filtered and evaporated in vacuo. The residue was purified on a silica gel flash chromatography column eluted with 30% ethyl acetate/hexane to afford 1.15 g (66%) of the title compound.

$^1$H NMR (300 MHz, $CDCl_3$, ppm): δ1.20–1.30 (t, 1H), 1.35–1.45 (t, 2H), 3.70 (s, 3H), 4.05–4.15 (m, 2H), 4.60 (s, 2H), 5.65 (s, 1H), 6.75–6.80 (d, 1H), 6.85–6.95 (m, 2H), 7.30–7.40 (m, 3H), 7.50–7.60 (m, 2H). FAB-MS: m/e 317 (M+1).

Step C: Preparation of methyl 2-(4-bromomethyl-2-ethoxyphenoxy)phenylacetate

To a stirred and cooled (0° C.) solution of 1.15 g (3.64 mmol) of the product of Step B dissolved in 18 mL of $CH_2Cl_2$ was added 1.51 g (4.55 mmol) of carbon tetrabromide and 1.19 g (4.55 mmol) of triphenylphosphine. After the addition the reaction mixture was stirred 30 minutes and allowed to warm to room temperature. The mixture was then evaporated in vacuo and purified on a silica gel flash chromatography column eluted with 15% ethyl acetate/hexane to afford 1.21 g (88%) of the title compound.

$^1$H NMR (300 MHz, $CDCl_3$, ppm): δ1.35–1.45 (t, 3H), 3.75 (s, 3H), 4.05–4.15 (m, 2H), 4.40 (s, 2H), 5.65 (s, 1H), 6.80–6.90 (m, 2H), 6.95 (s, 1H), 7.35–7.45 (m, 3H), 7.50–7.60 (m, 2H). FAB-MS: m/e 378, 380 (M+1).

Step E: Preparation of 3-[4-((1-carbomethoxy-1-phenyl)methoxy)-3-ethoxyphenyl]methyl-5,7-dimethyl-2-ethyl-3H-imidazo[4,5-b]pyridine The product of Step C (0.119 g, 0.31 mmol) was used to alkylate 0.055 g (0.28 mmol) of 5,7-dimethyl-2-ethylimidazo[4,5-b]pyridine (Example 24, Step C) according to the procedure described for Step B of Example 27, which after purification afforded 0.084 g (62%) of the title compound.

$^1$H NMR (400 MHz, $CDCl_3$, ppm): δ1.20–1.30 (t, 3H), 1.30–1.40 (t, 3H), 2.55 (s, 3H), 2.60 (s, 3H), 2.70–2.80 (m, 2H), 3.70 (s, 3H), 3.90–4.00 (m, 2H), 5.30 (s, 2H), 5.60 (s, 1H), 6.50–6.55 (d, 1H), 6.75–6.80 (m, 2H), 6.85 (s, 1H), 7.30–7.40 (m, 3H), 7.50–7.55 (m, 2H). FAB-MS: m/e 474 (M+1).

Step E: Preparation of 3-[4-((1-carboxy-1-phenyl)methoxy)-3-ethoxyphenyl]methyl-5,7-dimethyl-2-ethyl-3H-imidazo[4,5-b]pyridine Using the general procedure for ester hydrolysis described in Step E of Example 19, 0.080 g (0.17 mmol) of the product of Step D was converted to 0.069 g (88%) of the title compound.

$^1$H NMR (400 MHz, $CD_3OD$, ppm): δ1.20–1.30 (t, 3H), 1.30–1.40 (t, 3H), 2.55 (s, 3H), 2.60 (s, 3H), 2.80–2.90 (m, 2H), 3.95–4.05 (m, 2H), 5.45 (s, 2H), 5.50 (s, 1H), 6.50–6.55 (d, 1H), 6.80–6.85 (m, 2H), 7.25–7.35 (m, 3H), 7.50–7.55 (m, 2H).

EXAMPLE 35

3-[4-((1-Carboxy-1-phenyl)methoxy)-3-methylphenyl]-methyl-5,7-dimethyl,2,ethyl,3H-imidazo[4,5-b]-pyridine Step A: Preparation of methyl 2-(4-formyl-2-methylphenoxy)phenylacetate Using the $K_2CO_3$/acetone conditions for phenol alkylation described in Step A of Example 30, 0.50 g (3.68 mmol) of 4-hydroxy-3-methylbenzaldehyde was alkylated with 0.926 g (4.05 mmol) of methyl 2-bromophenylacetate to afford 1.00 g (96%) of the title compound.

$^1$H NMR (400 MHz, CDCl$_3$, ppm): δ2.40 (s, 3H), 3.70 (s, 3H), 5.70 (s, 1H), 6.80 (d, 1H), 7.35–7.45 (m, 3H), 7.55–7.60 (m, 2H), 7.65 (d, 1H), 7.70 (s, 1H), 9.85 (s, 1H). FAB-MS: m/e 285 (M+1).

Step B: Preparation of methyl 2-(4-hydroxymethyl-2-methylphenoxy)phenylacetate

A stirred solution of 1.00 g (3.52 mmol) of the product of Step A dissolved in 14 mL of methanol was treated with 0.067 g (1.8 mmol) of sodium borohydride at room-temperature. After 15 minutes the reaction mixture was partitioned between ethyl acetate and 1N hydrochloric acid, and the organic layer was separated. The product was washed with water, brine, dried (MgSO$_4$), filtered and evaporated in vacuo. The residue was purified on a silica gel flash chromatography column eluted with 30% ethyl acetate/hexane to afford 0.660 g (66%) of the title compound.

$^1$H NMR (400 MHz, CDCl$_3$, ppm): δ2.10 (s, 1H), 2.35 (s, 3H), 3.70 (s, 3H), 4.55 (s, 2H), 5.65 (s, 1H), 6.70 (d, 1H), 7.05 (d, 1H), 7.15 (s, 1H), 7.35–7.45 (m, 3H), 7.55–7.65 (m, 2H). FAB-MS: m/e 2.87 (M+1).

Step C: Preparation of methyl 2-(4-hydroxymethyl-2-methylphenoxy)phenylacetate

To a stirred and cooled (0° C.) solution of 0.660 g (2.31. mmol) of the product of Step B dissolved in 12 mL of CH$_2$Cl$_2$ was added 0,957 g (2.89 mmol) of carbon tetrabromide and 0.756 g (2.89 mmol) of triphenylphosphine. After the addition the reaction mixture was allowed to warm to room temperature and was stirred overnight. The mixture was then evaporated in vacuo and purified on a silica gel flash chromatography column eluted with 15% ethyl acetate/hexane to afford 0.704 g (87%) of the title compound.

$^1$H NMR (400 MHz, CDCl$_3$, ppm): δ2.30 (s, 3H), 3.70 (s, 3H), 4.45 (s, 2H), 5.60 (s, 1H), 6.65 (d, 1H), 7.10 (d, 1H), 7.20 (s, 1H), 7.35–7.45 (m, 3H), 7.55–7.60 (m, 2H). FAB-MS: m/e 2.69 (M+1).

Step D: Preparation of 3-[4-((1-carbomethoxy-1-phenyl)methoxy)-3-methylphenyl]methyl-5,7-dimethyl-2-ethyl-3H-imidazo[4,5-b]pyridine The product of Step C (0.110 g, 0.31 mmol) was used to alkylate 0.050 g (0.28 mmol) of 5,7-dimethyl-2-ethylimidazo[4,5-b]pyridine (Example 24, Step C) according to the procedure described for Step B of Example 27, which after purification afforded 0.041 g (33%) of the title compound.

$^1$H NMR (400 MHz, CDCl$_3$, ppm): δ1.20–1.30 (t, 3H), 2.25 (s, 3H), 2.55 (s, 3H), 2.60 (s, 3H), 2.70–2.80 (m, 2H), 3.65 (s, 3H), 5.35 (s, 2H), 5.55 (s, 1H), 6.60 (d, 1H), 6.80 (d, 1H), 6.85 (s, 1H), 6.95 (s, 1H), 7.30–7.40 (m, 3H), 7.50–7.55 (m, 2H). FAB-MS: m/e 444 (M+1).

Step E: Preparation of 3-[4-((1-carboxy-1-phenyl)methoxy)-3-methylphenyl]-methyl-5,7-dimethyl-2-ethyl-3H-imidazo[4,5-b]pyridine Using the general procedure for ester hydrolysis described in Step E of Example 19, 0.040 g (0.09 mmol) of the product of Step D was converted to 0.023 g (60%) of the title compound.

$^1$H NMR (400 MHz, CD$_3$OD, ppm): δ1.15–1.25 (t, 3H), 2.25 (s, 3H), 2.58 (s, 3H), 2.60 (s, 3H), 2.80–2.90 (m, 2H), 5.45 (s, 2H), 5.60 (s, 1H), 6.75 (d, 1H), 6.85 (d, 1H), 6.95 (s, 1H), 7.05 (s, 1H), 7.30–7.40 (m, 3H), 7.55–7.65 (m, 2H). FAB-MS: m/e 430 (M+1).

EXAMPLE 36

3-[4-((1-Carboxy-1-(2-methylphenyl))methoxy)-3-chlorophenyl]methyl-5,7-dimethyl-2-ethyl-3H-imidazo[4,5-b]pyridine Step A: Preparation of methyl 4-tert-butyldimethylsilyloxy-3-chlorobenzoate To a solution of 5.00 g (26.8 mmol) of methyl 3-chloro-4-hydroxybenzoate dissolved in 40 mL of CH$_2$Cl$_2$ was added 6.55 g (53.6 mmol) of 4-dimethylaminopyridine, 4.85 g (32.2 mmol) of tert-butyldimethylchlorosilane and the mixture was stirred at room temperature for 3.5 hours. The reaction mixture was filtered, diluted with ethyl acetate, washed with 0.1N HCl, saturated NaHCO$_3$, and brine. The product layer was then dried (MgSO$_4$), filtered and evaporated in vacuo to afford 8.05 g (100%) of the title compound.

$^1$H NMR (300 MHz, CDCl$_3$, ppm): δ0.25 (s, 6H), 1.00 (s, 9H), 3.85 (s, 3H), 6.85 (d, 1H), 7.80 (d, 1H), 8.05 (s, 1H). FAB-MS: m/e 301, 303 (M+1).

Step B: Preparation of 4-tert-butyldimethylsilyloxy-3-chlorobenzyl alcohol

To a stirred and cooled (0° C.) solution of 8.00 g (26.7 mmol) of the product of Step A dissolved in 50 mL of anhydrous THF was added 53.3 mL (53.3 mmol) of a 1M solution of lithium aluminum hydride in THF. After the addition was complete the reaction mixture was allowed to warm to room temperature and stirred 2 hours. The stirred reaction was then quenched by dropwise addition of 2.5 mL water, then 2.5 mL of 15% NaOH, and finally 7.5 mL water. The mixture was then filtered and concentrated in vacuo. The residue was dissolved in ethyl acetate, washed with 1N HCl, saturated NaHCO$_3$, dried (MgSO$_4$), and evaporated in vacuo to afford 4.0 g (53%) of the title compound.

$^1$H NMR (300 MHz, CDCl$_3$, ppm): δ0.20 (s, 6H), 1.00 (s, 9H), 1.80 (br s, 1H), 4.55 (s, 2H), 6.85 (d, 1H), 7.10 (d, 1H), 7.35 (s, 1H). FAB-MS: m/e 255,257 (M+1).

Step C: Preparation of 4-tert-butyldimethylsilyloxy-3-chlorobenzyl bromide

To a stirred and cooled (0° C.) solution of 4.00 g (14.1 mmol) of the product of Step B dissolved in 70 mL of CH$_2$Cl$_2$ was added 5.84 g (17.6 mmol) of carbon tetrabromide and 4.61 g (17.6 mmol) of triphenylphosphine. After the addition the reaction mixture was allowed to warm to room temperature and was stirred 3 hours. The mixture was then evaporated in vacuo and purified on a silica gel flash chromatography column eluted with 2% ethyl acetate/hexane to afford 4.50 g (92%) of the title compound.

$^1$H NMR (300 MHz, CDCl$_3$, ppm): δ0.20 (s, 6H), 1.00 (s, 9H), 4.40 (s, 2H), 6.80 (d, 1H), 7.15 (d, 1H), 7.35 (s, 1H).

Step D: Preparation of 3-(4-tert-butyldimethylsilyloxy-3-chlorophenyl)methyl-5,7-dimethyl-2-ethyl-3H-imidazo[4,5-b]pyridine The product of Step C (1.79 g, 5.15 mmol) was used to alkylate 0.750 g (4.29 mmol) of 5,7-dimethyl-2-ethylimidazo[4,5-b]pyridine (Example 24, Step C) according to the procedure described for Step B of Example 27, which after purification afforded 0.294 g (15%) of the title compound.

$^1$H NMR (300 MHz, CDCl$_3$, ppm): δ0.20 (s, 6H), 1.00 (s, 9H), 1.20–1.30 (t, 3H), 2.58 (s, 3H), 2.60 (s, 3H), 2.70–2.80 (m, 2H), 5.35 (s, 2H), 7.75 (d, 1H), 7.85–7.90 (m, 2H), 7.15 (s, 1H). FAB-MS: m/e 430, 432 (M+1).

Step E: Preparation of 3-(3-chloro-4-hydroxyphenyl)methyl-5,7-dimethyl-2-ethyl-3H-imidazo [4,5-b]pyridine To a solution of 0.294 g (0.661 mmol) of the product of Step D dissolved in 4 mL of THF was added 0.69 mL (0.69 mmol) of a 1.0M solution of tetra-n-butylammonium fluoride in THF, and the reaction mixture was stirred 2 hours at room temperature. The reaction was then concentrated in vacuo and purified by filtration through a silica gel pad eluted with chloroform. Evaporation of the filtrate and drying in vacuo afforded 0.188 g (87%) of the title compound.

$^1$H NMR (300 MHz, CD$_3$OD, ppm): δ1.25–1.35 (t, 3H), 2.65 (s, 3H), 2.67 (s, 3H), 2.85–2.95 (m, 2H), 5.45 (s, 2H), 6.90 (d, 1H), 6.95 (d, 1H), 7.05 (s, 1H), 7.15 (s, 1H). FAB-MS: m/e 316, 318 (M+1).

Step F: Preparation of 3-[4-((1-carbomethoxy-1-(2-methylphenyl))methoxy)-3-chlorophenyl]methyl-5,7-dimethyl-2-ethyl-3H-imidazo[4,5-b]pyridine To a suspension of 7 mg of a 60% oil dispersion of sodium hydride in 0.75 mL of DMF was added 0.050 g (0.16 mmol) of the product of Step E and the reaction mixture was stirred 10 minutes under an N$_2$ atmosphere. A solution of methyl 2-bromo-2'-methylphenylacetate (prepared from 2'-methylphenylacetic acid via a Hell-Volhard-Zelinsky reaction similar to Step A of Example 17) dissolved in 0.75 mL of DMF was then added and the reaction was stirred for 2 hours at room temperature. The reaction mixture was then partitioned between ethyl acetate and water, the organic layer was separated, dried (MgSO$_4$), filtered and evaporated. The residue was purified on a silica gel flash chromatography column eluted with EtOAc/hexane/CHCl$_3$ (50:40:10) to afford 0.070 g (92%) of the title compound.

$^1$H NMR (300 MHz, CDCl$_3$, ppm): δ1.25–1.35 (t, 3H), 2.45 (s, 3H), 2.60 (s, 3H), 3.65 (s, 3H), 2.75–2.85 (m, 2H), 3.70 (s, 3H), 5.35 (s, 2H), 5.60 (s, 1H), 6.75 (d, 1H), 6.85–6.95 (m, 2H), 7.15–7.40 (m, 4H), 7.55–7.65 (m, 1H). FAB-MS: m/e 478, 480 (M+1, 3:1 ratio).

Step G: Preparation of 3-[4-((1-carboxy-1-(2-methylphenyl))methoxy)-3-chlorophenyl]methyl-5,7-dimethyl-2-ethyl-3H-imidazo[4,5-b]pyridine Using the general procedure for ester hydrolysis described in Step E of Example 19, 0.040 g (0.15 mmol) of the product of Step F was converted to 0.066 g (97%) of the title compound.

$^1$H NMR (300 MHz, CD$_3$OD, ppm): d 1.25–1.35 (t, 3H), 2.50 (s, 3H), 2.63 (s, 3H), 2.65 (s, 3H), 2.85–2.95 (m, 2H), 5.50 (s, 2H), 5.80 (s, 1H), 6.95–7.10 (m, 3H), 7.20–7.30 (m, 4H), 7.60 (d, 1H). FAB-MS: m/e 464, 466 (M+1, 3:1 ratio).

EXAMPLE 37

3-[4-((1-Carboxy-1-phenyl)methoxy)-3-chloro-5-methoxyphenyl]methyl-5,7-dimethyl-2-ethyl-3H-imidazo[4,5-b]pyridine Preparation of methyl 2-(2-chloro-4-hydroxymethyl-6-methoxyphenoxy)-2-phenylacetate Using the K$_2$CO$_3$/acetone conditions for phenol alkylation described in Step A of Example 30, 0.50 g (2.62 mmol) of 3-chloro-4-hydroxy-5-methoxybenzaldehyde was alkylated with 0.668 g (2.92 mmol) of methyl 2-bromophenylacetate to afford 0.570 g (64%) of the title compound.

$^1$H NMR (300 MHz, CDCl$_3$, ppm): δ1.65–1.75 (t, 1H), 3.70 (s, 3H), 3.80 (s, 3H), 4.55 (d, 2H), 5.75 (s, 1H), 6.80 (s, 1H), 6.90 (s, 1H), 7.30–7.40 (m, 3H), 7.50–7.60 (m, 2H). FAB-MS: m/e 337,339 (M+1, 3:1 ratio).

Step B: Preparation of 2-(4-bromomethyl-2-chloro-6-methoxyphenoxy)-2-phenylacetate To a stirred and cooled (0° C.) solution of 0.570 g (1.69 mmol) of the product of Step A dissolved in 6 mL of CH$_2$Cl$_2$ was added 0.702 g (2.11 mmol) of carbon tetrabromide and 0.555 g (2.11 mmol) of triphenylphosphine. After the addition the reaction mixture was allowed to warm to room temperature and was stirred 4 hours. The mixture was then evaporated in vacuo and purified on a silica gel flash chromatography column eluted with 20% ethyl acetate/hexane to afford 0.580 g (86%) of the title compound.

$^1$H NMR (300 MHz, CDCl$_3$, ppm): δ3.75 (s, 3H), 3.80 (s, 3H), 4.35 (s, 2H), 5.65 (s, 1H), 6.80 (s, 1H), 6.95 (s, 1H), 7.30–7.40 (m, 3H), 7.50–7.60 (m, 2H). FAB-MS: m/e 398, 400, 402 (M+1).

Step C: Preparation of 3-[4-((1-carbomethoxy-1-phenyl)methoxy)-3-chloro-5-methoxyphenyl]methyl-5,7-dimethyl-2-ethyl-3H-imidazo[4,5-b]pyridine The product of Step B (0.126 g, 0.31 mmol) was used to alkylate 0.050 g (0.29 mmol) of 5,7-dimethyl-2-ethylimidazo[4,5-b]pyridine (Example 24, Step C) according to the procedure described for Step B of Example 27, which after purification afforded 0.092 g (65%) of the title compound.

$^1$H NMR (300 MHz, CDCl$_3$, ppm): δ1.20–1.30 (t, 2.55 (s, 3H), 2.60 (s, 3H), 2.70–2.80 (m, 2H), 3.65 (s, 3H), 3.70 (s, 3H), 5.30 (s, 2H), 5.70 (s, 1H) 6.63 (s, 1H), 6.68 (s, 1H), 6.90 (s, 1H), 7.25–7.35 (m, 3H), 7.45–7.55 (m, 2H). FAB-MS: m/e 494, 496 (M+1).

Step D: Preparation of 3-[4-((1-carboxy-1-phenyl)methoxy)-3-chloro-5-methoxyphenyl]methyl-5,7-dimethyl-2-ethyl-3H-imidazo[4,5-b]pyridine- Using the general procedure for ester hydrolysis described in Step E of Example 19, 0.090 (0.18 mmol) of the product of Step C was converted to 0.070 g (80%) of the title compound.

$^1$H NMR (300 MHz, CD$_3$OD, ppm): δ1.20–1.30 (t, 3H), 2.60 (s, 3H), 2.65 (s, 3H), 2.80–2.90 (m, 2H), 3.75 (s, 3H), 5.45 (s, 2H), 5.70 (s, 1H), 6.60 (s, 1H), 6.85 (s, 1H), 7.05 (s, 1H), 7.35–7.45 (m, 3H), 7.45–7.55 (m, 2H). FAB-MS: m/e 480, 482 (M+1, 3:1 ratio).

EXAMPLE 38

3-[4-((1-Carboxy-1-phenyl)methoxy)-3,5-dichlorophenyl]methyl-5,7-dimethyl-2-ethyl-3H-imidazo[4,5-b]pyridine Step A: Preparation of methyl 4-tert-butyldimethylsilyloxy-3,5-dichlorobenzoate To a solution of 10.00 g (45.2 mmol) of methyl 3,5-dichloro-4-hydroxybenzoate dissolved in 100 mL of CH$_2$Cl$_2$ was added 11.06 g (90.2 mmol) of 4-dimethylaminopyridine and 8.18 g (54.2 mmol) of tert-butyldimethylchlorosilane and the mixture was stirred under N$_2$ for 5 hours. The reaction mixture was then filtered and the filtrate was diluted with ethyl acetate. The solution was washed with water, 1N HCl, saturated NaHCO$_3$, dried (MgSO$_4$), filtered and evaporated. The residue was purified on a silica gel flash chromatography column eluted with 5% ethyl acetate/hexane to afford 7.70 g (51%) of the title compound.

$^1$H NMR (300 MHz, CDCl$_3$, ppm): δ0.30 (s, 6H), 1.00 (s, 9H), 3.90 (s, 3H), 7.95 (s, 2H). FAB-MS: m/e 335, 337, 339 (M+1).

Step B: Preparation of 4-tert-butyldimethylsilyloxy-3,5-dichlorobenzylalcohol

To a stirred and cooled (0° C.) solution of 7.70 g (23.0 mmol) of the product of Step A dissolved in 50 mL of anhydrous THF was added 23.0 mL (23.0 mmol) of a 1M solution of lithium aluminum hydride in THF. After the addition was complete the reaction mixture was allowed to warm to room temperature and stirred 3.5 hours. The stirred reaction was then quenched by dropwise addition of 0.88 mL water, then 0.88 mL of 15% NaOH, and finally 2.62 mL water. The reaction mixture was then filtered and concentrated in vacuo. The residue was dissolved in ethyl acetate, washed with 1N HCl, saturated NaHCO$_3$, dried (MgSO$_4$), and evaporated in vacuo to afford 1.83 g (26%) of the title compound.

$^1$H NMR (300 MHz, CDCl$_3$, ppm): δ0.30 (s, 6H), 1.05 (s, 9H), 1.80 (br s, 1H), 4.55 (s, 2H), 7.22 (s, 2H). FAB-MS: m/e 306 (M+1).

Step C: Preparation of 3,5-dichloro-4-hydroxybenzyl alcohol

To a solution of 1.83 g (5.96 mmol) of the product of Step B dissolved in 6 mL of THF was added 5.96 mL (5.96 mmol) of a 1M solution of tetra-n-butylammonium fluoride in THF and the reaction mixture was stirred at room temperature 30 minutes. The solution was then evaporated in vacuo and the residue was purified on a silica gel flash chromatography column eluted with 4% methanol/chloroform to afford 0.733 g (64%) of the title compound.

$^1$H NMR (300 MHz, CDCl$_3$, ppm): δ1.90–4.10 (br, 2H) 4.60 (s, 2H), 7.27 (s, 2H). FAB-MS: m/e 192 (M+1).

Step D: Preparation of methyl 2-(2,6-dichloro-4-hydroxymethylphenoxy)-2-phenylacetate Using the K$_2$CO$_3$/acetone conditions for phenol alkylation described in Step A of Example 30, 0.400 g (2.07 mmol) of the product of Step C was alkylated with 0.522 g (2.28 mmol) of methyl 2-bromophenylacetate to afford 0.144 g (20%) of the title compound.

$^1$H NMR (300 MHz, CDCl$_3$, ppm): δ1.70–1.80 (t, 3H), 3.75 (s, 3H), 4.55 (d, 2H), 5.75 (s, 1H), 7.22 (s, 2H), 7.30–7.40 (m, 3H), 7.45–7.55 (m, 2H). FAB-MS: m/e 341, 343,345 (M+1, 10:6:1 ratio).

Step E: Preparation of methyl 2-(4-bromomethyl-2,6-dichlorophenoxy)-2-phenylacetate To a stirred and cooled (0° C.) solution of 0.140 g (0.41 mmol) of the product of Step D dissolved in 2 mL of CH$_2$Cl$_2$ was added 0.170 g (0.51 mmol) of carbon tetrabromide and 0.135 g (0.51 mmol) of triphenylphosphine. After the addition the reaction mixture was allowed to warm to room temperature and was stirred overnight. The mixture was then evaporated in vacuo and purified on a silica gel flash chromatography column eluted with 15% ethyl acetate/hexane to afford 0.130 g (78%) of the title compound.

$^1$H NMR (300 MHz, CDCl$_3$, ppm): δ3.75 (s, 3H), 4.30 (s, 2H), 5.75 (s, 1H), 7.27 (s, 2H), 7.30–7.40 (m, 3H), 7.45–7.55 (m, 2H). FAB-MS: m/e 405 (M+1).

Step F: Preparation of 3-[4-((1-carbomethoxy-1-phenyl)methoxy)-3,5-dichlorophenyl]methyl-5,7-dimethyl-2-ethyl-3H-imidazo[4,5-b]pyridine The product of Step E (0.126 g, 0.31 mmol) was used to alkylate 0.050 g (0.29 mmol) of 5,7-dimethyl-2-ethylimidazo[4,5-b]pyridine (Example 24, Step C) according to the procedure described for Step B of Example 27, which after purification afforded 0.096 g (68%) of the title compound.

$^1$H NMR (300 MHz, CDCl$_3$, ppm): δ1.20–1.30 (t, 3H), 2.58 (s, 3H), 2.62 (s, 3H), 2.65–2.75 (m, 2H), 3.75 (s, 3H), 5.30 (s, 2H), 5.75 (s, 1H), 6.90 (s, 1H), 7.00 (s, 2H), 7.25–7.35 (m, 3H), 7.45–7.55 (m, 2H). FAB-MS: m/e 498, 500, 502 (M+1).

Step G: Preparation of 3-[4-((1-carboxy-1-phenyl)methoxy)-3,5-dichlorophenyl]methyl-5,7-dimethyl-2-ethyl-3H-imidazo[4,5-b]pyridine Using the general procedure for ester hydrolysis described in Step E of Example 19, 0.092 g (0.18 mmol) of the product of Step F was converted to 0.080 g (90%) of the title compound.

$^1$H NMR (300 MHz, CD$_3$OD, ppm): δ1.20–1.30 (t, 3H), 2.61 (s, 3H), 2.65 (s, 3H), 2.80–2.95 (m, 2H), 5.45 (s, 2H), 5.65 (s, 1H), 7.05 (s, 2H), 7.25–7.35 (m, 3H), 7.45–7.55 (m, 2H). FAB-MS: m/e 484, 486, 488 (M+1, 10:6:1 ratio).

EXAMPLE 39

3-[4-((1-Carboxy-1-phenyl)methoxy)-2-chlorophenyl]-methyl-5,7-dimethyl-2-ethyl-3H-imidazo[4,5-b]pyridine Step A: Preparation of methyl 2-(3-chloro-4-formylphenoxy)-2-phenylacetate Using the K$_2$CO$_3$/acetone conditions for phenol alkylation described in Step A of Example 30, 1.00 g (6.41 mmol) of 2-chloro-4-hydroxybenzaldehyde was alkylated with 1.61 g (7.05 mmol) of methyl 2-bromophenylacetate to afford 1.49 g (76%) of the title compound.

$^1$H NMR (300 MHz, CDCl$_3$, ppm): δ3.75 (s, 3H), 5.68 (s, 1H), 6.90 (d, 1H), 7.00 (s, 1H), 7.35–7.45 (m, 3H), 7.50–7.60 (m, 2H), 7.85 (d, 1H), 10.30 (s, 1H). FAB-MS: m/e 305, 307 (M+1).

Step B: Preparation of methyl 2-(3-chloro-4-hydroxymethylphenoxy)-2-phenylacetate A stirred solution of 1.49 g (4.90 mmol) of the product of Step A dissolved in 20 mL of methanol was treated with 0.093 g (2.46 mmol) of sodium borohydride at room temperature. After 5 minutes the reaction mixture was partitioned between ethyl acetate and 1N hydrochloric acid, and the organic layer was separated. The product was washed with water, brine, dried (MgSO$_4$), filtered and evaporated in vacuo. The residue was purified on a silica gel flash chromatography column eluted with 25% ethyl acetate/hexane to afford 1.380 g (92%) of the title compound.

$^1$H NMR (400 MHz, CDCl$_3$, ppm): δ1.80–1.85 (t, 1H), 3.75 (s, 3H), 4.70 (d, 2H), 5.60 (s, 1H), 6.85 (d, 1H), 7.00 (s, 1H), 7.30–7.45 (m, 4H), 7.50–7.60 (m, 2H).

Step C: Preparation of methyl 2-(4-bromomethyl-3-chlorophenoxy)-2-phenylacetate

To a stirred and cooled (0° C.) solution of 1.38 g (4.51 mmol) of the product of Step D dissolved in 18 mL of CH$_2$Cl$_2$ was added 1.87 g (5.64 mmol) of carbon tetrabromide and 1.48 g (5.64 mmol) of triphenylphosphine. After the addition the reaction mixture was allowed to warm to room temperature and was stirred 3 hours. The mixture was then evaporated in vacuo and purified on a silica gel flash chromatography column eluted with 10% ethyl acetate/hexane to afford 1.60 g (96%) of the title compound.

¹H NMR (400 MHz, CDCl₃, ppm): δ3.75 (s, 3H), 4.55 (s, 2H), 5.60 (s, 1H), 6.80 (d, 1H), 7.00 (s, 1H), 7.30 (d, 1H), 7.35–7.45 (m, 3H), 7.50–7.60 (m, 2H). FAB-MS: m/e 369, 371,373 (M+1).

Step D: Preparation of 3-[4-((1-carbomethoxy-1-phenyl)methoxy)-2-chlorophenyl]methyl-5,7-dimethyl-2-ethyl-3H-imidazo[4.5-b]pyridine The product of Step C (0.116 g, 0.31 mmol) was used to alkylate 0.050 g (0.29 mmol) of 5,7-dimethyl-2-ethylimidazo[4,5-b]pyridine (Example 24, Step C) according to the procedure described for Step B of Example 27, which after purification afforded 0.094 g (69%) of the title compound.

¹H NMR (400 MHz, CDCl₃, ppm): δ1.20–1.30 (t, 3H), 2.55 (s, 3H), 2.62 (s, 3H), 2.65–2.75 (m, 2H), 3.70 (s, 3H), 5.4.5 (s, 2H), 5.55 (s, 1H), 6.45 (d, 1H), 6.65 (d, 1H), 6.90 (s, 1H), 7.05 (s, 1H), 7.35–7.40 (m, 3H), 7.45–7.55 (m, 2H). FAB-MS: m/e 464, 466 (M+1, 3:1 ratio).

Step E: Preparation of 3-[4-((1-carboxy-1-phenyl)methoxy)-2-chlorophenyl]methyl-5,7-dimethyl-2-ethyl,3H-imidazo[4.5-b]pyridine Using the general procedure for ester hydrolysis described in Step E of Example 19, 0.090 g (0.18 mmol) of the product of Step D was converted to 0.030 g (34%) of the title compound.

¹H NMR (300 MHz, CD₃OD, ppm): δ1.25–1.35 (t, 3H), 2.60 (s, 3H), 2.65 (s, 3H), 2.80–2.90 (m, 2H), 5.55–5.65 (m, 3H), 6.50 (d, 1H), 6.85 (d, 1H), 7.05 (s, 1H), 7.15 (s, 1H), 7.35–7.45 (m, 3H), 7.55–7.65 (m, 2H). FAB-MS: m/e 450, 452 (M+1, 3:1 ratio).

EXAMPLE 40

3-[4-((1-Carboxy-1-(3-phenyl)propyloxy)phenyl]methyl-5,7-dimethyl-2-ethyl-3H-imidazo[4,5-b]pyridine Step A: Preparation of 3-[4-((1-carboethoxy-1-(3-phenyl)propoxy)phenyl]methyl-5,7-dimethyl-2-ethyl-3H-imidazo[4,5-b]pyridine To a suspension of 20 mg (0.18 mmol) of a 35% oil dispersion of KH in 0.4 mL of anhydrous DMF was added 0.050 g (0.18 mmol) of 5,7-dimethyl-2-ethyl-3-(4-hydroxyphenyl)methyl-3H-imidazo[4,5-b]pyridine (Example 24, Step E) and the reaction mixture was stirred under N₂ at room temperature. After 15 minutes, 0.050 g (0.18 mmol) of 18-crown-6 and a solution of 0.053 g (0.20 mmol) of ethyl 2-bromo-4-phenylbutanoate dissolved in 0.4 mL of DMF were added. The reaction mixture was stirred at room temperature 4 hours, then partitioned between ethyl acetate and water. The organic layer was separated, washed with water, dried (MgSO₄), filtered and evaporated. The residue was purified on a silica gel flash chromatography column eluted with 50% ethyl acetate/hexane to afford 0.063 g (75%) of the title compound.

¹H NMR (300 MHz, CDCl₃, ppm): δ1.17 (t, J=8 Hz, 3H), 1.27 (t, J=8 Hz, 3H), 2.11–2.30 (m, 2H), 2.56 (s, 3H), 2.60 (s, 3H), 2.70–2.90 (m, 4H), 4.15 (q, J=8 Hz, 2H), 4.50 (dd, J=6, 7 Hz, 1H), 5.35 (s, 2H), 6.74 (d, J=10 Hz, 2H), 6.86 (s, 1H), 7.04 (d, J=10 Hz, 2H), 7.10–7.28 (m, 5H). FAB-MS: m/e 472 (M+1).

Step B: Preparation of 3-[4-((1-carboxy-1-(3-phenyl)propoxy)phenyl]methyl-5,7-dimethyl-2-ethyl-3H-imidazo[4,5-b]pyridine Using the general procedure for ester hydrolysis described in Step E of Example 19, 0.063 g (0.13 mmol) of the product of Step A was converted to 0.047 g (80%) of the title compound.

¹H NMR (300 MHz, CD₃OD, ppm): δ1.27 (t, J=8 Hz, 3H), 2.16 (m, 2H), 2.63 (s, 3H), 2.66 (s, 3H), 2.80–2.95 (m, 4H), 4.55 (t, J=6 Hz, 1H), 5.52 (s, 2H), 6.86 (d, J=10 Hz, 2H), 7.07 (s, 1H), 7.12 (d, J=10 Hz, 1H), 7.15–7.32 (m, 5H). FAB-MS: m/e 444 (M+1).

EXAMPLE 41

3-[4-((1-Carboxy-1-(2-phenyl)ethoxy)phenyl]methyl-5,7-dimethyl-2-ethyl-3H-imidazo[4,5-b]pyridine Step A: Preparation of methyl 2-(4-hydroxymethylphenoxy)acetate Using the K₂CO₃/acetone conditions for phenol alkylation described in Step A of Example 30, 8.00 g (64.5. mmol) of 4-hydroxybenzyl alcohol was alkylated with 11.84 g (77.4 mmol) of methyl bromoacetate to afford 6.00 g (48%) of the title compound.

¹H NMR (300 MHz, CDCl₃, ppm): δ1.74 (br s, 1H), 3.76 (s, 3H), 4.61 (br s, 4H), 6.86 (d, J=10 Hz, 2H), 7.26 (d, J=10 Hz, 2H). FAB-MS: m/e 305 (M+1).

Step B: Preparation of methyl 2-(4-tert-butyldimethylsilyloxymethylphenoxy)acetate To a solution of 4.00 g (20.4 mmol) of the product of Step A dissolved in 30 mL of CH₂Cl₂ was added 5.00 g (40.8 mmol) of 4-dimethylaminopyridine and 3.69 g (24.5 mmol) of tert-butyldimethylchlorosilane and the mixture was stirred under N₂ for 5 hours. The reaction mixture was then filtered and the filtrate was diluted with ethyl acetate. The solution was washed with water, 1N HCl, saturated NaHCO₃, dried (MgSO₄), filtered and evaporated. Drying in vacuo afforded 6.30 g (99%) of the title compound.

¹H NMR (300 MHz, CDCl₃, ppm): δ0.09 (s, 6H), 0.94 (s, 9H), 3.80 (s, 3H), 4.63 (s, 2H), 4.68 (s, 2H), 6.86 (d, J=10 Hz, 2H), 7.26 (d, J=10 Hz, 2H). FAB-MS: m/e 311 (M+1).

Step C: Preparation of methyl 2-(4-tert-butyldimethylsilyloxymethylphenoxy)-3-phenylpropanoate A solution of 1.00 g (3.23 mmol) of the product of Step B dissolved in 4 mL of toluene was stirred under a N₂ atmosphere and cooled to 0° C. with an ice-water bath. To this solution was added 9.68 mL (4.85 mmol) of a 0.5M solution of potassium bis(trimethylsilyl)amide in toluene. After a 15 minute interval, 0.46 mL (3.88 mmol) of benzyl bromide was added and the reaction mixture was allowed to warm to room temperature and stirred 1 hour. Several milliliters of methanol were added to consume excess base, and the reaction was partitioned between ethyl acetate and 1N HCl. The organic layer was separated, washed with saturated NaHCO₃, brine, dried (MgSO₄), filtered and evaporated. The residue was purified on a silica gel flash chromatography column eluted with 15% ethyl acetate/hexane to afford 0.540 g (42%) of the title compound.

¹H NMR (300 MHz, CDCl₃, ppm): δ0.09 (s, 6H), 0.94 (s, 9H), 3.24 (m, 2H), 3.70 (s, 3H), 4.64 (s, 2H), 4.80 (dd, J=6,7 Hz, 1H), 6.80 (d, J=10 Hz, 2H), 7.09–7.35 (m, 7H). FAB-MS: m/e 401 (M+1).

Step D: Preparation of methyl 2-(4-hydroxymethylphenoxy)-3-phenylpropanoate

To a solution of 0.520 g (1.30 mmol) of the product of Step C dissolved in 3 mL of anhydrous TEF was added 1.3 mL (1.3 mmol) of a 1N solution of tetra-n-butylammonium fluoride in THF and the mixture was stirred at room temperature 1.5 hours. The mixture was then concentrated in vacuo and the residue was purified on a silica gel flash chromatography column eluted with 70% ethyl acetate/hexane to afford 0.230 g (62%) of the title compound.

¹H NMR (300 MHz, CDCl₃, ppm): δ1.55 (br s, 1H), 3.23 (m, 2H), 3.66 (s, 3H), 4.56 (d, J=9 Hz, 2H), 4.74 (dd, J=6,7 Hz, 1H), 6.83 (d, J=10 Hz, 2H), 7.10–7.30 (m, 7H). FAB-MS: m/e 285 (M+1).

Step E: Preparation of methyl 2-(4-bromomethylphenoxy)-3-phenylpropanoate

To a cooled (0° C.) solution of 0.230 g (0.80 mmol) of the product of Step D dissolved in 4 mL of CH₂Cl₂ was added 0.263 g (1.00 mmol) of carbon tetrabromide and 0.333 g (1.00 mmol) of triphenylphosphine. After 15 minutes at 0° C., the reaction mixture was allowed to warm to room temperature and was stirred for an additional 6 hours. The reaction was then concentrated in vacuo and purified on a silica gel flash chromatography column eluted with 5% ethyl acetate/hexane to afford 097 g (35%) of the title compound.

¹H NMR (300 MHz, CDCl₃, ppm): δ3.20 (m, 2H), 3.80 (s, 3H), 4.44 (s, 2H), 4.77 (dd, J=6, 7 Hz, 1H), 6.76 (d, J=10 Hz, 2H), 7.17–7.35 (m, 7H).

Step F: Preparation of 3-[4-((1-carboethoxy-1-(2-phenyl)ethoxy)phenyl]methyl-5,7-dimethyl-2-ethyl-3H-imidazo[4,5-b]pyridine The product of Step E (0.094 g, 0.27 mmol) was used to alkylate 0.040 g (0.23 mmol) of 5,7-dimethyl-2-ethylimidazo[4,5-b]pyridine (Example 24, Step C) according to the procedure described for Step B of Example 27, which after purification afforded 0.054 g (53%) of the title compound.

¹H NMR (300 MHz, CDCl₃, ppm): δ1.26 (t, J=8 Hz, 3H), 2.55 (s, 3H), 2.60 (s, 3H), 2.74 (q, J=8 Hz, 2H), 3.20 (m, 2H), 3.65 (s, 3H), 4.72 (dd, J=6, 7 Hz, 1H), 5.34 (s, 2H), 6.70 (d, J=10 Hz, 2H), 6.83 (s, 1H), 7.02 (d, J=10 Hz, 2H), 7.16–7.30 (m, 5H). FAB-MS: m/e 444 (M+1).

Step G: Preparation of 3-[4-((1-carboxy-1-(2-phenyl)ethoxy)phenyl]methyl-5,7-dimethyl-2-ethyl-3H-imidazo[4,5-b]pyridine Using the general procedure for ester hydrolysis described in Step E of Example 19, 0.054 g (0.12 mmol) of the product of Step A was converted to 0.042 g (81%) of the title compound.

¹H NMR (300 MHz, CD₃OD, ppm): δ1.25 (t, J=8 Hz, 3H), 2.60 (s, 3H), 4.63 (s, 3H), 4.85 (q, J=8 Hz, 2H), 3.18–3.25 (m, 2H), 4.78 (dd, J=6, 7 Hz, 1H), 5.45 (s, 2H), 6.80 (d., J=10 Hz, 2H), 7.02–7.10 (m, 3H), 7.15–7.35 (m, 5H). FAB-MS: m/e 430 (M+1).

EXAMPLE 42

3-[4-((1-Carboxy-1-phenyl)methoxy)-3-(2-propen-1-yl)phenyl]methyl-5,7-dimethyl-2-ethyl-3H-imidazo[4,5-b]pyridine Step A: Preparation of methyl 4-(2-propen-1-yl)oxybenzoate A 2 L flask was equipped with a mechanical stirrer, a reflux condenser and a stopper, then charged with 50.05 g (0.329 mol) of methyl 4-hydroxybenzoate, 960 mL of acetone, 22.50 g (1.625 mol) of anhydrous potassium carbonate, 80.5 mL (112.6 g, 0.932 mol) of allyl bromide and the mixture was stirred and refluxed for 14 hours. The mixture was cooled to room temperature, filtered and concentrated to an oil. The residual oil was purified by distillation (97° C.@0.03 mm Hg) to afford 53.52 g (86%) of the title compound.

¹H NMR (300 MHz, CDCl₃, ppm): δ3.84 (s, 3H), 4.56 (d, J=7 Hz, 2H), 5.28 (dd, J=3, 12 Hz, 1H), 5.40 (dd, J=3, 19Hz, 1H), 5.96–6.10 (m, 1H), 6.90 (d, J=10 Hz, 2H), 7.96 (d, J=10 Hz, 2H). FAB-MS: m/e 193 (M+1).

Step B: Preparation of methyl 4-hydroxy-3-(prop-2-en-1-yl)benzoate

A solution of 15.05 g (78.3 mmol) of the product of Step A in 25 mL of 1,2-dichlorobenzene was magnetically stirred and refluxed (183° C.) under an argon atmosphere for 18 hours. At this point, the reaction mixture was cooled to room temperature and applied to a 6 cm diameter by 18 cm silica gel flash chromatography column and eluted with 25% ethyl acetate-hexane to separate the 1,2-dichlorobenzene, then with 40% ethyl acetate-hexane to elute the product. The product fractions were concentrated in vacuo and the residual oil was crystallized from hexane to afford 13.70 g (91%) of the title compound.

¹H NMR (300 MHz, CDCl₃, ppm): δ3.42 (d, J=8 Hz, 2H), 3.88 (s, 3H), 5.14–5.20 (m, 2H), 5.48 (s, 1H), 5.94–6.06 (m, 1H), 6.82 (d, J=12 Hz, 1H), 7.80–7.85 (m, 2H). FAB-MS: m/e 193 (M+1).

Step C: Preparation of methyl 4-(tert-butyldimethylsilyloxy)-3-(2-propen-1-yl)benzoate To a solution of 5.168 g (26.9 mmol) of the product of Step B in 50 mL of dichloromethane was added 4.40 mL (2.95 mmol) of triethylamine, 4.46 g (2.95 mmol) of tert-butyldimethylchlorosilane, 0.100 g of 4-dimethylaminopyridine, and the reaction mixture was stirred at room temperature for 2 hours. The mixture was then diluted with 50 mL dichloromethane, washed with 100 mL 1N hydrochloric acid, dried (MgSO₄), filtered and evaporated. The residual oil (7.993 g, 97%) was used in the next step without further purification.

¹H NMR (300 MHz, CDCl₃, ppm): δ0.24 (s, 6H), 1.02 (s, 9H), 3.36 (d, J=8 Hz, 2H), 3.84 (s, 3H), 4.98–5.08 (m, 2H), 5.88–6.03 (m, 1H), 6.78 (d, J=11 Hz, 1H), 7.76–8.40 (m, 2H). FAB-MS: m/e 307 (M+1).

Step D: Preparation of 4-(tert-butyldimethylsilyloxy)3-(2-propen-1-yl)benzyl alcohol To a magnetically stirred solution of 8.523 g (28.0 mmol) of the product from Step C in 35 mL of anhydrous TBF was added 15.0 mL of a 1.0M solution of lithium aluminum hydride in THF, and the reaction mixture was stirred under a nitrogen atmosphere for 2 hours. At this point, the reaction was quenched by cautious addition of 10 mL water, the resulting precipitate was dissolved by addition of 1.0N hydrochloric acid and the product was extracted into ethyl acetate. The organic layer was separated, dried (MgSO₄), filtered and evaporated in vacuo to afford 7.258 g (93%) of the title compound.

¹H NMR (300 MHz, CDCl₃, ppm): δ0.20 (s, 6H), 1.00 (s, 9H), 3.34 (d, J=8 Hz, 2H), 3.84 (s, 1H), 4.57 (s, 2H), 4.97–5.07 (m, 2H), 5.88–6.03 (m, 1H), 6.86 (d, J=10 Hz, 1H), 7.05–7.14 (m, 2H). FAB-MS: m/e 279, 261 (M+1).

Step E: Preparation of 4-(tert-butyldimethylsilyl)3-(2-propen-1-yl)benzyl bromide To a magnetically stirred solution of 7.258 g (26 mmol) of the product from Step D and 10.281 g (31 mmol) of carbon tetrabromide in 50 mL of dry dichloromethane was slowly added 8.131 g (31 mmol) of triphenylphosphine at 0° C. under a nitrogen atmosphere. The reaction mixture was stirred 45 minutes and allowed to warm to room temperature. At this point, the reaction mixture was applied to a silica gel flash chromatography column and was eluted with dichloromethane. Evaporation of the product fractions and drying in vacuo afforded 7.651 g (86%) of the title compound as a viscous oil.

¹H NMR (300 MHz, CDCl₃, ppm): δ0.23 (s, 6H), 1.00 (s, 9H), 3.34 (d, J=8 Hz, 2H), 4.45 (s, 2H), 4.98–5.09 (m, 2H), 5.86–6.02 (m, 1H), 6.74 (d, J=10 Hz, 1H), 7.08–7.16 (m, 2H). FAB-MS: m/e 343,341 (M+1).

Step F: Preparation of 5,7-dimethyl-2-ethyl-3-[4-tert-butyldimethylsilyloxy-3-(2-propen-1-yl)phenyl]methyl,3H-imidazo[4,5-b]pyridine To a solution of 1.029 g (5.9 mmol) of 5,7-dimethyl.-2-ethylimidazo[4,5-b]pyridine (Example 24, Step C) dissolved in 10 mL of dry DMF was added 0.258 g (6.5 mmol) of a 60% oil dispersion of sodium hydride and the reaction mixture was stirred under a nitrogen atmosphere for 1 hour. At this point, hydrogen evolution had ceased, and a solution of 2.210 g of the product of Step E dissolved in 2.0 mL of dry DMF was added via syringe. The reaction was stirred an additional 2 hours at room temperature and then partitioned between ethyl acetate and water. The organic layer was extracted, washed with brine, dried (MgSO4), filtered and evaporated. The residual oil was purified on a silica gel flash chromatography column eluted with 50% ethyl acetate-hexane. Evaporation of the purified fraction and drying in vacuo afforded 1.519 g (59%) of the title compound.

$^1$H NMR (300 MHz, CDCl$_3$, ppm): δ0.16 (s, 6H), 0.96 (s, 9H), 1.27 (t, J=9 Hz, 3H), 2.57 (s, 3H), 2.60 (s, 3H), 2.76 (q, J=9 Hz, 2H), 3.28 (d, J=8 Hz, 2H), 4.93–5.03 (m, 2H), 5.33 (s, 2H), 5.81–5.95 (m, 1H), 6.64 (d, J=10 Hz, 1H), 6.76 (dd, J=3, 10 Hz, 1H), 6.86 (s, 1H), 7.00 (d, J=3 Hz, 1H). FAB-MS: m/e 436 (M+1).

Step G: Preparation of 5,7-dimethyl-2-ethyl-3-[4-hydroxy-3-(2-propen-1-yl)phenyl]methyl-3H-imidazo[4,5-b]pyridine To a solution of 1.519 g (3.48 mmol) of the product of Step F in 8.0 mL of anhydrous THF was added 3.6 mL of a 1.0 M solution of tetra-n-butylammonium fluoride in THF and the reaction mixture was stirred for 2.5 hours at room temperature. The reaction mixture was then evaporated in vacuo and the residual oil was chromatographed on a silica gel flash chromatography column eluted with ethyl acetate. The purified fractions were combined, evaporated and dried in vacuo to afford the title compound.

$^1$H NMR (300 MHz, CDCl$_3$, ppm): δ1.24 (t, J=9 Hz, 3H), 2.57 (s, 3H), 2.60 (s, 3H), 2.73 (q, J=9 Hz, 2H), 3.31 (d, J=8 Hz, 2H), 5.03–5.10 (m, 2H), 5.33 (s, 2H), 5.88–6.02 (m, 1H), 6.36 (d, J=10 Hz, 1H), 6.48 (dd, J=3,10 Hz, 1H), 6.84–6.89 (m, 2H), 7.37 (br s, 1H). FAB-MS: m/e 322 (MN+1).

Step H: Preparation of 5,7-dimethyl-2-ethyl-3-[4-((1-carbomethoxy-1-phenyl)methoxy)-3-(2-propen-1-yl)phenyl]-methyl-3H-imidazo[4,5-b]pyridine To a solution of 0.171 g (0.53 mmol) of the product of Step G dissolved in 2.5 mL of anhydrous DMF was added 0.023 g (0.58 mmol) of a 60% oil dispersion of sodium hydride and the reaction mixture was stirred under a nitrogen atmosphere for 30 minutes at room temperature. A solution of 0.134 g of methyl a-bromophenylacetate in 1.0 mL of DMF was then added via syringe and the reaction mixture was stirred an additional 1.5 hours. The reaction mixture was then partitioned between ethyl acetate and water, the organic layer was separated, dried (MgSO4), filtered and evaporated. The residual oil was purified on a silica gel flash chromatography column eluted with 75% ethyl acetate-hexane to afford after evaporation of the purified fractions and drying in vacuo 0.212 g (85%) of the title compound.

$^1$H NMR (300 MHz, CDCl$_3$, ppm): δ1.26 (t, J=9 Hz, 3H), 2.57 (s, 3H), 2.60 (s, 3H), 2.76 (q, J=9 Hz, 2H), 3.45 (d, J=8 Hz, 2H), 3.66 (s, 3H), 4.99–5.07 (m, 2H), 5.34 (s, 2H), 5.57 (s, 1H), 5.88–6.04 (m, 1H), 6.59 (d, J=10 Hz, 1H), 6.79 (dd, J=3, 10 Hz, 1H), 6.86 (s, 1H), 7.05 (d, J=3 Hz, 1H), 7.30–7.40 (m, 7.48–7.56 (m, 2H). FAB-MS: m/e 470 (M+1).

Step I: Preparation of 3-[4-((1-carboxy-1-phenyl)methoxy)-3-(2-propen-1-yl)phenyl]methyl-5,7-dimethyl-2-ethyl-3H-imidazo[4,5-b]pyridine To a solution of 0.141 g (0.30 mmol) of the product of Step H dissolved in 2.0 mL of methanol was added 0.25 mL of a 1.0N solution of sodium hydroxide and the reaction was stirred at room temperature for 2 hours. The reaction mixture was then adjusted to pH 7 with 1.0N hydrochloric acid and then partitioned between ethyl acetate and water. The organic layer was separated, dried (MgSO4), filtered, evaporated and then purified on a silica gel flash chromatography column eluted with chloroform-methanol-conc. ammonium hydroxide (80:15:1). Evaporation of the purified fractions arid drying in vacuo afforded 0.092 g (69%) of the title compound as a white amorphous solid.

$^1$H NMR (300 MHz, CD$_3$OD, ppm): δ1.27 (t, J=9 Hz, 3H), 2.61 (s, 3H), 2.64 (s, 3H), 2.89 (q, J=9 Hz, 2H), 3.40–3.52 (m, 2H), 4.95–5.06 (m, 2H), 5.53 (s, 2H), 5.73 (s, 1H), 5.94–6.13 (m, 1H), 6.84 (d, J=10 Hz, 1H), 6.95 (dd, J=3, 10 Hz, 1H), 7.06 (br s, 2H), 7.36–7.44 (m, 3H), 7.57–7.64 (m, 2H). FAB-MS: m/e 456 (M+1).

EXAMPLE 43

3-[4-((1-Carboxy-1-phenyl)methoxy)-3-propylphenyl]-methyl-5,7-dimethyl-2-ethyl-3H-imidazo[4,5-b]pyridine Step A: Preparation of 5,7-dimethyl-2-ethyl-3-[4-hydroxy-3-propylphenyl]methyl-3H-imidazo[4,5-b]pyridine A solution of 0.255 (0.79 mmol) of the product of Example 1, Step G in 10 mL ethanol was placed in a small Parr hydrogenation flask and 50 mg of a 10% palladium on carbon catalyst was added. The reaction mixture was then shaken in a Parr apparatus under a 45 psig hydrogen atmosphere for 1 hour at room temperature. The reaction mixture was then removed from the flask, filtered, evaporated and dried in vacuo to afford 0.239g (93%) of the title compound which was used in the next step without further purification.

$^1$H NMR (300 MHz, CDCl$_3$, ppm): δ0.90 (t, J=9 Hz, 3H), 1.24 (t, J=1.0 Hz, 3H), 1.50–1.62 (m, 2H), 2.48 (t, J=8 Hz, 2H), 2.56 (s, 3H), 2.59 (s, 3H), 2.72 (q, J=9 Hz, 2H), 5.32 (s, 3H), 6.23 (d, J=10 Hz, 1H), 6.38 (dd, J=3, 10 Hz, 1H), 6.79 (d, J=3 Hz, 1H), 6.87 (s, 1H), 7.68 (br s, 1H). FAB-MS: m/e 324 (M+1).

Step B: Preparation of 5,7-dimethyl-2-ethyl-3-[4-((1-carbomethoxy-1-phenyl)methoxy)-3-propylphenyl]-methyl-3H-imidazo[4,5-b]pyridine To a solution of 0.062 g (0.19 mmol) of the product of Step A in 1.5 mL of anhydrous DMF was added 8.4 mg of a 60% oil dispersion of sodium hydride and the reaction mixture was stirred under a nitrogen atmosphere. After the reaction mixture had stirred 30 minutes at room temperature, hydrogen evolution had ceased, and a solution of 0.048 g of methyl 2-bromophenylacetate in 0.5 mL of dry DMF was added via syringe. The reaction mixture was stirred an additional 1.5 hours and then partitioned between ethyl acetate and water. The organic layer was separated, washed with brine, dried (MgSO4), filtered, evaporated and then chromatographed on a silica gel flash chromatography column eluted with 50% ethyl acetate-hexane. The purified fractions were combined, evaporated and dried in vacuo to afford 59 mg (66%) of the title compound as a viscous oil.

$^1$H NMR (300 MHz, CDCl$_3$, ppm): δ0.90 (t, J=9 Hz, 3H), 1.25 (t, J=9 Hz, 3H), 1.54–1.68 (m, 2H), 2.56–2.66 (m, 2H), 2.58 (s, 3H), 2.62 (s, 3H), 2.76. (g, J=9 Hz, 2H), 3.66 (s, 3H), 5.35 (s, 2H), 5.57 (s, 1H), 6.59 (d, J=10 Hz, 1H), 6.81 (dd, J=3,10 Hz, 1H), 6.87 (s, 1H), 6.99 (d, J=3 Hz, 1H), 7.28–7.40 (m, 3H), 7.49–7.56 (m, 2H). FAB-MS: m/e 472 (M+1).

Step C: Preparation of 3-[4-((1-carboxy-1-phenyl)methoxy)-3-propylphenyl]methyl-5,7-dimethyl-2-ethyl-3H-imidazo[4,5-b]pyridine To a solution of 0.042 g (0.09 mmol) of the product of Step B dissolved in 1.0 mL of methanol was added 0.1 mL of a 1.0N solution of sodium hydroxide and the reaction mixture was stirred for 3 hours at room temperature. The reaction mixture was then adjusted to pH 7 with 1.0N hydrochloric acid and then partitioned between ethyl acetate and water. The organic layer was separated, dried (MgSO$_4$), filtered, evaporated and then purified on a silica gel flash chromatography column eluted with chloroform-methanol-conc. ammonium hydroxide (80:15:1). Evaporation of the purified fractions and drying in vacuo afforded 0.021 g (51%) of the title compound as a white amorphous solid.

$^1$H NMR (300 MHz, CD$_3$OD, ppm): δ0.90 (t, J=8 Hz, 3H), 1.26 (t, J=9 Hz, 3H), 1.53–1.67 (m, 2H), 2.61 (s, 3H), 2.65 (s, 3H), 2.66–2.80 (m, 2H), 2.86 (q, J=8 Hz, 2H), 5.49 (s, 2H), 5.54 (s, 1H), 6.80 (d, J=10 Hz, 1H), 6.90 (dd, 3–2, 10 Hz, 1H), 6.98 (d, J=2 Hz, 1H), 7.06 (s, 1H), 7.30–7.44 (m, 3H), 7.60–7.66 (m, 2H). FAB-MS: m/e 458 (M+1).

EXAMPLE 44

3-[4-((1-Carboxy-1-(2-methylphenyl))methoxy)-3-propylphenyl]methyl-5,7-dimethyl-2-ethyl-3H-imidazo[4,5-b]pyridine Step A: Preparation of 5,7-dimethyl-2-ethyl-3-[4-((1-carbormethoxy-1-(2-methylphenyl))methoxy)-3-propylphenyl]-methyl-3H-imidazo[4,5-b]pyridine To a suspension of 5.9 mg (2.45 mmol) of a 60% oil dispersion of NaH in 0.8 mL of DMF was added 0.066 g (0.20 mmol) of 5,7-dimethyl-2-ethyl-3-[4-hydroxy-3-propylphenyl]methyl-3H-imidazo[4,5-b]pyridine (Example 43, Step A) and the mixture was stirred at room temperature. After 20 minutes, a solution of 0.060 g (2.45 mmol) of methyl 2-bromo-2'-methylphenylacetate (prepared from 2'-methylphenylacetic acid via a Hell-Volhard-Zelinsky reaction similar to Step A of Example 17) dissolved in 0.5 mL of DMF was added and the reaction mixture was stirred an additional 1.5 hours. The reaction was then partitioned between ethyl acetate and water, the organic layer was separated, washed with water, dried (MgSO$_4$), filtered and evaporated in vacuo. The residue was purified on a silica gel flash chromatography column eluted with 50% ethyl acetate/hexane to afford 0.082 g (83%) of the title compound.

$^1$H NMR (300 MHz, CDCl$_3$, ppm): δ0.90 (t, J=9 Hz, 3H), 1.25 (t, J=8 Hz, 3H), 1.50–1.65 (m, 2H), 2.44 (s, 3H), 2.56 (s, 3H), 2.60 (s, 3H), 2.52–2.65 (m, 2H), 2.75 (q, J=8 Hz, 2H), 3.67 (s, 3H), 5.34 (s, 2H), 5.74 (s, 1H), 6.55 (d, J=10 Hz, 1H), 6.78 (dd, J=2, 10 Hz, 1,H), 6.86 (s, 1H), 6.98 (d, J=2 Hz, 1H), 7.15–7.28 (m, 3H), 7.50–7.56 (m, 1H). FAB-MS: m/e 486 (M+1).

Step B: Preparation of 3-[4-((1-carboxy-1-(2-methylphenyl))methoxy)-3-propylphenyl]methyl-5,7-dimethyl-2-ethyl-3H-imidazo[4,5-b]pyridine Using the general procedure for ester hydrolysis described in Step E of Example 19, 0.076 g (0.16 mmol) of the product of Step A was converted to 0.040 g (54%) of the title compound.

$^1$H NMR (300 MHz, CD$_3$OD, ppm): δ0.88 (t, J=9 Hz, 3H), 1.27 (t, J=8 Hz, 3H), 1.50–1.65 (m, 2H), 2.49 (s, 3H) 2.62 (s, 3H), 2.65 (s, 3H), 2.55–2.70 (m, 2H), 2.88 (q, J=8 Hz, 2H), 5.48 (s, 2H), 5.83 (s, 1H), 6.78 (d, J=10 Hz, 1H), 6.90 (dd, J=2, 10 Hz, 1H), 6.99 (d, J=2 Hz, 1H), 7.06 (s, 1H), 7.20–7.27 (m, 3H), 7.54–7.60 (m, 1H). FAB-MS: m/e 472 (M+1).

EXAMPLE 45

3-[4-((1-Carboxy-1-(2-chlorophenyl))methoxy)-3-propylphenyl]methyl-5,7,-dimethyl-2-ethyl-3H-imidazo[4,5-b]pyridine Step A: Preparation of 5,7-dimethyl-2-ethyl-3-[4-((1-carbomethoxy-1-(2-chlorophenyl))methoxy)-3-propylphenyl]-methyl-3H-imidazo[4,5-b]pyridine To a suspension of 6.3 mg (2.63 mmol) of a 60% oil dispersion of NaH in 1.0 mL of DMF was added 0.071 g (0.22 mmol) of 5,7-dimethyl-2-ethyl-3-[4-hydroxy-3-propylphenyl]methyl-3H-imidazo[4,5-b]pyridine (Example 43, Step A) and the mixture was stirred at room temperature. After 20 minutes, a solution of 0.069 g (0.26 mmol) of methyl 2-bromo-2'-chlorophenylacetate (Example 4, Step A) dissolved in 0.75 mL of DMF was added and the reaction mixture was stirred an additional 2 hours. The reaction was then partitioned between ethyl acetate and water, the organic layer was separated, washed with water, dried (MgSO$_4$), filtered and evaporated in vacuo. The residue was purified on a silica gel flash chromatography column eluted with 50% ethyl acetate/hexane to afford 0.098 g (88%) of the title compound.

$^1$H NMR (300 MHz, CDCl$_3$, ppm): δ0.89 (t, J=9 Hz, 3H), 1.26 (t, J=8 Hz, 3H), 2.55 (s, 3H), 2.59 (s, 3H), 2.52–2.63 (m, 2H), 2.74 (q, J=8 Hz, 2H), 3.70 (s, 3H), 5.34 (s, 2H), 6.03 (s, 1H), 6.62 (d, J=10 Hz, 3H), 6.78 (dd, J=2, 10 Hz, 1H), 6.86 (s, 1H), 6.97 (d, J=2 Hz, 1H), 7.24–7.32 (m, 2H), 7.34–7.42 (m, 1H), 7.57–7.64 (m, 1H). FAB-MS: m/e 506 (M+1).

Step B: Preparation of 3-[4-((1-carboxy-1-(2-chlorophenyl))methoxy)-3-propylphenyl]methyl-5,7-dimethyl-2-ethyl-3H-imidazo[4,5-b]pyridine Using the general procedure for ester hydrolysis described in Step E of Example 19, 0.098 g (0.19 mmol) of the product of Step A was converted to 0.072 g (76%) of the title compound.

$^1$H NMR (300 MHz, CD$_3$OD, ppm): δ0.85 (t, J=9 Hz, 3H), 1.25 (t, J=8 Hz, 3H), 1.60–21.74 (m, 2H), 2.61 (s, 3H), 2.64 (s, 3H), 2.52–2.60 (m, 2H), 2.88 (q, J=8 Hz, 2H), 5.49 (s, 2H), 6.04 (s, 1H), 6.80 (d, J=10 Hz, 1H), 6.92 (dd, J=2, 10 Hz, 1H), 6.98 (d, J=2 Hz, 1H), 7.06 (s, 1H), 7.33–7.39 (m, 2H), 7.44–7.50 (m, 1H), 7.64–7.70 (m, 1H). FAB-MS: m/e 492 (M+1).

EXAMPLE 46

3-[4-((1-Carboxy-1-phenyl)methoxy)-3-(1-methylcyclohex-1-yl)phenyl]methyl-5,7-dimethyl-2-ethyl-3H-imidazo[4,5-b]pyridine Step A: Preparation of methyl 2-(2-(1-methylcyclohex-1-yl)-4-methylphenoxy)-2-phenylacetate Using the K₂CO₃/acetone conditions for phenol alkylation described in Step A of Example 30, 0.496 g (2.4.3 mmol) of 2-(1-methylcyclohex-1-yl)-4-methylphenol was alkylated with 0.834 g (3.64 mmol) of methyl 2-bromophenylacetate to afford 0.780 g (91%) of the title compound.

¹H NMR (300 MHz, CDCl₃, ppm): δ1.41 (s, 3H), 1.36–1.80 (m, 8H), 2.20–2.34 (m, 2H), 2.27 (s, 3H), 3.70 (s, 3H), 5.64 (s, 1H), 6.70 (d, J=10 Hz, 1H), 6.87 (dd, J=2, 10 Hz, 1H), 7.16 (d, J=2 Hz, 1H), 7.32–7.44 (m, 3H), 7.55,–7.63 (m, 2H). FAB-MS: m/e 353 (M+1).

Step B: Preparation of methyl 2-(4-bromomethyl-2-(1-methylcyclohex-1-yl)phenoxy)-2-phenylacetate To a solution of 0.780 g (2.21 mmol) of the product of Step A dissolved in 12 mL of CCl₄ was added 0.394 g (2.21 mmol) of N-bromosuccinimide and 20 mg (catalytic amount) of AIBN. The mixture was stirred and refluxed under a N₂ atmosphere for 6 hours. The mixture was then cooled, filtered and evaporated in vacuo. The residue was purified on a silica gel flash chromatography column eluted with 7% ethyl acetate/hexane to afford 0.203 g (21%) of the title compound.

¹H NMR (300 MHz, CDCl₃, ppm): δ1.36 (s, 3H), 1.34–1.80 (m, 8H), 2.18–2.30 (m, 2H), 3.70 (s, 3H), 4.46 (s, 2H), 5.65 (s, 1H), 6.71 (d, J=10 Hz, 1H), 7.10 (dd, J=2, 10 Hz, 1H), 7.35 (d, J=2 Hz, 1H), 7.32–7.44 (m, 3H), 7.50–7.58 (m, 2H). FAB-MS: m/e 433 (M+1).

Step C: Preparation of 3-[4-((1-carbomethoxy-1-phenyl)methoxy)-3-(1-methylcyclohex-1-yl)phenyl]methyl-5,7-dimethyl-2-ethyl-3H-imidazo[4,5-b]pyridine To a suspension of 18 mg (0.47 mmol) of a 60% oil dispersion of NaH in 1.0 mL of DMF was added 0.083 g (0.47 mmol) of 5,7-dimethyl-2-ethyl-3-[4-hydroxy-3-propylphenyl]methyl-3H-imidazo[4,5-b]pyridine (Example 43, Step A) and the mixture was stirred at room temperature. After 20 minutes, a solution of 0.203 g (0.47 mmol) of the product of Step B dissolved in 0.75 mL of DMF was added and the reaction mixture was stirred an additional 2 hours. The reaction was then partitioned between ethyl acetate and water, the organic layer was separated, washed with water, dried (MgSO₄), filtered and evaporated in vacuo. The residue was purified on a silica gel flash chromatography column eluted with 50% ethyl acetate/hexane to afford 0.097 g (39%) of the title compound.

¹H NMR (300 MHz, CDCl₃, ppm): δ1.28 (t, J=8 Hz, 3H), 1.33 (s, 3H), 1.20–1.70 (m, 8H), 2.13–2.24 (m, 2H), 2.55 (s, 3H), 2.60 (s, 3H), 2.82 (q, J=8 Hz, 2H), 3.66 (m, 3H), 5.34 (s, 2H), 5.58 (s, 1H), 6.53 (d, J=10 Hz, 1H), 6.77 (dd, J=2, 10 Hz, 1H), 6.85 (s, 1H), 7.26–7.40 (m, 4H), 7.50–7.58 (m, 2H). FAB-MS: m/e 526 (M+1).

Step D: Preparation of 3-[4-((1-carboxy-1-phenyl)methoxy)-3-(1-methylcyclohex-1-yl)phenyl]methyl-5,7-dimethyl-2-ethyl-3H-imidazo[4,5-b]pyridine Using the general procedure for ester hydrolysis described in Step E of Example 19, 0.097 g (0.18 mmol) of the product of Step C was converted to 0.056 g (59%) of the title compound.

¹H NMR (300 MHz, CD₃OD, ppm): δ1.01 (t, J=8 Hz, 1H), 1.34 (s, 3H), 1.20–1.70 (m, 8H), 2.08–2.20 (m, 2H), 2.40 (s, 3H), 2.54 (s, 3H), 2.88 (q, J=8 Hz, 2H), 5.25 (d, J=16 Hz, 1H), 5.37 (d, J=16 Hz, 1H), 5.60 (s, 1H), 6.73–6.86 (m, 3H), 7.32–7.47 (m, 4H), 7.64–7.74 (m, 2H). FAB-MS: m/e 512 (M+1).

EXAMPLE 47

3-[4-((1-Carboxy-1-(4-chlorophenyl))methoxy)-3-propylphenyl]methyl-5,7-dimethyl-2-ethyl-3H-imidazo[4,5-b]pyridine Step A: Preparation of 5,7-dimethyl-2-ethyl-3-[4-((1-carbomethoxy-1-(4-chlorophenyl))methoxy)-3-propylphenyl]methyl-3H-imidazo[4,5-b]pyridine Using the K₂CO₃/acetone conditions for phenol alkylation described in Step A of Example 30, 5,7-dimethyl-2-ethyl-3-[4-hydroxy-3-propylphenyl]methyl-3H-imidazo[4,5-b]pyridine (Step A, Example 43) was alkylated with methyl 2-bromo-2-(4-chlorophenyl)acetate (Step A, Example 3). Standard workup and purification by flash chromatography afforded a 50% yield of the title compound.

¹H NMR (200 MHz, CDCl₃, ppm): δ7.49 (d, 2H), 7.36 (d, 2H), 7.02 (d, 1H), 6.90 (s, 1H), 6.82 (dd, 1H), 6.57 (d, 1H), 5.54 (s, 1H), 5.38 (br s, 2H), 3.67 (s, 3H), 2.86 (q, 2H), 2.66 (s, 3H), 2.6 (s, 3H), 2.5 (t, 2H), 1.7–1.5 (m, 2H), 1.15 (t, 3H), 0.9 (t, 3H). FAB-MS: m/e 506 (M+1).

Step B: Preparation of 5,7-dimethyl-2-ethyl-3-[4-((1-carboxy-1-(4-chlorophenyl))methoxy)-3-propylphenyl]methyl-3H-imidazo[4,5-b]pyridine Using the general procedure for ester hydrolysis described in Step E of Example 19, the product of Step A was converted to the title compound in 77% yield.

¹H NMR (200 MHz, CDCl₃, ppm): δ7.56 (d, 2H), 7.25 (d, 2H), 7.15 (d, 1H), 6.988 (d, 2H), 6.8 (br s, 1H), 5.44 (s, 1H), 5.41 (s, 2H), 2.9–2.72 (q, 2H), 2.6 (s, 3H), 2.56 (s, 3H), 2.3–1.95 (br m, 2H), 1.65–1.44 (m, 2H), 1.27 (t, 3H), 0.84 (t, 3H). FAB-MS: m/e 492 (M+1), 530 (M+K).

EXAMPLE 48

3-[4-((1-Carboxy-1-(2-methoxyphenyl))methoxy)-3-propylphenyl]methyl-5,7-dimethyl-2-ethyl-3H-imidazo[4,5-b]pyridine Step A: Preparation of 5,7-dimethyl-2-ethyl-3-[4-((1-carbomethoxy-1-(2-methoxyphenyl))methoxy)-3-propylphenyl]methyl-3H-imidazo [4,5-b]pyridine Using the K₂CO₃/acetone conditions for phenol alkylation described in Step A of Example 30, 5,7-dimethyl-2-ethyl-3-[4-hydroxy-3-propylphenyl]methy 1-3H-imidazo[4,5-b]pyridine (Step A, Example 43) was alkylated with methyl 2-bromo-2-(2-methoxy)acetate. Standard workup and purification by flash chromatography afforded a 69% yield of the title compound.

¹H NMR (400 MHz, CDCl₃, ppm): δ7.6 (d, 1H), 7.38 (dd, 1H), 6.98 (dd, 1H), 6.875 (s, 1H), 6.866 (dd, 1H), 6.8–6.75 (m, 2H), 6.62 (d, 1H), 5.975 (s, 1H), 5.35 (ABq, 2H), 3.85 (s, 3H), 3.68 (s, 3H), 2.79 (q, 2H), 2.62(s 3H), 2.575 (s, 3H), 2.466 (dd, 1H), 1.65–1.47 (m, 2H), 1.27 (t, 3H), 0.9 (t, 3H). FAB-MS: m/e 502 (M+1).

Step B: Preparation of 5,7-dimethyl-2-ethyl-3-[4-((1-carboxy-1-(2-methoxyphenyl))methoxy)-3-propylphenyl]methyl-3H-imidazo[4,5-b]pyridine Using the general procedure for ester hydrolysis described in Step E of Example 19, the product of Step A was converted to the title compound in 58% yield.

¹H NMR (400 MHz, CDCl₃, ppm): δ7.8 (d, 1H), 7.4 (dd, 1H), 7.16 (d, 1H), 6.99 (d, 1H), 6.875 (s, 1H), 6.825 (d, 1H), 6.775 (d, 1H), 6.72 (d, 1H), 6.02 (br s, 1H), 5.33 (ABq, 2H), 3.83 (s, 3H), 2.72 (q, 2H), 2.575 (s, 3H), 2.49 (s, 3H), 1.7–1.47 (m, 2H), 0.97 (t, 3H), 0.9 (t, 3H). FAB-MS: m/e 488 (M+1).

EXAMPLE 49

3-[4-((1-Carboxy-1-(2,5-dibromo-3,4-dimethoxyphenyl))methoxy)-3-propylphenyl]methyl-5,7-dimethyl-2-ethyl-3H-imidazo[4,5-b]pyridine Step A: Preparation of methyl 2,2',5'-tribromo-3,4-dimethoxyphenylacetate A mixture of 5.0 g (25 mmol) of 3',4'-dimethoxyphenylacetic acid and thionyl chloride 2.32 mL (1.25 sq.) was stirred and refluxed while bromine (4.5 mL, 3.5 sq.) was added dropwise to the reaction mixture. The reaction was refluxed overnight then cooled. Methanol (30 mL) was cautiously added and the reaction mixture was stirred an additional 1 hour at room temperature. The mixture was then evaporated in vacuo, and the residue was purified on a silica gel flash chromatography column eluted with 10% ethyl acetate/hexane to afford 0.80 g (7%) of the title compound.

$^1$H NMR (400 MHz, CDCl$_3$, ppm): δ7.37 (s, 1H), 5.94 (s, 2H), 3.88 (s, 3H), 3.85 (s, 3H), 3.79 (s, 3H). FAB-MS: m/e 445 (M+1).

Step B: Preparation of 5,7-dimethyl-2-ethyl-3-[4-((1-carbomethoxy-1-(2,5-dibromo-3,4-dimethoxyphenyl))methoxy)-3-propylphenyl]methyl-3H-imidazo[4,5-b]pyridine Using the K$_2$CO$_3$/acetone conditions for phenol alkylation described in Step A of Example 30, 5,7-dimethyl-2-ethyl-3-[4-hydroxy-3-propylphenyl]methyl-3H-imidazo[4,5-b]pyridine (Step A, Example 43) was alkylated with the product of Step A. Standard workup and purification by flash chromatography afforded a 65% yield of the title compound.

$^1$H NMR (400 MHz, CDCl$_3$, ppm): δ7.15 (s, 1H), 6.98 (dd, 1H), 6.86 (s, 1H), 6.79 (dd, 1H), 6.5485 (d, 1H, 8.42 Hz), 6.042 (s, 1H), 5.33 (ABq, 2H), 3.825 (s, 3H), 3.8 (s, 3H), 3,713 (s, 3H), 2.76 (q, 2H, 7.6 Hz), 2.592 (s, 3H), 2.561 (s, 3H), 2.477 (dd, 2H, 7.65 Hz, 7.6 Hz), 1.675–1.45 (m, 2H), 1.268 (t, 3H), 0.889 (t, 3H). FAB-MS: m/e 688, 690, 692 (M+1).

Step C: Preparation of 5,7-dimethyl-2-ethyl-3-[4-((1-carboxy-1-(2,5-dibromo-3,4-dimethoxyphenyl))methoxy)-3-propylphenyl]methyl-3H-imidazo[4,5-b]pyridine Using the general procedure for ester hydrolysis described in Step E of Example 19, the product of Step B was converted to the title compound in 72% yield.

$^1$H NMR (400 MHz, CDCl$_3$, ppm): δ7.25 (br s, 1H), 6.97 (s, 1H), 6.94 (s, 1H), 6.82 (br s, 1H), 6.68 (br s, 1H), 5.41 (s, 3H), 3.80 (s, 3H), 3.78 (s, 3H), 2.80 (m, 2H), 2.58 (s, 3H), 2.56 (s, 3H), 2.22 (m, 2H), 1.8–1.45 (m, 2H), 1.25 (t, 3H), 0.84 (t, 3H). FAB-MS: m/e 675 (M+1).

EXAMPLE 50

3-[4-((1-Carboxy-1-(3,4-dimethoxyphenyl))methoxy)-3-propylphenyl]methyl-5,7-dimethyl-2-ethyl-3H-imidazo[4,5-b]pyridine Step A: Preparation of 5,7-dimethyl-2-ethyl-3-[4-((1-carbomethoxy-1-(3,4-dimethoxyphenyl))methoxy)-3-propylphenyl]methyl-3H-imidazo[4,5-b]pyridine To a solution of 63 mg (0.09,mmol) of the product of Step A of Example 49 in methanol was added 5 mg of palladium chloride, 20 mg of sodium borohydride and the mixture was stirred at room temperature for 2 hours. The reaction mixture was evaporated in vacuo, and the residue was purified on a silica gel flash chromatography column eluted with 50% ethyl acetate/hexane to afford 22 mg (45%) of the title compound.

$^1$H NMR (400 MHz, CDCl$_3$, ppm): δ7.07 (s, 1H), 7.04 (d, 1H, 8.13 Hz), 6.97 (s, 1H), 6.85 (s, 1H), 6.85 (d, 1H), 6.78 (dd, 1H), 6.57 (d, 1H), 5.48 (s, 1H), 5.33 ( s, 1H), 3.86 ( s, 3H), 3.85 ( s, 3H), 3.65 ( s, 3H), 2.75 (q, 2H, 7.52 Hz), 2.59 (s, 3H), 2.56 (s, 3H), 2.65–2.5 (m, 2H), 1.72–1.47 (m, 2H), 1.252 (t, 3H, 7.69 Hz), 0.89 (t, 3H, 7.34 Hz). FAB-MS: m/e 532 (M+1).

Step B: Preparation of 5,7-dimethyl-2-ethyl-3-[4-((1-carboxy-1-(3,4-dimethoxyphenyl))methoxy)-3-propylphenyl]methyl-3H-imidazo[4,5-b]pyridine Using the general procedure for ester hydrolysis described in Step E of Example 19, the product of Step A was converted to the title compound in 90% yield.

$^1$H NMR (400 MHz, CDCl$_3$, ppm): δ7.2 (s, 1H), 7.14 (d, 1H), 6.98 (s, 1H), 6.84 (d, 1H), 6.82 (s, 1H), 6.74 (d, 1H), 6.65 (d, 1H), 5.5 (s, 1H), 5.3 (ABq, 2H), 3.86 (s, 3H), 3.84 (s, 3H), 2.62 (q, 2H), 2.7–2.55 (m, 2H), 2.52 (s, 3H), 2.39 (s, 3H), 1.7–1.47 (m, 2H), 1.22 (t, 3H), 0.89 (t, 3H). FAB-MS: m/e 518 (M+1).

EXAMPLE 51

3-[4-((1-Carboxy-1-phenyl)methoxy)-3,5-dipropylphenyl]methyl-5,7-dimethyl-2-ethyl-3H-imidazo[4,5-b]pyridine Step A: Preparation of methyl 3-(2-propen-1-yl)-4-(2-propen-1-yloxy)benzoate A solution of 3.04 g (15.8 mmol) of methyl 4-hydroxy-3-propenylbenzoate (Example 42, Step B) was refluxed with anhydrous potassium carbonate (4.37 g, 2 equiv) and allyl bromide (3.5 mL, 2.5 equiv) in acetone overnight. The mixture was filtered through Celite and the filter cake was washed with more acetone and dichloromethane. After removing the solvents, the resulting oil was distilled under high vacuum to give 3.2 g (87%) of the title compound.

$^1$H NMR (400 MHz, CDCl$_3$, ppm): δ7.87 (dd, 1H), 7.83 (d, 1H), 6.83 (d, 1H), 6.07–5.92 (m, 2H), 5.41 (dd, 1H), 5.27 (dd, 1H), 5.07 (dd, 1H), 5.05 (dd, 1H), 4.58 (d, 2H), 3.83 (s, 3H), 3.4 (d, 2H).

Step B: Preparation of methyl 4-hydroxy-3,5-di(2-propen-1-yl)benzoate

The product of Step A (3.2g, 13.8 mmol) was refluxed in 1,2-dichlorobenzene for 3 days in the presence of a catalytic amount of BHT (10 mg). Flash column chromatography of the mixture using hexane and then 10% and 20% ethyl acetate in hexane afforded 3.1 g (97%) of the title compound.

$^1$H NMR (200 MHz, CDCl$_3$, ppm): δ7.73 (s, 2H), 6.12–5.92 (m, 2H), 5.63 (s, 1H), 5.21 (dd, 2H), 5.15 (dd, 2H), 3.87 (s, 3H), 3.43 (dd, 4H). FAB-MS: m/e 232 (M+1).

Step C: Preparation of methyl 4-tert-butyldimethylsilyloxy-3,5-di(2-propen-1-yl)benzoate The product of Step B (3.1 g, 13.36 mmol) was treated with tert-butyldimethylsilyl chloride (2.22 g, 1.1 equiv), triethylamine (3 mL) and DMAP (0.1 equiv) in dichloromethane overnight. The mixture was concentrated and flash chromatographed with 5% and then 10% ethyl acetate in hexane to furnish 4.5 g (97%) of the title compound.

$^1$H NMR (200 MHz, CDCl$_3$, ppm): δ7.72 (s, 2H), 6.02–5.30 (m, 2H), 5.12 (dd, 2H), 5.07 (dd, 2H), 3.86 (s, 3H), 3.38 (dd, 4H, 7 Hz), 1.02 (s, 9H), 0.21 (s, 6H).

Step D: Preparation of methyl 4-tert-butyldimethylsilyloxy-3,5-dipropylbenzoate

A solution of 5.0 g (14.45 mmol) of the product of Step C in 250 mL ethanol containing 5% Rh/C (0.25 g) was shaken under a 40 psi pressure of hydrogen. Upon completion of reduction, the mixture was filtered through Celite, the filter cake was washed with methanol and dichloromethane. Removal of solvents afforded 4.55 g (90%) of the title compound.

¹H NMR (200 MHz, CDCl₃, ppm): δ7.66 (s, 2H), 3.84 (s, 3H), 2.54 (dd, 4H, 7.91 Hz, 7.41 Hz), 1.56 (sextet, 4H), 0.98 (s, 9H), 0.899 (t, 6H), 0.18 (s, 6H).

Step E: Preparation of 4-tert-butyldimethylsilyloxy-3,5-dipropylbenzyl alcohol

Lithium aluminum hydride (9 mL of a 1M solution in THF) was added cautiously to a solution of the product of Step D at 0° C., and the reaction mixture was stirred overnight. Ethyl acetate was added to the mixture, cooled to 0° C. and treated with cold 1N HCl. After separating the organic phase, the aqueous phase was extracted with a mixture of ethyl acetate-ether-dichloromethane. The combined organic extracts were dried and concentrated. The concentrated material was purified by flash column chromatography using 20% ethyl acetate in hexane to afford 4.2 g (92%) of the title compound.

¹H NMR (400 MHz, CDCl₃, ppm): δ6.95 (s, 2H), 4.54 (s, 2H), 2.52 (dd, 4H), 1.55 (sextet, 4H), 0.99 (s, 9H), 0.90 (t, 6H), 0.16 (s, 6H).

Step F: Preparation of 5,7-dimethyl-2-ethyl-3-[4-tert-butyldimethylsilyloxy-3,5-dipropylphenyl]methyl-3H-imidazo[4,5-b]pyridine To a solution of 4.2 g (13.0 mmol) of the product of Step E, 2.5 g (14.0 mmol) of 5,7-dimethyl-2-ethylimidazo[4,5-b]pyridine (Example 24, Step C), and 5.62 (20.0 mmol) of triphenylphosphine dissolved in 40 mL of THF, was added 3.396 g (20.0 mmol) of diethyl azodicarboxylate and the mixture was stirred for 1 hour. The reaction mixture was then concentrated in vacuo and the residual oil was purified on a silica gel flash chromatography column eluted with 25–40% ethyl acetate/hexane to afford 5 g (80%) of the title compound.

¹H NMR (400 MHz, CDCl₃, ppm): δ6.84 (s, 1H), 6.71 (s, 2H), 5.29 (s, 2H), 2.75 (q, 2H), 2.57 (s, 3H), 2.55 (s, 3H), 2.4 (dd, 4H), 1.42 (sextet, 4H), 1.27 (t, 3H), 0.94 (s, 9H), 0.8 (t, 6H), 0.10 (s, 6H).

Step G: Preparation of 5,7-dimethyl-2-ethyl-3-[4-hydroxy-3,5-dipropylphenyl]methyl-3H-imidazo[4,5-b]pyridine A THF solution of 5.0 g (10.44 mmol) of the product of Step F was treated with tetrabutylammonium fluoride (1.2 equiv, 1M solution in THF) overnight. THF was removed in vacuo and the residue was flash chromatographed using 30–50% ethyl acetate in hexane as eluent to afford 3.35 g (88%) of the title compound.

¹H NMR (400 MHz, CDCl₃, ppm): δ6.86 (s, 1H), 6.81 (s, 1H), 6.73 (s, 2H), 5.37 (s, 1H), 5.30 (s, 2H), 2.76 (q, 2H), 2.6 (s, 3H), 2.56 (s, 3H), 2.44 (dd, 4H), 1.52 (sextet, 4H), 1.23 (t, 3H), 0.88 (t, 6H).

Step H: Preparation of 5,7-dimethyl-2-ethyl-3-[4-((1-carbomethoxy-1-phenyl)methoxy)-3,5-dipropylphenyl]methyl-3H-imidazo[4,5-b]pyridine Using the K₂CO₃/acetone conditions for phenol alkylation described in Step A of Example 30, the product of Step G was alkylated with methyl 2-bromophenylacetate. Standard workup and purification by flash chromatography afforded a 96% yield of the title compound.

¹H NMR (400 MHz, CDCl₃, ppm): δ7.44–7.42 (m, 2H), 7.37–7.31 (m, 3H), 6.88 (s, 1H), 6.74 (s, 2H), 5.38 (s, 1H), 5.33 (s, 2H), 3.7 (s, 3H), 2.80 (q, 2H), 2.62 (s, 3H), 2.57 (s, 3H), 2.38 (dd, 2H), 2.3–2.25 (m, 2H), 1.55–1.47 (m, 2H), 1.46–1.37 (m, 2H), 1.36 (t, 3H), 0.86 (t, 3H), 0.72 (t, 3H). FAB-MS: m/e 514 (M+1).

Step I: Preparation of 3-[4-((1-carboxy-1-phenyl)methoxy)-3,5-dipropylphenyl]methyl-5,7-dimethyl-2-ethyl-3H-imidazo[4,5-b]pyridine Using the general procedure for ester hydrolysis described in Step E of Example 19, the product of Step H was converted to the title compound in 80% yield.

¹H NMR (400 MHz, CDCl₃, ppm): δ7.47–7.34 (m, 2H), 7.33–7.22 (m, 3H), 6.92 (s, 1H), 6.69 (s, 2H), 5.35 (br s, 3H), 2.78 (g, 2H), 2.58 (s, 3H), 2.55 (s, 3H), 2.62–2.25 (m, 4H), 1.45–1.28 (m, 4H), 1.2 (t, 3H), 0.7 (t, 6H). FAB-MS: m/e 500 (M+1).

EXAMPLE 52

3-[4-((1-Carboxy-1-(2-methoxyphenyl))methoxy)-3,5-dipropylphenyl]methyl-5,7-dimethyl-2-ethyl-3H-imidazo[4,5-b]pyridine Step A: Preparation of 3-[4-((1-carbomethoxy-1-(2-methoxyphenyl))methoxy)-3,5-dipropylphenyl]methyl-5,7-dimethyl-2-ethyl-3H-imidazo[4,5-b]pyridine Using the K₂CO₃/acetone conditions for phenol alkylation described in Step A of Example 30, the product of Step G was alkylated with methyl 2-bromo-(2'-methoxy)phenylacetate. Standard workup and purification by flash chromatography afforded the title compound.

¹H NMR (400 MHz, CDCl₃, ppm): δ7.62 (dd, 1H, J=2.1, 1.9 Hz), 7.40 (dd, 1H), 7.30 (dd, 1H), 6.86 (s, 1H), 6.72 (s, 2H), 6.70 (dd, 1H), 5.37 (s), 5.35 (s), 5.32 (s, 2H), 3.69 (s, 3H), 3.68 (s, 3H), 2.74 (q, 2H, J=7.5 Hz), 2.61 (s, 3H), 2.56 (s, 3H), 2.34–2.19 (m, 4H), 1.50–1.29 (m, 4H), 1.23 (t, 3H, 7.54 Hz), 0.74 (t, 6H, J=7.3 Hz). FAB-MS: m/e 544 (M+1).

Step B: Preparation of 3-[4-((1-carboxy-1-(2-methoxyphenyl))methoxy)-3,5-dipropylphenyl]methyl-5,7-dimethyl-2-ethyl-3H-imidazo[4,5-b]pyridine Using the general procedure for ester hydrolysis described in Step E of Example 19, the product of Step A was converted to the title compound in 77% yield.

¹H NMR (400 MHz, CDCl₃, ppm): δ7.72–7.66 (m), 7.55 (br s, 1H), 7.52–7.48 (m), 7.35 (dd, 1H), 6.86 (s, 1H), 6.72 (s, 2H), 6.69 (dd, 1H), 5.38 (s, 1H), 5.30 (ABq, 2H), 3.64 (s, 3H), 2.76 (q, 2H, 7.6 Hz), 2.55 (s, 3H), 2.52 (s, 3H), 2.28 (m, 4H), 1.50–1.18 (m, 4H), 1.13 (t, 3H), 0.74 (t, 6H). FAB-MS: m/e 608 (M+2K).

EXAMPLE 53

3-[4-((1-Carboxy-1-(2,5-dibromo-3,4-dimethoxyphenyl))methoxy)-3,5-dipropylphenyl]methyl-5,7-dimethyl-2-ethyl-3H-imidazo[4,5-b]pyridine Step A: Preparation of 3-[4-((1-carbomethoxy-1-(2,5-dibromo-3,4-dimethoxyphenyl))methoxy)-3,5-dipropylphenyl]methyl-5,7-dimethyl-2-ethyl-3H-imidazo[4,5-b]pyridine Using the K₂CO₃/acetone conditions for phenol alkylation described in Step A of Example 30, the product of Step G was alkylated with methyl 2,2',5'-tribromo-3',4'-dimethoxyphenylacetate (Step A, Example). Standard workup and purification by flash chromatography afforded a 60% yield of the title compound.

¹H NMR (400 MHz, CDCl₃, ppm): δ7.36 (s, 1H), 6.89 (s, 1H), 6.75 (s, 2H), 5.55 (s, 1H), 5.34 (ABq, 2H), 3.88 (s, 3H), 3.84 (s, 3H), 3.69 (s, 3H), 2.78 (q, 2H), 2.62 (s, 3H), 2.41–2.20 (m, 4H), 1.45–1.32 (m, 4H), 0.85 (t, 3H), 0.74 (t, 6H). FAB-MS: m/e 732 (M+1).

Step B: Preparation of 3-[4-((1-carboxy-1-(2,5-dibromo-3,4-dimethoxyphenyl))methoxy)-3,5-dipropylphenyl]methyl-5,7-dimethyl-2-ethyl-3H-imidazo[4,5-b]pyridine Using the general procedure for ester hydrolysis described in Step E of Example 19, the product of Step A was converted to the title compound.

$^1$H NMR (400 MHz, CD$_3$OD, ppm): δ7.45 (br s, 1H), 7.01 (s, 1H), 6.75 (s, 2H), 5.51 (s, 1H), 5.44 (ABq, 2H), 3.88 (s, 3H), 3.78 (s, 3H), 3.34 (s, 3H), 2.82 (q, J=7.5 Hz, 2H), 2.59 (s, 3H), 2.57 (s, 3H), 2.24–2.40 (m, 4H), 1.38–1.52 (m, 2H), 1.24–1.36 (m, 2H), 1.20 (t, J=7.5 Hz, 3H), 0.74 (t, J=7.5 Hz, 6H). FAB-MS: m/e 716 (M+1).

EXAMPLE 54

3-[4-N-((1-Carboxy-1-phenyl)methyl)-N-methylaminophenyl]methyl-5,7-dimethyl-2-ethyl-3H-imidazo[4,5-b]pyridine Step A: Preparation of 5,7-dimethyl-2-ethyl-3-(4-nitrophenyl)methyl-3H-imidazo[4,5-b]pyridine To a solution of 5.0 g (1.0 eq, 28.6 mmol) 5,7-dimethyl-2-ethylimidazo[4,5-b]pyridine in 30 mL DMF under N$_2$ at rt was added 1.37 g (1.2 eq, 34.3 mmol) of a 60% oil dispersion of NaB. After stirring for 5 minutes, 8.64 g (1.4 eq, 40.0 mmol) of p-nitrobenzyl bromide was added. The dark brown mixture was stirred for 2 hours under a blanket of N$_2$ at rt. The mixture was diluted with 1 L CH$_2$Cl$_2$ and washed with 500 mL H$_2$O and 500 mL saturated aqueous NaCl. The organic phase was dried over MgSO$_4$ and concentrated to a yellow oil. The oil was flash chromatographed with 50% ethyl acetate/hexane. The product containing fractions were combined and concentrated to a yellow oil which crystallized on standing, yielding 6.81 g (76.8%) of the title compound.

$^1$H NMR (300 MHz, CDCl$_3$, ppm): δ8.15 (d, 2H), 7.27 (d, 2H), 6.92 (s, 1H), 5.55 (s, 2H), 2.77 (q, 2H), 2.64 (s, 3H), 2.57 (s, 3H), 1.32 (t, 3H). FAB-MS: m/e 325 (M+1).

Step B: Preparation of 5,7-dimethyl-2-ethyl-3-(4-aminophenyl)methyl-3H-imidazo[4,5-b]pyridine To a solution of 6.81 g (21.0 mmol) of the product of Step A dissolved in 75 mL methanol in a high pressure reaction vessel was added 0.3 g 5% palladium on carbon. The resulting suspension was pressurized to 40 psi with H$_2$ and shaken for 2 hours. The solution was filtered through a pad of celite and the filtrate concentrated to a gray-green oil which crystallized on standing. The crude material was flash chromatographed with 50% ethyl acetate/hexane and 3% methanol/ethyl acetate to yield 5.0 g (85%) of the title compound.

$^1$H NMR (300MHz, CD$_3$OD, ppm): δ6.85 (s, 1H), 6.80 (d, 2H), 6.52 (d, 2H), 5.26 (s, 2H), 2.72 (q, 2H), 2.49 (s, 3H), 2.49 (s, 6H), 1.12 (t, 3H). FAB-MS: m/e 281 (M+1).

Step C: Preparation of 5,7-dimethyl-2-ethyl-3-(4-N-(tert-butyloxycarbonyl)aminophenyl)methyl-3H-imidazo[4,5-b]pyridine To a solution of 1.0 g (3.57 mmol) of of the product of Step B dissolved in 20 mL CH$_2$Cl$_2$ was added 0.75 mL (5.36 mmol, 1.5 eq) of triethylamine and 1.23 mL (5.36 mmol, 1.5 eq) of di-tert-butyl dicarbonate. The resulting solution was stirred for 18 hours. The products had crystallized out of solution after that time period. The suspension was diluted with 500 mL of CH$_2$Cl$_2$ (which promoted dissolution of the products) and washed with 200 mL H$_2$O at pH 9 (NaOH). The organic phase was dried over Na$_2$SO$_4$, filtered and concentrated to a pale yellow oil. The oil was flash chromatographed with 50% ethyl acetate/hexane to yield 450 mg (33%) of the title compound as a white powder.

$^1$H NMR (300 MHz, CDCl$_3$, ppm): δ7.26 (d, 2H), 7.04 (d, 2H), 6.89 (s, 1H), 6.63 (br s, 1H), 5.39 (s, 2H), 2.77 (g, 2H), 2.62 (s, 3H), 2.59 (s, 3H), 1.49 (s, 9H), 1.29 (t, 3H). FAB-MS: m/e 381 (M+1).

General procedure for alkylation of N-BOC protected amines:

Step D: Preparation of 5,7-dimethyl-2-ethyl-3-(4-N-(tert-butyloxycarbonyl)-N-methylaminophenyl)methyl-3H-imidazo[4,5-b]pyridine To a solution of 100 mg of the product of Step C dissolved in 4 mL of DMF was added 16 mg (0.39 mmol, 1.5 eq) of a 60% oil dispersion of NaH. This mixture was stirred for 5 minutes until evolution of hydrogen ceased, and then 32.8 mL (73.8 mg, 0.52 mmol, 2.0 eq) of methyl iodide was added. The solution was then stirred for 18 hours. The excess NaH was quenched with methanol and then all volatiles were removed in vacuo. The resultant brown oil was purified on a silica gel flash chromatography column eluted with 50% ethyl acetate/hexane. The product fractions were combined and concentrated to give a pale yellow oil which was used directly in the next step.

$^1$H NMR (400 MHz, CDCl$_3$, ppm): δ7.12 (d, 2H), 7.04 (d, 2H), 6.87 (s, 1H), 5.40 (s, 2H), 3.18 (s, 3H), 2.77 (q, 2H), 2.60 (s, 3H), 2.56 (s, 3H), 1.49 (s, 9H), 1.27 (t, 3H). FAB-MS: m/e 395 (M+1).

General procedure for deprotection of N-BOC nines:

Step E: Preparation of 5,7-dimethyl-2-ethyl-3-(4-N-methylaminophenyl)methyl-3H-imidazo[4,5-b]pyridine Dissolved the product of Step D in 2.0 mL CH$_2$Cl$_2$ and added 2.0 mL TFA. Solution was stirred for 3 hours. Volatiles were removed in vacuo and the compound was dissolved in methanol. 2.0 mL saturated aqueous NaHCO$_3$ was added to neutralize the excess TFA. The methanol was then concentrated and the H$_2$O azeotroped with toluene. The compound was taken up in CHCl$_3$ and the excess NaHCO$_3$ was filtered out through a celite pad. The solution was concentrated yield 9 mg (94%) of a pale yellow oil.

$^1$H NMR (400 MHz, CDCl$_3$, ppm): δ6.97 (d, 2H), 6.85 (s, 1H), 6.4.8 (d, 2H), 5.32 (s, 2H), 3.73 (br s, 3H), 2.79 (q, 2H), 2.76 (s, 3H), 2.61 (s, 3H), 2.59 (s, 3H), 1.28 (t, 3H). FAB-MS: m/e 295 (M+1).

General procedure for phenylaminophenylacetic acid synthesis:

Step F: Preparation of 3-[4-N-((1-carbomethoxy-1-phenyl)methyl)-N-methylaminophenyl]methyl-5,7-dimethyl-2-ethyl-3H-imidazo[4,5-b]pyridine To a solution of 72.3 mg (0.25 mmol) of the product of Step E dissolved in 2.0 mL DMF was added 15 mg (0.37 mmol, 1.5 eq) of a 60% oil dispersion of NaH, and the reaction mixture was stirred at room temperature. After evolution of hydrogen had ceased, 95.5 mL (0.49 mmol, 2.0 eq) of methyl-2-bromophenylacetate was added. The resulting solution was stirred for 80 hours under N$_2$ at rt. The excess NaH was quenched with methanol and the volatiles were removed in vacuo. The resultant oil was purified on a silica gel flash chromatography column eluted with 50% ethyl acetate/hexane to yield 80.7 mg (73%) of the title compound as a pale yellow oil.

$^1$H NMR (400 MHz, CDCl$_3$, ppm): δ7.29–7.38 (m, 3H), 7.22 (d, 2H), 7.05 (d, 2H), 6.87 (s, 1H), 6.74 (d, 2H), 5.69 (s, 1H), 5.36 (s, 2H), 3.74 (s, 3H), 2.82 (q, 2H), 2.73 (s, 3H), 2.61 (s, 3H), 2.59 (s, 3H), 1.51 (t, 3H). FAB-MS: m/e 443 (M+1).

Step G: Preparation of 3-[4-N-((1-carboxy-1-phenyl)-methyl)-N-methylaminophenyl]methyl-5,7-dimethyl-2-ethyl,3H-imidazo[4,5-b]pyridine To a solution of the product of Step F dissolved in 3.0 mL methanol, was added 3.0 mL of 3N NaOH, and the solution was stirred for 7 days. The methanol was removed in vacuo and the H$_2$O was removed by azeotropic distillation with toluene. The product was taken up in CHCl$_3$ and the excess NaOH filtered through a celite pad. The CHCl$_3$ was concentrated and the resultant oil was purified on a 20 cm×20 cm×500 mm silica gel preparatory TLC plate, developed with a solution of CHCl$_3$/MeOH/NH$_4$OH (80:20:2). The product was extracted from the silica gel with 100 mL of 10% methanol/CHCl$_3$. The solution was concentrated and the resultant oil triturated with ether to yield 61 mg (78.2%) of the title compound as a white powder.

$^1$H NMR (400 MHz, CDCl$_3$, ppm): δ7.00 (s, 5H), 6.77 (s, 1H), 6.70 (d, 2H), 6.43 (d, 2H), 5.15 (s, 1H), 5.12 (s, 2H), 2.68 (q, 2H), 2.57 (s, 3H), 2.40 (s, 6H), 1.20 (t, 3H). FAB-MS: m/e 429 (M+1).

EXAMPLE 55

3-[4-N-((1-Carboxy-1-phenyl)methyl)-N-ethylaminophenyl]methyl-5,7-dimethyl-2-ethyl-3H-imidazo[4,5-b]pyridine Step A: Preparation of 5,7-dimethyl-2-ethyl-3-(4-N-(tert-butyloxycarbonyl)-N-ethylaminophenyl)methyl-3H-imidazo[4,5-b]pyridine Using the general procedure for the alkylation of N-BOC protected amines described in Step D of Example 54, 5,7-dimethyl-2-ethyl-3-(4-N-(tertbutyloxycarbonyl)aminophenyl)methyl-3H-imidazo[4,5-b]pyridine (Step C, Example 54) was alkylated with ethyliodide. Standard workup and purification by flash chromatography afforded the title compound.

$^1$H NMR (300 MHz, CDCl$_3$, ppm): δ7.09 (s, 4H), 6.90 (s, 1H), 5.44 (s, 2H), 3.62 (q, 2H), 2.80 (q, 2H), 2.64 (s, 3H), 2.59 (s, 3H), 1.40 (s, 9H), 1.28 (t, 3H), 1.09 (t, 3H). FAB-MS: m/e 409 (M+1).

Step B: Preparation of 5,7-dimethyl-2-ethyl-3-(4-N-ethylaminophenyl)methyl-3H-imidazo[4,5-b]pyridine Using the general procedure for deprotection of N-BOC amines described in Step E of Example 54, the product of Step A was converted to the title compound.

$^1$H NMR (300 MHz, CDCl$_3$, ppm): δ6.97 (d, 2H), 6.87 (s, 1H), 6.49 (d, 2H), 3.10 (q, 2H), 2.80 <q, 2H), 2.62 (s, 3H), 2.60 (s, 3H), 1.29 (t, 3H), 1.21 (t, 3H). FAB-MS: m/e 308 (M+1).

Step C: Preparation of 3-[4-N-((1-carbomethoxy-1-phenyl)methyl)-N-ethylaminophenyl]methyl-5,7-dimethyl-2-ethyl-3H-imidazo[4,5-b]pyridine Using the general procedure for the phenylaminophenylacetic acid synthesis described in Step F of Example 54, the product of Step B was alkylated with methyl 2-bromophenylacetate. Standard workup and purification by flash chromatography afforded the title compound.

$^1$H NMR (200 MHz, CDCl$_3$, ppm): δ7.24–7.40 (m 5H), 7.05 (d, 2H), 6.88 (s, 1H), 6.72 (d, 2H), 5.49 (s, 1H), 5.37 (s, 2H), 4.73 (s, 3H), 3.28 (q, 2H), 2.83 (q, 2H), 2.62 (s, 3H), 2.60 (s, 3H), 1.31 (t, 3H), 0.86 (t, 3H). FAB-MS: m/e 457 (M+1).

Step D: Preparation of 3-[4-N-((1-carboxy-1-phenyl)-methyl)-N-ethylaminophenyl]methyl-5,7-dimethyl-2-ethyl-3H-imidazo[4,5-b]pyridine Using the general procedure for ester hydrolysis described in Step E of Example 19, the product of Step C was converted to the title compound.

$^1$H NMR (400 MHz, CDCl$_3$, ppm): δ7.05 (m, 5H), 6.75 (s, 1H), 6.72 (d, 2H), 6.42 (d, 2H), 5.21 (s, 1H), 5.14 (s, 2H), 3.12 (q, 2H), 2.73 (q, 2H), 2.58 (s, 3H), 2.37 (s, 3H), 1.24 (t, 3H). FAB-MS: m/e 443 (M+1).

EXAMPLE 56

3-[4-N-((1-Carboxy-1-phenyl)methyl)-N-propylaminophenyl]methyl-5,7-dimethyl-2-ethyl-3H-imidazo[4,5-b]pyridine Step A: Preparation of 5,7-dimethyl-2-ethyl-3-(4-N-(tert-butyloxycarbonyl)-N-propylaminophenyl)methyl-3H-imidazo[4,5-b]pyridine Using the general procedure for the alkylation of N-BOC protected amines described in Step D of Example 54, 5,7-dimethyl-2-ethyl-3-(4-N-(tertbutyloxycarbonyl)aminophenyl)methyl-3H-imidazo[4,5-b]pyridine (Step C, Example 54) was alkylated with propyl bromide. Standard workup and purification by flash chromatography afforded the title compound.

$^1$H NMR (300 MHz, CDCl$_3$, ppm): δ7.09 (s,4H), 6.89 (s, 1H), 5.44 (s, 2H), 3.52 (t, 2H), 2.79 (q, 2H), 2.63 (s, 3H), 2.59 (s, 3H), 1.50 (m, 2H), 1.40 (s, 9H), 1.28 (t, 3H), 0.84 (t, 3H). FAB-MS: m/e 423 (M+1).

Step B: Preparation of 5,7-dimethyl-2-ethyl-3-(4-N-propylaminophenyl)methyl-3H-imidazo[4,5-b]pyridine Using the general procedure for deprotection of N-BOC amines described in Step E of Example 54, the product of Step A was converted to the title compound.

$^1$H NMR (300 MHz, CDCl$_3$, ppm): δ6.97 (d, 2H), 6.88 (s, 1H), 6.49 (d, 2H), 5.33 (s, 2H), 3.02 (t, 2H), 2.80 (q, 2H), 2.62 (s, 3H), 2.60 (s, 3H), 1.60 (m, 2H), 1.30 (t, 3H), 0.98 (t, 3H). FAB-MS: m/e 323 (M+1).

Step C: Preparation of 3-[4-N-((1-carbomethoxy-1-phenyl)methyl)-N-propylaminophenyl]methyl-5,7-dimethyl-2-ethyl-3H-imidazo[4,5-b]pyridine Using the general procedure for the phenylaminophenylacetic acid synthesis described in Step F of Example 54, the product of Step B was alkylated with methyl 2-bromophenylacetate. Standard workup and purification by flash chromatography afforded the title compound.

$^1$H NMR (400 MHz, CDCl$_3$, ppm): δ7.22–7.38 (m, 5H), 7.04 (d, 2H), 6.88 (s, 1H), 6.70 (d, 2H), 5.49 (s, 1H), 5.37 (s, 2H), 3.72 (t, 2H), 2.83 (q, 2H), 2.62 (s, 3H), 2.60 (s, 3H), 1.44 (m, 2H), 1.33 (t, 3H), 0.89 (t, 3H). FAB-MS: m/e 471 (M+1).

Step D: Preparation of 3-[4-N-((1-carboxy-1-phenyl)-methyl)-N-propylaminophenyl]methyl-5,7-dimethyl-2-ethyl-3H-imidazo[4,5-b]pyridine Using the general procedure for ester hydrolysis described in Step E of Example 19, the product of Step C was converted to the title compound.

$^1$H NMR (400 MHz, CDCl$_3$, ppm): δ7.20 (br s, 2H), 7.06 (br s, 3H), 6.78 (s, 1H), 6.73 (d, 2H), 6.52 (d, 2H), 5.11 (br s, 3H), 2.9 7 (m, 2H), 2.71 (q, 2H), 2.57 (s, 3H), 2.42 (s, 3H), 1.23 (t, 3H), 0.87 (m, 3H), 0.46 (t, 3H). FAB-MS: m/e 457 (M+1).

EXAMPLE 57

3-[4-N-((1-Carboxy-1-phenyl)methyl)aminophenyl]-methyl-5,7-dimethyl-2-ethyl-3H-imidazo[4,5-b]pyridine Step A: Preparation of 3-[4-N-((1-carbomethoxy-1-phenyl)methyl)aminophenyl]methyl-5,7-dimethyl-2-ethyl-3H-imidazo[4,5-b]pyridine To a solution of 0.50 g (1.79 mmol) of 5,7-dimethyl-2-ethyl-3-(4-aminophenyl)methyl-3H-imidazo [4,5-b]pyridine (Step B, Example 54) in 4.0 mL DMF, was added 143 mg (3.57 mmol, 2.0 eq) of a 60% oil dispersion of NaH. When evolution of hydrogen ceased (approximately 5 min.), 1.04 mL (5.36 mmol, 3.0 eq) of methyl 2-bromophenylacetate was added, and the mixture was stirred for 18 hours. The DMF was removed in vacuo and the resultant brown oil was flash chromatographed with 2:1 ethyl acetate/hexane to yield 0.690 g (90%) of a yellow-green powder.

$^1$H NMR (400 MHz, CDCl$_3$, ppm): δ7.42 (d, 2H), 7.23–7.35 (m, 3H), 6.89 (d, 2H), 6.85 (s, 1H), 6.43 (d, 2H), 5.28 (s, 2H), 4.97–5.01 (m, 1H), 3.69 (s, 3H), 2.77 (q, 2H), 2.60 (s, 3H), 2.56 (s, 3H), 1.25 (t, 3H). FAB-MS: m/e 429 (M+1).

Step B: Preparation of 3-[4-N-((1-carboxy-1-phenyl)-methyl)aminophenyl]methyl-5,7-dimethyl-2-ethyl-3H-imidazo[4,5-b]pyridine To a solution of 0.45 g of the product of Step A dissolved in 5.0 mL methanol, was added 3.0 mL of 3N NaOH solution, and the mixture was stirred for 30 minutes. The methanol was removed in vacuo and the water was removed by azeotropic distillation with toluene. The toluene was removed in vacuo, then the product was redissolved in CHCl$_3$ and excess NaOH was removed by filtration of the suspension through a celite pad. The filtrate was concentrated to a clear oil and purified on a silica gel flash chromatography column eluted with CHCl$_3$/MeOH/NH$_4$OH (80:15:1). The product fractions were combined and concentrated. The resultant oil was triturated with ether to yield 396 mg (91%) of the title compound as a white powder.

$^1$H NMR (300 MHz, CDCl$_3$, ppm): δ7.48 (d, 2H), 7.40 (s, 1H), 7.20–7.34 (m, 4H), 6.91 (s, 1H), 6.87 (d, 2H), 5.31 (s, 2H), 4.89 (br s, 1H), 2.78 (q, 2H), 2.59 (s, 6H), 1.24 (t, 3H). FAB-MS: m/e 415 (M+1).

EXAMPLE 58

3-[4-N-((1-Carboxy-1-phenyl)methyl)-N-allylaminophenyl]methyl-5,7-dimethyl-2-ethyl-3H-imidazo[4,5-b]pyridine General procedure for alkylation of secondary amines with LiN(TMS)$_2$:

Step A: Preparation of 3-[4-N-((1-carbomethoxy-1-phenyl)methyl)-N-allylaminophenyl]methyl 5,7-dimethyl-2-ethyl-3H-imidazo[4,5-]pyridine To a solution of 0.30 g (0.70 mmol) of 3-[4-N-((1-carbomethoxy-1-phenyl)methyl)aminophenyl]methyl-5,7-dimethyl-2-ethyl-3H-imidazo[4,5-b]pyridine (Step A, Example 57) in 1.5 mL THF, 0.84 mL (0.84 mmol, 1.2 eq) of 1M lithium bis(trimethylsilyl)amide in THF was added producing a dark brown solution with evolution of hydrogen gas. After stirring the solution for 5 minutes, 96.1 mL (1.05 mmol, 1.5 eq) of allyl iodide was added. The resultant yellow solution was stirred for 18 hours. The solution was concentrated to a yellow oil which was flash chromatographed with 50% ethyl acetate/hexane. The product fractions were combined and concentrated to yield 173 mg (53%) of a pale yellow oil.

$^1$H NMR (400 MHz, CDCl$_3$, ppm): δ7.52 (d, 2H), 7.22–7.33 (m, 3H), 6.98 (s, 1H), 6.78 (d, 2H), 6.23 (d, 2H), 5.52–5.65 (ddd, 1H), 5.26 (s, 1H), 5.23 (s, 2H), 5.03 (dd, 1H), 4.96 (dd, 1H), 3.62 (s, 3H), 3.18 (d, 2H), 2.71 (q, 2H), 2.57 (s, 3H), 2.54 (s, 3H), 1.21 (t, 3H). FAB-MS: m/e 469 (M+1).

Step B: Preparation of 3-[4-N-((1-carboxy-1-phenyl)-methyl)-N-allylaminophenyl]methyl-5,7-dimethyl-2-ethyl-3H-imidazo[4,5-b]pyridine Using the general procedure for ester hydrolysis described in Step E of Example 19, the product of Step A was converted to the title compound.

$^1$H NMR (400 MHz, CD$_3$OD, ppm): δ7.53 (d, 2H), 7.22 (t, 3H), 7.12 (t, 1H), 6.97 (s, 1H), 6.68 (d, 2H), 6.22 (d, 2H), 5.67–5.74 (m, 1H), 5.29 (s, 2H), 3.36 (dd, 1H), 3.07 (dd, 1H), 2.78 (q, 2H), 2.57 (s, 3H), 2.56 (s, 3H), 1.15 (t, 3H). FAB-MS: m/e 455 (M+1).

EXAMPLE 59

3-[4-N-((1-Carboxy-1-phenyl)methyl)-N-iso-butylaminophenyl]methyl-5,7-dimethyl-2-ethyl-3H-imidazo[4,5-b]pyridine Step A: Preparation of 3-[4-N-((1-carbomethoxy-1-phenyl)methyl)-N-iso-butylaminophenyl]methyl-5,7-dimethyl-2-ethyl-3H-imidazo [4,5-b]pyridine Using the general procedure for the alkylation of secondary amines with LiN(TMS)$_2$ described in Step A of Example 58, 3-[4-N-((1-carbomethoxy-1-phenyl)methyl)aminophenyl]methyl-5,7-dimethyl-2-ethyl-3H-imidazo[4,5-b]pyridine (Step A, Example 57) was alkylated with iso-butyl bromide. Standard workup and purification by flash chromatography afforded the title compound.

$^1$H NMR (400 MHz, CDCl$_3$, ppm): δ7.49 (d, 2H), 7.18–7.30 (m, 3H), 6.83 (s, 1H), 6.77 (d, 2H), 6.20 (d, 2H), 5.49 (s, 1H), 5.22 (s, 2H), 3.61 (s, 3H), 2.70 (q, 2H), 2.57 (s, 3H), 2.54 (s, 3H), 2.45 (d, 2H), 1.63 (m, 1H), 1.18 (t, 3H), 0.81 (d, 3H), 0.75 (d, 3H). FAB-MS: m/e 485 (M+1).

Step B: Preparation of 3-[4-N-((1-carboxy-1-phenyl)-methyl)-N-iso-butylaminophenyl]methyl-5,7-dimethyl-2-ethyl-3H-imidazo[4,5-b]pyridine Using the general procedure for ester hydrolysis described in Step E of Example 19, the product of Step A was converted to the title compound.

$^1$H NMR (400 MHz, CD$_3$OD, ppm): δ7.49 (d, 2H), 7.17 (t, 2H), 7.08 (t, 1H), 6.96 (s, 1H), 6.68 (d, 2H), 6.21 (d, 2H), 5.27 (s, 2H), 2.76 (q, 2H), 2.57–2.63 (m, 1H), 2.56 (s, 3H), 2.55 (s, 3H), 2.31 (dd, 1H), 1.65–1.71 (m, 1H), 1.12 (t, 3H), 0.93 (d, 3H), 0.76 (d, 3H). FAB-MS: m/e 471 (M+1).

EXAMPLE 60

3-[4-N-((1-Carboxy-1-phenyl)methyl)-N-cyclopropylmethylaminophenyl]methyl-5,7-dimethyl-2-ethyl-3H-imidazo[4.5-b]pyridine Step A: Preparation of 3-[4-N-((1-carbomethoxy-1-phenyl)methyl)-N-cyclopropylmethylaminophenyl]-methyl-5,7-dimethyl-2-ethyl-3H-imidazo[4,5-b]pyridine Using the general procedure for the alkylation of secondary amines with LiN(TMS)$_2$ described in Step A of Example 58, 3-[4-N-((1-carbomethoxy-1-phenyl)methyl)aminophenyl]methyl-5,7-dimethyl-2-ethyl-3H-imidazo[4,5-b]pyridine (Step A, Example 57) was alkylated with cyclopropylmethyl bromide. Standard workup and purification by flash chromatography afforded the title compound.

¹H NMR (400 MHz, CDCl₃, ppm): δ7.49 (d, 2H), 7.29 (t, 2H), 7.24 (d, 1H), 6.83 (s, 1H), 6.78 (d, 2H), 6.22 (d, 2H), 5.52 (s, 1H), 5.23 (s, 2H), 3.63 (s, 3H), 2.73 (q, 2H), 2.67 (dd, 1H), 2.57 (s, 3H), 2.55 (s, 3H), 2.09 (dd, 1H), 1.22 (t, 3H), 0.55–0.65 (m, 1H), 0.36 (dt, 2H), −0.06 (m, 2H). FAB-MS: m/e 483 (M+1).

Step B: Preparation of 3-[4-N-((1-carboxy-1-phenyl)methyl)-N-cyclopropylmethylaminophenyl]methyl-5,7-dimethyl-2-ethyl-3H-imidazo [4,5-b]pyridine Using the general procedure for ester hydrolysis described in Step E of Example 19, the product of Step A was converted to the title compound. FAB-MS: m/e 485 (M+1).

EXAMPLE 61

3-[4-N-((1-Carboxy-1-phenyl)methyl)-N-sec-butylaminophenyl]methyl-5,7-dimethyl-2-ethyl-3H-imidazo[4,5-b]pyridine Step A: Preparation of 3-[4-N-((1-carbomethoxy-1-phenyl)methyl)-N-sec-butylaminophenyl]methyl-5,7-dimethyl-2-ethyl-3H-imidazo [4,5-b]pyridine Using the general procedure for the alkylation of secondary amines with LiN(TMS)₂ described in Step A of Example 58, 3-[4-N-((1-carbomethoxy-1-phenyl)methyl)aminophenyl]methyl-5,7-dimethyl-2-ethyl-3H-imidazo[4,5-b]pyridine (Step A, Example 57) was alkylated with sec-butyl bromide. Standard workup and purification by flash chromatography afforded the title compound.

¹H NMR (400 MHz, CDCl₃, ppm): δ7.53–7.59 (m, 3H), 7.20–7.30 (m, 2H), 6.82 (s, 1H), 6.79 (d, 2H), 6.24 (d, 2H), 5.23 (s, 2H), 4.36 (s, 1H), 3.55 (s, 3H), 2.72 (q, 2H), 2.58 (s, 3H), 2.55 (s, 3H), 2.10 (m, 1H), 1.20 (t, 3H), 0.82–0.90 (m, 5H), 0.80 (d, 3H). FAB-MS: m/e 485 (M+1).

Step B: Preparation of 3-[4-N-((1-carboxy-1-phenyl)methyl)-N-sec-butylaminophenyl]methyl-5,7-dimethyl-2-ethyl-3H-imidazo[4,5-b]pyridine Using the general procedure for ester hydrolysis described in Step E of Example 19, the product of Step A can be converted to the title compound.

EXAMPLE 62

3-[4-N-((1-Carboxy-1-phenyl)methyl)-N-iso-propylaminophenyl]methyl-5,7-dimethyl-2-ethyl-3H-imidazo[4,5-b]pyridine Step A: Preparation of 3-[4-N-((1-carbomethoxy-1-phenyl)methyl)-N-iso-propylaminophenyl]methyl-5,7-dimethyl-2-ethyl-3H-imidazo [4,5-b]pyridine Using the general procedure for the alkylation of secondary amines with LiN(TMS)₂ described in Step A of Example 58, 3-[4-N-((1-carbomethoxy-1-phenyl)methyl)aminophenyl]methyl-5,7-dimethyl-2-ethyl-3H-imidazo[4,5-b]pyridine (Step A, Example 57) was alkylated with iso-propyl bromide. Standard workup and purification by flash chromatography afforded the title compound.

¹H NMR (400 MHz, CDCl₃, ppm): δ7.57 (d, 2H), 7.21–7.30 (m, 3H), 6.90 (br s, 1H), 6.81 (d, 2H) 6.25 (d, 2H), 5.27 (s, 2H), 4.42 (s, 1S), 3.56 (s, 3H), 2.73–2.82 (m, 2H), 2.64 (s, 3H), 2.57 (s, 3H), 2.49 (m, 1H), 1.24 (m, 3H), 0.88 (d, 3H), 0.80 (d, 3H). FAB-MS: m/e 471 (M+1).

Step B: Preparation of 3-[4-N-((1-carboxy-1-phenyl)methyl)-N-iso-propylaminophenyl]methyl-5,7-dimethyl-2-ethyl,3H-imidazo[4,5-b]pyridine Using the general procedure for ester hydrolysis described in Step E of Example 19, the product of Step A can be converted to the title compound.

EXAMPLE 63

3-[4-N-((1-(Tetrazol-5-yl)-1-phenyl)methyl)-N-methylaminophenyl]methyl-5,7-dimethyl-2-ethyl-3H-imidazo [4,5-b]pyridine Step A: Preparation of 3-[4-N-((1-cyano-1-phenyl)methyl)-N-methylaminophenyl]methyl-5,7-dimethyl-2-ethyl-3H-imidazo[4,5-b]pyridine To a solution of 75 mg (0.26 mmol) of 5,7-dimethyl-2-ethyl-3-(4-N-methylaminophenyl)methyl-3H-imidazo[4,5-b]pyridine (Step E, Example 54) dissolved in 1.0 mL methanol and 1.0 mL acetic acid was added 51.9 uL (0.51 mmol) benzaldehyde and 25 mg (0.38 mmol) potassium cyanide. The mixture was stirred for 24 hours at room temperature, then evaporated in vacuo. The residual oil was purified on a silica gel flash chromatography column to afford 101 mg (97%) of the title compound.

¹H NMR (400 MHz, CDCl₃, ppm): δ7.32–7.40 (m, 3H), 7.24 (d, 2H), 7.08 (d, 2H), 6.90 (s, 1H), 6.75 (d, 2H), 5.65 (s, 1H), 5.35 (s, 2H), 2.88 (q, 2H), 2.75 (s, 3H), 2.62 (s, 3H), 2.58 (s, 3H), 1.50 (t, 3H). FAB-MS: m/e 410 (M+1).

Step B: Preparation of 3-[4-N-((1-(tetrazol-5-yl)-1-phenyl)methyl)-N-methylaminophenyl]methyl-5,7-dimethyl-2-ethyl-3H-imidazo[4,5-b]pyridine To a solution of 101 mg (0.25 mmol) of the product of Step A dissolved in 5.0 mL toluene was added 154 mg (0.75 mmol) of trimethylstannyl azide, and the mixture was stirred and heated at reflux for 24 hours. The reaction mixture was evaporated in vacuo, the residue was redissolved in 5.0 mL THF and then treated with 0.5 mL of a 1.0N HCl solution at 0° C. After stirring for 10 minutes, the reaction mixture was concentrated in vacuo, and the water was removed by azeotropic distillation with toluene. After evaporation, the residue was purified on a silica gel preparative layer chromatography plate eluted with CHCl₃/MeOH/NH₄OH (80:20:2). The product bands were collected and the product removed from the silica gel by elution with 10% methanol/chloroform. Evaporation of the filtrate and recrystallization of the residue from dichloromethane/hexanes afforded 90 mg (80%) of the title compound as a white powder.

¹H NMR (400 MHz, CD₃OD, ppm): δ7.20–7.30 (m, 3H), 7.10 (d, 2H), 6.97 (d, 2H), 6.82 (d, 2H), 6.52 (s, 1H), 5.40 (s, 2H), 2.83 (q, 2H), 2.80 (s, 3H), 2.58 (s, 3H), 2.57 (s, 3H), 1.22 (t, 3H). FAB-MS: m/e 453 (M+1).

EXAMPLE 64

3-[4-(1-Carboxy-1-phenyl)methoxy-3-propylphenyl]-methyl-5-carbomethoxy-2-ethyl-7-methyl-3H-imidazo [4,5-b]pyridine Step A: Preparation of 2-ethyl-7-methylimidazo [4,5-b]pyridine-4-oxide A solution of 28 g (174 mmol) of 2-ethyl-7-methylimidazo[4,5-b]pyridine (described in European Patent Application #400,974, May 12, 1990) and m-chloroperbenzoic acid (80–90%, 44.6 g) in CHCl₃ (300 mL) was heated at reflux for 0.5 hours. The mixture was concentrated and purified (SiO₂, 100% CH₂Cl₂ gradient to 30% CH$_2$Cl$_2$/MeOH) to give 29.8 g of the title compound as a solid.

$^1$H NMR (300 MHz, CD$_3$OD, ppm): δ8.13 (d, 1H, J=6 Hz), 7.13 (d, 1H, J=6 Hz), 3.01 (q, 2H, J=7.5 Hz), 2.60 (s, 3H), 1.46 (t, 3H, J=7.5 Hz).

Step B: Preparation of 5-chloro-2-ethyl-7-methylimidazo[4,5-b]pyridine

A mixture of 29.75 g (0.168 mol) of the product of Step A, CHCl$_3$ (25 mL) and POCl$_3$ (160 mL) was heated to 80° C. for 1 hour. After pouring over ice, the mixture was neutralized by careful addition of NH$_4$OH and extracted with EtOAc. Concentration gave 23.8 g of the title compound as a solid.

$^1$H NMR (250 MHz, CDCl$_3$, ppm): δ7.07 (s, 1H) 3.10 (q, 2H, J=7.5 Hz), 2.67 (s, 3H), 1.48 (t, 3H, J=7.5 Hz).

Step C: Preparation of 5-bromo-2-ethyl-7-methylimidazo[4,5-b]pyridine

A mixture of 22.2 g (0.113 mol) of the product of Step B in 30% HBr-HOAc was heated to 100° C. for 19 hours. The mixture was poured onto ice, neutralized with NH$_4$OH, extracted (5×EtOAc), and the organic layers were concentrated to give 15 g (1$^{st}$ crop) of the title compound as a solid after crystallization from EtOAc.

$^1$H NMR (300 MHz, CDCl$_3$, ppm): δ7.22 (s, 1H) 3.13 (q, 2H, J=7.5 Hz), 2.66 (s, 3H), 1.47 (t, 3H, J=7.5 Hz).

Step D: Preparation of 3-benzyl-5-bromo-2-ethyl-7-methylimidazo[4,5-b]pyridine

To a solution of 10 g (39 mmol) of the product of Step C in DMF (70 mL) at rt was added NaH (1.3 g of an 80% oil dispersion, 43 mmol). After 20 minutes benzyl bromide (5.15 mL, 43 mmol) was added and the reaction was stirred for 16 hours. The mixture was poured onto 500 g of ice and the solid residue was filtered, washed with water and air dried to give 13 g of the title compound.

$^1$H NMR (300 MHz, CDCl$_3$, ppm): δ 7.33-7.22 (m, 3H), 7.19 (s, 1H), 7.11-7.07 (m, 2H), 5.42 (s, 2H), 2.76 (q, 2H, J=7.5 Hz), 2.63 (s, 3H), 1.29 (t, 3H, J=7.5 Hz).

Step E: Preparation of 3-benzyl-5-cyano-2-ethyl-7-methylimidazo[4,5-b]pyridine

A mixture of 620 mg (1.8 mmol) of the product of Step D and CuCN (806 mg, 9.0 mmol) was heated in pyridine (4 mL) at reflux for 10 hours under nitrogen. The reaction was cooled, then water (50 mL), KCN (1.17 g), and EtOAc (20 mL) were added and the mixture was heated to 50° C. for 5 min. Cooling and extraction with EtOAc (2×50 mL) gave 467 mg of the title compound as a tan solid.

$^1$H NMR (400 MHz, CDCl$_3$, ppm): δ7.40 (s, 1H), 7.35-7.20 (m. 3H), 7.18-7.07 (m, 2H), 5.44 ( s, 2H), 2.83 (q, 2H, J=7.5 Hz), 2.67 (s, 3H), 1.32 (t, 3H, J=7.5 Hz).

Step F: Preparation of methyl 3-benzyl-2-ethyl-7-methylimidazo[4,5-b]pyridine-5-carboxylate A solution of 440 mg (1.59 mmol) of the product of Step E in H$_2$SO$_4$ (4 mL) and H$_2$O (4 mL) was heated to 80° C. for 8 hours. The reaction was cooled, MeOH (150 mL) was added, then conc NH$_4$OH was added until the mixture turned basic. The white solid (NH$_4$)$_2$SO$_4$ was filtered and washed with MeOH. The water and MeOH were removed in vacuo and and the residue was taken up in MeOH and then filtered to remove any remaining (NH$_4$)$_2$SO$_4$. After concentrating, and removal of water from the residue by evaporation from toluene, anhydrous 3% HCl—MeOH (50 mL) was added and the mixture was stirred overnight at ft. Filtration, concentration, and extraction from 5% aqueous Na$_2$CO$_3$ with CH$_2$Cl$_2$ gave 750 mg of the crude title compound as a solid.

$^1$H NMR (300 MHz, CDCl$_3$, ppm): δ7.93 (s, 1H) 7.38-7.29 (m, 3H), 7.12-7.03 (m, 2H), 5.53 (s, 2H), 3.96 (s, 3H), 2.78 (q, 2H, J=7.5 Hz), 2.70 (s, 3H), 1.29 (t, 3H, J=7.5 Hz ).

Step G: Preparation of methyl 2-ethyl-7-methylimidazo [4,5-b]pyridine-5-carboxylate A mixture of 750 mg of the crude product of Step F in MeOH (30 mL), concentrated aqueous HCl (1 mL), and 100 mg of moist Pearlman's catalyst were shaken under 1 atm. H$_2$ for 24 hours. The reaction was incomplete so 100 mg more of the catalyst was added and the reaction was shaken as described above for an additional 24 hours. Filtration, concentration, and extraction from dilute NH$_4$OH with EtOAc followed by drying (Na$_2$SO$_4$), concentration, and purification (SiO$_2$, 5% MeOH/EtOAc) gave 250 mg of the title compound as a solid.

$^1$H NMR (400 MHz, CDCl$_3$, ppm): δ7.90 (s, 1H), 4.00 (s, 3H), 3.10 (q, 2H, J=7.5 Hz), 2.71 (s, 3H), 1.38 (t, 3H, J=7.5 Hz).

Step H: Preparation of 4-hydroxy-3-(2-propen-1-yl)benzyl alcohol

To a solution of approximately 7.26 g (2.6 mmol) of crude 4-tert-butyldimethylsilyloxy-3-(prop-2-enyl)benzyl alcohol (Step D of Example 42) dissolved in 50 mL of anhydrous THF was added 26 mL (2.6 mmol) of tetra-n-butylammonium fluoride and the reaction mixture was stirred at room temperature for 16 hours. The mixture was then evaporated in vacuo and the residual oil was purified on a silica gel flash chromatography column eluted with 5% methanol/chloroform to afford 3.386 g (79%) of the title compound as a colorless oil.

$^1$H NMR (300 MHz, CDCl$_3$, ppm): δ2.12 (br s, 1H), 3.35 (d, J=8 Hz, 2H), 4.54 (s, 3H), 5.05-5.15 (m, 2H), 5.90 (br s, 1H), 5.90-6.05 (m, 1H), 6.70 (d, J=10 Hz, 1H), 7.02-7.10 (m, 2H). FAB-MS: m/e 165 (M+1).

Step I: Preparation of 4-hydroxy-3-propylbenzyl alcohol

To a solution of 0.370 g (2.25 mmol) of the product of Step H dissolved in 25 mL of absolute ethanol was added 53 mg of a 5% rhodium on carbon catalyst and the mixture was shaken under a 40 psig pressure of hydrogen on a Parr apparatus. After 30 minutes, the reaction mixture was removed, filtered and evaporated in vacuo. The residue was purified on a silica gel flash chromatography column eluted with 35% ethyl acetate/hexane to afford the title compound.

$^1$H NMR (300 MHz, CDCl$_3$, ppm): δ0.95 (t, J=8 Hz, 3H), 1.55-1.68 (m, 2H), 2.22 (br s, 1H), 2.57 (t, J=8 Hz, 2H), 4.56 (s, 2H), 5.93 (br s, 1), 6.66 (d, J=10 Hz, 1H), 7.00 (dd, J=2, 10 Hz, 1H), 7.08 (d, J=2 Hz, 1H). FAB-MS: m/e 167 (M+1).

Step J: Preparation of methyl (4-hydroxymethyl-2-propylphenoxy)-2-phenylacetate

To a solution of 0.484 g (2.91 mmol) of the product of Step I dissolved in 12 mL of acetone were added 0.667 g (2.91 mmol) of methyl 2-bromophenylacetate, 0.804 g (5.82 mmol) of anhydrous K$_2$CO$_3$ and the mixture was stirred and heated at reflux for 5 hours. The mixture was then cooled, filtered and evaporated in vacuo. The residual oil was purified on a silica gel flash chromatography column eluted with 30% ethyl acetate/hexane to afford 0.756 g (83%) of the title compound.

$^1$H NMR (300 MHz, CDCl$_3$, ppm): δ0.95 (t, J=8 Hz, 3H), 1.58 (br s, 1H), 1.60-1.75 (m, 2H), 2.70 (t, J=8 Hz, 2H), 3.68 (s, 3H), 4.57 (m, 2H), 5.62 (s, 1H), 6.68 (d, J=10 Hz, 1H), 7.07 (dd, J=2, 10 Hz, 1H), 7.16 (d, J=2 Hz, 1H), 7.32–7.44 (m, 3H), 7.55–7.60 (m, 2H). FAB-MS: m/e 315 (M+1).

Step K: Preparation of methyl 2-(4-tert-butyldimethylsilyloxymethyl-2-propylphenoxy)-2-phenylacetate To a solution of 2.34 g (7.45 mmol) of the product of Step 3 in DMF (30 mL) were added imidazole (609 mg, 8.94 mmol) and tert-butyldimethylchlorosilane (1.35 g, 8.94 mmol) at 0° C. The solution was stirred at room temperature for 18 hours, and was then poured into 100 mL of ethyl acetate and washed with 1120 (2×). The water layer was extracted with ethyl acetate (2×). The combined organic layer was washed with 1120 (3×) and brine, and was dried over anhydrous MgSO4. After concentration the mixture was purified by flash chromatography (hexane: EtOAc=10:1) to give 1.96 g of the title compound as a clear oil.

1H NMR (400 MHz, CDCl3, ppm): δ7.58 (dd, 2H, J=8.4, 1.8 Hz), 7.42–7.30 (m, 3H), 7.09 (d, 1H, J=1.8 Hz), 7.03 (dd, 1H, J=8.4, 1.8 Hz), 6.67 (d, 1H, J=8.3 Hz), 5.61 (s, 1H), 4.63 (s, 2H), 3.68 (s, 3H), 2.69 (t, 2H, J=7.8 Hz), 1.72–1.60 (m, 2H), 0.94 (t, 2H, J=7.4 Hz), 0.90 (s, 9H), 0.06 (s, 6H).

Step L: Preparation of 2-(4-tert-butyldimethylsilyloxymethyl-2-propylphenoxy)-2-phenylacetic acid To a solution of 1.875 g (4.38 mmol) of the product of Step K in methanol (20 mL) was added 1N NaOH (4.82 mL, 4.82 mmol) at rt. The solution was stirred at rt for 3 hours. After the solvent was evaporated under reduced pressure, the residue was dissolved in H2O (30 mL) and washed with ethyl acetate (30 mL). The aqueous layer was acidified to pH=3 with 2N HCl. A milky emulsion was extracted with ethyl acetate (3×). The combined organic layer was washed with brine, and was dried over anhydrous MgSO4. Concentration afforded 0.929 g of the title compound as a colorless glass.

1H NMR (400 MHz, CDCl3, ppm): δ7.56 (d, 2H, J=6.2 Hz), 7.42–7.32 (m, 3H), 7.09 (s, 1H), 7.02 (d, 1H, J=8.3 Hz), 6.67 (d, 1H, J=8.2 Hz), 5.60 (s, 1H), 4.62 (s, 2H), 2.67 (t, 2H, J=7.4 Hz), 1.70–1.57 (m, 2H), 0.93 (t, 3H.. J=7.2 Hz), 0.90 (s, 9H), 0.05 (s, 6H).

Step M: Preparation of tert-Butyl 2-(4-tert-butyldimethylsilyloxymethyl-2-propylphenoxy)-2-phenylacetate To a solution of 929 mg (2.24 mmol) of the product of Step L in benzene were added oxalyl chloride (234 mL, 2.69 mmol) and one drop of DMF at 0° C. The solution was stirred at rt for 45 minutes. After concentration the residue was dissolved in CH2Cl2 (10 mL). The solution was added to a solution of tert-butyl alcohol (253 mL, 2.69 mmol) and Et3N in CH2Cl2 (10 mL) at 0° C. The solution was stirred at rt for 3 hours. The mixture was poured into EtOAc (50 mL) and washed with H2O (1×) and brine, and dried over anhydrous MgSO4. Concentration gave 778 mg of the title compound as a slightly yellow glass.

1H NMR (300 MHz, CDCl3, ppm): δ7.60–7.30 (m, 5H), 7.09 (s, 1H), 7.03 (d, 1H, J=8.3 Hz), 6.68 (d, 1H, J=8.2 Hz), 5.49 (s, 1H), 4.62 (s, 2H), 2.80–2.60 (m, 2H), 1.80–1.55 (m, 2H), 1.33 (s, 9H), 0.93 (t, 3H), 0.90 (s, 9H), 0.05 (s, 6H).

Step N: Preparation of tert-butyl 2-(4-hydroxymethyl-2-propylphenoxy)-2-phenylacetate To a solution of 778 mg (1.59 mmol) of the product of Step 3 in THF (5 mL) was added 1N tetra-n-butylammonium fluoride solution in THF (2.69 mL, 2.69 mmol). After the solution was stirred at rt for 2 hours, it was poured into EtOAc (50 mL) and washed with H2O and brine, and dried over anhydrous MgSO4. Concentration afforded 839 mg of the title compound as a yellow glass.

1H NMR (400 MHz, CDCl3, ppm): δ7.60–7.30 (m, 5H), 7.20–7.08 (m, 2H), 6.68 (d, 1H, J=8.2 Hz), 5.18 (s, 1H), 4.52 ( s, 2H), 2.75–2.60 (m, 2H), 1.75–1.60 (m, 2H), 1.33 (s, 9H), 0.93 (t, 3H).

Step O: Preparation of tert-butyl 2-(4-bromomethyl-2-propylphenoxy)-2-phenylacetate To a solution of 839 mg of the crude product from Step N in CH2Cl2 (20 mL) were added triphenylphosphine (525 mg, 2 mmol) and carbon tetrabromide (663 mg, 2 mmol) at 0° C. The solution was stirred at 0° C. for 1 hour and at rt for 15 hours. The solution was poured into EtOAc (100 mL). After the precipitate was removed, the filtrate was washed with H2O and brine, and dried over anhydrous MgSO4. Concentration afforded 302 mg of the title compound as a white solid.

1H NMR (400 MHz, CDCl3, ppm): δ7.57 (d, 2H, J=6.2 Hz), 7.41–7.33 (m, 3H), 7.17 (d, 1H, J=2.0 Hz), 7.10 (dd, 1H, J=8.3, 2.0 Hz), 6.67 (d, 1H, J=8.2 Hz), 5.49 (s, 1H), 4.52 (s, 2H), 2.75–2.65 (m, 2H), 1.76–1.62 (m, 2H), 1.34 (s, 9H), 0.96 (t, 3H, J=7.2 Hz).

Step P: Preparation of 3-[4-((1-carbo-tert-butoxy-1-phenyl)methoxy)-3-propylphenyl]methyl-5-carbomethoxy-2-ethyl-7-methyl-3H-imidazo [4,5-b]pyridine To a 25 mL round bottom flask were placed 41.8 mg (0.19 mmol) of methyl 2-ethyl-7-methylimidazo[4,5-b]pyridine-5-carboxylate (the product of Step G of this Example) and a 60% oil dispersion of NaH (5 mg, 0.21 mmol). The flask was evacuated and filled with nitrogen. Dry DMF (2 mL) was added to the mixture dropwise at 0° C. The solution was stirred at rt for 5 minutes. To the solution was added 80 mg (0.19 mmol) of tert-butyl 2-(4-bromomethyl-2-propylphenoxy)-2-phenylacetate (Step O) in dry DMF (2 mL) at rt. After the solution was stirred at rt for 15 hours, it was poured into EtOAc (10 mL) and washed with H2O and brine, and dried over anhydrous MgSO4. Concentration followed by purification by flash chromatography. (hexane: EtOAc=2:1) afforded 63.6 mg of the title compound as a colorless glass.

1H NMR (400 MHz, CDCl3, ppm): δ7.92 (s, 1H), 7.52 (d, 2H, J=7.0 Hz), 7.40–7.30 (m, 3H), 6.99 (d, 1H, J=2.0 Hz), 6.83 (dd, 1H, J=8.3, 2.0 Hz), 6.61 (d, 1H, J=8.4 Hz), 5.44 (s, 2H), 5.43 (s, 1H), 3.97 (s, 2.79 (q, 2H, J=7.5 Hz), 2.70 (s, 3H), 2.65–2.55 (m, 2H), 1.70–1.55 (m, 2H), 1.3 (s, 9H), 1.25 (t, 3H, J=8.3 Hz), 0.89 (t, 3H, J=7.3 Hz).

Step Q: Preparation of 3-[4-((1-carboxy-1-phenyl)methoxy)-3-propylphenyl]methyl-5-carbomethoxy-2-ethyl-7-methyl-3H-imidazo[4,5-b]pyridine To a solution of 21.4 mg (0.038 mmol) of the product of Step P in CH2Cl2 (1 mL) was added TFA (0.4 mL, 5.19 mmol) at ft. The solution was stirred at rt for 2 hours. The crude mixture was directly purified by flash chromatography eluted with CHCl3/MeOH/NH4OH (100:10:1) to give 11 mg of the title compound as a white solid.

1H NMR (400 MHz, CD3OD, ppm): δ7.84 (s, 1H), 7.55–7.42 (br m, 2H), 7.25–7.13 (m, 3H), 6.96 (s, 1H), 6.88–6.62 (br m, 2H), 5.43 (s, 3H), 3.87 (s, 3H), 2.81 (q, 2H, J=7.5 Hz), 2.58 (s, 3H), 2.50–2.40 (m, 2H), 1.53–1.37 (m, 2H), 1.16 (t, 3H, J=7.5 Hz), 0.74 (t, 3H, J=6.6 Hz). FAB-MS: m/e 524 (M+Na), 540 (M+K).

EXAMPLE 65

3-[4-((1-carboxy-1-phenyl)methoxy)-3-propylphenyl]-methyl-5-carboxy-2-ethyl-7-methyl-3H-imidazo[4,5-b]pyridine Step A: Preparation of 3-[4-((1-carbo-tert-butoxy-1-phenyl)methoxy)-3-propyl phenyl]methyl-5-carboxy-2-ethyl-7-methyl-3H-imidazo[4,5-b]pyridine To a solution of 63 mg (0.113 mmol) of 3-[4-((1-carbo-tert-butoxy-1-phenyl)methoxy)-3-propylphenyl]methyl-5-carbomethoxy-2-ethyl-7-methyl-3H-imidazo[4,5-b]pyridine (from step M of Example 64) in MeOH (2 mL) was added 1N NaOH (136 mL, 0.136 mmol) at rt. The solution was refluxed for 3 hours. After the evaporation of the solvent the residue was taken up in H$_2$O and acidified to pH=3 with 2N hydrochloric acid. A white precipitate was collected and dried in a vacuum oven (60° C.) for 3 hours to afford 47 mg of the title compound as a white solid.

$^1$H NMR (400 MHz, CDCl$_3$, ppm): δ8.0 (s, 1H), 7.52 (d, 2H, J=6.9 Hz), 7.38–7.32 (m, 3H), 6.93 (s, 1H), 6.79 (dd, 1H, J=6.8, 1.1 Hz), 6.63 (d, 1H, J=8.4 Hz), 5.44 (s, 1H), 5.37 (s, 2H), 2.85 (q, 2H, J=6.7 Hz), 2.72 (s, 3H), 2.67–2.60 (m, 2H), 1.68–1.56 (m, 2H), 1.30 (s, 9H), 1.30 (t, 3H, J=8.3 Hz), 0.90 (t, 3H, J=6.5 Hz). FAB-MS: m/e 544 (M+1).

Step B: Preparation of 3-[4-((1-carboxy-1-phenyl)methoxy)-3-propylphenyl]methyl-5-carboxy-2-ethyl-7-methyl-3H-imidazo[4,5-b]pyridine To a solution of 3-[4-((1-carbo-t-butoxy-1-phenyl)methoxy)-3-propylphenyl]methyl-5-carboxy-2-ethyl-7-methyl-3H-imidazo[4,5-b]pyridine (47 mg, 0.087 mmol) in CHCl$_3$ (3 mL) was added TFA (0.5 mL) at −20° C. The solution was warmed to rt and was stirred at rt for 12 hours. After evaporation of the solvent the crude mixture was purified by flash chromatography eluted with CHCl$_3$/MeOH/AcOM (90:5:5) to give 31 mg of the title compound as a white solid.

$^1$H NMR (400 MHz, CD$_3$OD, ppm): δ7.90 (br s, 1H), 7.52 (d, 2H, J=7.1 Hz), 7.30–7.20 (m, 3H), 6.97 (s, 1H), 6.90–6.80 (m, 1H), 6.78–6.68 (m, 1H), 5.49 (br s, 2H), 5.47 (s, 1H), 2.90–2.75 (m, 2H), 2.61 (s, 3H), 2.54–2.45 (m, 2H), 1.55–1.45 (m, 2H), 1.17 (t, 3H, J=7.5 Hz), 0.77 (t, 3H, J=7.3 FAB-MS: m/e 510 (M+Na), 526 (M+K).

EXAMPLE 66

3-[4-(1-Carboxy-1-phenyl)methoxy)-3-propylphenyl]-methyl-5-carbobenzyloxy-2-ethyl-7-methyl-3H-imidazo [4,5-b]pyridine Step A: Preparation of 3-[4-((1-carbo-tert-butoxy-1-phenyl)methoxy)-3-propylphenyl]methyl-5-carbobenzyloxy-2-ethyl-7-methyl-3H-imidazo [4,5-b]pyridine To a solution of 23.3 mg (0.043 mmol) of 3-[4-(1-carbo-tert-butoxy-1-phenyl)methoxy-3-propylphenyl]-methyl-5-carboxy-2-ethyl-7-methyl-3H-imidazo [4,5-b]pyridine (from step A of Example 65) and bis(2-oxo-3-oxazolidinyl)phosphinic chloride (13.1 mg, 0.052 mmol) in CH$_2$Cl$_2$ (2 mL) were added triethylamine (7.2 mL, 0.052 mmol) and benzyl alcohol (5.4 mL, 0.052 mmol) at ft. The solution was stirred at rt for 15 hours. The solution was poured into EtOAc (20 mL) and was washed with H$_2$O and brine, and dried over anhydrous MgSO$_4$. After evaporation of the solvent, the mixture was purified by flash chromatography (hexanes: EtOAc=2:1) to afford 9.3 mg of the title compound as a colorless glass.

$^1$H NMR (400 MHz, CDCl$_3$): d 7.91 (s, 1H), 7.53–7.29 (m, 10H), 7.40–7.30 (m, 3H), 6.99 (s, 1H), 6.87 (d, 1H, J=8.4 Hz), 6.61 (d, 1H, J=8.4 Hz), 5.43 (s, 5H), 2.79 (q, 2H, J=7.5 Hz), 2.68 (s, 3H), 2.65–2.55 (m, 2H), 1.70–1.55 (m, 2H), 1.3 (s, 9H), 1.28 (t, 3H, J=8.3 Hz ), 0.88 ( t, 3H. J=7.3 Hz ).

Step B: Preparation of 3-[4-((1-carboxy-1-phenyl)methoxy)-3-propylphenyl]methyl-5-carbobenzyloxy-2-ethyl-7-methyl-3H-imidazo[4,5-b]pyridine To a solution of 3-[4-(1-carbo-tert-butoxy-1-phenyl)-methoxy-3-propylphenyl]methyl-5-carbobenzyloxy-2-ethyl-7-methyl-3H-imidazo[4,5-b]pyridine (9 mg, 0.014 mmol) in CH$_2$Cl$_2$ (1 mL) was added TFA (0.4 mL) at rt dropwise. The solution was stirred at rt for 2.5 hours. After evaporation of the solvent the crude mixture was purified by flash chromatography eluted with CHCl$_3$/MeOH/NH$_4$OH (80:15:1), to give 3.8 mg of the title compound as a white solid.

$^1$H NMR (400 MHz, CD$_3$OD, ppm): δ7.90 (s, 1H), 7.54 (d, 2H, J=7.0), 7.43 (d, 2H, J=7.1 Hz), 7.35–7.20 (m, 6H), 7.0 (s, 1H), 6.95–6.85 (m, 1H), 6.75–6.70 (m, 1H), 5.46 (s, 2H) , 5.38 (s, 3H), 2.86 (q, 21t, J=7.6 Hz), 2.61 (s, 3H) , 2.70–2.60 (m, 1H), 2.50–2.40 (m, 1H), 1.48–1.37 (m , 2H), 1.20 (t, 3H, J=8.3 Hz), 0.73 (t, 3H, J=7.3 Hz) FAB-MS: m/e 600 (M+Na), 616 (M+K).

EXAMPLE 67

3-[4-(1-(Hydroxymethoxyphosphoryl)-1-(2-methylphenyl))methoxyphenyl]methyl-5,7-dimethyl-2-ethyl-3H-imidazo[4,5-b]pyridine Step A: Preparation of dimethyl 2-hydroxy-2-(2'-methylphenyl)methylphosphonate To a solution of dimethyl phosphite (1.340 g, 12.18 mmol) and o-tolualdehyde (1.50 mL, 1.06 equiv) at rt was added NEt$_3$ (3 drops). After standing at rt for 48 h the reaction mixture, containing the product which had solidified, was dissolved in CH$_2$Cl$_2$ and washed with H$_2$O, dried over anhydrous MgSO$_4$ and concentrated in vacuo. The product was recrystallized from a mixture of Et$_2$O/Hex providing 2.21 g (79%) of the titled compound. Rf=0.5 (9:1CH$_2$Cl$_2$/MeOH).

$^1$H NMR (200 MHz, CDCl$_3$, ppm): 6 2.36 (s, 3H), 3.63 (d, 3H), 3.68 (d, 3H), 4.57 (bm, 1H), 5.29 (dd, 1H), 7.09–7.30 (comp m, 3H), 7.67 (bd, 1H).

Step B: Preparation of dimethyl 2-bromo-2-(2'-methylphenyl)methylphosphonate

To a solution of the product from step A (0.284 g, 1.23 mmol) and CBr$_4$ (0.410 g, 1.0 equiv) in CH$_2$Cl$_2$ (5 mL) at rt was added PPh$_3$ (0.322 g, 1.0 equiv). After standing at rt for 2 days the mixture was concentrated in vacuo and the residue was purified by flash chromatography on a silica column using Hex/EtOAc (1:1) providing 0.174 g (48%) of the titled compound. Rf=0.48 (2:1EtOAc/Hex).

$^1$H NMR (300 MHz, CDCl$_3$, ppm): 5 2.38 (s, 3H), 3.61 (d, 3H), 3.86 (d,. 3H), 5.16 (d, 1H), 7.12–7.28 (comp m, 3H), 7.86 (bd, 1H).

Step C: Preparation of dimethyl 2-(4-hydroxymethylphenoxy)-2-(2'-methylphenyl)methylphosphonate To a solution of p-hydroxybenzyl alcohol (0.315 g, 2.54 mmol) in dry DMF (3 mL) under N$_2$ at rt was added 80% NaH in oil (76 mg, 1.0 equiv). After H$_2$ evolution ceased, a solution of the product of Step B (0.324 g, 1.11 mmol) in DMF (1 mL) was added. The mixture was stirred overnight at rt and the next day the blue-green solution was quenched with a solution of sat'd NH$_4$Cl and the solvent removed in vacuo. The residue was partially dissolved in EtOAc, dried over anhydrous MgSO4, filtered and concentrated in vacuo. The product was purified by flash chromatography on a silica column using Hex/EtOAc (1:3) to afford 85 mg (23%) of the titled compound. Rf=0.17 (1:1EtOAc/Hex).

1H NMR (200 MHz, CDCl3, ppm): δ2.53 (dd, 3H), 3.72 (d, 3H), 3.80 (d, 3H), 4.57 (s, 2H), 5.69 (d, 1H), 6.81 (d, 2H), 7.13–7.26 (comp m, 5H), 7.59 (bm, 1H).

Step D: Preparation of dimethyl 2-(4-bromomethylphenoxy)-2-(2'-methylphenyl)methylphosphonate To a solution of the product of Step C (0.112 g, 0.333 mmol) and CBr4 (0.253 g, 2.28 equiv) in dry CH2Cl2 (1 mL) was added PPh3 (0.200 g 2.29 equiv). The reaction mixture was stirred at rt overnight and then concentrated in vacuo. The product was purified by flash chromatography on a silica column using Hex/EtOAc (1:1) to afford 78 mg (59%) of the titled compound. Rf=0.46 (2:1 EtOAc/Hex).

1H NMR (300 MHz, CDCl3, ppm) δ2.48 (s, 3H), 3.68 (d, 3H), 3.76 (d, 3H), 4.39 (s, 2H), 5.63 (d, 1H), 6.71 (d, 2H), 7.12–7.25 (comp m, 5H), 7.59 (bm, 1H).

Step E: Preparation of 3-[4-(1-(Hydroxymethoxyphosphoryl)-1-(2-methylphenyl))methoxyphenyl]methyl-5,7-dimethyl-2-ethyl-3H-imidazo[4,5-b]pyridine and 3-[4-(1-(dimethoxyphosphoryl)-1-(2-methylphenyl))methoxyphenyl]methyl-5,7-dimethyl-2-ethyl-3H-imidazo[4,5-b]pyridine To a solution a solution of 5,7-dimethyl-2-ethylimidazopyridine (68.0 mg, 0.389 mmol) in dry DMF (1 mL) under N2 at rt was added 80% NaH in oil (17.5 mg, 1.5 equiv). When H2 evolution ceased a solution of the product of Step D (78.0 mg, 0.195 mmol) in dry DMF (0.5 mL) was added via syringe. After stirring for 3 h the reaction mixture was quenched with a solution of sat'd NH4Cl. The solvent was removed in vacuo and the residue was dissolved in CH2Cl2, dried over anhydrous MgSO4, filtered and concentrated in vacuo. The residue was purified by flash chromatography on a silica gel column eluted first with CHCl3/MeOH (25:1) then with CHCl3/MeOH/NH4OH (40:10:1) to afford the phosphonate mono and diesters. The diester (7.8 mg) was obtained in 9% yield. Rf=0.32 (20:1 CHCl3/MeOH).

1H NMR (200 MHz, CDCl3, ppm): δ1.27 (t, 3H), 2.48 (d, 3H), 2.57 (s, 3H), 2.62 (s, 3H), 2.75 (q, 2H), 3.69 (d, 3H), 3.79 (d, 3H), 5.33 (s, 2H), 5.61 (d, 1H), 6.72 (d, 2H), 6.87 (s, 1H), 6.98 (d, 2H), 7.19 (d, 3H), 7.52 (bm, 1H).

The monoester (39.0 mg) was obtained in 46% yield. Rf=0.41 (40:10:1 CHCl3/MeOH/NH4OH).

1H NMR (300 MHz, CD3OD, ppm): δ1.19 (t, 3H), 2.25 (s, 3H), 2.58 (s, 3H), 2.61 (s, 3H), 2.80 (q, 2H), 3.59 (d, 3H), 5.41 (s, 2H), 5.55 (d, 1H), 6.77 (d, 2H), 6.95 (d, 2H), 7.00 (s, 1H), 7.03–7.18 (comp m, 3H), 7.51 (bm, 1H).

What is claimed is:

1. A compound of structural formula I, wherein:

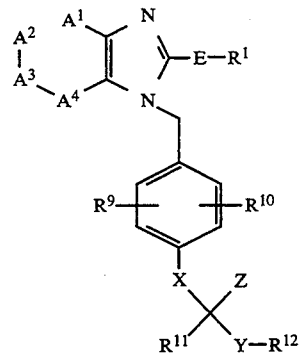

or a pharmaceutically acceptable salt, wherein:
$R^1$ is:
- (a) $(C_1-C_6)$-alkyl, $(C_2-C_6)$-alkenyl or $(C_2-C_6)$-alkynyl each of which is unsubstituted or substituted with a substituent selected from the group consisting of:
  - i) aryl as defined below in $R^1$ (b),
  - ii) $(C_3-C_7)$-cycloalkyl,
  - iii) Cl, Br, I, F,
  - iv) OH,
  - v) $NH_2$,
  - vi) $NH(C_1-C_4)$-alkyl,
  - vii) $N[(C_1-C_4)$-alkyl$)]_2$,
  - viii) $NHSO_2R^2$,
  - ix) $CF_3$,
  - x) $COOR^2$, or
  - xi) $SO_2NMR^{2a}$; and
- (b) aryl, wherein aryl is defined as phenyl or naphthyl which is unsubstituted, mono- or disubstituted with substituents selected from the group consisting of:
  - i) Cl, Br, I, F,
  - ii) $(C_1-C_4)$-alkyl,
  - iii) $(C_1-C_4)$-alkoxy,
  - iv) $NO_2$,
  - v) $CF_3$,
  - vi) $SO_2NR^{2a}R^{2a}$,
  - vii) $(C_1-C_4)$-alkylthio,
  - viii) hydroxy,
  - ix) amino,
  - x) $(C_3-C_7)$-cycloalkyl,
  - xi) $(C_3-C_{10})$-alkenyl; and
- (c) heteroaryl, wherein heteroaryl is defined as a 5- or 6-membered heteroaromatic moiety which can contain one or two members selected from the group consisting of N, O, S, and wherein the heteroaryl is unsubstituted, mono- or disubstituted with substituents selected from the group consisting of:
  - i) Cl, Br, I, F,
  - ii) OH,
  - iii) SH,
  - iv) $NO_2$,
  - v) $(C_1-C_4)$-alkyl,
  - vi) $(C_2-C_4)$-alkenyl,
  - vii) $(C_2-C_4)$-alkynyl,
  - viii) $(C_1-C_4)$-alkoxy, or
  - ix) $CF_3$, or
- (d) $(C_1-C_4)$-perfluoroalkyl; and
—$A^1$—$A^2$—$A^3$—$A^4$— is

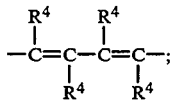

E is:
(a) a single bond,
(b) —S(O)$_n$(CH$_2$)$_s$—, or
(c) —O—; and n is 0 to 2; and
s is 0 to 5; and R$^2$ is:
(a) H, or
(b) (C$_1$-C$_6$)-alkyl; and R$^{2a}$ is:
(a) R$^2$,
(b) CH$_2$-aryl, or
(c) aryl; and R$^4$ groups are independently:
(a) H,
(b) (C$_1$-C$_6$)-alkyl, (C$_2$-C$_6$)-alkenyl, or (C$_2$-C$_6$)-alkynyl, each of which is unsubstituted or substituted with:
 i) OH,
 ii) (C$_1$-C$_4$)-alkoxy,
 iii) CO$_2$R$^2$,
 iv) OCOR$^2$,
 v) CONMR$^{2a}$,
 vi) CON(R$^{2a}$)$_2$,
 vii) N(R$^{2a}$)C(=O)R$^2$,
 viii) NH$_2$,
 ix) (C$_1$-C$_4$)-alkylamino,
 x) di[(C$_1$-C$_4$)-alkyl]amino,
 xi) —S—(C$_1$-C$_4$)-alkyl,
 xii) aryl,
 xiii) heteroaryl,
(c) Cl, Br, I, F,
(d) CF$_3$,
(e) CO$_2$R$^{2a}$,
(f) C(=O)N(R$^{2a}$)$_2$,
(g) —C(=O)-aryl,
(h) (C$_3$-C$_7$)-cycloalkyl,
(i) —OR$^{24}$,
(j) —SH,
(k) —S(O)$_n$—(C$_1$-C$_4$)-alkyl,
(l) —SO$_3$H,
(m) —NR$^2$R$^{21}$,
(n) —NR$^2$C(=O)R$^{21}$,
(o) —NR$^2$COOR$^{21}$,
(p) —SO$_2$NR$^{2a}$R$^{2a}$,
(q) —NO$_2$,
(r) —NHSO$_2$—(C$_1$-C$_4$)-alkyl, or
(s) when R$^4$ groups are on adjacent carbon atoms they may join to form a phenyl ring; and R$^5$ is:
(a) H, or
(b) (C$_1$-C$_6$)-alkyl or (C$_2$-C$_6$)-alkenyl, optionally substituted with:
 i) hydroxy, or
 ii) (C$_1$-C$_4$)-alkoxy; and R$^{5a}$ is
(a) R$^5$, or
(b) (C$_1$-C$_4$)-acyl; and R$^6$ is:
(a) H,
(b) (C$_1$-C$_6$)-alkyl, or
(c) (C$_1$-C$_6$)-alkyl substituted with hydroxy; and R$^{6a}$ is:
(a) R$^6$, or
(b) (C$_1$-C$_6$)-alkyl substituted with:
 i) CO$_2$R$^2$,
 ii) CONMR$^2$,
 iii) CON(R$^2$)$_2$; and R$^9$ and R$^{10}$ are independently:
(a) H,
(b) (C$_1$-C$_6$)-alkyl, unsubstituted or substituted with (C$_3$-C$_7$)-cycloalkyl,
(c) (C$_2$-C$_6$)-alkenyl,
(d) (C$_2$-C$_6$)-alkynyl,
(e) Cl, Br, F, I,
(f) (C$_1$-C$_6$)-alkoxy,
(g) when R$^9$ and R$^{10}$ are on adjacent carbons, they can be joined to form a phenyl ring,
(h) perfluoro-(C$_1$-C$_6$)-alkyl,
(i) (C$_3$-C$_7$)-cycloalkyl, unsubstituted or substituted with (C$_1$-C$_6$)-alkyl,
(j) aryl,
(k) (C$_1$-C$_6$)-alkyl-S(O)$_n$—(CH$_2$)$_n$—,
(l) hydroxy-(C$_1$-C$_6$)-alkyl,
(m) —CF$_3$,
(n) —CO$_2$R$^{2a}$,
(o) —OH,
(p) —NR$^2$R$^{21}$,
(q) —[(C$_1$-C$_6$)-alkyl]NR$^2$R$^{21}$,
(r) —NO$_2$,
(s) —(CH$_2$)$_n$—SO$_2$—N(R$^2$)$_2$,
(t) —NR$^2$CO—(C$_1$-C$_4$)-alkyl, or
(u) —CON(R$^2$)$_2$;

X is:
(a) —O—,
(b) —S(O)$_n$—,
(c) —NR$^{13}$—
(d) —CH$_2$O—,
(e) —CH$_2$S(O)$_n$,
(f) —CH$_2$NR$^{13}$—,
(g) —OCH$_2$—,
(h) —NR$^{13}$CH$_2$—,
(i) —S(O)$_n$CH$_2$—,
(j) —CH$_2$—,
(k) —(CH$_2$)$_2$—,
(l) single bond, or
(m) —CH=, wherein Y and R$^{12}$ are absent forming a —C=C— bridge to the carbon bearing Z and R$^{11}$;

Y is:
(a) single bond,
(b) —O—,
(c) —S(O)$_n$—,
(d) —NR$^{13}$—,
(e) —CH$_2$—; and except that X and Y are not defined in such a way that the carbon atom to which Z is attached is also simultaneously bonded to two heteroatoms (O, N, S, SO, SO$_2$);

R$^{11}$ and R$^{12}$ are independently:
(a) H,
(b) (C$_1$-C$_6$)-alkyl, unsubstituted or substituted with a substituent selected from the group consisting of:
 (i) aryl,
 (ii) (C$_3$-C$_7$)-cycloalkyl,
 (iii) NR$^2$R$^{21}$,
 (iv) morpholin-4-yl,
 (v) OH,
 (vi) CO$_2$R$^{2a}$, or (vii) $CON(R^2)_2$,
(c) aryl or aryl-$(C_1-C_2)$-alkyl, unsubstituted or substituted with 1 to 3 substituents selected from the group consisting of:
  (i) C, Br, I, F,
  (ii) $(C_1-C_6)$-alkyl,
  (iii) $[(C_1-C_5)$-alkenyl$]CH_2—$,
  (iv) $[(C_1-C_5)$-alkynyl$]CH_2—$,
  (v) $(C_1-C_6)$-alkyl-$S(O)_n—(CH_2)_n—$,
  (vi) $—CF_3$,
  (vii) $—CO_2R^{2a}$,
  (viii) $—OH$,
  (ix) $—NR^2R^{21}$,
  (x) $—NO_2$,
  (xi) $—NR^2COR^2$,
  (xii) $—CON(R^2)_2$,
  (xiii) $—G^1—[(C_1-C_6)$-alkyl$]—R^{27}$,
  (xiv) $—N[CH_2CH_2]_2Q^1$, or
  (xv) $—P(O)[O—(C_1-C_4)$-alkyl$]_2$, and can additionally be substituted with 1 or 2 substituents selected from the group consisting of: Br, Cl or F,
(d) $(C_3—C_7)$-cycloalkyl, or
(e) when Y is single bond, $R^{11}$ and $R^{12}$ can be joined to form a ring of 5 to 7 carbon atoms, the ring can be benzo-fused and one carbon of which can be replaced with a heteroatom selected from the group consisting of: O, $S(O)_n$ and $NR^{26}$; and $G^1$ is: a single bond, O, $S(O)_n$ or $NR^{27}$; and
$Q^1$ is: O, $S(O)_n$ or $NR^{26}$; and
$R^{13}$ is:
  (a) H,
  (b) $(C_1-C_6)$-alkyl,
  (c) aryl as defined in $R^1$(b),
  (d) aryl-$(C_1-C_6)$-alkyl-$(C=O)—$,
  (e) $(C_1-C_6)$-alkyl-$(C=O)—$,
  (f) $[(C_2-C_5)$-alkenyl$]CH_2—$,
  (g) $[(C_2-C_5)$-alkynyl$]CH_2—$, or
  (h) aryl-$CH_2—$; and Z is:
  (a) $—CO_2H$,
  (b) $—CO_2R^{28}$,
  (c) -tetrazol-5-yl,
  (d) $—CONH$-tetrazol-5-yl,
  (e) $—CONHSO_2$-aryl, wherein aryl is as defined in $R^1$(b),
  (f) $—CONHSO_2$-$(C_1-C_8)$-alkyl, wherein the alkyl group is unsubstituted or substituted with a substituent selected from the group consisting of: $—OH$, $—SH$, $—O(C_1-C_4)$-alkyl, $—S—(C_1-C_4)$-alkyl, $—CF_3$, Cl, Br, F, I, $—NO_2$, $—CO_2H$, $—CO_2$-$(C_1-C_4)$-alkyl, $—NH_2$, $NH[(C_1-C_4)$-alkyl], or $—N[(C_1-C_4)$-alkyl$]_2$,
  (g) $—CONHSO_2$-$(C_1-C_4)$-perfluoroalkyl,
  (h) $—CONHSO_2$-heteroaryl,
  (i) $—CONHSO_2NR^{2a}R^{2a}$,
  (j) $—SO_2NHCO$-aryl, wherein aryl is as defined in $R^1$(b),
  (k) $—SO_2NHCO$-$(C_1-C_8)$-alkyl, wherein the alkyl group is unsubstituted or substituted with a substituent selected from the group consisting of: $—OH$, $—SH$, $—O(C_1-C_4)$-alkyl, $—S$-$(C_1-C_4)$-alkyl, $—CF_3$, Cl, Br, F, I, $—NO_2$, $—CO_2H$, $—CO_2$-$(C_1-C_4)$-alkyl, $—NH_2$, $—NH[(C_1-C_4)$-alkyl], or $—N[(C_1-C_4)$-alkyl$]_2$,
  (l) $—SO_2NHCO$-$(C_1-C_4)$-perfluoroalkyl,
  (m) $—SO_2NHCO$-heteroaryl,
  (n) $—SO_2CONR^{2a}R^{2a}$,
  (o) $—PO(OH)_2$,
  (p) $—PO(OR^2)_2$, or
  (q) $—PO(OH)(OR^2)$; and $R^{20}$ is:
  (a) H,
  (b) $(C_1-C_6)$-alkyl,
  (c) allyl,
  (d) $(C_3-C_6)$-cycloalkyl,
  (e) $(C_1-C_4)$-acyl,
  (f) benzyl, or
  (g) phenyl; and $R^{21}$ is:
  (a) H, or
  (b) $(C_1-C_4)$-alkyl, unsubstituted or substituted with:
    i) $NH_2$,
    ii) $NH[(C_1-C_4)$-alkyl],
    iii) $N[(C_1-C_4)$-alkyl$]_2$,
    iv) $CO_2H$,
    v) $CO_2(C_1-C_4)$-alkyl,
    vi) OH,
    vii) $SO_3H$, or
    viii) $SO_2NH_2$; and $R^{25}$ is:
  (a) H,
  (b) $(C_1-C_6)$-alkyl,
  (c) aryl,
  (d) aryl-$(C_1-C_5)$-alkyl; and $R^{26}$ is:
  (a) H,
  (b) $(C_1-C_4)$-alkyl,
  (c) $(C_1-C_4)$-alkoxyl,
  (d) aryl,
  (e) aryl-$(C_1-C_4)$-alkyl,
  (f) $CO_2R^{2a}$,
  (g) $CON(R^2)_2$,
  (h) $SO_2R^{2a}$,
  (i) $SO_2N(R^2)_2$,
  (j) $P(O)[(C_1-C_4)$-alkoxyl$]_2$, or
  (k) imidazol-2-yl or imidazol-4-yl, in which the imidazolyl can be substituted with $(C_1-C_4)$-alkyl; and $R^{27}$ is:
  (a) OH,
  (b) $NR^2R^{21}$,
  (c) $CO_2R^{2a}$,
  (d) $CON(R^2)_2$,
  (e) $S(O)_n$—$(C_1-C_4)$-alkyl,
  (f) $N(CH_2CH_2)_2Q'$; and $R^{28}$ is:
  (a) $(C_1-C_4)$-alkyl,
  (b) $CHR^{29}—O—COR^{30}$,
  (c) $CH_2CH_2—N[(C_1-C_2)$-alkyl$]_2$,
  (d) $CH_2CH_2—N[CH_2CH_2]_2O$,
  (e) $(CH_2CH_2O)_y—O—[(C_1-C_4)$-alkyl], wherein y is 1 or 2,
  (f) arl or $CH_2$-aryl, wherein aryl is unsubstituted or substituted with $CO_2—(C_1-C_4)$-alkyl,

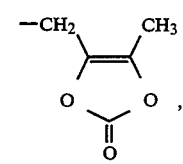  (g)

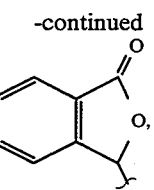
(h)

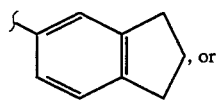
(i) , or

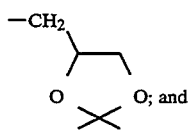
; and $R^{29}$ and $R^{30}$ independently are $(C_1-C_6)$-alkyl or phenyl.

2. The compound as recited in claim 1 wherein:
$R^1$ is:
 (a) $(C_1-C_6)$-alkyl or $(C_2-C_6)$-alkenyl or $(C_2-C_6)$-alkynyl each of which is unsubstituted or substituted with a substituent selected from the group consisting of:
  i) $(C_1-C_4)$-alkylthio,
  ii) $(C_1-C_4)$-alkoxy,
  iii) $CF_3$,
  iv) $CF_2-CF_3$, or
  v) $(C_3-C_5)$-cycloalkyl,
 (b) $(C_1-C_4)$-perfluoroalkyl, or
 (c) $(C_3-C_5)$-cycloalkyl; and
E is:
 (a) single bond,
 (b) —S—, or
 (c) —O—; and
$R^2$ is:
 (a) H, or
 (b) $(C_1-C_6)$-alkyl; and
$R^{2a}$ is:
 (a) $R^2$,
 (b) benzyl, or
 (c) phenyl; and
$R^4$ groups are independently:
 (a) H,
 (b) $(C_1-C_6)$-alkyl, which is unsubstituted or substituted with:
  i) OH,
  ii) $CO_2 R^2$,
  iii) $NH_2$,
  iv) $(C_1-C_4)$-alkylamino,
  v) di[$(C_1-C_4)$-alkylamino,
 (c) Cl, Br, I, F,
 (d) $CF_3$,
 (e) $CO_2R^{2a}$,
 (f) $C(=O)NR^{2a}R^{2a}$,
 (g) —C(=O)-aryl, wherein aryl is defined as phenyl or naphthyl which is unsubstituted, mono- or disubstituted with substituents selected from the group consisting of:
  i) Cl, Br, I, F,
  ii) $(C_1-C_4)$-alkyl,
  iii) $(C_1-C_4)$-alkoxy,
  iv) $NO_2$,
  v) $CF_3$,
  vi) $SO_2NR^{2a}R^{2a}$,
  vii) $(C_1-C_4)$-alkylthio,
  viii) hydroxy,
  ix) amino,
  x) $(C_3-C_7)$-cycloalkyl,
  xi) $(C_3-C_{10})$-alkenyl,
 (h) $(C_3-C_7)$-cycloalkyl, or
 (i) —$OR^{22}$,
 (j) —S—$(C_1-C_4)$-alkyl,
 (k) —N[$(C_1-C_4)$-alkyl]$_2$,
 (l) —NHC(=O)$(C_1-C_4)$-alkyl,
 (m) —NHCOO$(C_1-C_4)$-alkyl,
 (n) —$SO_2NH(C_1-C_4)$-alkyl,
 (o) —$NO_2$,
 (p) —$NHSO_2CH_3$,
 (q) when $R^4$ groups are on adjacent carbon atoms they may join to form a phenyl ring; and
$R^5$ is:
 (a) H, or
 (b) $(C_1-C_6)$-alkyl, which is unsubstituted or substituted with: hydroxyl, or $(C_1-C_4)$-alkoxy; and
$R^{5a}$ is
 (a) H,
 (b) $(C_1-C_4)$-alkyl, or
 (c) $(C_1-C_4)$-acyl; and
$R^{6a}$ is:
 (a) H, or
 (b) $(C_1-C_4)$-alkyl; and
$R^{13}$ is:
 (a) H,
 (b) $(C_1-C_6)$-alkyl,
 (c) phenyl or naphthyl,
 (d) phenyl-$(C_1-C_6)$-alkyl-(C=O)— or naphthyl-$(C_1-C_6)$-alkyl-(C=O)—, or
 (e) $(C_1-C_6)$-alkyl-(C=O)—; and
Z is:
 (a) —$CO_2H$,
 (b) —$CO_2R^{28}$,
 (c) -tetrazol-5-yl,
 (d) —CONH(tetrazol-5-yl),
 (e) —$CONHSO_2$-aryl, wherein aryl is as defined in $R^4$(g),
 (f) —$CONHSO_2$—$(C_1-C_4)$-alkyl,
 (g) —$CONHSO_2$—$(C_1-C_4)$-perfluoroalkyl,
 (h) —$CONHSO_2$-heteroaryl, wherein heteroaryl is defined as a 5 or 6 membered aromatic ring containing one or two heteroatoms selected from the group consisting of O, N, or S;
 (i) —$CONHSO_2NR^{2a}R^{2a}$,
 (j) —$SO_2NHCO$-aryl, wherein aryl is as defined in $R^4$(g),
 (k) —$SO_2NHCO$-$(C_1-C_6)$-alkyl,
 (l) —$SO_2NHCO$-$(C_1-C_4)$-perfluoroalkyl,
 (m) —$SO_2NHCO$-heteroaryl, wherein heteroaryl is defined as a 5 or 6 membered aromatic ring containing one or two heteroatoms selected from the group consisting of O, N, or S,
 (n) —$SO_2NHCONR^{2a}R^{2a}$.

3. The compound as recited in claim 2 which is a compound of structural formula II:

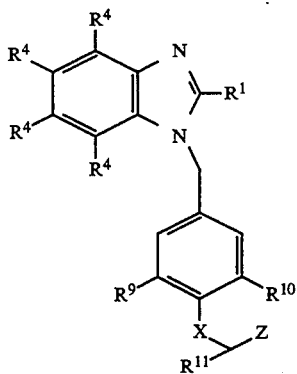

II wherein,

R² is:
(a) H,
(b) $(C_1-C_6)$-alkyl; and $R^{2a}$ is:
(a) $R^2$,
(b) benzyl, or
(c) phenyl; and $R^4$ groups are independently:
(a) H,
(b) $(C_1-C_6)$-alkyl, which is unsubstituted or substituted with:
  i) OH,
  ii) $CO_2R^{2a}$,
  iii) $NH_2$,
  iv) $(C_1-C_4)$-alkylamino,
  v) di[$(C_1-C_4)$-alkyl]amino,
(c) Cl, Br, I, F,
(d) $CF_3$,
(e) $CO_2R^{2a}$,
(f) $C(=O)NR^{2a}R^{2a}$,
(g) $(C_3-C_7)$-cycloalkyl,
(h) —C(=O)-phenyl or —C(=O)-naphthyl,
(i) —$OR^{22}$,
(j) —N[$(C_1-C_4)$-alkyl]$_2$,
(k) —NHC(=O)$(C_1-C_4)$-alkyl,
(l) —$NHCO_2(C_1-C_4)$-alkyl,
(m) —$SO_2NH$—$(C_1-C_4)$-alkyl,
(n) —$SO_2NH$-aryl,
(o) —$NO_2$,
(p) —$NHSO_2CH_3$, $R^5$ is:
(a) H, or
(b) $(C_1-C_6)$-alkyl, unsubstituted or substituted with: hydroxyl, or $CO_2R^2$; and $R^{5a}$ is
(a) H,
(b) $(C_1-C_4)$-alkyl, or
(c) $(C_1-C_4)$-acyl; and $R^{6a}$ is:
(a) H, or
(b) $(C_1-C_4)$-alkyl; and $R^9$ and $R^{10}$ are independently:
(a) H,
(b) $(C_1-C_6)$-alkyl, unsubstituted or substituted with $(C_3-C_7)$-cycloalkyl,
(c) $(C_2-C_6)$-alkenyl,
(d) $(C_2-C_6)$-alkynyl,
(e) Cl, Br, F, I,
(f) $(C_1-C_6)$-alkoxy, (g) when $R^9$ and $R^{10}$ are on adjacent carbons, they can be joined to form an aryl ring,
(h) $(C_1-C_6)$-perfluoroalkyl,
(i) $(C_3-C_7)$-cycloalkyl, unsubstituted or substituted with $(C_1-C_6)$-alkyl, or
(j) phenyl; and X is:
(a) —O—,
(b) —S(O)$_n$—,
(c) —$NR^{13}$—
(d) —$CH_2O$—,
(e) —$CH_2S(O)_n$,
(f) —$CH_2NR^{13}$—,
(g) —$OCH_2$—,
(h) —$NR^{13}CH_2$—,
(i) —$S(O)_nCH_2$—, or
(j) single bond; and $R^{11}$ is:
(a) H,
(b) $(C_1-C_6)$-alkyl, unsubstituted or substituted with:
  i) phenyl or naphthyl, or
  ii) $(C_3-C_7)$-cycloalkyl,
(c) phenyl or naphthyl,
(d) phenyl-$(C_1-C_2)$-alkyl or naphthyl-$(C_1-C_2)$-alkyl, or
(e) $(C_3-C_7)$-cycloalkyl; and $R^{13}$ is:
(a) H,
(b) $(C_1-C_6)$-alkyl,
(c) phenyl or naphthyl as defined in $R^1$(b),
(d) phenyl-$(C_1-C_6)$-alkyl-(C=O)— or naphthyl-$(C_1-C_6)$-alkyl-(C=O)—, or
(e) $(C_1-C_6)$-alkyl-(C=O)—; and Z is:
(a) —$CO_2H$,
(b) —$CO_2$—$(C_1-C_6)$-alkyl,
(c) -tetrazol-5-yl,
(d) —CONH(tetrazol-5-yl),
(e) —$CONHSO_2$-phenyl or —$CONHSO_2$-naphthyl, wherein phenyl or naphthyl is unsubstituted or substituted as defined in $R^1$(b),
(f) —$CONHSO_2$—$(C_1-C_4)$-alkyl,
(g) —$CONHSO_2$—$(C_1-C_4)$-perfluoroalkyl,
(h) —$CONHSO_2$-heteroaryl, where in heteroaryl is a 5 or 6 membered aromatic ring containing one or two heteroatoms selected from the group consisting of O, N, or S,
(i) —$CONHSO_2NR^{2a}R^{2a}$,
(j) —$SO_2NHCO$-phenyl or —$SO_2NHCO$-naphthyl, wherein phenyl or naphthyl is unsubstituted or substituted as defined in $R^1$(b),
(k) —$SO_2NHCO$-$(C_1-C_4)$-alkyl,
(l) —$SO_2NHCO$-$(C_1-C_4)$-perfluoroalkyl,
(m) —$SO_2NHCO$-heteroaryl, wherein heteroaryl is a 5 or 6 membered aromatic ring containing one or two heteroatoms selected from the group consisting of O, N, or S,
(n) —$SO_2NHCONR^{2a}R^{2a}$,
(o) —$PO(OH)_2$,
(p) —$PO(OR^2)_2$, or
(q) —$PO(OH)(OR^2)$.

4. The compound as recited in claim 3, wherein:
$R^1$ is:
(a) $(C_1-C_6)$-alkyl, $(C_2-C_6)$-alkenyl or $(C_2-C_6)$-alkynyl, each of which is unsubstituted or substituted with a substituent selected from the group consisting of:

i) $(C_1-C_4)$-alkylthio,
   ii) $(C_1-C_4)$-alkoxy,
   iii) $CF_3$,
   iv) $CF_2CF_3$, or
   v) $(C_3-C_5)$-cycloalkyl, or
   (b) $(C_1-C_4)$-perfluoroalkyl; and
$R^9$ and $R^{10}$ are each independently
   a) $(C_1-C_6)$-alkyl,
   b) $(C_1-C_6)$-alkoxy,
   c) F, Cl, Br, I,
   d) $(C_3-C_7)$-cycloalkyl or
   e) phenyl; and
X is:
   (a) —O—,
   (b) $NR^{13}$, or
   (c) —$CH_2$—;
$R^{11}$ is:
   a) phenyl or naphthyl, or
   b) phenyl-$(C_1-C_2)$-alkyl or naphthyl-$(C_1-C_2)$-alkyl; and
Z is:
   a) —COOH,
   b) -tetrazol-5-yl,
   c) —$CONHSO_2$—$(C_1-C_4)$-alkyl,
   d) —$CONHSO_2$—$(C_1-C_4)$-phenyl or —$CONHSO_2$-$(C_1-C_4)$-naphthyl, wherein phenyl or naphthyl is unsubstituted or substituted as defined in $R^1$(b),
   e) —$CONHSO_2$—$(C_1-C_4)$-heteroaryl, or
   f) —CONH (tetrazol-5-yl).

5. The compound of structural formula I as recited in claim 1 which is selected from the group consisting of:
2-butyl-1-[4-(1-carboxy-1-phenyl)methoxyphenyl]-methylbenzimidazole;
2-butyl-1-[4-(1-carboxy-1-phenyl)methoxyphenyl]-methyl-7-methylbenzimidazole;
1-[4-(1-carboxy-1-phenyl)methoxyphenyl]methyl-7-methyl-2-propylbenzimidazole;
1-[4-(1-carboxy-1-phenyl)methoxyphenyl]methyl-5,7-dimethyl-2-ethylbenzimidazole;
1-[4-(1-carboxy-1-(2-chlorophenyl))methoxyphenyl]-methyl-5,7-dimethyl-2-ethylbenzimidazole;
1-[4-(1-carboxy-1-(2-methylphenyl))methoxyphenyl]-methyl-5,7-dimethyl-2-ethylbenzimidazole;
1-[4-(1-carboxy-1-(2,6-dichlorophenyl))methoxyphenyl]methyl-5,7-dimethyl-2-ethylbenzimidazole;
1-[4-(1-carboxy-1-(2-nitrophenyl))methoxyphenyl]-methyl-5,7-dimethyl-2-ethylbenzimidazole;
1-[4-(1-carboxy-1-(2-trifluormethylphenyl))methoxy-phenyl]methyl-5,7-dimethyl-2-ethylbenzimidazole;
1-[4-(1-carboxy-1-(2-ethoxyphenyl))methoxyphenyl]-methyl-5,7-dimethyl-2-ethylbenzimidazole;
1-[4-(1-carboxy-1-(1-naphthyl))methoxyphenyl]methyl-5,7-dimethyl-2-ethylbenzimidazole;
1-[4-(1-carboxy-1-(2,6-dimethylphenyl))methoxy-phenyl]methyl-5,7-dimethyl-2-ethylbenzimidazole;
1-[4-(N-(1-carboxy-1-(2-chlorophenyl))methyl-)aminophenyl]methyl-5,7-dimethyl-2-ethylbenzimidazole;
1-[4-(N-(1-carboxy-1-(2-chlorophenyl))methyl)-N-methyl)aminophenyl]methyl-5,7-dimethyl-2-ethyl-benzimidazole;
1-[4-(N-(1-carboxy-1-(2-chlorophenyl))methyl-N-acetyl)aminophenyl]methyl-5,7 -dimethyl-2-ethyl-benzimidazole;
1-[4-(1-carboxy-1-(2-chlorophenyl))methylthio-phenyl]methyl-5,7-dimethyl-2-ethylbenzimidazole;
1-[4-(1-carboxy-1-(2-chlorophenyl))methylsulfinyl-phenyl]methyl-5,7-dimethyl-2-ethylbenzimidazole;
1-[4-(1-carboxy-1-(2-chlorophenyl))methylsulfonyl-phenyl]methyl-5,7-dimethyl-2-ethylbenzimidazole;
1-[4-(1-carboxy-1-(2-chlorophenyl))methoxy-3-methylphenyl]methyl-5,7-dimethyl-2-ethylben-zimidazole;
1-[4-(1-carboxy-1-(2-chlorophenyl))methoxy-3-ethyl-phenyl]methyl-5,7-dimethyl-2-ethylbenzimidazole;
1-[4-(1-carboxy-1-(2-chlorophenyl))methoxy-3-propylphenyl]methyl-5,7-dimethyl-2-ethylben-zimidazole;
1-[4-(1-carboxy-1-(2-chlorophenyl))methoxy-3-chlorophenyl]methyl-5,7-dimethyl-2-ethylben-zimidazole;
1-[4-(1-carboxy-1-(2-chlorophenyl))methoxy-3,5-dichlorophenyl]methyl-5,7-dimethyl-2-ethylben-zimidazole;
1-[4-(1-carboxy-1-(2-chlorophenyl))methoxyphenyl]-methyl-2-ethyl-5-hydroxymethyl-7-methylben-zimidazole;
5-carboxy-1-[4-(1-carboxy-1-(2-chlorophenyl))me-thoxyphenyl]methyl-2-ethyl-7-methylben-zimidazole;
5-carbomethoxy-1-[4-(1-carboxy-1-(2-chlorophenyl)-)methoxyphenyl]methyl-2-ethyl-7-methylben-zimidazole;
1-[4-(1-carboxy-1-(2-chlorophenyl))methoxyphenyl]-methyl-2,5-diethyl-7-methylbenzimidazole;
1-[4-(1-carboxy-1-(2-chlorophenyl))methoxyphenyl]-methyl-2,5,7-triethylbenzimidazole;
1-[4-(1-carboxy-1-(2-chlorophenyl))methoxyphenyl]-methyl-2-ethyl-4,5,7-triethylbenzimidazole;
1-[4-(1-carboxy-1-(2-chlorophenyl))methoxyphenyl]-methyl-5,7-dimethyl-2-ethyl-4-hydroxyben-zimidazole;
5,7-dimethyl-2-ethyl-1-[4-(1-tetrazoly-5-yl)-1-(2-chlorophenyl))methoxyphenyl]methylben-zimidazole;
5,7-dimethyl-2-ethyl-1-[4-(1-tetrazol-5-yl)-1-(2-methylphenyl))methoxyphenyl]methylben-zimidazole;
5,7-dimethyl-2-ethyl-1-[4-(1-tetrazol-5-yl)-1-(2-ethox-yphenyl))methoxyphenyl]methylbenzimidazole;
5,7-dimethyl-2-ethyl-1-[4-(1-tetrazol-5-yl)-1-(2-tri-fluoromethylphenyl))methoxy-3-methoxyphenyl]-methylbenzimidazole;
5,7-dimethyl-2-ethyl-1-[4-N-(1-tetrazol-5-yl)-1-(2-chlorophenyl))methylaminophenyl]methylben-zimidazole;
5,7-dimethyl-2-ethyl-1-[4-(1-tetrazol-5-yl)-1-(2-chlorophenyl))methyl-N -methylaminophenyl]me-thylbenzimidazole;
5,7-dimethyl-2-ethyl-1-[4-(1-tetrazol-5-yl)-1-(2-chlorophenyl))methylthiophenyl]methylben-zimidazole;
5,7-dimethyl-2-ethyl-1-[4-(1-tetrazol-5-yl)-1-(2-chlorophenyl))methylsulfinylphenyl]methylben-zimidazole;
5,7-dimethyl-2-ethyl-1-[4-(1-tetrazol-5-yl)-1-(2-chlorophenyl))methylsulfonylphenyl]methylben-zimidazole;
2-ethyl-5-hydroxymethyl-7-methyl-1-[4-(1-tetrazol-5-yl)-1-(2-chlorophenyl)) methoxyphenyl]methyl-benzimidazole;
5-carboxy-7-methyl-2-ethyl-1-[4-(1-(tetrazol-5-yl)-1-(2-chlorophenyl)) methoxyphenyl]methylben-zimidazole;

5-carbomethoxy-2-ethyl-7-methyl-1-[4-(1-(tetrazol-5-yl)-1-(2-chlorophenyl)) methoxyphenyl]methylbenzimidazole;

2,5-diethyl-7-methyl-1-[4-(1-(tetrazol-5-yl)-1-(2-chlorophenyl))methoxyphenyl]methylbenzimidazole;

1-[4-(1-tetrazol-5-yl)-1-(2-chlorophenyl))methoxyphenyl]methyl-2,5,7-triethylbenzimidazole;

2-ethyl-1-[4-(1-tetrazol-5-yl)-1-(2-chlorophenyl))methoxyphenyl]methyl-4,5,7-trimethylbenzimidazole;

5,7-dimethyl-2-ethyl-4-hydroxy-1-[4-(1-(tetrazol-5-yl)-1-(2-chlorophenyl)) -methoxyphenyl]methylbenzimidazole;

5,7-dimethyl-2-ethyl-1-[4-(1-(N-phenylsulfonyl)-carboxamido-1-(2-chlorophenyl))methoxyphenyl]methylbenzimidazole;

5,7-dimethyl-2-ethyl-1-[4-(1-(N-trifluoromethylsulfonyl)carboxamido-1-(2chlorophenyl))methoxyphenyl]methylbenzimidazole;

5,7-dimethyl-2-ethyl-1-[4-(1-(N-methylsulfonyl)carboxamido-1-(2-chlorophenyl))methoxyphenyl]methylbenzimidazole.

6. A pharmaceutical composition useful in the treatment of hypertension which comprises a pharmaceutically acceptable carrier and a therapeutically effective amount of a compound of claim 1.

7. The composition of claim 6 which includes another antihypertensive agent selected from a diuretic, an angiotensin converting enzyme inhibitor a calcium channel blocker and a b-blocker which are members selected from the group consisting of:

amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, parryline hydrochloride, polythiazide, prazosin, propranolol, *rauwolfia serpentina*, rescinnsmine, resetpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapzil, enalaprilat, fosinopril sodium, lisinopril, pentopril, quinapril hydrochloride, ramapril, reprotide, zofenopril calcium, diflusinal, diltiazem, felodipine, nicardipine, nifedipine, niludipine, nimodipine, nisoldipine, nitrendipine, and the like, as well as admixtures and combinations thereof.

8. A method of treating hypertension which comprises administering to a patient in need of such treatment a therapeutically effective amount of a compound of claim 1.

9. An ophthalmological formulation for the treatment of ocular hypertension comprising an ophthalmologically acceptable carrier and an effective ocular antihypertensive amount of a compound of claim 1.

10. A method of treating ocular hypertension comprising topical ocular administration to a patient in need of such treatment of an effective ocular antihypertensive amount of a compound of claim 1.

11. A method of treating cognitive dysfunction, anxiety, or depression comprising administering to a patient in need of such treatment, a therapeutically effective amount of a compound of claim 1.

* * * * *

UNITED STATES PATENT AND TRADEMARK OFFICE
CERTIFICATE OF CORRECTION

PATENT NO. : 5,449,682

DATED : September 12, 1995

INVENTOR(S) : William J. Greenlee, David Hangauer, Arthur A. Patchett, Thomas F. Walsh, Kenneth J. Fitch, Daljit S. Dhanoa and Ralph A. Rivero It is certified that error appears in the above-indentified patent and that said Letters Patent is hereby corrected as shown below:

Column 182, in Claim 1, line 34 read:

xi) $SO_2NMR^{2a}$; and should read:

xi) $SO_2NHR^{2a}$; and

Column 183, in Claim 1, line 30 read:

v) $CONMR^{2a}$, should read:

v) $CONHR^{2a}$,

Column 184, in Claim 1, line 6 read:

ii) $CONMR^2$ , should read:

ii) $CONHR^2$ ,

Column 185, in Claim 1, line 5 read:

i) C, Br, I, F, should read:

i) Cl, Br, I, F,

UNITED STATES PATENT AND TRADEMARK OFFICE
CERTIFICATE OF CORRECTION

PATENT NO. : 5,449,682
DATED : September 12, 1995
INVENTOR(S) : William J. Greenlee, David Hangauer, Arthur A. Patchett, Thomas F. Walsh, Kenneth J. Fitch, Daljit S. Dhanoa and Ralph A. Rivero It is certified that error appears in the above-indentified patent and that said Letters Patent is hereby corrected as shown below:

Column 186, in Claim 1, line 56 read:

d) $CH_2CH_2-N[CH_2CH_2[_2O,$ should read:

d) $CH_2CH_2-N[CH_2CH_2]_2O,$

Column 187, in Claim 1, between lines 15 and 19 read:

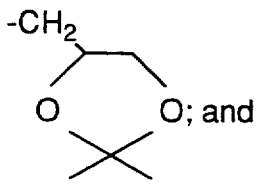

should read:

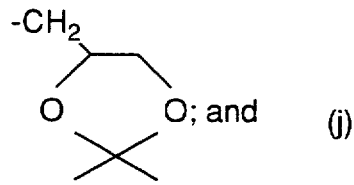

(j)

Column 194, in Claim 7, line 3 read:

parryline hydrochloride, should read:

pargyline hydrochloride,

UNITED STATES PATENT AND TRADEMARK OFFICE
CERTIFICATE OF CORRECTION

PATENT NO. : 5,449,682
DATED : September 12, 1995
INVENTOR(S) : William J. Greenlee, David Hangauer, Arthur A. Patchett, Thomas F. Walsh, Kenneth J. Fitch, Daljit S. Dhanoa and Ralph A. Rivero It is certified that error appears in the above-indentified patent and that said Letters Patent is hereby corrected as shown below:

Column 194, in Claim 7, line 5 read:
  resetpine, should read:
  reserpine,

Column 194, in Claim 7, line 12 read:
  enalapzil, should read:
  enalapril,

Column 194, in Claim 7, line 14 read:
  reprotide, should read:
  teprotide,

Signed and Sealed this

Twenty-sixth Day of December, 1995

Attest:

BRUCE LEHMAN

*Attesting Officer*     *Commissioner of Patents and Trademarks*